US012637458B2

(12) United States Patent
Tate et al.

(10) Patent No.: US 12,637,458 B2
(45) Date of Patent: May 26, 2026

(54) IMIDAZO[1,2-A]PYRIDINE COMPOUNDS AND THEIR USE IN THERAPY

(71) Applicants: Imperial College Innovations Limited, London (GB); MyricX Pharma Limited, London (GB)

(72) Inventors: Edward William Tate, London (GB); Andrew Simon Bell, London (GB); Roger Bonnert, Geneva (CH); Robin Carr, London (GB); Timothy John Ritchie, London (GB)

(73) Assignees: IMPERIAL COLLEGE INNOVATIONS LIMITED, London (GB); MYRICX PHARMA LIMITED, London (GB)

( * ) Notice: Subject to any disclaimer, the term of this patent is extended or adjusted under 35 U.S.C. 154(b) by 395 days.

(21) Appl. No.: 18/026,684

(22) PCT Filed: Sep. 17, 2021

(86) PCT No.: PCT/GB2021/052425
§ 371 (c)(1),
(2) Date: Mar. 16, 2023

(87) PCT Pub. No.: WO2022/058745
PCT Pub. Date: Mar. 24, 2022

(65) Prior Publication Data
US 2024/0166643 A1 May 23, 2024

(30) Foreign Application Priority Data
Sep. 18, 2020 (GB) ..................................... 2014736

(51) Int. Cl.
| | |
|---|---|
| *C07D 471/04* | (2006.01) |
| *A61K 45/06* | (2006.01) |
| *A61P 35/00* | (2006.01) |
| *C07D 487/08* | (2006.01) |
| *C07D 495/04* | (2006.01) |

(52) U.S. Cl.
CPC ............ *C07D 471/04* (2013.01); *A61K 45/06* (2013.01); *A61P 35/00* (2018.01); *C07D 487/08* (2013.01); *C07D 495/04* (2013.01)

(58) Field of Classification Search
CPC .. C07D 471/04; C07D 487/08; C07D 495/04; A61P 35/00; A61K 45/06
See application file for complete search history.

(56) References Cited

U.S. PATENT DOCUMENTS

| | | | |
|---|---|---|---|
| 3,763,156 A | 10/1973 | Woitun et al. | |
| 3,939,268 A | 2/1976 | Nickl et al. | |
| 4,423,049 A | 12/1983 | Temple, Jr. | |
| 7,244,735 B2 | 7/2007 | Straub et al. | |
| 8,993,757 B2 | 3/2015 | Huisman et al. | |
| 10,220,034 B2 | 3/2019 | Zlotnick et al. | |
| 10,227,329 B2 | 3/2019 | Brubaker et al. | |
| 10,308,637 B2 * | 6/2019 | McDonald ........... | C07D 471/04 |
| 10,759,804 B2 | 9/2020 | Bell et al. | |
| 11,466,011 B2 | 10/2022 | Bell et al. | |
| 2022/0064158 A1 | 3/2022 | Tate et al. | |
| 2022/0071960 A1 | 3/2022 | Tate et al. | |
| 2022/0280484 A1 | 9/2022 | Tate et al. | |
| 2022/0411431 A1 | 12/2022 | Bell et al. | |

FOREIGN PATENT DOCUMENTS

| | | |
|---|---|---|
| WO | WO 2005/068468 A2 | 7/2005 |
| WO | WO 2013/041457 A1 | 3/2013 |
| WO | WO 2015/057945 A1 | 4/2015 |
| WO | WO 2017/001812 A1 | 1/2017 |
| WO | WO 2018/017983 A1 | 1/2018 |
| WO | WO 2020/128473 A1 | 6/2020 |

(Continued)

OTHER PUBLICATIONS

Bell et al. "Selective Inhibitors of Protozoan Protein N-myristoyltransferases as Starting Points for Tropical Disease Medicinal Chemistry Programs", PLOS Neglected Tropical Diseases, vol. 6, Issue 4, Apr. 24, 2012, pp. 1-9.
Database Registry Chemical Abstracts Service, XP055891355, Feb. 14, 2013.
Database Registry Chemical Abstracts Service, XP055891363, Dec. 22, 2013.
Database Registry Chemical Abstracts Service, XP055891367, Dec. 27, 2013.

(Continued)

*Primary Examiner* — Kamal A Saeed
*Assistant Examiner* — Quincy Mckoy
(74) *Attorney, Agent, or Firm* — Birch, Stewart, Kolasch & Birch, LLP

(57) ABSTRACT

The invention relates to compounds of Formula (I): and related aspects.

Formula (I)

23 Claims, 6 Drawing Sheets

(56)            References Cited

FOREIGN PATENT DOCUMENTS

| WO | WO 2020/128475 A1 | 6/2020 |
| WO | WO 2022/090746 A1 | 5/2022 |

OTHER PUBLICATIONS

Database Registry Chemical Abstracts Service, XP055891373, Jan. 1, 2014.

Database Registry Chemical Abstracts Service, XP055891375, Jan. 7, 2014.

Database Registry Chemical Abstracts Service, XP055891379, Jan. 15, 2014.

Database Registry Chemical Abstracts Service, XP055891384, Feb. 26, 2014.

Database Registry Chemical Abstracts Service, XP055891386, Mar. 7, 2016.

Database Registry Chemical Abstracts Service, XP055891389, Mar. 9, 2016.

Database Registry Chemical Abstracts Service, XP055891392, Apr. 19, 2017.

Database Registry Chemical Abstracts Service, XP055901359, Feb. 15, 2013.

Database Registry Chemical Abstracts Service, XP55865845, Apr. 19, 2011.

International Search Report (PCT/ISA/210) issued in PCT/GB2021/052425, dated Feb. 24, 2022.

Written Opinion of the International Searching Authority (PCT/ISA/237) issued in PCT/GB2021/052425, dated Feb. 24, 2022.

STN Registry, CAS No. 1282577-98-3, Apr. 19, 2011, 1 page total.

Bell, "N-Myristoyltransferase as a Drug Target: A (Chemical) Space Odyssey", Imperial College London, Institute of Chemical Biology, Department of Chemistry, Jun. 26, 2017, pp. 1-314, with 4 Appendices.

Database Registry Chemical Abstracts Service, CAS Registry No. 1485379-70-1 and 1489988-32-0. Dec. 2, 2013 and Dec. 8, 2013.

Database Registry Chemical Abstracts Service, CAS Registry No. 1420967-38-9 and 1420898-89-9, XP055891359, Feb. 15, 2013 and Feb. 14, 2013.

* cited by examiner (a)

(b)

Concentration of Example
Compound 3

(Error bars: SD; N = 4, 72h)

Concentration of Example
Compound 2

(Error bars: SD; N = 4, 72h)

(a)

(b)

Concentration of Example Compound 3

(Error bars: SD; N = 4, 72h)

Concentration of Example Compound 2

(Error bars: SD; N = 4, 72h)

(a)

Concentration of Example
Compound 3

(Error bars: SD; N = 3, 96h)

(b)

Concentration of Example
Compound 2

(Error bars: SD, N = 3, 96h)

IMIDAZO[1,2-A]PYRIDINE COMPOUNDS AND THEIR USE IN THERAPY

FIELD OF INVENTION

This invention relates to compounds of formula (I) and salts thereof which have activity as inhibitors of N-myristoyl transferase (NMT) especially the human forms thereof. The invention also relates to uses of such compounds as medicaments, in particular in the prevention or treatment of a disease or disorder in which inhibition of N-myristoyl transferase provides a therapeutic or prophylactic effect. Such diseases include hyperproliferative disorders (such as B-cell lymphoma and leukaemia) and viral infections (such as human rhinovirus, HIV, poliovirus, foot and mouth disease, enterovirus 71 and pox virus infections). Microbial infections (such as protozoan infections such as malaria and leishmaniasis and fungal infections) may also be treated.

BACKGROUND TO THE INVENTION

N-myristoyl transferase (NMT) is a monomeric enzyme, which is ubiquitous in eukaryotes. NMT catalyses an irreversible co-translational transfer of myristic acid (a saturated 14-carbon fatty acid) from myristoyl-Coenzyme A (myr-CoA) to a protein substrate containing an N-terminal glycine with formation of an amide bond (Farazi, T. A., G. Waksman, and J. I. Gordon, *J. Biol. Chem.,* 2001. 276(43): p. 39501-39504). N-myristoylation by NMT follows an ordered Bi—Bi mechanism. Myr-CoA binds to NMT in the first NMT binding pocket prior to the binding of a protein substrate (Rudnick, D. A., C. A. McWherter, W. J. Rocque, et al., *J. Biol. Chem.,* 1991. 266(15): p. 9732-9739). The bound myr-CoA facilitates the opening of a second binding pocket where the protein substrate binds. Following binding of the protein substrate, transfer of myristate to the protein substrate takes place via a nucleophilic addition-elimination reaction, finally with the release of CoA and the myristoylated protein.

There are two types of human NMT, human NMT1 (HsNMT1) and human NMT2 (HsNMT2). Inhibition of human NMT has been suggested as a target for treating or preventing various diseases or disorders, for example hyperproliferative disorders (for example cancers, e.g. human colorectal cancer, gallbladder carcinoma, brain tumors, and lymphomas such as B-cell lymphoma) (Resh M D. 1993. Biochern. Biophys.Acta 1115, 307-22; Bertiaume L G, Beuachamp E, WO2017011907), and viral infections such as HIV (Gottlinger H G, Sodroski J G, Haseltine W A. 1989. Proc. Nat. Acad. Sci. USA 86:5781-85; Bryant M L, Ratner L. 1990. Proc. Natl. Acad. Sci. USA 87:523-27), human rhinovirus (RV, formally abbreviated as HRV) (Davis M P, Bottley, G, Beales L P, Killington, R A, Rowlands D J, Tuthill, T J, 2008 Journal of Virology 82 4169-4174; Mousnier A, Bell A S, Swieboda D P, Morales-Sanfrutos J, Perez-Dorado I, Brannigan J A, Newman J, Ritzefeld M, Hutton, J A, Guedan A, Asfor A S, Robinson, S W, Hopkins-Navratilova 1, Wilkinson A J, Johnston S L, Leatherbarrow R J, Tuthill T J, Solari R, Tate E W 2018 Nature Chemistry 10 (6) 599-606), Corbic Ramljak I, Stanger J, Real-Hohn A. Dreier D, Wimmer L., Redlberger-Fritz M, Fischl W, Klingel K, Mihovilovic M D, Blaas D, Kowalski H, PLOS Pathogens 14(8): e1007203 and dengue virus 2019 Microbiology e00831 Suwanmanee S., Mahakhunkijcharoen Y., Ampawong, S., Leaungwutiwong P., Missé, D, Luplertlop, N. As NMT plays a key role in protein trafficking, mediation of protein-protein interactions, stabilization of protein structures and signal transduction in living systems, inhibition of the NMT enzyme has the potential to disrupt multi-protein pathways. This is an attractive characteristic to reduce the risk of the development of resistance in, for example, treatment or prevention of hyperproliferative disorders and microbial infections.

Biochemical analysis has shown high conservation of myr-CoA binding sites, but divergent peptide binding specificities between human and fungal and parasitic NMTs (Johnson, D. R., R. S. Bhatnagar, J. I. Gordon, et al., *Annu. Rev. Biochem.,* 1994. 63: p. 869-914). As a consequence, NMT can be viewed as a target with the potential for the development of selective non-peptidic inhibitors.

NMT fungal and mammalian enzymes from various sources have been well characterized, see for example the following references: *Saccharomyces cerevisiae* (Duronio, R. J., D. A. Towler, R. O. Heuckeroth, et al., *Science,* 1989. 243(4892): p. 796-800), *Candida albicans* (Wiegand, R. C., C. Carr, J. C. Minnerly, et al., *J. Biol. Chem.,* 1992. 267(12): p. 8591-8598) and *Cryptococcus neoformans* (Lodge, J. K., R. L. Johnson, R. A. Weinberg, et al., *J. Biol. Chem.,* 1994. 269(4): p. 2996-3009), human NMT1 (McIlhinney, R. A. J. and K. McGlone, *Exp. Cell Res.,* 1996. 223: p. 348-356) and human NMT2 (Giang, D. K. and B. F. Cravatt, *J. Biol. Chem.,* 1998. 273: p. 6595-6598).

NMT has also been characterised in protozoan parasites. See for example the following references: *Plasmodium falciparum* (Pf) (Gunaratne, R. S., M. Sajid, I. T. Ling, et al., *Biochem. J.,* 2000. 348: p. 459-463), *Plasmodium vivax* (Pv), *Leishmania major* (Lm) (Price, H. P., M. R. Menon, C. Panethymitaki, et al., *J. Biol. Chem.,* 2003. 278(9): p. 7206-7214), *Leishmania donovani* (Ld) (Branningan, J. A., B. A. Smith, Z. Yu, et al., *J. Mol. Biol.,* 2010. 396: p. 985-999) and *Trypanosoma brucei* (Tb) (Price, H. P., M. R. Menon, C. Panethymitaki, et al., *J. Biol. Chem.,* 2003. 278(9): p. 7206-7214.

Several myristoylated proteins have been observed in protozoans and their functions have been determined. These proteins and the processes in which they are involved suggest that N-myristoylation may play a role in multiple pathways in the biology of parasites. Inhibition of myristoylation could thus disrupt multiple pathways. The potential for the development of resistance should thus be smaller than for some other targets. To date, only a single isoform of NMT has been found in each protozoan organism investigated. If it is correct that there is only a single isoform, then that will also assist in reducing the potential for the development of resistance.

As described above, there are two binding pockets in NMT. One is the myr-CoA binding pocket and the other is the peptide binding pocket. Most NMT inhibitors reported to date target the peptide binding pocket. Most NMT inhibitors developed to date have been targeted to fungal N-myristoyl transferases.

Compounds active as inhibitors of NMT have previously been disclosed, see for example WO00/37464 (Roche), WO2010/026365 (University of Dundee), WO2013/083991 (Imperial Innovations Limited), WO2017/001812 (Imperial Innovations Limited), WO20201128473 (Imperial College Innovations Limited) and WO2020/128475 (Imperial College Innovations Limited).

In addition, Bell et al disclosed the results of a high throughput screening study carried out to identify inhibitors of NMT, and disclosed the compounds PF-03531814 (1-(5-chloro-2-{[2-(dimethylamino)ethyl]amino}pyrimidin-4-yl)-N-[(5-methylpyrazin-2-yl)methyl]azetidine-3-carboxamide) and PF-03531549 (1-(5-chloro-2-{[2-(dimethylamino)

ethyl]amino}pyrimidin-4-yl)-N-[(2,4-difluorophenyl)methyl]azetidine-3-carboxamide) as having selective activity for *Plasmodium falciparum* NMT over both human NMTs (PLoS Neglected Tropical Diseases, 2012, 6, e1625).

PF-03531814

PF-03531549

There remains a need in the art for further compounds active as inhibitors of N-myristoyl transferase, particularly the human forms thereof.

SUMMARY OF THE INVENTION

A compound of Formula (I), or a pharmaceutically acceptable ester, amide, carbamate or salt thereof, including salts of such esters, amides or carbamates:

Formula (I)

wherein:

$n_1$ is 1 or 2; $n_2$ is 1 or 2;

$X^1$ is selected from the group consisting of $CR^x$ and N;

when present, $R^x$ is selected from the group consisting of hydrogen, halogen, and $-C_{1-4}$alkyl optionally substituted by 1, 2 or 3 substituents, each substituent being independently selected from the group consisting of halogen, $-OH$, $-OCH_3$, and $-OCF_3$;

$R^1$ is selected from the group consisting of hydrogen; $-C_{1-4}$alkyl optionally substituted by 1, 2 or 3 substituents, each substituent being independently selected from the group consisting of halogen, $-OCH_3$, and $-OCF_3$; and $-C_{3-6}$cycloalkyl optionally substituted by 1, 2 or 3 substituents, each substituent being independently selected from the group consisting of halogen, $-CH_3$, $-OCH_3$, and $-OCF_3$;

$R^2$ is selected from the group consisting of hydrogen; $-C_{1-4}$alkyl optionally substituted by 1, 2 or 3 substituents, each substituent being independently selected from the group consisting of halogen, $-OCH_3$, and $-OCF_3$; and $-C_{3-6}$cycloalkyl optionally substituted by 1, 2 or 3 substituents, each substituent being independently selected from the group consisting of halogen, $-CH_3$, $-OCH_3$, and $-OCF_3$;

or $R^1$ and $R^2$ are linked such that together with the atom to which they are attached they form a $C_{3-6}$cycloalkyl group or a 3- to 6-membered non-aromatic heterocyclyl group comprising 1 heteroatom selected from the group consisting of O and N, wherein said $C_{3-6}$cycloalkyl group or 3- to 6-membered non-aromatic heterocyclyl group is optionally substituted by 1 or 2 substituents, each substituent being independently selected from the group consisting of halogen, $-OH$, $-CH_3$, $-OCH_3$, and $-OCF_3$;

$R^3$ is selected from the group consisting of hydrogen; $-C_{1-4}$alkyl optionally substituted by 1, 2 or 3 substituents, each substituent being independently selected from the group consisting of halogen, $-OH$, $-OCH_3$, and $-OCF_3$; and $-C_{3-6}$cycloalkyl optionally substituted by 1, 2 or 3 substituents, each substituent being independently selected from the group consisting of halogen, $-OH$, $-CH_3$, $-OCH_3$, and $-OCF_3$;

or $R^1$ and $R^3$ are linked such that together with the atoms to which they are attached they form a 3- to 6-membered non-aromatic heterocyclyl group comprising 1 N heteroatom, wherein said 3- to 6-membered non-aromatic heterocyclyl group is optionally substituted by 1 or 2 substituents, each substituent being independently selected from the group consisting of halogen, $-CH_3$, $-OH$, $-OCH_3$, and $-OCF_3$;

$X^2$ is selected from the group consisting of $CR^4$ and N;

when present, $R^4$ is selected from the group consisting of hydrogen; halogen; $-C_{1-4}$alkyl optionally substituted by 1, 2 or 3 substituents, each substituent being independently selected from the group consisting of halogen, $-OH$, $-OCH_3$, $-OCF_3$, and $-NR^aR^b$;

$R^{5a}$ and $R^{5d}$ are independently selected from the group consisting of hydrogen; halogen; methyl optionally substituted by 1, 2 or 3 substituents, each substituent being independently selected from the group consisting of halogen, $-OH$, $-OCH_3$, and $-OCF_3$; and methoxy optionally substituted by 1, 2 or 3 substituents, each substituent being independently selected from the group consisting of halogen, $-OH$, $-OCH_3$, and $-OCF_3$;

$R^{5b}$ and $R^{5c}$ are independently selected from the group consisting of hydrogen; halogen; $-C_{1-4}$alkyl optionally substituted by 1, 2 or 3 substituents, each substituent being independently selected from the group consisting of halogen, —OH, —OCH$_3$, and —OCF$_3$; —O—C$_{1-4}$alkyl optionally substituted by 1, 2 or 3 substituents, each substituent being independently selected from the group consisting of halogen, —OH, —OCH$_3$, and —OCF$_3$; and C$_{3-6}$cycloalkyl optionally substituted by 1, 2 or 3 substituents, each substituent being independently selected from the group consisting of halogen, —CH$_3$, —OH, —OCH$_3$, and —OCF$_3$;

or R$^{5b}$ and R$^{5c}$ are linked such that together with the atoms to which they are attached they form a 6-membered aryl group or a 5- or 6-membered aromatic heterocyclyl group comprising 1 or 2 heteroatoms selected from the group consisting of S, O and N, wherein said 6-membered aryl group or 5- or 6-membered aromatic heterocyclyl group is optionally substituted by 1 or 2 substituents, each substituent being independently selected from the group consisting of halogen, —OH, —OCH$_3$, and —OCF$_3$;

R$^6$ is selected from the group consisting of hydrogen and methyl;

when present, each R$^7$ is —C$_{1-4}$alkyl optionally substituted by 1, 2 or 3 substituents, each substituent being independently selected from the group consisting of halogen, —OH, —OCH$_3$, and —OCF$_3$;

R$^8$ is selected from the group consisting of hydrogen; halogen; —OH; —CN; —C$_{1-4}$alkyl optionally substituted by 1, 2 or 3 substituents, each substituent being independently selected from the group consisting of halogen, —OH, —CN, and methoxy optionally substituted by 1, 2 or 3 halogen; —C$_{3-6}$cycloalkyl optionally substituted by 1, 2 or 3 substituents, each substituent being independently selected from the group consisting of halogen, —CH$_3$, —OH, —CN, and methoxy optionally substituted by 1, 2 or 3 halogen; —C$_{1-4}$alkenyl optionally substituted by 1, 2 or 3 substituents, each substituent being independently selected from the group consisting of halogen, —OH, —CN, and methoxy optionally substituted by 1, 2 or 3 halogen; and —O—C$_{1-4}$alkyl optionally substituted by 1, 2 or 3 substituents, each substituent being independently selected from the group consisting of halogen, —OH, CN and methoxy optionally substituted by 1, 2 or 3 halogen; R$^9$ is selected from the group consisting of hydrogen, and —C$_{1-4}$alkyl optionally substituted by 1, 2 or 3 substituents, each substituent being independently selected from the group consisting of halogen, —OH, —OCH$_3$, and —OCF$_3$; or R$^8$ and R$^9$ are linked such that together with the atoms to which they are attached they form a 6-membered aryl group, a C$_{5-6}$cycloalkyl group, or a 5- or 6-membered aromatic heterocyclyl group comprising 1 or 2 heteroatoms selected from N, O and S, and wherein said 6-membered aryl group, C$_{5-6}$cycloalkyl group or 5- to 6-membered aromatic heterocyclyl group is optionally substituted by 1, 2 or 3 substituents, each substituent being independently selected from the group consisting of halogen; —OH; —CN; —C$_{1-4}$alkyl optionally substituted by 1, 2 or 3 substituents, each substituent being independently selected from the group consisting of halogen, —OH, and methoxy optionally substituted by 1, 2 or 3 halogen; and —O—C$_{1-4}$alkyl optionally substituted by 1, 2 or 3 substituents, each substituent being independently selected from the group consisting of -halogen, —OH, and methoxy optionally substituted by 1, 2 or 3 halogen;

6 p is 0, 1, or 2;

Z is a 5- to 13-membered non-aromatic heterocyclyl group comprising 1, 2 or 3 heteroatoms selected from N, O and S, wherein at least one of the heteroatoms is N, and wherein said 5- to 13-membered non-aromatic heterocyclyl group is optionally substituted with 1, 2, 3 or 4 substituents, each substituent being independently selected from the group consisting of halogen; —C$_{1-6}$alkyl optionally substituted by 1, 2 or 3 substituents, each substituent being independently selected from the group consisting of halogen, —OH, and —OC$_{1-3}$alkyl optionally substituted by 1, 2 or 3 halogen; —O—C$_{1-6}$alkyl optionally substituted by 1, 2 or 3 substituents, each substituent being independently selected from the group consisting of halogen, —OH, and —O—C$_{1-3}$alkyl optionally substituted by 1, 2 or 3 halogen; NR$^c$R$^d$; and C$_{3-6}$cycloalkyl optionally substituted by 1, 2 or 3 substituents, each substituent being independently selected from the group consisting of halogen, —OH, and —O—C$_{1-3}$alkyl optionally substituted by 1, 2 or 3 halogen; or when two substituents are on adjacent ring positions they may be linked such that together with the atoms to which they are attached they form a C$_{3-6}$cycloalkyl group or a 4- to 6-membered non-aromatic heterocyclyl group comprising 1 heteroatom selected from the group consisting of O and N, wherein said C$_{3-6}$cycloalkyl group or 4- to 6-membered non-aromatic heterocyclyl group is optionally substituted by 1 or 2 substituents, each substituent being independently selected from the group consisting of halogen; —C$_{1-6}$alkyl optionally substituted by 1, 2 or 3 substituents, each substituent being independently selected from the group consisting of halogen, —OH, and —OC$_{1-3}$alkyl optionally substituted by 1, 2 or 3 halogen; and —O—C$_{1-6}$alkyl optionally substituted by 1, 2 or 3 substituents, each substituent being independently selected from the group consisting of halogen, —OH, and —O—C$_{1-3}$alkyl optionally substituted by 1, 2 or 3 halogen;

R$^c$ and R$^d$ are independently selected from the group consisting of hydrogen; —C$_{1-6}$alkyl optionally substituted by 1, 2 or 3 substituents, each substituent being independently selected from the group consisting of halogen, —OCH$_3$, and —OCF$_3$; and C$_{3-6}$cycloalkyl optionally substituted by 1, 2 or 3 substituents, each substituent being independently selected from the group consisting of halogen, —CH$_3$, —OH, —OCH$_3$, and —OCF$_3$; or Z is —NR$^{10}$R$^{11}$, wherein R$^{10}$ is selected from the group consisting of hydrogen and —C$_{1-4}$alkyl; and R$^{11}$ is a 5- to 10-membered non-aromatic heterocyclyl group comprising 1, 2 or 3 heteroatoms selected from N, O and S, wherein at least one of the heteroatoms is N, and wherein said 5- to 10-membered non-aromatic heterocyclyl group is optionally substituted with 1, 2, 3 or 4 substituents independently selected from the group consisting of halogen; —OH; —C$_{1-6}$alkyl optionally substituted by 1, 2 or 3 substituents, each substituent being independently selected from the group consisting of halogen, —OH, and —OC$_{1-3}$alkyl optionally substituted by 1, 2 or 3 halogen; and —O—C$_{1-6}$alkyl optionally substituted by 1, 2 or 3 substituents, each substituent being independently selected from the group consisting of halogen, —OH, and —O—C$_{1-3}$alkyl optionally substituted by 1, 2 or 3 halogen; and when present, each R$^a$ and R$^b$ are independently selected from the group consisting of hydrogen and —C$_{1-4}$alkyl.

The invention also provides a compound of Formula (I), or a pharmaceutically acceptable ester, amide, carbamate or salt thereof, including salts of such esters, amides or carbamates:

Formula (I)

wherein:

$n_1$ is 1 or 2; $n_2$ is 1 or 2;

$X^1$ is selected from the group consisting of $CR^x$ and N;

when present, $R^x$ is selected from the group consisting of hydrogen, halogen, and —$C_{1-4}$alkyl optionally substituted by 1, 2 or 3 substituents, each substituent being independently selected from the group consisting of halogen, —OH, —$OCH_3$, and —$OCF_3$;

$R^1$ is selected from the group consisting of hydrogen; —$C_{1-4}$alkyl optionally substituted by 1, 2 or 3 substituents, each substituent being independently selected from the group consisting of halogen, —$OCH_3$, and —$OCF_3$; and —$C_{3-6}$cycloalkyl optionally substituted by 1, 2 or 3 substituents, each substituent being independently selected from the group consisting of halogen, —$CH_3$, —$OCH_3$, and —$OCF_3$;

$R^2$ is selected from the group consisting of hydrogen; —$C_{1-4}$alkyl optionally substituted by 1, 2 or 3 substituents, each substituent being independently selected from the group consisting of halogen, —$OCH_3$, and —$OCF_3$; and —$C_{3-6}$cycloalkyl optionally substituted by 1, 2 or 3 substituents, each substituent being independently selected from the group consisting of halogen, —$CH_3$, —$OCH_3$, and —$OCF_3$;

or $R^1$ and $R^2$ are linked such that together with the atom to which they are attached they form a $C_{3-6}$cycloalkyl group or a 3- to 6-membered non-aromatic heterocyclyl group comprising 1 heteroatom selected from the group consisting of O and N, wherein said $C_{3-6}$cycloalkyl group or 3- to 6-membered non-aromatic heterocyclyl group is optionally substituted by 1 or 2 substituents, each substituent being independently selected from the group consisting of halogen, —OH, —$CH_3$, —$OCH_3$, and —$OCF_3$;

$R^3$ is selected from the group consisting of hydrogen; —$C_{1-4}$alkyl optionally substituted by 1, 2 or 3 substituents, each substituent being independently selected from the group consisting of halogen, —OH, —$CH_3$, —$OCH_3$, and —$OCF_3$; and —$C_{3-6}$cycloalkyl optionally substituted by 1, 2 or 3 substituents, each substituent being independently selected from the group consisting of halogen, —OH, —$OCH_3$, and —$OCF_3$;

or $R^1$ and $R^3$ are linked such that together with the atoms to which they are attached they form a 3- to 6-membered non-aromatic heterocyclyl group comprising 1 N heteroatom, wherein said 3- to 6-membered non-aromatic heterocyclyl group is optionally substituted by 1 or 2 substituents, each substituent being independently selected from the group consisting of halogen, —OH, —$CH_3$, —$OCH_3$, and —$OCF_3$;

$X^2$ is selected from the group consisting of $CR^4$ and N;

when present, $R^4$ is selected from the group consisting of hydrogen; halogen; —$C_{1-4}$alkyl optionally substituted by 1, 2 or 3 substituents, each substituent being independently selected from the group consisting of halogen, —OH, —$OCH_3$, and —$OCF_3$; and —$NR^aR^b$;

$R^{5a}$ and $R^{5d}$ are independently selected from the group consisting of hydrogen; halogen; methyl optionally substituted by 1, 2 or 3 substituents, each substituent being independently selected from the group consisting of halogen, —OH, —$OCH_3$, and —$OCF_3$; and methoxy optionally substituted by 1, 2 or 3 substituents, each substituent being independently selected from the group consisting of halogen, —OH, —$OCH_3$, and —$OCF_3$;

$R^{5b}$ and $R^{5c}$ are independently selected from the group consisting of hydrogen; halogen; —$C_{1-4}$ alkyl optionally substituted by 1, 2 or 3 substituents, each substituent being independently selected from the group consisting of halogen, —OH, —$OCH_3$, and —$OCF_3$; —O—$C_{1-4}$alkyl optionally substituted by 1, 2 or 3 substituents, each substituent being independently selected from the group consisting of halogen, —OH, —$OCH_3$, and —$OCF_3$; and $C_{3-6}$cycloalkyl optionally substituted by 1, 2 or 3 substituents, each substituent being independently selected from the group consisting of halogen, —$CH_3$, —OH, —$OCH_3$, and —$OCF_3$;

or $R^{5b}$ and $R^{5c}$ are linked such that together with the atoms to which they are attached they form a 6-membered aryl group or a 5- or 6-membered aromatic heterocyclyl group comprising 1 or 2 heteroatoms selected from the group consisting of S, O and N, wherein said 6-membered aryl group or 5- or 6-membered aromatic heterocyclyl group is optionally substituted by 1 or 2 substituents, each substituent being independently selected from the group consisting of halogen, —OH, —$OCH_3$, and —$OCF_3$;

$R^6$ is selected from the group consisting of hydrogen and methyl;

when present, each $R^7$ is —$C_{1-4}$alkyl optionally substituted by 1, 2 or 3 substituents, each substituent being independently selected from the group consisting of halogen, —OH, —$OCH_3$, and —$OCF_3$;

$R^8$ is selected from the group consisting of hydrogen; halogen; —OH; —CN; —$C_{1-4}$alkyl optionally substituted by 1, 2 or 3 substituents, each substituent being independently selected from the group consisting of halogen, —OH, —CN, and methoxy optionally substituted by 1, 2 or 3 halogen; —$C_{3-6}$cycloalkyl optionally substituted by 1, 2 or 3 substituents, each substituent being independently selected from the group consisting of halogen, —$CH_3$, —OH, —CN, and methoxy optionally substituted by 1, 2 or 3 halogen; —$C_{1-4}$alkenyl optionally substituted by 1, 2 or 3 substituents, each substituent being independently selected from the group consisting of halogen, —OH, —CN, and methoxy optionally substituted by 1, 2 or 3 halogen; and —O—$C_{1-4}$alkyl optionally substituted by 1, 2 or 3 substituents, each substituent being independently selected from the group consisting of halogen, —OH, CN and methoxy optionally substituted by 1, 2 or 3 halogen;

$R^9$ is selected from the group consisting of hydrogen, and —$C_{1-4}$alkyl optionally substituted by 1, 2 or 3 substituents, each substituent being independently selected from the group consisting of halogen, —OH, —$OCH_3$, and —$OCF_3$; or $R^8$ and $R^9$ are linked such that together with the atoms to which they are attached they form a 6-membered aryl group or a 5- or 6-membered aromatic heterocyclyl group comprising 1 or 2 heteroatoms selected from N, O and S, and wherein said 6-membered aryl group or 5- to 6-membered aromatic heterocyclyl group is optionally substituted by 1, 2 or 3 substituents, each substituent being independently selected from the group consisting of halogen; —OH; —CN; —$C_{1-4}$ alkyl optionally substituted by 1, 2 or 3 substituents, each substituent being independently selected from the group consisting of halogen, —OH, and methoxy optionally substituted by 1, 2 or 3 halogen; and —O—$C_{1-4}$alkyl optionally substituted by 1, 2 or 3 substituents, each substituent being independently selected from the group consisting of -halogen, —OH, and methoxy optionally substituted by 1, 2 or 3 halogen;

p is 0, 1, or 2;

Z is a 5- to 13-membered non-aromatic heterocyclyl group comprising 1, 2 or 3 heteroatoms selected from N, O and S, wherein at least one of the heteroatoms is N, and wherein said 5- to 10-membered non-aromatic heterocyclyl group is optionally substituted with 1, 2, 3 or 4 substituents, each substituent being independently selected from the group consisting of halogen; —$C_{1-6}$alkyl optionally substituted by 1, 2 or 3 substituents, each substituent being independently selected from the group consisting of halogen, —OH, and —$OC_{1-3}$-alkyl optionally substituted by 1, 2 or 3 halogen; and —O—$C_{1-6}$alkyl optionally substituted by 1, 2 or 3 substituents, each substituent being independently selected from the group consisting of halogen, —OH, and —O—$C_{1-3}$alkyl optionally substituted by 1, 2 or 3 halogen; or Z is —$NR^{10}R^{11}$, wherein $R^{10}$ is selected from the group consisting of hydrogen and —$C_{1-4}$alkyl; and $R^{11}$ is a 5- to 10-membered non-aromatic heterocyclyl group comprising 1, 2 or 3 heteroatoms selected from N, O and S, wherein at least one of the heteroatoms is N, and wherein said 5- to 10-membered non-aromatic heterocyclyl group is optionally substituted with 1, 2, 3 or 4 substituents, independently selected from the group consisting of halogen; —OH; —$C_{1-6}$alkyl optionally substituted by 1, 2 or 3 substituents, each substituent being independently selected from the group consisting of halogen, —OH, and —$OC_{1-3}$alkyl optionally substituted by 1, 2 or 3 halogen; and —O—$C_{1-6}$alkyl optionally substituted by 1, 2 or 3 substituents, each substituent being independently selected from the group consisting of halogen, —OH, and —O—$C_{1-3}$alkyl optionally substituted by 1, 2 or 3 halogen; and when present, each $R^a$ and $R^b$ are independently selected from the group consisting of hydrogen and —$C_{1-4}$alkyl.

The compounds of the invention have surprisingly been found to have activity as inhibitors of N-myristoyl transferase, and in particular have been found to be very potent inhibitors of human N-myristoyl transferase 1. The compounds of the invention have also surprisingly been found to have good metabolic stability. These advantages are expected to make the compounds of the invention especially useful for use in treating and preventing diseases in which inhibition of N-myristoyl transferase provides a therapeutic or prophylactic effect, for example diseases include hyperproliferative disorders (such as B-cell lymphoma and leukaemia), viral infections (such as human rhinovirus, HIV, poliovirus, foot and mouth disease, enterovirus 71 infections and pox virus infections). The compounds may also be useful in the prevention or treatment e.g. treatment of protozoan infections (such as malaria and leishmaniasis) and fungal infections.

The invention also provides a pharmaceutical composition comprising a compound of the invention and a pharmaceutically acceptable carrier.

The invention also provides a compound of the invention or a pharmaceutical composition of the invention for use as a medicament.

The invention also provides a compound of the invention or a pharmaceutical composition of the invention for use in the prevention or treatment of a disease or disorder in which inhibition of N-myristoyl transferase provides a therapeutic or prophylactic effect.

The invention also provides use of compound of the invention for the manufacture of a medicament for the prevention or treatment of a disease or disorder in which inhibition of N-myristoyl transferase provides a therapeutic or prophylactic effect.

The invention also provides a method of treating or preventing a disease or disorder in which inhibition of N-myristoyl transferase provides a therapeutic or prophylactic effect in a mammal, which comprises administering to the mammal a therapeutically effective amount of a compound of the invention or pharmaceutical composition of the invention.

The invention also provides a kit of parts comprising: (a) a first pharmaceutical composition comprising a compound of the invention and a pharmaceutically acceptable carrier; and (b) a second pharmaceutical composition comprising a further therapeutic agent, suitably a further N-myristoyl transferase inhibitor, and a pharmaceutically acceptable carrier.

DETAILED DESCRIPTION OF THE INVENTION

Figure 1:
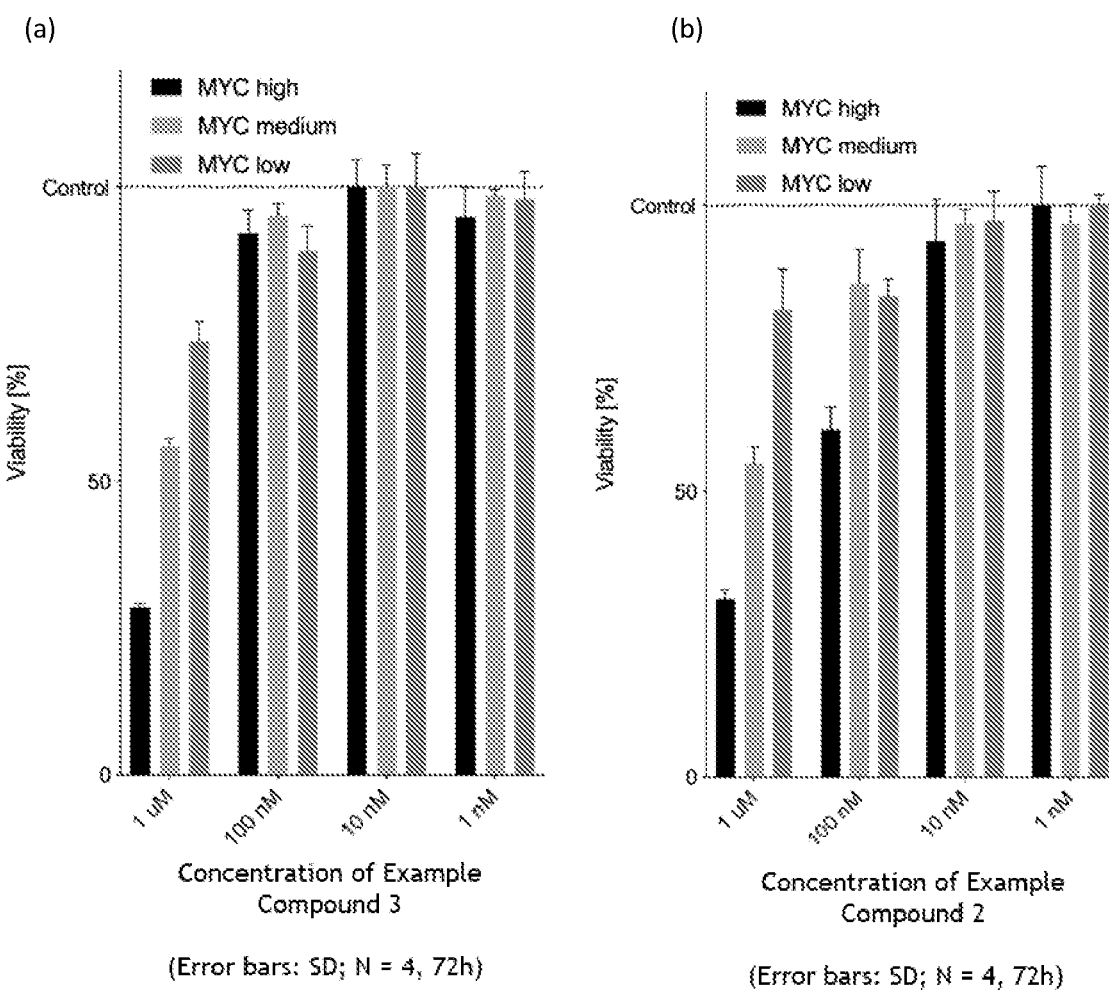
FIG. 1a shows the metabolic viability of the P-493-6 cell line treated with Example Compound 3 at the shown concentrations for 72 hours, with different expression levels of c-MYC induced.
FIG. 1b shows the metabolic viability of the P-493-6 cell line treated with Example Compound 2 at the shown concentrations for 72 hours, with different expression levels of c-MYC induced.

The present invention provides compounds that are NMT inhibitors. The term "NMT inhibitor" as used herein is intended to cover any moiety which binds to NMT and inhibits its activity. The inhibitors may act as competitive inhibitors, or partial competitive inhibitors. The inhibitor may bind to NMT at the myr-CoA binding pocket or at the peptide binding pocket (or inhibit NMT through another mechanism). Compounds of the present invention suitably bind and inhibit NMT through the peptide binding pocket.

Definitions

The following definitions apply to the terms as used throughout this specification, unless otherwise limited in specific instances.

As used herein, the term "alkyl" means both straight and branched chain saturated hydrocarbon groups. Examples of alkyl groups include methyl, ethyl, n-propyl, iso-propyl, n-butyl, t-butyl, i-butyl, sec-butyl, pentyl and hexyl groups. Among unbranched alkyl groups, there are suitably methyl, ethyl, n-propyl, iso-propyl, n-butyl groups such as methyl, ethyl, n-propyl and n-butyl.

Among branched alkyl groups, there may be mentioned iso-propyl, t-butyl, i-butyl, 1-ethylpropyl and 1-ethylbutyl groups e.g. t-butyl, i-butyl, 1-ethylpropyl and 1-ethylbutyl groups.

As used herein, the term "alkoxy" (e.g. methoxy) means the group O-alkyl (e.g. O-methyl), where "alkyl" is used as described above. Examples of alkoxy groups include methoxy and ethoxy groups. Other examples include propoxy and butoxy.

As used herein, the term "alkenyl" means both straight and branched chain unsaturated hydrocarbon groups with at least one carbon carbon double bond. Examples of alkenyl groups include ethenyl, propenyl, butenyl, pentenyl and hexenyl. Suitable alkenyl groups include ethenyl, 1-propenyl, 2-propenyl and but-2-enyl.

As used herein, the term "cycloalkyl" means a saturated group in a ring system. A cycloalkyl group can be mono-cyclic or bicyclic. A bicyclic group may, for example, be fused or bridged.

Examples of monocyclic cycloalkyl groups include cyclopropyl, cyclobutyl, cyclopentyl, cyclohexyl, cycloheptyl, cyclooctyl. Examples of bicyclic cycloalkyl groups include bicyclooctane, bicyclononane, bicyclodecane (decalin) and bicyclooctane. A further example of a cycloalkyl groups is an adamantane. Suitable examples of monocyclic cycloalkyl groups include cyclopropyl, cyclobutyl, cyclopentyl and cyclohexyl. Other examples of monocyclic cycloalkyl groups are cycloheptyl and cyclooctyl. Examples of bicyclic cycloalkyl groups include bicyclo [2. 2.1]hept-2-yl. Suitably, the cycloalkyl group is monocyclic. A cycloalkyl group e.g. $C_{3-6}$cycloalkyl may be joined to the remainder of the molecule through a single carbon atom, for example:

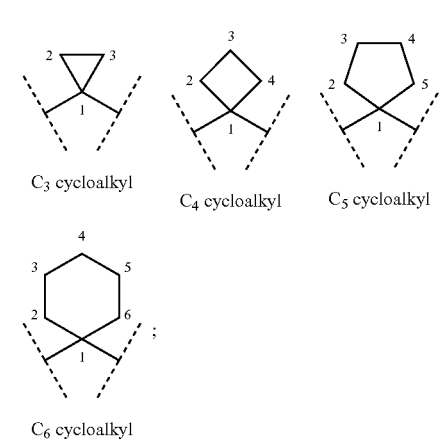

$C_3$ cycloalkyl          $C_4$ cycloalkyl          $C_5$ cycloalkyl $C_6$ cycloalkyl or via a bond, for example:

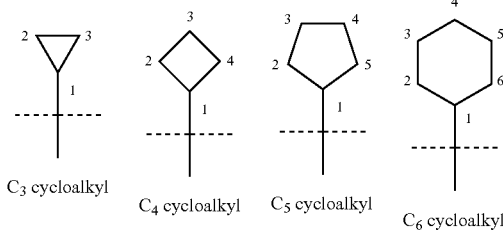

$C_3$ cycloalkyl          $C_4$ cycloalkyl          $C_5$ cycloalkyl          $C_6$ cycloalkyl wherein the dashed line indicates the connection to the remainder of the compound.

As used herein, the term "aryl" means a carbocyclic aromatic ring system, such as phenyl.

As used herein, the term "halogen" or "halo" means fluorine, chlorine, bromine or iodine. Fluorine, chlorine and bromine are suitable, and fluorine and chlorine are particularly suitable.

As used herein, the term "heterocyclyl" (or heterocycle) means an aromatic or a non-aromatic cyclic group of carbon atoms wherein from one to four of the carbon atoms is/are replaced by one or more heteroatoms independently selected from nitrogen (N), oxygen (O) or sulfur (S). A heterocyclyl (or heterocycle) group may, for example, be monocyclic or bicyclic. In a bicyclic heterocyclyl (or heterocycle) group there may be one or more heteroatoms in each ring, or only in one of the rings. A heteroatom may be S, O or N, and is suitably O or N.

Examples of monocyclic non-aromatic heterocyclyl (or heterocycle) groups include aziridinyl, azetidinyl, pyrrolidinyl, imidazolidinyl, pyrazolidinyl, piperidinyl, piperazinyl, tetrahydrofuranyl, tetrahydropyranyl, morpholinyl, thiomorpholinyl, azepanyl and diazepanyl (for example 1,4-diazepanyl, 1,1-diazepanyl or 1,5-diazepanyl, and suitably 1,4-diazepanyl).

Examples of bicyclic non-aromatic heterocyclyl (or heterocycle) groups include diazabicycloheptanyl (for example 3,6-diazabicyclo[3.2.0]heptanyl), 1H-octahydropyrrolo[3,4-b]pyridinyl, 2,5-diazabicyclo[2.2.1]heptanyl, cis-octahydro-pyrrolo[3,4-b]pyridinyl, cis-octahydro-pyrrolo[3,4-c]pyridi-nyl, 3,7-diazabicyclo[3.3.1]nonanyl, 2,6-diazaspiro[3.3] heptanyl, octahydropyrrolo[3,2-b]pyrrolyl, 1,7-diazaspiro [4.4]nonanyl, 1,8-diazaspiro[4.5]decanyl, decahydro-2,7-naphthyridinyl, 2,8-diazaspiro[5.5]undecanyl, 3,6-diazabicyclo[3.2.0]heptane, 2,8-diazaspiro[4.5]decanyl, octahydropyrrolo[3,4-c]pyrrolyl, trans-octahydro-1H-pyr-rolo[3,4-b]pyridinyl, 2,6-diazaspiro[4.5]decanyl, 2,7-diaz-aspiro[4.5]decanyl, 1,7-diazaspiro[3.5]nonanyl, 1,6-diaz-aspiro[3.5]nonanyl, 2,6-diazaspiro[3.5]nonanyl, 2,7-diaza-spiro[3.5]nonanyl, (4aR,8aR)-decahydro-1,5-naphthyridinyl, 3,9-diazaspiro[5.5]undecanyl, (3aS,6aS)-octahydropyrrolo[2,3-c]pyrrolyl, 2,9-diazaspiro[6.6] tridecanyl, 3,8-diazabicyclo[4.2.0]octanyl, 3,7-diazabicyclo [4.2.0]octanyl, 9,9-dimethyl-3,7-diazabicyclo[3.3.1] nonanyl, cis-octahydro-pyrrolo[3,4-c]pyridinyl, cis-Decahydro-1,7-naphthyridinyl, 2,7-diazabicyclo[4.2.0] octanyl, (4aS,7aS)-octahydropyrrolo[3,4-b][1,4]oxazinyl, 2,6-diazaspiro[3.4]octanyl, 1,9-diazaspiro[6.6]tridecanyl, (4aS,8aS)-decahydro-1,5-naphthyridinyl, trans-decahydro-1,7-naphthyridine, (1S,2S)-2,5-diazabicyclo[2.2.1]heptanyl, trans-decahydro-1,7-naphthyridinyl, rac-(4aR,8aR)-octa-hydro-2H-pyrido[4,3-b]morpholinyl, decahydro-1,6-naph-thyridinyl, octahydro-1H-pyrrolo[3,2-c]pyridinyl, rac-(3aR, 6aR)-octahydropyrrolo[2,3-c]pyrrolyl, and decahydropyrrolo[3,2-c]azepinyl.

Examples of monocyclic aromatic heterocyclyl (or heterocycle) groups include furanyl, thienyl, pyrrolyl, oxazolyl, thiazolyl, imidazolyl, oxadiazolyl, thiadiazolyl, pyridyl, triazolyl, triazinyl, tetrazolyl, pyridazyl, isothiazolyl, isoxazolyl, pyrazinyl, pyrazolyl and pyrimidinyl.

Examples of bicyclic aromatic heterocyclyl groups (or heterocycle) include quinoxalinyl, quinazolinyl, pyridopy-razinyl, benzoxazolyl, benzothiophenyl, benzimidazolyl, naphthyridinyl, quinolinyl, benzofuranyl, indolyl, benzothi-azolyl, oxazolyl[4,5-b]pyridyl, pyridopyrimidinyl, isoquino-linyl and benzodioxazolyl.

Further examples of bicyclic aromatic heterocyclyl groups include those in which one of the rings is aromatic and the other is non-aromatic, such as dihydrobenzofuranyl, indanyl, indolinyl, isoindolinyl, tetrahydroisoquinolinyl, tet-rahydroquinolyl and benzoazepanyl.

Compound of the Invention

The invention provides a compound of Formula (I), or a pharmaceutically acceptable ester, amide, carbamate or salt thereof, including salts of such esters, amides or carbamates. The compounds of the present invention are NMT inhibitors.

In one embodiment, a compound of Formula (I), or a pharmaceutically acceptable ester, amide, carbamate or salt thereof is provided. In one embodiment, the compound of formula (I) is provided in the form of a salt of the pharmaceutically acceptable ester, amide, or carbamate thereof. In one embodiment, the pharmaceutically acceptable ester, amide, or carbamate of the compound of formula (I) are not salts. In one embodiment, a compound of formula (I) is provided in the form of a pharmaceutically acceptable ester. In one embodiment, a compound of formula (I) is provided in the form of a pharmaceutically acceptable amide. In one embodiment, a compound of formula (I) is provided in the form of a pharmaceutically acceptable carbamate. In one embodiment, a compound of formula (I) is provided in the form of a pharmaceutically acceptable salt. In one embodiment, a compound of formula (I) is provided.

The present inventors have found that compounds of formula (I) are inhibitors of human NMT, HsNMT1 and HsNMT2. In particular, the data in the present application shows that the compounds are especially potent human NMT 1 inhibitors as they have very low micromolar or nanomolar $IC_{50}$ values for human NMT1 (HsNMT1) (it is well established that HsNMT1 and HsNMT2 are generally inhibited to the same degree by NMT inhibitor compounds (PLoS Neglected Tropical Diseases 6(4): e1625)). The present inventors have also found that compounds of formula (I) are inhibitors of *P. vivax* NMT.

To further test the potency of the compounds of the invention, certain compounds of the invention were tested in metabolic activity cellular assays using 8 different cancer cell lines. Compounds of the invention inhibited metabolic activity in each of the metabolic activity assays, and thus are expected to be useful as agents for preventing and/or treating cancer, by virtue of being inhibitors of human NMT1 and/or NMT2.

$EC_{50}$ values for *Plasmodium falciparum* (Pf) NMT were measured for certain compounds of the invention by measuring the amount of parasite DNA in human erythrocytes incubated with synchronous *Plasmodium falciparum* late stage trophozoites. Certain compounds of the invention inhibited parasitic infection of the cells in the assay. A compound of the invention has also been shown to reduce *P. falciparum* parasite burden in mice engrafted with human erythrocytes Thus the compounds of the invention are expected to be useful as agents for preventing and/or treating protozoan infections, such as malaria, by virtue of being inhibitors of protozoan NMT, such as Pf NMT.

The compounds of the present invention, as well as being potent, combine this with good metabolic stability. The results of Examples (e) and (f) below show the rat hepato-cyte half-life, rat iv half-life and the rat oral bioavailability of a various Example Compounds of the invention.

The combination of the above-mentioned properties makes the compounds of the present invention especially suitable for use as medicaments, and in particular medicaments for oral administration.

The compounds of the invention may contain chiral (asymmetric) centers or the molecule as a whole may be chiral. The individual stereoisomers (enantiomers and diastereoisomers) and mixtures of these are within the scope of the present invention.

For the avoidance of doubt, an embodiment or more or most suitable aspect of any one feature of a compound of the invention may be combined with any embodiment or more or most suitable aspect of another feature of a compound of the invention of the invention to create a further embodiment.

Limitations described herein for compounds of formula (I) apply equally to compounds of formula (Ia), (Ib), (Ic), (Id), (Ie), (If), (Ig), (Ih), (Ij), (Ik), (Im), (In), (Io), (Ip) and (Iq).

Where substituents are indicated as being optionally substituted in formula (I) in the embodiments and preferences set out below, the optional substituent may be attached to an available carbon atom, which means a carbon atom which is attached to a hydrogen atom i.e. a C—H group or the optional substituent may be attached to an available nitrogen atom, which means a nitrogen atom which is attached to a hydrogen atom i.e. a N—H group. The optional substituent replaces the hydrogen atom attached to the carbon atom or the hydrogen atom attached to the nitrogen atom.

Suitably, in one embodiment the relevant group is substituted. In another embodiment, the relevant group is unsubstituted.

In the compound of formula (I), $n_1$ is 1 or 2, and $n_2$ is 1 or 2. In certain suitable embodiments, $n_1$ is 1, and $n_2$ is 1 or 2. In especially suitable embodiments, $n_1$ is 1, and $n_2$ is 1. In such embodiments, the compound of formula (I) is a compound of formula (Ia):

(Ia)

In the compound of formula (I), $X^1$ is selected from the group consisting of $CR^x$ and N. Suitably, $X^1$ is N. In such embodiments, the compound of formula (I) is a compound of formula (Ib):

(Ib)

In the compound of formula (I), when present, $R^x$ may be selected from the group consisting of hydrogen, halogen, and —$C_{1-4}$alkyl optionally substituted by 1, 2 or 3 substituents, each substituent being independently selected from the group consisting of halogen, —OH, —$OCH_3$, and —$OCF_3$. Suitably $R^x$ is selected from the group consisting of hydrogen, halogen (suitably F or Cl), and —$C_{1-4}$alkyl optionally substituted by a halogen (suitably F or Cl), —$OCH_3$, or —$OCF_3$. More suitably $R^x$ is selected from the group consisting of hydrogen, F, Cl and —$C_{1-4}$alkyl. Even more suitably $R^x$ is hydrogen.

In the compound of formula (I), $R^1$ may be selected from the group consisting of hydrogen; —$C_{1-4}$alkyl optionally substituted by 1, 2 or 3 substituents, each substituent being independently selected from the group consisting of halogen, —$OCH_3$, and —$OCF_3$; and —$C_{3-6}$cycloalkyl optionally substituted by 1, 2 or 3 substituents, each substituent being independently selected from the group consisting of halogen, —$CH_3$, —$OCH_3$, and —$OCF_3$;

$R^2$ may be selected from the group consisting of hydrogen; —$C_{1-4}$alkyl optionally substituted by 1, 2 or 3 substituents, each substituent being independently selected from the group consisting of halogen, —$OCH_3$, and —$OCF_3$; and —$C_{3-6}$cycloalkyl optionally substituted by 1, 2 or 3 substituents, each substituent being independently selected from the group consisting of halogen, —$CH_3$, —$OCH_3$, and —$OCF_3$; or $R^1$ and $R^2$ may be linked such that together with the atom to which they are attached they form a $C_{3-6}$cycloalkyl group or a 3- to 6-membered non-aromatic heterocyclyl group comprising 1 heteroatom selected from the group consisting of O and N, wherein said $C_{3-6}$cycloalkyl group or 3- to 6-membered non-aromatic heterocyclyl group is optionally substituted by 1 or 2 substituents, each substituent being independently selected from the group consisting of halogen, —OH, —$CH_3$, —$OCH_3$, and —$OCF_3$.

In certain suitable embodiments, $R^1$ is selected from the group consisting of hydrogen and —$C_{1-4}$ alkyl optionally substituted by 1, 2 or 3 substituents, each substituent being independently selected from the group consisting of halogen, —$OCH_3$, and —$OCF_3$. More suitably, $R^1$ is selected from the group consisting of hydrogen and —$C_{1-4}$alkyl. Even more suitably, $R^1$ is selected from the group consisting of hydrogen and —$C_{1-3}$alkyl. Even more suitably, $R^1$ is selected from the group consisting of hydrogen and methyl. Even more suitably, $R^1$ is methyl.

In certain suitable embodiments, $R^2$ is selected from the group consisting of hydrogen and —$C_{1-4}$ alkyl optionally substituted by 1, 2 or 3 substituents, each substituent being independently selected from the group consisting of halogen, —$OCH_3$, and —$OCF_3$. More suitably, $R^2$ is selected from the group consisting of hydrogen and —$C_{1-4}$alkyl. Even more suitably, $R^2$ is selected from the group consisting of hydrogen and —$C_{1-3}$alkyl. Even more suitably, $R^2$ is selected from the group consisting of hydrogen and methyl. Even more suitably, $R^2$ is methyl.

In certain suitable embodiments, $R^1$ and $R^2$ are independently selected from the group consisting of hydrogen, and —$C_{1-4}$alkyl optionally substituted by 1, 2 or 3 substituents, each substituent being independently selected from the group consisting of halogen, —$OCH_3$, and —$OCF_3$ (for example, $R^1$ is —$C_{1-4}$alkyl optionally substituted by 1, 2 or 3 substituents, each substituent being independently selected from the group consisting of halogen, —$OCH_3$, and —$OCF_3$, and $R^2$ is —$C_{1-4}$alkyl optionally substituted by 1, 2 or 3 substituents, each substituent being independently selected from the group consisting of halogen, —$OCH_3$, and —$OCF_3$; or $R^1$ is —$C_{1-4}$alkyl optionally substituted by 1, 2 or 3 substituents, each substituent being independently selected from the group consisting of halogen, —$OCH_3$, and —$OCF_3$, and $R^2$ is hydrogen; or $R^1$ is hydrogen and $R^2$ is hydrogen). More suitably, $R^1$ and $R^2$ are independently selected from the group consisting of hydrogen and —$C_{1-4}$alkyl (for example, $R^1$ is —$C_{1-4}$alkyl and $R^2$ is —$C_{1-4}$alkyl; or $R^1$ is —$C_{1-4}$alkyl and $R^2$ is hydrogen; or $R^1$ is hydrogen and $R^2$ is hydrogen). Even more suitably, $R^1$ and $R^2$ are independently selected from the group consisting of hydrogen and —$C_{1-3}$alkyl (for example, $R^1$ is —$C_{1-3}$alkyl and $R^2$ is —$C_{1-3}$alkyl; or $R^1$ is —$C_{1-3}$alkyl and $R^2$ is hydrogen; or $R^1$ is hydrogen and $R^2$ is hydrogen). Even more suitably, $R^1$ and $R^2$ are independently selected from the group consisting of hydrogen and methyl (for example, $R^1$ is methyl and $R^2$ is methyl; or $R^1$ is methyl and $R^2$ is hydrogen; or $R^1$ is hydrogen and $R^2$ is hydrogen).

In certain suitable embodiments, $R^1$ is —$C_{1-4}$alkyl optionally substituted by 1, 2 or 3 substituents, each substituent being independently selected from the group consisting of halogen, —$OCH_3$, and —$OCF_3$; and $R^2$ is —$C_{1-4}$alkyl optionally substituted by 1, 2 or 3 substituents, each substituent being independently selected from the group consisting of halogen, —$OCH_3$, and —$OCF_3$. More suitably, $R^1$ is —$C_{1-4}$alkyl; and $R^2$ is —$C_{1-4}$alkyl. Even more suitably, $R^1$ is —$C_{1-3}$alkyl; and $R^2$ is —$C_{1-3}$ alkyl. Even more suitably, $R^1$ is methyl; and $R^2$ is methyl.

In another suitable embodiment, $R^1$ is —$C_{1-4}$alkyl optionally substituted by 1, 2 or 3 substituents, each substituent being independently selected from the group consisting of halogen, —$OCH_3$, and —$OCF_3$; and $R^2$ is hydrogen. More suitably, $R^1$ is —$C_{1-4}$alkyl; and $R^2$ is -hydrogen. Even more suitably, $R^1$ is —$C_{1-3}$alkyl; and $R^2$ is hydrogen. Even more suitably, $R^1$ is methyl; and $R^2$ is hydrogen.

In one suitable embodiment, $R^1$ is hydrogen and $R^2$ is hydrogen.

In another embodiment, $R^1$ and $R^2$ may be linked such that together with the atom to which they are attached they form a $C_{3-6}$cycloalkyl group (i.e. cyclopropyl group, cyclobutyl group, cyclopentyl group, or cyclohexyl group) or a 3- to 6-membered non-aromatic heterocyclyl group (i.e. a 3-, 4-, 5- or 6-membered non-aromatic heterocyclyl group) comprising 1 heteroatom selected from the group consisting of O and N, wherein said $C_{3-6}$cycloalkyl group or 3- to 6-membered non-aromatic heterocyclyl group is optionally substituted by 1 or 2 substituents, each substituent being independently selected from the group consisting of halogen, —OH, —$CH_3$, —$OCH_3$, and —$OCF_3$. For example, $R^1$ and $R^2$ are linked such that together with the atom to which they are attached they form a $C_{3-5}$cycloalkyl group (i.e. cyclopropyl group, cyclobutyl group, or cyclopentyl group) or a 3- to 5-membered non-aromatic heterocyclyl group (i.e. a 3-, 4- or 5-membered non-aromatic heterocyclyl group) comprising 1 heteroatom selected from the group consisting of O and N, wherein said $C_{3-5}$cycloalkyl group or 3- to 5-membered non-aromatic heterocyclyl group is optionally substituted by 1 or 2 substituents, each substituent being independently selected from the group consisting of halogen, —$CH_3$, —OH, —$OCH_3$, and —$OCF_3$. Also for example, $R^1$ and $R^2$ are linked such that together with the atom to which they are attached they form a $C_{3-5}$cycloalkyl group, wherein said $C_{3-5}$cycloalkyl group is optionally substituted by 1 or 2 substituents, each substituent being independently selected from the group consisting of halogen, —$CH_3$, —OH, —$OCH_3$, and —$OCF_3$. Also for example, $R^1$ and $R^2$ are linked such that together with the atom to which they are attached they form a $C_{3-5}$cycloalkyl group, wherein said $C_{3-5}$cycloalkyl group is optionally substituted by 1 substituent selected from the group consisting of halogen, —$CH_3$, —OH, —$OCH_3$, and —$OCF_3$. Also for example, $R^1$ and $R^2$ are linked such that together with the atom to which they are attached they form a $C_{3-5}$cycloalkyl group.

In another embodiment, $R^1$ and $R^2$ are linked such that together with the atom to which they are attached they form a $C_{3-6}$cycloalkyl group (i.e. cyclopropyl group, cycobutyl group, cyclopentyl group, or cyclohexyl group) wherein said $C_{3-6}$cycloalkyl group is optionally substituted by 1 substituent selected from the group consisting of halogen, —$CH_3$, —OH, —$OCH_3$, and —$OCF_3$. For example, $R^1$ and $R^2$ are linked such that together with the atom to which they are attached they form a $C_{3-6}$cycloalkyl group (i.e. cyclopropyl group, cyclobutyl group, cyclopentyl group, or cyclohexyl group).

For the avoidance of doubt, in embodiments in wherein $R^1$ and $R^2$ are linked, $R^1$ and $R^3$ are not linked.

$R^3$ may be selected from the group consisting of hydrogen; —$C_{1-4}$alkyl optionally substituted by 1, 2 or 3 substituents, each substituent being independently selected from the group consisting of halogen, —OH, —$OCH_3$, and —$OCF_3$; and —$C_{3-6}$cycloalkyl optionally substituted by 1, 2 or 3 substituents, each substituent being independently selected from the group consisting of halogen, —OH, —$CH_3$, —$OCH_3$, and —$OCF_3$. Suitably, $R^3$ is selected from the group consisting of hydrogen and —$C_{1-4}$alkyl optionally substituted by 1, 2 or 3 substituents, each substituent being independently selected from the group consisting of halogen, —$OCH_3$, and —$OCF_3$. More suitably, $R^3$ is selected from the group consisting of hydrogen and —$C_{1-4}$alkyl optionally substituted by 1, 2 or 3 F atoms. Even more suitably, $R^3$ is selected from the group consisting of hydrogen and —$C_{1-3}$alkyl optionally substituted by 1, 2 or 3 F atoms. Even more suitably, $R^3$ is selected from the group consisting of hydrogen and methyl optionally substituted by 1, 2 or 3 F atoms. For example, $R^3$ is hydrogen; or $R^3$ is methyl; or $R^3$ is —$CF_3$.

In another embodiment, $R^1$ and $R^3$ may be linked such that together with the atoms to which they are attached they form a 3- to 6-membered non-aromatic heterocyclyl group (i.e. a 3-, 4-, 5- or 6-membered non-aromatic heterocyclyl group) comprising 1 N heteroatom, wherein said 3- to 6-membered non-aromatic heterocyclyl group is optionally substituted by 1 or 2 substituents, each substituent being independently selected from the group consisting of halogen, —$CH_3$, —OH, —$OCH_3$, and —$OCF_3$ e.g. halogen, —OH, —$OCH_3$, and —$OCF_3$. For example, $R^1$ and $R^3$ are linked such that together with the atoms to which they are attached they form a 4- to 6-membered non-aromatic heterocyclyl group (i.e. a 4-, 5- or 6-membered non-aromatic heterocyclyl group) comprising 1 N heteroatom, wherein said 4- to 6-membered non-aromatic heterocyclyl group is optionally substituted by 1 or 2 substituents, each substituent being independently selected from the group consisting of halogen, —$CH_3$, —OH, —$OCH_3$, and —$OCF_3$ e.g. halogen, —OH, —$OCH_3$, and —$OCF_3$. Also for example, $R^1$ and $R^3$ are linked such that together with the atoms to which they are attached they form a 5- or 6-membered non-aromatic heterocyclyl group comprising 1 N heteroatom, wherein said 5- or 6-membered non-aromatic heterocyclyl group is optionally substituted by 1 or 2 substituents, each substituent being independently selected from the group consisting of halogen, —$CH_3$, —OH, —$OCH_3$, and —$OCF_3$ e.g halogen, —OH, —$OCH_3$, and —$OCF_3$. Also for example, $R^1$ and $R^3$ are linked such that together with the atoms to which they are attached they form a 5- or 6-membered non-aromatic heterocyclyl group comprising 1 N heteroatom, wherein said 5- or 6-membered non-aromatic heterocyclyl group is optionally substituted by 1 substituent selected from the group consisting of halogen, —$CH_3$, —OH, —$OCH_3$, and —$OCF_3$ e.g. halogen, —OH, —$OCH_3$, and —$OCF_3$. Also for example, $R^1$ and $R^3$ are linked such that together with the atoms to which they are attached they form a 5- or 6-membered non-aromatic heterocyclyl group comprising 1 N heteroatom.

In another embodiment, $R^1$ and $R^3$ are linked such that together with the atoms to which they are attached they form a 4- or 5-membered non-aromatic heterocyclyl group comprising 1 N heteroatom, wherein said 4- or 5-membered non-aromatic heterocyclyl group is optionally substituted by 1 substituent selected from the group consisting of halogen, —CH$_3$, —OH, —OCH$_3$, and —OCF$_3$ e.g. halogen, —OH, —OCH$_3$, and —OCF$_3$. For example, R$^1$ and R$^3$ are linked such that together with the atoms to which they are attached they form a 4- or 5-membered non-aromatic heterocyclyl group comprising 1 N heteroatom.

For the avoidance of doubt, in embodiments in wherein R$^1$ and R$^3$ are linked, R$^1$ and R$^2$ are not linked.

In the compound of formula (I), X$^2$ is selected from the group consisting of CR$^4$ and N. Suitably, X$^2$ is CR$^4$. In such embodiments, the compound of formula (I) is a compound of formula (Ic):

(Ic)

When present, R$^4$ may be selected from the group consisting of hydrogen; halogen; —C$_{1-4}$alkyl optionally substituted by 1, 2 or 3 substituents, each substituent being independently selected from the group consisting of halogen, —OH, —OCH$_3$, —OCF$_3$, and —NR$^a$R$^b$. Suitably, R$^4$ is selected from the group consisting of hydrogen; halogen; and —C$_{1-4}$alkyl optionally substituted by 1, 2 or 3 substituents, each substituent being independently selected from the group consisting of halogen, —OH, —OCH$_3$, and —OCF$_3$. More suitably, R$^4$ is selected from the group consisting of hydrogen; halogen; and —C$_{1-4}$alkyl optionally substituted by 1 substituent selected from the group consisting of halogen, —OH, —OCH$_3$, and —OCF$_3$. Even more suitably, R$^4$ is selected from the group consisting of hydrogen and —C$_{1-4}$alkyl. In one especially suitable embodiment, R$^4$ is selected from the group consisting of hydrogen and methyl, for example R$^4$ is hydrogen.

Alternatively, R$^4$ is selected from the group consisting of hydrogen and —C$_{1-4}$alkyl optionally substituted by 1, 2 or 3 substituents, each substituent being independently selected from the group consisting of halogen, —OCH$_3$, and —OCF$_3$. More suitably, R$^4$ is selected from the group consisting of hydrogen and methyl optionally substituted by 1, 2 or 3 F atoms, for example R$^4$ is hydrogen; or R$^4$ is methyl; or R$^4$ is —CF$_3$.

When present, each R$^a$ and R$^b$ may be independently selected from the group consisting of hydrogen and —C$_{1-4}$alkyl. Suitably each R$^a$ and R$^b$ may be independently selected from the group consisting of hydrogen and methyl. For example, R$^a$ is hydrogen and R$^b$ is hydrogen; or R$^a$ is methyl and R$^b$ is hydrogen; or R$^a$ is methyl and R$^b$ is methyl.

In one suitable embodiment of the invention, R$^3$ and R$^4$ are each hydrogen.

In the compound of formula (I), R$^{5a}$ and R$^{5b}$ are independently selected from the group consisting of hydrogen; halogen; methyl optionally substituted by 1, 2 or 3 substituents, each substituent being independently selected from the group consisting of halogen, —OH, —OCH$_3$, and —OCF$_3$; and methoxy optionally substituted by 1, 2 or 3 substituents, each substituent being independently selected from the group consisting of halogen, —OH, —OCH$_3$, and —OCF$_3$. Suitably, R$^{5a}$ and R$^{5d}$ are independently selected from the group consisting of hydrogen; F; Cl; methyl optionally substituted by 1 substituent selected from the group consisting of halogen, —OH, —OCH$_3$, and —OCF$_3$; and methoxy optionally substituted by 1 substituent selected from the group consisting of halogen, —OH, —OCH$_3$, and —OCF$_3$. More suitably, R$^{5a}$ and R$^{5d}$ are independently selected from the group consisting of hydrogen; F; Cl; methyl and methoxy. Even more suitably, R$^{5a}$ and R$^{5d}$ are independently selected from the group consisting of hydrogen and methyl. In one very suitable embodiment R$^{5a}$ and R$^{5d}$ are each hydrogen.

In certain suitable embodiments, R$^{5a}$ is hydrogen and R$^{5d}$ is selected from the group consisting of hydrogen; halogen; methyl optionally substituted by 1, 2 or 3 substituents, each substituent being independently selected from the group consisting of halogen, —OH, —OCH$_3$, and —OCF$_3$; and methoxy optionally substituted by 1, 2 or 3 substituents, each substituent being independently selected from the group consisting of halogen, —OH, —OCH$_3$, and —OCF$_3$. Suitably, R$^{5a}$ is hydrogen and R$^{5d}$ is selected from the group consisting of hydrogen; F; Cl; methyl optionally substituted by 1 substituent selected from the group consisting of halogen, —OH, —OCH$_3$, and —OCF$_3$; and methoxy optionally substituted by 1 substituent selected from the group consisting of halogen, —OH, —OCH$_3$, and —OCF$_3$. More suitably, R$^{5a}$ is hydrogen and R$^{5d}$ is selected from the group consisting of hydrogen; F; Cl; methyl and methoxy. Even more suitably R$^{5a}$ is hydrogen and R$^{5d}$ is independently selected from the group consisting of hydrogen and methyl.

In certain suitable embodiments, R$^{5d}$ is hydrogen and R$^{5a}$ is selected from the group consisting of hydrogen; halogen; methyl optionally substituted by 1, 2 or 3 substituents, each substituent being independently selected from the group consisting of halogen, —OH, —OCH$_3$, and —OCF$_3$; and methoxy optionally substituted by 1, 2 or 3 substituents, each substituent being independently selected from the group consisting of halogen, —OH, —OCH$_3$, and —OCF$_3$. More suitably, R$^{5d}$ is hydrogen and R$^{5a}$ is selected from the group consisting of hydrogen; F; Cl; methyl optionally substituted by 1 substituent selected from the group consisting of halogen, —OH, —OCH$_3$, and —OCF$_3$; and methoxy optionally substituted by 1 substituent selected from the group consisting of halogen, —OH, —OCH$_3$, and —OCF$_3$. Even more suitably, R$^{5d}$ is hydrogen and R$^{5a}$ is selected from the group consisting of hydrogen; F; Cl; methyl and methoxy. Even more suitably R$^{5d}$ is hydrogen and R$^{5a}$ is independently selected from the group consisting of hydrogen and methyl.

In the compound of formula (I), R$^{5b}$ and R$^{5c}$ may be independently selected from the group consisting of hydrogen; halogen; —C$_{1-4}$alkyl optionally substituted by 1, 2 or 3 substituents, each substituent being independently selected from the group consisting of halogen, —OH, —OCH$_3$, and —OCF$_3$; —O—C$_{1-4}$alkyl optionally substituted by 1, 2 or 3 substituents, each substituent being independently selected from the group consisting of halogen, —OH, —OCH$_3$, and —OCF$_3$; and C$_{3-6}$cycloalkyl optionally substituted by 1, 2 or 3 substituents, each substituent being independently selected from the group consisting of halogen, —CH₃, —OH, —OCH₃, and —OCF₃;

> or R$^{5b}$ and R$^{5c}$ may be linked such that together with the atoms to which they are attached they form a 6-membered aryl group or a 5- or 6-membered aromatic heterocyclyl group comprising 1 or 2 heteroatoms selected from the group consisting of S, O and N, wherein said 6-membered aryl group or 5- or 6-membered aromatic heterocyclyl group is optionally substituted by 1 or 2 substituents, each substituent being independently selected from the group consisting of halogen, —OH, —OCH₃, and —OCF₃.

In certain suitable embodiments, R$^{5b}$ and R$^{5c}$ are independently selected from the group consisting of hydrogen; halogen; —C$_{1-4}$alkyl optionally substituted by 1, 2 or 3 substituents, each substituent being independently selected from the group consisting of halogen, —OH, —OCH₃, and —OCF₃; —O—C$_{1-4}$alkyl optionally substituted by 1, 2 or 3 substituents, each substituent being independently selected from the group consisting of halogen, —OH, —OCH₃, and —OCF₃; and C$_{3-6}$cycloalkyl optionally substituted by 1, 2 or 3 substituents, each substituent being independently selected from the group consisting of halogen, —CH₃, —OCH₃, —OH, —OCH₃, and —OCF₃, such as halogen, —CH₃, —OH, —OCH₃, and —OCF₃. More suitably, R$^{5b}$ and R$^{5c}$ are independently selected from the group consisting of hydrogen; halogen; —C$_{1-4}$alkyl optionally substituted by 1 substituent selected from the group consisting of halogen, —OH, —OCH₃, and —OCF₃; and —O—C$_{1-4}$ alkyl optionally substituted by 1 substituent selected from the group consisting of halogen, —OH, —OCH₃, and —OCF₃; and C$_{3-6}$ cycloalkyl optionally substituted by 1 substituent selected from the group consisting of halogen, —CH₃, —OH, —OCH₃, and —OCF₃.

More suitably, R$^{5b}$ and R$^{5c}$ are independently selected from the group consisting of hydrogen; halogen; and —C$_{1-4}$alkyl optionally substituted by 1 substituent selected from the group consisting of halogen, —OH, —OCH₃, and —OCF₃. Even more suitably, R$^{5b}$ and R$^{5c}$ are independently selected from the group consisting of hydrogen; F; Cl; and —C$_{1-4}$alkyl, such as R$^{5b}$ and R$^{5c}$ are each independently hydrogen.

In one especially suitable embodiment, R$^{5a}$ and R$^{5d}$ are hydrogen, and R$^{5b}$ and R$^{5c}$ are selected from the group consisting of hydrogen, halogen and —C$_{1-4}$alkyl optionally substituted by 1, 2 or 3 substituents, each substituent being independently selected from the group consisting of halogen, —OH, —OCH₃, and —OCF₃ groups. For example, R$^{5a}$ and R$^{5d}$ are hydrogen, and R$^{5b}$ and R$^{5c}$ are selected from the group consisting of hydrogen, halogen and —C$_{1-4}$alkyl optionally substituted by 1 substituent selected from the group consisting of halogen, —OH, —OCH₃, and —OCF₃ groups.

In certain suitable embodiments, R$^{5b}$ is hydrogen and R$^{5c}$ is selected from the group consisting of hydrogen; halogen; —C$_{1-4}$alkyl optionally substituted by 1, 2 or 3 substituents, each substituent being independently selected from the group consisting of halogen, —OH, —OCH₃, and —OCF₃; —O—C$_{1-4}$alkyl optionally substituted by 1, 2 or 3 substituents, each substituent being independently selected from the group consisting of halogen, —OH, —OCH₃, and —OCF₃; and C$_{3-6}$cycloalkyl optionally substituted by 1, 2 or 3 substituents, each substituent being independently selected from the group consisting of halogen, —CH₃, —OH, —OCH₃, and —OCF₃. More suitably, R$^{5b}$ is hydrogen and R$^{5c}$ is selected from the group consisting of hydrogen;

halogen; —C$_{1-4}$alkyl optionally substituted by 1 substituent selected from the group consisting of halogen, —OH, —OCH₃, and —OCF₃; and —O—C$_{1-4}$alkyl optionally substituted by 1 substituent selected from the group consisting of halogen, —OH, —OCH₃, and —OCF₃; and C$_{3-6}$cycloalkyl optionally substituted by 1 substituent selected from the group consisting of halogen, —OH, —CH₃, —OCH₃, and —OCF₃.

More suitably, R$^{5b}$ is hydrogen and R$^{5c}$ is selected from the group consisting of hydrogen; halogen; and —C$_{1-4}$alkyl optionally substituted by 1 substituent selected from the group consisting of halogen, —OH, —OCH₃, and —OCF₃. Even more suitably, R$^{5b}$ is hydrogen and R$^{5c}$ is selected from the group consisting of hydrogen; F; Cl; and —C$_{1-4}$alkyl (for example, hydrogen; F; Cl; and methyl). In such embodiments, suitably R$^{5a}$ and R$^{5d}$ are each hydrogen.

In one especially suitable embodiment, R$^{5c}$ is hydrogen and R$^{5c}$ is selected from the group consisting of hydrogen; F; and Cl. In such an embodiment, suitably R$^{5a}$ and R$^{5d}$ are each hydrogen.

In one especially suitable embodiment, R$^{5c}$ is hydrogen and R$^{5b}$ is selected from the group consisting of hydrogen; F; and Cl. In such an embodiment, suitably R$^{5a}$ and R$^{5d}$ are each hydrogen.

In certain suitable embodiments, R$^{5c}$ is hydrogen and R$^{5b}$ is selected from the group consisting of hydrogen; halogen; —C$_{1-4}$alkyl optionally substituted by 1, 2 or 3 substituents, each substituent being independently selected from the group consisting of halogen, —OH, —OCH₃, and —OCF₃; —O—C$_{1-4}$alkyl optionally substituted by 1, 2 or 3 substituents, each substituent being independently selected from the group consisting of halogen, —OH, —OCH₃, and —OCF₃; and C$_{3-6}$cycloalkyl optionally substituted by 1, 2 or 3 substituents, each substituent being independently selected from the group consisting of halogen, —CH₃, —OH, —OCH₃, and —OCF₃. More suitably, R$^{5c}$ is hydrogen and R$^{5d}$ is selected from the group consisting of hydrogen; halogen; —C$_{1-4}$alkyl optionally substituted by 1 substituent selected from the group consisting of halogen, —OH, —OCH₃, and —OCF₃; and —O—C$_{1-4}$alkyl optionally substituted by 1 substituent selected from the group consisting of halogen, —OH, —OCH₃, and —OCF₃; and C$_{3-6}$cycloalkyl optionally substituted by 1 substituent selected from the group consisting of halogen, —CH₃, —OH, —OCH₃, and —OCF₃. More suitably, R$^{5c}$ is hydrogen and R$^{5b}$ is selected from the group consisting of hydrogen; halogen; and —C$_{1-4}$alkyl optionally substituted by 1 substituent selected from the group consisting of halogen, —OH, —OCH₃, and —OCF₃. Even more suitably, R$^{5c}$ is hydrogen and R$^{5b}$ is selected from the group consisting of hydrogen; F; Cl; and —C$_{1-4}$alkyl (for example, hydrogen; F; Cl; and methyl). In such embodiments, suitably R$^{5a}$ and R$^{5d}$ are each hydrogen.

In one especially suitable embodiment, R$^{5b}$ is hydrogen and R$^{5c}$ is selected from the group consisting of hydrogen and C$_{1-4}$alkyl (for example hydrogen and methyl). In such an embodiment, suitably R$^{5a}$ and R$^{5d}$ are each hydrogen. In one especially suitable embodiment, R$^{5a}$, R$^{5b}$, R$^{5c}$ and R$^{5d}$ are each hydrogen.

In certain other embodiments, R$^{5b}$ and R$^{5c}$ are linked such that together with the atoms to which they are attached they form a 6-membered aryl group or a 5- or 6-membered aromatic heterocyclyl group comprising 1 or 2 heteroatoms selected from the group consisting of S, O and N, wherein said 6-membered aryl group or 5- or 6-membered aromatic heterocyclyl group is optionally substituted by 1 or 2 substituents, each substituent being independently selected from the group consisting of halogen, —OH, —OCH₃, and —$OCF_3$. For example, $R^{5b}$ and $R^{5c}$ are linked such that together with the atoms to which they are attached they form a 6-membered aryl group or a 5- or 6-membered aromatic heterocyclyl group comprising 1 or 2 heteroatoms selected from the group consisting of O and N, wherein said 6-membered aryl group or 5- or 6-membered aromatic heterocyclyl group is optionally substituted by 1 or 2 substituents, each substituent being independently selected from the group consisting of halogen, —OH, —$OCH_3$, and —$OCF_3$. Also for example, $R^{5b}$ and $R^{5c}$ are linked such that together with the atoms to which they are attached they form a 6-membered aryl group or a 5- or 6-membered aromatic heterocyclyl group comprising 1 or 2 N heteroatoms, wherein said 6-membered aryl group or 5- or 6-membered aromatic heterocyclyl group optionally substituted by 1 or 2 substituents, each substituent being independently selected from the group consisting of halogen, —OH, —$OCH_3$, and —$OCF_3$. For example, $R^{5b}$ and $R^{5c}$ are linked such that together with the atoms to which they are attached they form a 6-membered aryl group or a 5- or 6-membered aromatic heterocyclyl group comprising 1 or 2 N heteroatoms. In such embodiments, $R^{5a}$ and $R^{5d}$ may be, for example, each hydrogen.

In the compound of formula (I), $R^6$ may be selected from the group consisting of hydrogen and methyl. Suitably, $R^6$ is hydrogen.

In one suitable embodiment of the invention, $R^3$, $R^4$ and $R^6$ are each hydrogen.

In the compound of formula (I), p is 0, 1, or 2. For example, p may be 0 or 1. In certain suitable embodiments, p is 0.

In one suitable embodiment of the invention, $R^6$ is hydrogen; and p is 0. In another suitable embodiment of the invention, $R^3$, $R^4$ and $R^6$ are each hydrogen; and p is 0.

In the compound of formula (I), when present, each $R^7$ may be —$C_{1-4}$alkyl optionally substituted by 1, 2 or 3 substituents, each substituent being independently selected from the group consisting of halogen, —OH, —$OCH_3$, and —$OCF_3$. Suitably, when present, each $R^7$ is independently —$C_{1-4}$alkyl optionally substituted by 1 substituent selected from the group consisting of halogen, —OH, —$OCH_3$, and —$OCF_3$. More suitably, when present, each $R^7$ is independently —$C_{1-4}$alkyl. In another suitable embodiment, when present, each $R^7$ may be methyl optionally substituted by 1 substituent selected from the group consisting of halogen, —OH, —$OCH_3$, and —$OCF_3$.

In the compound of formula (I), $R^8$ may be selected from the group consisting of hydrogen; halogen; —OH; —CN; —$C_{1-4}$alkyl optionally substituted by 1, 2 or 3 substituents, each substituent being independently selected from the group consisting of halogen, —OH, —CN, and methoxy optionally substituted by 1, 2 or 3 halogen; —$C_{3-6}$cycloalkyl optionally substituted by 1, 2 or 3 substituents, each substituent being independently selected from the group consisting of halogen, —$CH_3$, —OH, —CN, and methoxy optionally substituted by 1, 2 or 3 halogen; —$C_{1-4}$alkenyl (such as —$C_{2-4}$alkenyl) optionally substituted by 1, 2 or 3 substituents, each substituent being independently selected from the group consisting of halogen, —OH, —CN, and methoxy optionally substituted by 1, 2 or 3 halogen; and —O—$C_{1-4}$alkyl optionally substituted by 1, 2 or 3 substituents, each substituent being independently selected from the group consisting of halogen, —OH, CN and methoxy optionally substituted by 1, 2 or 3 halogen. Suitably, $R^8$ is selected from the group consisting of hydrogen; halogen; —$C_{1-4}$alkyl optionally substituted by 1, 2 or 3 substituents, each substituent being independently selected from the group consisting of halogen, —OH, —CN, and methoxy optionally substituted by 1, 2 or 3 halogen; —$C_{3-4}$cycloalkyl optionally substituted by 1, 2 or 3 substituents, each substituent being independently selected from the group consisting of halogen, —$CH_3$, —OH, —CN, and methoxy optionally substituted by 1, 2 or 3 halogen (e.g. 1, 2 or 3 F atoms); —$C_{1-4}$alkenyl (such as —$C_{2-4}$alkenyl) optionally substituted by 1, 2 or 3 substituents, each substituent being independently selected from the group consisting of halogen, —OH, —CN, and methoxy optionally substituted by 1, 2 or 3 halogen; and —O—$C_{1-4}$alkyl optionally substituted by 1, 2 or 3 substituents, each substituent being independently selected from the group consisting of halogen, —OH, CN and methoxy optionally substituted by 1, 2 or 3 halogen. More suitably, $R^8$ is selected from the group consisting of hydrogen; halogen (e.g. F or Cl); —$C_{1-4}$alkyl optionally substituted by 1, 2 or 3 substituents, each substituent being independently selected from the group consisting of halogen, —OH, —CN, and methoxy optionally substituted by 1, 2 or 3 halogen; and —O—$C_{1-4}$alkyl optionally substituted by 1, 2 or 3 substituents, each substituent being independently selected from the group consisting of halogen, —OH, CN and methoxy optionally substituted by 1, 2 or 3 halogen. Even more suitably, $R^8$ is selected from the group consisting of hydrogen; halogen (e.g. F or Cl); —$C_{1-4}$alkyl optionally substituted by 1 substituent, selected from the group consisting of halogen, —OH, —CN, and methoxy optionally substituted by 1, 2 or 3 halogen; and —O—$C_{1-4}$alkyl optionally substituted by 1 substituent, selected from the group consisting of halogen, —OH, CN and methoxy optionally substituted by 1, 2 or 3 halogen. Even more suitably, $R^8$ is selected from the group consisting of hydrogen; halogen (e.g. F or Cl); —$C_{1-4}$alkyl optionally substituted by 1 substituent, selected from the group consisting of halogen, and methoxy optionally substituted by 1, 2 or 3 halogen; and —O—$C_{1-4}$alkyl optionally substituted by 1 substituent, selected from the group consisting of halogen, and methoxy optionally substituted by 1, 2 or 3 halogen. Even more suitably, $R^8$ is selected from the group consisting of hydrogen; halogen; —$C_{1-4}$alkyl; and —O—$C_{1-4}$alkyl. For example, $R^8$ is selected from the group consisting of hydrogen; halogen; methyl; and methoxy.

Alternatively, $R^8$ is selected from the group consisting of hydrogen; halogen (e.g. F or Cl); methyl optionally substituted by 1, 2 or 3 substituents, each substituent being independently selected from the group consisting of halogen, —OH, —CN, and methoxy optionally substituted by 1, 2 or 3 halogen; and methoxy optionally substituted by 1, 2 or 3 substituents, each substituent being independently selected from the group consisting of halogen, —OH, CN and methoxy optionally substituted by 1, 2 or 3 halogen. Suitably, $R^8$ is selected from the group consisting of hydrogen; halogen (e.g. F or Cl); methyl optionally substituted by 1, 2 or 3 substituents, each substituent being independently selected from the group consisting of halogen, and methoxy optionally substituted by 1, 2 or 3 halogen; and methoxy optionally substituted by 1, 2 or 3 substituents, each substituent being independently selected from the group consisting of halogen, and methoxy optionally substituted by 1, 2 or 3 halogen. More suitably, $R^8$ is selected from the group consisting of hydrogen; halogen (e.g. F or Cl); methyl optionally substituted by 1, 2 or 3 F atoms, and methoxy optionally substituted by 1, 2 or 3 F atoms. For example, $R^a$ is selected from the group consisting of hydrogen; halogen; methyl; —$CF_3$; methoxy; and —$OCF_3$. Suitably, $R^8$ is $CF_3$. Suitably, $R^8$ is Cl.

In another embodiment, $R^8$ is selected from the group consisting of hydrogen; halogen; —OH; —CN; —$C_{1-3}$alkyl optionally substituted by 1, 2 or 3 substituents, each substituent being independently selected from the group consisting of halogen (e.g. F), —OH, —CN, and methoxy optionally substituted by 1, 2 or 3 halogen (e.g. 1, 2 or 3 F atoms); —$C_{3-4}$cycloalkyl optionally substituted by 1, 2 or 3 substituents, each substituent being independently selected from the group consisting of halogen (e.g. F), —OH, —$CH_3$, —CN, and methoxy optionally substituted by 1, 2 or 3 halogen (e.g. 1, 2 or 3 F atoms); and —O—$C_{1-3}$alkyl optionally substituted by 1, 2 or 3 substituents, each substituent being independently selected from the group consisting of halogen (e.g. F), —OH, —CN, and methoxy optionally substituted by 1, 2 or 3 halogen (e.g. 1, 2 or 3 F atoms). In such an embodiment, suitably $R^9$ is hydrogen.

In the compound of formula (I), $R^9$ may be selected from the group consisting of hydrogen and —$C_{1-4}$alkyl optionally substituted by 1, 2 or 3 substituents, each substituent being independently selected from the group consisting of halogen, —OH, —$OCH_3$, and —$OCF_3$. Suitably, $R^9$ is selected from the group consisting of hydrogen and —$C_{1-4}$alkyl optionally substituted by 1 substituent selected from the group consisting of halogen, —OH, —$OCH_3$, and —$OCF_3$. More suitably, $R^9$ is selected from the group consisting of hydrogen and —$C_{1-4}$alkyl. More suitably, $R^9$ is selected from the group consisting of hydrogen, and methyl. In one especially suitable embodiment, $R^9$ is hydrogen.

Alternatively, $R^9$ is selected from the group consisting of hydrogen and methyl optionally substituted by 1, 2 or 3 substituents, each substituent being independently selected from the group consisting of halogen, —OH, —$OCH_3$, and —$OCF_3$. Suitably, $R^9$ is selected from the group consisting of hydrogen and methyl optionally substituted by 1, 2 or 3 F atoms. For example, $R^9$ is hydrogen; or $R^9$ is methyl; or $R^9$ is —$CF_3$.

In one suitable embodiment of the invention, $R^6$ and $R^9$ are each hydrogen; and p is 0. In another suitable embodiment of the invention, $R^3$, $R^4$, $R^6$ and $R^9$ are each hydrogen; and p is 0.

In the compound of formula (I), $R^8$ and $R^9$ may be linked such that together with the atoms to which they are attached they form a 6-membered aryl group, $C_{5-6}$cycloalkyl group or a 5- or 6-membered aromatic heterocyclyl group comprising 1 or 2 heteroatoms (for example, 1 heteroatom) selected from N, O and S, and wherein said 6-membered aryl group, $C_{5-6}$cycloalkyl group or 5- to 6-membered aromatic heterocyclyl group is optionally substituted by 1, 2 or 3 substituents, each substituent being independently selected from the group consisting of halogen; —OH; —CN; —$C_{1-4}$alkyl optionally substituted by 1, 2 or 3 substituents, each substituent being independently selected from the group consisting of halogen, —OH, and methoxy optionally substituted by 1, 2 or 3 halogen; and —O—$C_{1-4}$alkyl optionally substituted by 1, 2 or 3 substituents, each substituent being independently selected from the group consisting of -halogen, —OH, and methoxy optionally substituted by 1, 2 or 3 halogen.

In the compound of formula (I), $R^8$ and $R^9$ are linked such that together with the atoms to which they are attached they form a 6-membered aryl group, a $C_{5-6}$cycloalkyl group or a 5- or 6-membered aromatic heterocyclyl group comprising 1 or 2 heteroatoms (for example, 1 heteroatom) selected from N, O and S, and wherein said 6-membered aryl group, $C_{5-6}$cycloalkyl group or 5- or 6-membered aromatic hetero-cyclyl group is optionally substituted by 1, 2 or 3 substituents (e.g. 1 substituent), each substituent being independently selected from the group consisting of halogen; —OH; —CN; —$C_{1-3}$alkyl optionally substituted by 1, 2 or 3 substituents, each substituent being independently selected from the group consisting of halogen, —OH, —$OCH_3$, and —$OCF_3$; and —O—$C_{1-}$alkyl optionally substituted by 1, 2 or 3 substituents, each substituent being independently selected from the group consisting of -halogen, —OH, —$OCH_3$, and —$OCF_3$.

In one suitable embodiment, $R^8$ and $R^9$ are linked such that together with the atoms to which they are attached they form a $C_{5-6}$cycloalkyl group, wherein said $C_{5-6}$cycloalkyl group is optionally substituted by 1, 2 or 3 (e.g. 1 substitutent) substituents, each substituent being independently selected from the group consisting of halogen; —OH; —CN; —$C_{1-4}$alkyl optionally substituted by 1, 2 or 3 substituents, each substituent being independently selected from the group consisting of halogen, —OH, and methoxy optionally substituted by 1, 2 or 3 halogen; and —O—$C_{1-4}$alkyl optionally substituted by 1, 2 or 3 substituents, each substituent being independently selected from the group consisting of -halogen, —OH, and methoxy optionally substituted by 1, 2 or 3 halogen.

In one suitable embodiment, $R^8$ and $R^9$ are linked such that together with the atoms to which they are attached they form a $C_{5-6}$cycloalkyl group, wherein said $C_{5-6}$cycloalkyl group is optionally substituted by 1, 2 or 3 substituents (e.g. 1 substituent) selected from the group consisting of halogen; —OH; —CN; —$C_{1-3}$alkyl optionally substituted by 1, 2 or 3 substituents, each substituent being independently selected from the group consisting of halogen, —OH, —$OCH_3$, and —$OCF_3$; and —O—$C_{1-3}$alkyl optionally substituted by 1, 2 or 3 substituents, each substituent being independently selected from the group consisting of -halogen, —OH, —$OCH_3$, and —$OCF_3$.

Even more suitably, $R^8$ and $R^9$ are linked such that together with the atoms to which they are attached they form a $C_5$cycloalkyl group, wherein said $C_5$cycloalkyl group is optionally substituted by 1, 2 or 3 (e.g. 1 substitutent) substituents, each substituent being independently selected from the group consisting of halogen; —OH; —CN; —$C_{1-4}$alkyl optionally substituted by 1, 2 or 3 substituents, each substituent being independently selected from the group consisting of halogen, —OH, and methoxy optionally substituted by 1, 2 or 3 halogen; and —O—$C_{1-4}$alkyl optionally substituted by 1, 2 or 3 substituents, each substituent being independently selected from the group consisting of -halogen, —OH, and methoxy optionally substituted by 1, 2 or 3 halogen.

Even more suitably, $R^8$ and $R^9$ are linked such that together with the atoms to which they are attached they form a $C_5$cycloalkyl group, wherein said $C_5$cycloalkyl group is optionally substituted by 1, 2 or 3 substituents (e.g. 1 substituent) selected from the group consisting of halogen; —OH; —CN; —$C_{1-3}$alkyl optionally substituted by 1, 2 or 3 substituents, each substituent being independently selected from the group consisting of halogen, —OH, —$OCH_3$, and —$OCF_3$; and —O—$C_{1-3}$alkyl optionally substituted by 1, 2 or 3 substituents, each substituent being independently selected from the group consisting of -halogen, —OH, —$OCH_3$, and —$OCF_3$.

Alternatively, $R^8$ and $R^9$ may be linked such that together with the atoms to which they are attached they form a 6-membered aryl group or a 5- or 6-membered aromatic heterocyclyl group comprising 1 or 2 heteroatoms selected from N, O and S, and wherein said 6-membered aryl group or 5- to 6-membered aromatic heterocyclyl group is optionally substituted by 1, 2 or 3 substituents, each substituent being independently selected from the group consisting of halogen; —OH; —CN; —$C_{1-4}$alkyl optionally substituted by 1, 2 or 3 substituents, each substituent being independently selected from the group consisting of halogen, —OH, and methoxy optionally substituted by 1, 2 or 3 halogen; and —O—$C_{1-4}$alkyl optionally substituted by 1, 2 or 3 substituents, each substituent being independently selected from the group consisting of -halogen, —OH, and methoxy optionally substituted by 1, 2 or 3 halogen. For example, $R^6$ and $R^9$ may be linked such that together with the atoms to which they are attached they form a 6-membered aryl group or a 5- or 6-membered aromatic heterocyclyl group comprising 1 or 2 heteroatoms selected from N and O, and wherein said 6-membered aryl group or 5- to 6-membered aromatic heterocyclyl group is optionally substituted by 1, 2 or 3 substituents, each substituent being independently selected from the group consisting of halogen; —OH; —CN; —$C_{1-4}$alkyl optionally substituted by 1, 2 or 3 substituents, each substituent being independently selected from the group consisting of halogen, —OH, and methoxy optionally substituted by 1, 2 or 3 halogen; and —O—$C_{1-4}$alkyl optionally substituted by 1, 2 or 3 substituents, each substituent being independently selected from the group consisting of -halogen, —OH, and methoxy optionally substituted by 1, 2 or 3 halogen. Also for example, $R^8$ and $R^9$ may be linked such that together with the atoms to which they are attached they form a 6-membered aryl group or a 5- or 6-membered aromatic heterocyclyl group comprising 1 or 2 heteroatoms selected from N and O, and wherein said 6-membered aryl group or 5- to 6-membered aromatic heterocyclyl group is optionally substituted by 1, 2 or 3 substituents, each substituent being independently selected from the group consisting of halogen (e.g. F or Cl); —$C_{1-4}$alkyl optionally substituted by 1, 2 or 3 substituents, each substituent being independently selected from the group consisting of halogen, —OH, and methoxy optionally substituted by 1, 2 or 3 halogen; and —O—$C_{1-4}$alkyl optionally substituted by 1, 2 or 3 substituents, each substituent being independently selected from the group consisting of -halogen, —OH, and methoxy optionally substituted by 1, 2 or 3 halogen.

In another embodiment, $R^8$ and $R^9$ may be linked such that together with the atoms to which they are attached they form a 6-membered aryl group or a 5- or 6-membered aromatic heterocyclyl group comprising 1 or 2 heteroatoms (for example, 1 heteroatom) selected from N and O, and wherein said 6-membered aryl group or 5- to 6-membered aromatic heterocyclyl group is optionally substituted by 1, 2 or 3 substituents, each substituent being independently selected from the group consisting of halogen (e.g. F or Cl); —$C_{1-4}$alkyl optionally substituted by 1 substituent, selected from the group consisting of halogen, and methoxy optionally substituted by 1, 2 or 3 halogen; and —O—$C_{1-4}$alkyl optionally substituted by 1 substituent, selected from the group consisting of halogen, and methoxy optionally substituted by 1, 2 or 3 halogen. For example, $R^8$ and $R^9$ may be linked such that together with the atoms to which they are attached they form a 6-membered aryl group or a 5- or 6-membered aromatic heterocyclyl group comprising 1 or 2 heteroatoms (for example, 1 heteroatom) selected from N and O, and wherein said 6-membered aryl group or 5- to 6-membered aromatic heterocyclyl group is optionally substituted by 1 or 2 substituents, each substituent being independently selected from the group consisting of halogen (e.g. F or Cl); —$C_{1-4}$alkyl optionally substituted by 1 substituent, selected from the group consisting of halogen, and methoxy optionally substituted by 1, 2 or 3 halogen; and —O—$C_{1-4}$alkyl optionally substituted by 1 substituent, selected from the group consisting of halogen, and methoxy optionally substituted by 1, 2 or 3 halogen. For example, $R^8$ and $R^9$ may be linked such that together with the atoms to which they are attached they form a 6-membered aryl group or a 5- or 6-membered aromatic heterocyclyl group comprising 1 or 2 heteroatoms (for example, 1 heteroatom) selected from N and O, and wherein said 6-membered aryl group or 5- to 6-membered aromatic heterocyclyl group is optionally substituted by 1 or 2 substituents, each substituent being independently selected from the group consisting of halogen; —$C_{1-4}$alkyl; and —O—$C_{1-4}$alkyl. Also, for example, $R^8$ and $R^9$ may be linked such that together with the atoms to which they are attached they form a 6-membered aryl group or a 5- or 6-membered aromatic heterocyclyl group comprising 1 or 2 heteroatoms (for example, 1 heteroatom) selected from N and O, and wherein said 6-membered aryl group or 5- to 6-membered aromatic heterocyclyl group is optionally substituted by 1 or 2 substituents, each substituent being independently selected from the group consisting of hydrogen; halogen; methyl; and methoxy. In a further embodiment, $R^8$ and $R^9$ may be linked such that together with the atoms to which they are attached they form a 6-membered aryl group or a 5- or 6-membered aromatic heterocyclyl group comprising 1 or 2 heteroatoms (for example, 1 heteroatom) selected from N and O.

Alternatively, in one embodiment $R^8$ and $R^9$ may be linked such that together with the atoms to which they are attached they form a 6-membered aryl group or a 5- or 6-membered aromatic heterocyclyl group comprising 1 or 2 heteroatoms (for example, 1 heteroatom) selected from N and O, and wherein said 6-membered aryl group or 5- to 6-membered aromatic heterocyclyl group is optionally substituted by 1 or 2 substituents, each substituent being independently selected from the group consisting of halogen (e.g. F or Cl); methyl optionally substituted by 1, 2 or 3 substituents, each substituent being independently selected from the group consisting of halogen, —OH, —CN, and methoxy optionally substituted by 1, 2 or 3 halogen e.g. halogen, —OH and methoxy optionally substituted by 1, 2 or 3 halogen; and methoxy optionally substituted by 1, 2 or 3 substituents, each substituent being independently selected from the group consisting of halogen, —OH, CN and methoxy optionally substituted by 1, 2 or 3 halogen e.g. halogen, —OH and methoxy optionally substituted by 1, 2 or 3 halogen. For example, $R^8$ and $R^9$ may be linked such that together with the atoms to which they are attached they form a 6-membered aryl group or a 5- or 6-membered aromatic heterocyclyl group comprising 1 or 2 heteroatoms (for example, 1 heteroatom) selected from N and O, and wherein said 6-membered aryl group or 5- to 6-membered aromatic heterocyclyl group is optionally substituted by 1 or 2 substituents, each substituent being independently selected from the group consisting of halogen (e.g. F or Cl); methyl optionally substituted by 1, 2 or 3 substituents, each substituent being independently selected from the group consisting of halogen, and methoxy optionally substituted by 1, 2 or 3 halogen; and methoxy optionally substituted by 1, 2 or 3 substituents, each substituent being independently selected from the group consisting of halogen, and methoxy optionally substituted by 1, 2 or 3 halogen. Also for example, $R^8$ and $R^9$ may be linked such that together with the atoms to which they are attached they form a 6-membered aryl group or a 5- or 6-membered aromatic heterocyclyl group comprising 1 or 2 heteroatoms (for example, 1 heteroatom) selected from N and O, and wherein said 6-membered aryl group or 5- to 6-membered aromatic heterocyclyl group is optionally substituted by 1 or 2 substituents, each substituent being independently selected from the group consisting of halogen (e.g. F or Cl); methyl optionally substituted by 1, 2 or 3 F atoms, and methoxy optionally substituted by 1, 2 or 3 F atoms. Also for example, $R^8$ and $R^9$ may be linked such that together with the atoms to which they are attached they form a 6-membered aryl group or a 5- or 6-membered aromatic heterocyclyl group comprising 1 or 2 heteroatoms (for example, 1 heteroatom) selected from N and O, and wherein said 6-membered aryl group or 5- to 6-membered aromatic heterocyclyl group is optionally substituted by 1 or 2 substituents, each substituent being independently selected from the group consisting of halogen; methyl; —$CF_3$; methoxy; and —$OCF_3$.

Alternatively, in one embodiment $R^8$ and $R^9$ are linked such that together with the atoms to which they are attached they form a 5- or 6-membered aromatic heterocyclyl group comprising 1 or 2 heteroatoms (for example, 1 heteroatom) selected from N, O and S, and wherein the 5- or 6-membered aromatic heterocyclyl group is optionally substituted by 1, 2 or 3 substituents, each substituent being independently selected from the group consisting of halogen; —OH; —CN; —$C_{1-4}$ alkyl optionally substituted by 1, 2 or 3 substituents, each substituent being independently selected from the group consisting of halogen, —OH, and methoxy optionally substituted by 1, 2 or 3 halogen; and —O—$C_{1-4}$alkyl optionally substituted by 1, 2 or 3 substituents, each substituent being independently selected from the group consisting of -halogen, —OH, and methoxy optionally substituted by 1, 2 or 3 halogen.

Alternatively, in one embodiment $R^8$ and $R^9$ are linked such that together with the atoms to which they are attached they form a 5- or 6-membered aromatic heterocyclyl group comprising 1 or 2 heteroatoms (for example, 1 heteroatom) selected from N, O and S, and wherein the 5- or 6-membered aromatic heterocyclyl group is optionally substituted by 1 substituent selected from the group consisting of halogen; —OH; —CN; —$C_{1-3}$alkyl optionally substituted by 1, 2 or 3 substituents, each substituent being independently selected from the group consisting of halogen, —OH, —$OCH_3$, and —$OCF_3$; and —O—$C_{1-3}$alkyl optionally substituted by 1, 2 or 3 substituents, each substituent being independently selected from the group consisting of -halogen, —OH, —$OCH_3$, and —$OCF_3$.

In one suitable embodiment, $R^8$ and $R^9$ are linked such that together with the atoms to which they are attached they form a 5-membered aromatic heterocyclyl group comprising 1 or 2 heteroatoms (for example, 1 heteroatom) selected from N, O and S, and wherein the 5-membered aromatic heterocyclyl group is optionally substituted by 1, 2 or 3 substituents, each substituent being independently selected from the group consisting of halogen; —OH; —CN; —$C_{1-4}$alkyl optionally substituted by 1, 2 or 3 substituents, each substituent being independently selected from the group consisting of halogen, —OH, and methoxy optionally substituted by 1, 2 or 3 halogen; and —O—$C_{1-4}$alkyl optionally substituted by 1, 2 or 3 substituents, each substituent being independently selected from the group consisting of -halogen, —OH, and methoxy optionally substituted by 1, 2 or 3 halogen; In one suitable embodiment, $R^8$ and $R^9$ are linked such that together with the atoms to which they are attached they form a 5-membered aromatic heterocyclyl group comprising 1 or 2 heteroatoms (for example, 1 heteroatom) selected from N, O and S, and wherein the 5-membered aromatic heterocyclyl group is optionally substituted by 1 substituent selected from the group consisting of halogen; —OH; —CN; —$C_{1-3}$alkyl optionally substituted by 1, 2 or 3 substituents, each substituent being independently selected from the group consisting of halogen, —OH, —$OCH_3$, and —$OCF_3$; and —O—$C_{1-3}$alkyl optionally substituted by 1, 2 or 3 substituents, each substituent being independently selected from the group consisting of -halogen, —OH, —$OCH_3$, and —$OCF_3$.

In one suitable embodiment, $R^8$ and $R^9$ are linked such that together to the atoms to which they are attached they form a 5-membered aromatic heterocyclyl group selected from the group consisting of:

In one suitable embodiment, the 5-membered heterocyclyl group is selected from the group consisting of:

In one suitable embodiment, the 5-membered heterocyclyl group is:

In one suitable embodiment, the 5-membered heterocyclyl group is:

In one suitable embodiment, the 5-membered heterocyclyl group is:

In one suitable embodiment, the 5-membered heterocyclyl group is:

For the avoidance of doubt, within such embodiments denotes the point of attachment, wherein for example is equivalent to In the compound of formula (I), Z may be a 5- to 13-membered non-aromatic heterocyclyl group comprising 1, 2 or 3 heteroatoms selected from N, O and S, wherein at least one of the heteroatoms is N, and wherein said 5- to 13-membered non-aromatic heterocyclyl group is optionally substituted with 1, 2, 3 or 4 substituents (for example 1, 2 or 3 substituents; or 1 or 2 substituents; or 1 substituent), each substituent being independently selected from the group consisting of halogen; —$C_{1-6}$alkyl optionally substituted by 1, 2 or 3 substituents, each substituent being independently selected from the group consisting of halogen, —OH, and —O$C_{1-3}$alkyl optionally substituted by 1, 2 or 3 halogen; —O—$C_{1-6}$alkyl optionally substituted by 1, 2 or 3 substituents, each substituent being independently selected from the group consisting of halogen, —OH, and —O—$C_{1-3}$alkyl optionally substituted by 1, 2 or 3 halogen; $NR^cR^d$; and $C_{3-6}$cycloalkyl optionally substituted by 1, 2 or 3 substituents, each substituent being independently selected from the group consisting of halogen, —OH, and —O—$C_{1-3}$alkyl optionally substituted by 1, 2 or 3 halogen; or when two substituents are on adjacent ring positions they may be linked such that together with the atoms to which they are attached they form a $C_{3-6}$cycloalkyl group or a 4- to 6-membered non-aromatic heterocyclyl group comprising 1 heteroatom selected from the group consisting of O and N, wherein said $C_{3-6}$cycloalkyl group or 4- to 6-membered non-aromatic heterocyclyl group (i.e. a 4-, 5- or 6-membered non-aromatic heterocyclyl group) is optionally substituted by 1 or 2 substituents, each substituent being independently selected from the group consisting of halogen; —$C_{1-6}$alkyl optionally substituted by 1, 2 or 3 substituents, each substituent being independently selected from the group consisting of halogen, —OH, and —O$C_{1-3}$alkyl optionally substituted by 1, 2 or 3 halogen; and —O—$C_{1-6}$alkyl optionally substituted by 1, 2 or 3 substituents, each substituent being independently selected from the group consisting of halogen, —OH, and —O—$C_{1-3}$alkyl optionally substituted by 1, 2 or 3 halogen;

$R^c$ and $R^d$ are independently selected from the group consisting of hydrogen; —$C_{1-6}$alkyl optionally substituted by 1, 2 or 3 substituents, each substituent being independently selected from the group consisting of halogen, —$OCH_3$, and —$OCF_3$; and $C_{3-6}$cycloalkyl optionally substituted by 1, 2 or 3 substituents, each substituent being independently selected from the group consisting of halogen, —$CH_3$, —OH, —$OCH_3$, and —$OCF_3$;

or Z is —$NR^{10}R^{11}$.

In the compound of formula (I), Z may be a 5- to 13-membered non-aromatic heterocyclyl group comprising 1, 2 or 3 heteroatoms selected from N, O and S, wherein at least one of the heteroatoms is N, and wherein said 5- to 13-membered non-aromatic heterocyclyl group is optionally substituted with 1, 2, 3 or 4 substituents (for example 1, 2 or 3 substituents; or 1 or 2 substituents; or 1 substituent), each substituent being independently selected from the group consisting of halogen; —$C_{1-6}$alkyl optionally substituted by 1, 2 or 3 substituents, each substituent being independently selected from the group consisting of halogen, —OH, and —$OC_{1-3}$alkyl optionally substituted by 1, 2 or 3 halogen; —O—$C_{1-6}$alkyl optionally substituted by 1, 2 or 3 substituents, each substituent being independently selected from the group consisting of halogen, —OH, and —O—$C_{1-3}$-alkyl optionally substituted by 1, 2 or 3 halogen;

or Z is —$NR^{10}R^{11}$.

Alternatively, Z may be a 5- to 13-membered non-aromatic heterocyclyl group comprising 1, 2 or 3 heteroatoms selected from N, O and S, wherein at least one of the heteroatoms is N, and wherein said 5- to 13-membered non-aromatic heterocyclyl group is optionally substituted with 1, 2, 3 or 4 substituents (for example 1, 2 or 3 substituents; or 1 or 2 substituents; or 1 substituent), each substituent being independently selected from the group consisting of $NR^cR^d$; and $C_{3-6}$cycloalkyl optionally substituted by 1, 2 or 3 substituents, each substituent being independently selected from the group consisting of halogen, —OH, and —O—$C_{1-3}$alkyl optionally substituted by 1, 2 or 3 halogen; or when two substituents are on adjacent ring positions they may be linked such that together with the atoms to which they are attached they form a $C_{3-6}$cycloalkyl group or a 4- to 6-membered non-aromatic heterocyclyl group comprising 1 heteroatom selected from the group consisting of O and N, wherein said $C_{3-6}$cycloalkyl group or 4- to 6-membered non-aromatic heterocyclyl group is optionally substituted by 1 or 2 substituents, each substituent being independently selected from the group consisting of halogen; —$C_{1-6}$alkyl optionally substituted by 1, 2 or 3 substituents, each substituent being independently selected from the group consisting of halogen, —OH, and —$OC_{1-3}$-alkyl optionally substituted by 1, 2 or 3 halogen; and —O—$C_{1-6}$alkyl optionally substituted by 1, 2 or 3 substituents, each substituent being independently selected from the group consisting of halogen, —OH, and —O—$C_{1-3}$alkyl optionally substituted by 1, 2 or 3 halogen;

$R^c$ and $R^d$ are independently selected from the group consisting of hydrogen; —$C_{1-6}$alkyl optionally substituted by 1, 2 or 3 substituents, each substituent being independently selected from the group consisting of halogen, —$OCH_3$, and —$OCF_3$; and $C_{3-6}$cycloalkyl optionally substituted by 1, 2 or 3 substituents, each substituent being independently selected from the group consisting of halogen, —$CH_3$, —OH, —$OCH_3$, and —$OCF_3$;

or Z is —$NR^{10}R^{11}$.

Alternatively, Z may be a 5- to 10-membered non-aromatic heterocyclyl group comprising 1, 2 or 3 heteroatoms selected from N, O and S, wherein at least one of the heteroatoms is N, and wherein said 5- to 10-membered non-aromatic heterocyclyl group is optionally substituted with 1, 2, 3 or 4 substituents (for example 1, 2 or 3 substituents; or 1 or 2 substituents; or 1 substituent), each substituent being independently selected from the group consisting of halogen; —$C_{1-6}$alkyl optionally substituted by 1, 2 or 3 substituents, each substituent being independently selected from the group consisting of halogen, —OH, and —$OC_{1-3}$-alkyl optionally substituted by 1, 2 or 3 halogen; and —O—$C_{1-6}$alkyl optionally substituted by 1, 2 or 3 substituents, each substituent being independently selected from the group consisting of halogen, —OH, and —O—$C_{1-3}$alkyl optionally substituted by 1, 2 or 3 halogen;

or Z is —$NR^{10}R^{11}$.

In embodiments wherein Z is a 5- to 13-membered non-aromatic heterocyclyl group (i.e. a 5-, 6-, 7-, 8-, 9-, 10-, 11-, 12-, or 13-membered non-aromatic heterocyclyl group), suitably a N heteroatom is directly attached to 6-membered aromatic heterocyclyl group of formula (I) comprising $X^1$.

In embodiments wherein Z is a 5- to 13-membered non-aromatic heterocyclyl group, Z may be an aziridinyl, azetidinyl, pyrrolidinyl, imidazolidinyl, pyrazolidinyl, piperidinyl, piperazinyl, tetrahydrofuranyl, tetrahydropyranyl, morpholinyl, thiomorpholinyl, azepanyl, diazepanyl (for example 1,4-diazepanyl, 1,1-diazepanyl or 1,5-diazepanyl, and suitably 1,4-diazepanyl), diazabicycloheptanyl (for example 3,6-diazabicyclo[3.2.0]heptanyl), 1H-octahydropyrrolo[3,4-b]pyridinyl, 2,5-diazabicyclo[2.2.1]heptanyl, cis-octahydro-pyrrolo[3,4-b]pyridinyl, cis-octahydro-pyrrolo[3,4-c]pyridinyl, 3,7-diazabicyclo[3.3.1]nonanyl, 2,6-diazaspiro[3.3]heptanyl, octahydropyrrolo[3,2-b]pyrrolyl, 1,7-diazaspiro[4.4]nonanyl, 1,8-diazaspiro[4.5]decanyl, decahydro-2,7-naphthyridinyl, 2,8-diazaspiro[5.5]undecanyl, 3,6-diazabicyclo[3.2.0]heptane, 2,8-diazaspiro[4.5]decanyl, octahydropyrrolo[3,4-c]pyrrolyl, trans-octahydro-1H-pyrrolo[3,4-b]pyridinyl, 2,6-diazaspiro[4.5]decanyl, 2,7-diazaspiro[4.5]decanyl, 1,7-diazaspiro[3.5]nonanyl, 1,6-diazaspiro[3.5]nonanyl, 2,6-diazaspiro[3.5]nonanyl, 2,7-diaza-spiro[3.5]nonanyl, (4aR,8aR)-decahydro-1,5-naphthyridinyl, 3,9-diazaspiro[5.5]undecanyl, (3aS,6aS)-octahydropyrrolo[2,3-c]pyrrolyl, 2,9-diazaspiro[6.6]tridecanyl, 3,8-diazabicyclo[4.2.0]octanyl, 3,7-diazabicyclo[4.2.0]octanyl, 9,9-dimethyl-3,7-diazabicyclo[3.3.1]nonanyl, cis-octahydro-pyrrolo[3,4-c]pyridinyl, cis-Decahydro-1,7-naphthyridinyl, 2,7-diazabicyclo[4.2.0]octanyl, (4aS,7aS)-octahydropyrrolo[3,4-b][1,4]oxazinyl, 2,6-diazaspiro[3.4]octanyl, 1,9-diazaspiro[6.6]tridecanyl, (4aS,8aS)-decahydro-1,5-naphthyridinyl, trans-decahydro-1,7-naphthyridine, (1S,2S)-2,5-diazabicyclo[2.2.1]heptanyl, trans-decahydro-1,7-naphthyridinyl, rac-(4aR,8aR)-octahydro-2H-pyrido[4,3-b]morpholinyl, decahydro-1,6-naphthyridinyl, octahydro-1H-pyrrolo[3,2-c]pyridinyl, rac-(3aR,6aR)-octahydropyrrolo[2,3-c]pyrrolyl, or decahydropyrrolo[3,2-c]azepinyl group. Suitably an N heteroatom of the heterocyclyl group directly attached to 6-membered aromatic heterocyclyl group of formula (I) comprising $X^1$.

In embodiments wherein Z is a 5- to 13-membered non-aromatic heterocyclyl group, suitably the Z is a 5- to 13-membered non-aromatic heterocyclyl group (i.e. a 5-, 6-, 7-, 8-, 9-, 10-, 11-, 12-, or 13-membered non-aromatic heterocyclyl group) comprising 1, 2 or 3 heteroatoms selected from N and O, wherein at least one of the heteroatoms is N, and wherein said 5- to 13-membered non-aromatic heterocyclyl group is optionally substituted with 1, 2, 3 or 4 substituents (for example 1, 2 or 3 substituents; or 1 or 2 substituents; or 1 substituent). In such embodiment, suitably a N heteroatom is directly attached to 6-membered aromatic heterocyclyl group of formula (I) comprising $X^1$. For example, Z is a 5- to 10-membered non-aromatic heterocyclyl group, suitably the Z is a 5- to 10-membered non-aromatic heterocyclyl group (i.e. a 5-, 6-, 7-, 8-, 9-, or 10-membered non-aromatic heterocyclyl group) comprising 1, 2 or 3 heteroatoms selected from N and O, wherein at least one of the heteroatoms is N, and wherein said 5- to 10-membered non-aromatic heterocyclyl group is optionally substituted with 1, 2, 3 or 4 substituents (for example 1, 2 or 3 substituents; or 1 or 2 substituents; or 1 substituent). In such embodiment, suitably a N heteroatom is directly attached to 6-membered aromatic heterocyclyl group of formula (I) comprising $X^1$.

Alternatively, wherein Z is a 5- to 13-membered non-aromatic heterocyclyl group, suitably Z is a 6- to 10-membered non-aromatic heterocyclyl group (i.e. a 6-, 7-, 8-, 9- or 10-membered non-aromatic heterocyclyl group) comprising 1, 2 or 3 heteroatoms selected from N, O and S, wherein at least one of the heteroatoms is N, and wherein said 6 to 10-membered non-aromatic heterocyclyl group is optionally substituted with 1, 2, 3 or 4 substituents (for example 1, 2 or 3 substituents; or 1 or 2 substituents; or 1 substituent). More suitably Z is a 6- to 10-membered non-aromatic heterocyclyl group comprising 2 or 3 heteroatoms selected from N, O and S, wherein at least one of the heteroatoms is N, and wherein said 6- to 10-membered non-aromatic heterocyclyl group is optionally substituted with 1, 2, 3 or 4 substituents (for example 1, 2 or 3 substituents; or 1 or 2 substituents; or 1 substituent). More suitably Z is a 6- to 10-membered non-aromatic heterocyclyl group comprising 2 or 3 heteroatoms selected from N, O and S, wherein at least one of the heteroatoms is N, and wherein said 6- to 10-membered non-aromatic heterocyclyl group is optionally substituted with 1, 2, 3 or 4 substituents (for example 1, 2 or 3 substituents; or 1 or 2 substituents; or 1 substituent). Even more suitably Z is a 6- to 10-membered non-aromatic heterocyclyl group comprising 2 or 3 heteroatoms selected from N and O, wherein at least one of the heteroatoms is N, and wherein said 6- to 10-membered non-aromatic heterocyclyl group is optionally substituted with 1, 2, 3 or 4 substituents (for example 1, 2 or 3 substituents; or 1 or 2 substituents; or 1 substituent). In such embodiment, suitably a N heteroatom is directly attached to 6-membered aromatic heterocyclyl group of formula (I) comprising $X^1$.

Alternatively, wherein Z is a 5- to 13-membered non-aromatic heterocyclyl group, suitably Z is a 5- to 8-membered non-aromatic heterocyclyl group (i.e. a 5-, 6-, 7- or 8-membered non-aromatic heterocyclyl group) comprising 1, 2 or 3 heteroatoms selected from N, O and S, wherein at least one of the heteroatoms is N, and wherein said 5- to 8-membered non-aromatic heterocyclyl group is optionally substituted with 1, 2, 3 or 4 substituents (for example 1, 2 or 3 substituents; or 1 or 2 substituents; or 1 substituent). More suitably Z is a 5- to 8-membered non-aromatic heterocyclyl group comprising 2 or 3 heteroatoms selected from N, O and S, wherein at least one of the heteroatoms is N, and wherein said 5- to 8-membered non-aromatic heterocyclyl group is optionally substituted with 1, 2, 3 or 4 substituents (for example 1, 2 or 3 substituents; or 1 or 2 substituents; or 1 substituent). More suitably Z is a 5- to 8-membered non-aromatic heterocyclyl group comprising 2 or 3 heteroatoms selected from N, O and S, wherein at least one of the heteroatoms is N, and wherein said 5- to 8-membered non-aromatic heterocyclyl group is optionally substituted with 1, 2, 3 or 4 substituents (for example 1, 2 or 3 substituents; or 1 or 2 substituents; or 1 substituent). Even more suitably Z is a 5- to 8-membered non-aromatic heterocyclyl group comprising 2 or 3 heteroatoms selected from N and O, wherein at least one of the heteroatoms is N, and wherein said 5- to 8-membered non-aromatic heterocyclyl group is optionally substituted with 1, 2, 3 or 4 substituents (for example 1, 2 or 3 substituents; or 1 or 2 substituents; or 1 substituent). In such embodiment, suitably a N heteroatom is directly attached to 6-membered aromatic heterocyclyl group of formula (I) comprising $X^1$.

In one suitable embodiment, wherein Z is a 5- to 13-membered non-aromatic heterocyclyl group, suitably Z is a 6-membered non-aromatic heterocyclyl group comprising 1, 2 or 3 heteroatoms selected from N, O and S, wherein at least one of the heteroatoms is N, and wherein said 6-membered non-aromatic heterocyclyl group is optionally substituted with 1, 2, 3 or 4 substituents (for example 1, 2 or 3 substituents; or 1 or 2 substituents; or 1 substituent). More suitably Z is a 6-membered non-aromatic heterocyclyl group comprising 2 or 3 heteroatoms selected from N, O and S, wherein at least one of the heteroatoms is N, and wherein said 6-membered non-aromatic heterocyclyl group is optionally substituted with 1, 2, 3 or 4 substituents (for example 1, 2 or 3 substituents; or 1 or 2 substituents; or 1 substituent). More suitably Z is a 6-membered non-aromatic heterocyclyl group comprising 2 or 3 heteroatoms selected from N, O and S, wherein at least one of the heteroatoms is N, and wherein said 6-membered non-aromatic heterocyclyl group is optionally substituted with 1, 2, 3 or 4 substituents (for example 1, 2 or 3 substituents; or 1 or 2 substituents; or 1 substituent). Even more suitably Z is a 6-membered non-aromatic heterocyclyl group comprising 2 or 3 heteroatoms selected from N and O, wherein at least one of the heteroatoms is N, and wherein said 6-membered non-aromatic heterocyclyl group is optionally substituted with 1, 2, 3 or 4 substituents (for example 1, 2 or 3 substituents; or 1 or 2 substituents; or 1 substituent). In such embodiment, suitably a N heteroatom is directly attached to 6-membered aromatic heterocyclyl group of formula (I) comprising $X^1$.

In embodiments wherein Z is optionally substituted (for example, optionally substituted with 1, 2, 3, or 4 substituents; or optionally substituted with 1, 2, or 3 substituents; or optionally substituted with 1 or 2 substituents; or optionally substituted with 1 substituent), each substituent may be independently selected from the group consisting of halogen; —$C_{1-6}$alkyl optionally substituted by 1, 2 or 3 substituents, each substituent being independently selected from the group consisting of halogen, —OH, and —$OC_{1-3}$alkyl optionally substituted by 1, 2 or 3 halogen; and —O—$C_{1-6}$alkyl optionally substituted by 1, 2 or 3 substituents, each substituent being independently selected from the group consisting of halogen, —OH, and —O—$C_{1-3}$alkyl optionally substituted by 1, 2 or 3 halogen. Suitably, each substituent is independently selected from the group consisting of halogen; —$C_{1-4}$alkyl optionally substituted by 1, 2 or 3 substituents, each substituent being independently selected from the group consisting of halogen, —OH, and —$OC_{1-3}$alkyl optionally substituted by 1, 2 or 3 halogen; and —O—$C_{1-4}$alkyl optionally substituted by 1, 2 or 3 substituents, each substituent being independently selected from the group consisting of halogen, —OH, and —O—$C_{1-3}$alkyl optionally substituted by 1, 2 or 3 halogen. More suitably, each substituent is independently selected from the group consisting of halogen; —$C_{1-4}$alkyl optionally substituted by 1 substituent selected from the group consisting of halogen, —OH, and —$OC_{1-3}$alkyl optionally substituted by 1, 2 or 3 halogen; and —O—$C_{1-4}$alkyl optionally substituted by 1 substituent selected from the group consisting of halogen, —OH, and —O—$C_{1-3}$alkyl optionally substituted by 1, 2 or 3 halogen. More suitably, each substituent is independently selected from the group consisting of halogen; —$C_{1-4}$alkyl optionally substituted by 1 substituent selected from the group consisting of halogen and —$OC_{1-3}$alkyl optionally substituted by 1, 2 or 3 halogen; and —O—$C_{1-4}$alkyl optionally substituted by 1 substituent selected from the group consisting of halogen and —O—$C_{1-3}$alkyl optionally substituted by 1, 2 or 3 halogen (for example, each substituent is independently —$C_{1-4}$alkyl optionally substituted by 1 substituent selected from the group consisting of halogen and —$OC_{1-3}$alkyl optionally substituted by 1, 2 or 3 halogen). Even more suitably, each substituent is independently selected from the group consisting of halogen; —$C_{1-4}$alkyl optionally substituted by 1 substituent selected from the group consisting of F and —OC$_{1-3}$alkyl optionally substituted by 1, 2 or 3 F atoms; and —O—C$_{1-4}$alkyl optionally substituted by 1 substituent selected from the group consisting of F and —O—C$_{1-3}$alkyl optionally substituted by 1, 2 or 3 F atoms (for example, each substituent is independently —C$_{1-4}$alkyl optionally substituted by 1 substituent selected from the group consisting of F and —OC$_{1-3}$alkyl optionally substituted by 1, 2 or 3 F atoms).

Alternatively, each substituent is independently selected from the group consisting of halogen; —C$_{1-4}$alkyl optionally substituted by 1, 2 or 3 substituents, each substituent being independently selected from the group consisting of halogen and —OC$_{1-3}$alkyl optionally substituted by 1, 2 or 3 halogen; and —O—C$_{1-4}$alkyl optionally substituted by 1, 2 or 3 substituents, each substituent being independently selected from the group consisting of halogen and —O—C$_{1-}$-alkyl optionally substituted by 1, 2 or 3 halogen (for example, each substituent is independently —C$_{1-4}$alkyl optionally substituted by 1, 2 or 3 substituents, each substituent being independently selected from the group consisting of halogen and —OC$_{1-3}$alkyl optionally substituted by 1, 2 or 3 halogen). More suitably, each substituent is independently selected from the group consisting of halogen; —C$_{1-4}$alkyl optionally substituted by 1, 2 or 3 substituents, each substituent being independently selected from the group consisting of halogen and methoxy optionally substituted by 1, 2 or 3 halogen; and —O—C$_{1-4}$alkyl optionally substituted by 1, 2 or 3 substituents, each substituent being independently selected from the group consisting of halogen and methoxy optionally substituted by 1, 2 or 3 halogen. Even more suitably, each substituent is independently selected from the group consisting of halogen; —C$_{1-4}$alkyl optionally substituted by 1, 2 or 3 substituents, each substituent being independently selected from the group consisting of F and methoxy optionally substituted by 1, 2 or 3 F atoms; and —O—C$_{1-4}$alkyl optionally substituted by 1, 2 or 3 substituents, each substituent being independently selected from the group consisting of F and methoxy optionally substituted by 1, 2 or 3 F atoms.

In another suitable embodiment, each substituent of Z is independently selected from the group consisting of halogen; methyl optionally substituted by 1, 2 or 3 substituents, each substituent being independently selected from the group consisting of F and methoxy optionally substituted by 1, 2 or 3 F atoms; and methoxy optionally substituted by 1, 2 or 3 substituents, each substituent being independently selected from the group consisting of F and methoxy optionally substituted by 1, 2 or 3 F atoms (for example, each substituent is independently; methyl optionally substituted by 1, 2 or 3 substituents, each substituent being independently selected from the group consisting of F and methoxy optionally substituted by 1, 2 or 3 F atoms).

In one suitable embodiment, wherein Z is a 5- to 13-membered non-aromatic heterocyclyl group, suitably Z is:

-continued (or suitably Z is

);

(and even more suitably Z is or )

wherein
〰 denotes the point of attachment.
m may be 0, 1, 2 or 3. Suitably m is 0, 1 or 2. More suitably m is 1 or 2.
r may be 0, 1, 2 or 3. Suitably r is 0, 1 or 2. In certain embodiments, suitably r is 1 or 2. In certain embodiments, suitably r is 0 or 1.
s may be 0, 1, 2 or 3. Suitably s is 0, 1 or 2. In certain embodiments, suitably s is 1 or 2. In certain embodiments, suitably s is 0 or 1. More suitably s is 0.

$R^{12}$ may be selected from the group consisting of hydrogen and —$C_{1-6}$alkyl optionally substituted by 1, 2 or 3 substituents, each substituent being independently selected from the group consisting of halogen and —$OC_{1-3}$alkyl optionally substituted by 1, 2 or 3 halogen.

Suitably, $R^{12}$ is selected from the group consisting of hydrogen and —$C_{1-4}$alkyl optionally substituted by 1, 2 or 3 substituents, each substituent being independently selected from the group consisting of halogen and —$OC_{1-3}$alkyl optionally substituted by 1, 2 or 3 halogen. More suitably, $R^{12}$ is selected from the group consisting of hydrogen and —$C_{1-4}$alkyl optionally substituted by 1, 2 or 3 substituents, each substituent being independently selected from the group consisting of halogen and methoxy optionally substituted by 1, 2 or 3 halogen. More suitably, $R^{12}$ is selected from the group consisting of hydrogen and —$C_{1-4}$alkyl optionally substituted by 1 substituent selected from the group consisting of halogen and methoxy optionally substituted by 1, 2 or 3 halogen (e.g. 1, 2, or 3 F atoms). More suitably, $R^{12}$ is selected from the group consisting of —$C_{1-4}$alkyl optionally substituted by 1, 2 or 3 substituents, each substituent being independently selected from the group consisting of halogen and —$OC_{1-3}$alkyl optionally substituted by 1, 2 or 3 halogen. Even more suitably, $R^{12}$ is selected from the group consisting of hydrogen and methyl. Even more suitably, $R^{12}$ is hydrogen. Even more suitably, $R^{12}$ is methyl.

In one suitable embodiment, Z is

Suitably, Z is

Suitably, Z is

When present, each $R^{13}$ is independently selected from the group consisting of halogen; —$C_{1-6}$alkyl optionally substituted by 1, 2 or 3 substituents, each substituent being independently selected from the group consisting of halogen, —OH, and —$OC_{1-4}$alkyl optionally substituted by 1, 2 or 3 halogen; and —O—$C_{1-6}$alkyl optionally substituted by 1, 2 or 3 substituents, each substituent being independently selected from the group consisting of halogen, —OH, —$O$—$C_{1-3}$alkyl optionally substituted by 1, 2 or 3 halogen; $NR^cR^d$; and $C_{3-6}$cycloalkyl optionally substituted by 1, 2 or 3 substituents, each substituent being independently selected from the group consisting of halogen, —OH, and —$OC_{1-3}$alkyl optionally substituted by 1, 2 or 3 halogen; or when two substituents are on adjacent ring positions they may be linked such that together with the atoms to which they are attached they form a $C_{3-6}$cycloalkyl group or a 4- to 6-membered non-aromatic heterocyclyl group comprising 1 heteroatom selected from the group consisting of O and N, wherein said $C_{3-6}$cycloalkyl group or 4- to 6-membered non-aromatic heterocyclyl group is optionally substituted by 1 or 2 substituents, each substituent being independently selected from the group consisting of halogen; —$C_{1-6}$alkyl optionally substituted by 1, 2 or 3 substituents, each substituent being independently selected from the group consisting of halogen, —OH, and —$OC_{1-3}$alkyl optionally substituted by 1, 2 or 3 halogen; and —O—$C_{1-6}$alkyl optionally substituted by 1, 2 or 3 substituents, each substituent being independently selected from the group consisting of halogen, —OH, and —O—$C_{1-3}$alkyl optionally substituted by 1, 2 or 3 halogen;

$R^c$ and $R^d$ are independently selected from the group consisting of hydrogen; —$C_{1-6}$alkyl optionally substituted by 1, 2 or 3 substituents, each substituent being independently selected from the group consisting of halogen, —$OCH_3$, and —$OCF_3$; and $C_{3-6}$cycloalkyl optionally substituted by 1, 2 or 3 substituents, each substituent being independently selected from the group consisting of halogen, —$CH_3$, —OH, —$OCH_3$, and —$OCF_3$.

Suitably, the two substituents on adjacent ring positions are one $R^{12}$ and one $R^{13}$. Alternatively, the two substituents on adjacent ring positions are both $R^{13}$.

Alternatively, when m is 0 or 1, r is 2 or 3 and two $R^{13}$ groups are on adjacent ring positions, said two $R^{13}$ are linked such that together with the atoms to which they are attached they form a $C_{3-6}$cycloalkyl group or a 4- to 6-membered non-aromatic heterocyclyl group comprising 1 heteroatom selected from the group consisting of O and N, wherein said $C_{3-6}$cycloalkyl group or 4- to 6-membered non-aromatic heterocyclyl group (i.e. a 4-, 5- or 6-membered non-aromatic heterocyclyl group) is optionally substituted by 1 or 2 substituents, each substituent being independently selected from the group consisting of halogen; —$C_{1-6}$alkyl optionally substituted by 1, 2 or 3 substituents, each substituent being independently selected from the group consisting of halogen, —OH, and —$OC_{1-3}$alkyl optionally substituted by 1, 2 or 3 halogen; and —O—$C_{1-6}$alkyl optionally substituted by 1, 2 or 3 substituents, each substituent being independently selected from the group consisting of halogen, —OH, and —O—$C_{1-3}$alkyl optionally substituted by 1, 2 or 3 halogen. Suitably, the two $R^{13}$ groups join to form a $C_{3-6}$cycloalkyl group, such as a cyclopropyl group which is suitably unsubstituted.

Alternatively, when r is 1, 2 or 3 and one $R^{13}$ group is at an adjacent ring position to N—$R^{12}$, said $R^{13}$ and $R^{12}$ are linked such that together with the atoms to which they are attached they form a 5- or 6-membered non-aromatic heterocyclyl group comprising 1 N heteroatom and optionally 1 heteroatom selected from the group consisting of O and N, wherein said 5- or 6-membered non-aromatic heterocyclyl group is optionally substituted by 1 or 2 substituents, each substituent being independently selected from the group consisting of halogen; —C$_{1-6}$alkyl optionally substituted by 1, 2 or 3 substituents, each substituent being independently selected from the group consisting of halogen, —OH, and —OC$_{1-3}$alkyl optionally substituted by 1, 2 or 3 halogen; and —O—C$_{1-6}$alkyl optionally substituted by 1, 2 or 3 substituents, each substituent being independently selected from the group consisting of halogen, —OH, and —O—C$_{1-3}$alkyl optionally substituted by 1, 2 or 3 halogen; and when present, each R$^{14}$ is independently selected from the group consisting of halogen; —C$_{1-3}$alkyl optionally substituted by 1, 2 or 3 substituents, each substituent being independently selected from the group consisting of halogen, —OH, and —OC$_{1-4}$alkyl optionally substituted by 1, 2 or 3 halogen; and —O—C$_{1-6}$alkyl optionally substituted by 1, 2 or 3 substituents, each substituent being independently selected from the group consisting of halogen, —OH, and —O—C$_{1-3}$alkyl optionally substituted by 1, 2 or 3 halogen.

In one suitable embodiment, when present each R$^{13}$ is independently NR$^c$R$^d$ or C$_{3-6}$cycloalkyl optionally substituted by 1, 2 or 3 substituents, each substituent being independently selected from the group consisting of halogen, —OH, and —OC$_{1-3}$alkyl optionally substituted by 1, 2 or 3 halogen. In one suitable embodiment, each R$^{13}$ is independently NR$^c$R$^d$.

Even more suitably, each R$^{13}$ is independently C$_{3-6}$cycloalkyl optionally substituted by 1, 2 or 3 substituents, each substituent being independently selected from the group consisting of halogen, —OH, and —OC$_{1-3}$alkyl optionally substituted by 1, 2 or 3 halogen. Even more suitably, each R$^{13}$ is independently cyclopropyl, which is suitably unsubstituted.

In one embodiment, R$^c$ is hydrogen. In a second embodiment, R$^c$ is —C$_{1-6}$alkyl optionally substituted by 1, 2 or 3 substituents, each substituent being independently selected from the group consisting of halogen, —OCH$_3$, and —OCF$_3$. In a third embodiment, R$^c$ is C$_{3-6}$cycloalkyl optionally substituted by 1, 2 or 3 substituents, each substituent being independently selected from the group consisting of halogen, —CH$_3$, —OH, —OCH$_3$, and —OCF$_3$.

Suitably, R$^c$ is unsubstituted —C$_{1-6}$alkyl, such as methyl, ethyl and propyl, in particular methyl and ethyl, especially methyl.

Suitably, R$^c$ is unsubstituted C$_{3-6}$cycloalkyl, such as cyclopropyl, cyclobutyl and cyclopentyl, in particular cyclopropyl.

In one embodiment, R$^d$ is hydrogen. In a second embodiment, R$^d$ is —C$_{1-6}$alkyl optionally substituted by 1, 2 or 3 substituents, each substituent being independently selected from the group consisting of halogen, —OCH$_3$, and —OCF$_3$. In a third embodiment, R$^d$ is C$_{3-6}$cycloalkyl optionally substituted by 1, 2 or 3 substituents, each substituent being independently selected from the group consisting of halogen, —CH$_3$, —OH, —OCH$_3$, and —OCF$_3$.

Suitably, R$^d$ is unsubstituted —C$_{1-6}$alkyl, such as methyl, ethyl and propyl, in particular methyl and ethyl, especially methyl.

Suitably, R$^d$ is unsubstituted C$_{3-6}$cycloalkyl, such as cyclopropyl, cyclobutyl and cyclopentyl, in particular cyclopropyl.

In one embodiment, R$^c$ is hydrogen and R$^d$ is methyl which is suitably unsubstituted. In a second embodiment, R$^c$ and R$^d$ are each methyl which are suitably unsubstituted. In a third embodiment, R$^c$ and R$^d$ are each hydrogen.

Alternatively, when present, each R$^{13}$ may be independently selected from the group consisting of halogen; —C$_{1-}$

42

$_6$alkyl optionally substituted by 1, 2 or 3 substituents, each substituent being independently selected from the group consisting of halogen, —OH, and —OC$_{1-4}$alkyl optionally substituted by 1, 2 or 3 halogen; and —O—C$_{1-6}$alkyl optionally substituted by 1, 2 or 3 substituents, each substituent being independently selected from the group consisting of halogen, —OH, and —O—C$_{1-3}$alkyl optionally substituted by 1, 2 or 3 halogen;

or, when m is 0 or 1, r is 2 or 3 and two R$^{13}$ groups are on adjacent ring positions, said two R$^{13}$ are linked such that together with the atoms to which they are attached they form a C$_{4-6}$cycloalkyl group (i.e. a cyclobutyl, cyclopentyl or cyclohexyl group) or a 4- to 6-membered non-aromatic heterocyclyl group (i.e. a 4-, 5- or 6-membered non-aromatic heterocyclyl group) comprising 1 heteroatom selected from the group consisting of O and N, wherein said C$_{4-6}$cycloalkyl group or 4- to 6-membered non-aromatic heterocyclyl group is optionally substituted by 1 or 2 substituents, each substituent being independently selected from the group consisting of halogen; —C$_{1-6}$alkyl optionally substituted by 1, 2 or 3 substituents, each substituent being independently selected from the group consisting of halogen, —OH, and —OC$_{1-4}$alkyl optionally substituted by 1, 2 or 3 halogen; and —O—C$_{1-6}$alkyl optionally substituted by 1, 2 or 3 substituents, each substituent being independently selected from the group consisting of halogen, —OH, and —O—C$_{1-3}$alkyl optionally substituted by 1, 2 or 3 halogen;

or, when r is 1, 2 or 3 and one R$^{13}$ group is at an adjacent ring position to N—R$^{12}$, said R$^{13}$ and R$^{12}$ are linked such that together with the atoms to which they are attached they form a 5- or 6-membered non-aromatic heterocyclyl group comprising 1 N heteroatom and optionally 1 heteroatom selected from the group consisting of O and N, wherein said 5- or 6-membered non-aromatic heterocyclyl group is optionally substituted by 1 or 2 substituents, each substituent being independently selected from the group consisting of halogen; —C$_{1-6}$alkyl optionally substituted by 1, 2 or 3 substituents, each substituent being independently selected from the group consisting of halogen, —OH, and —OC$_{1-3}$alkyl optionally substituted by 1, 2 or 3 halogen; and —O—C$_{1-6}$alkyl optionally substituted by 1, 2 or 3 substituents, each substituent being independently selected from the group consisting of halogen, —OH, and —O—C$_{1-3}$alkyl optionally substituted by 1, 2 or 3 halogen.

Suitably, when present, each R$^{13}$ is independently selected from the group consisting of halogen; —C$_{1-6}$alkyl optionally substituted by 1, 2 or 3 substituents, each substituent being independently selected from the group consisting of halogen, —OH, and —OC$_{1-4}$alkyl optionally substituted by 1, 2 or 3 halogen; and —O—C$_{1-6}$alkyl optionally substituted by 1, 2 or 3 substituents, each substituent being independently selected from the group consisting of halogen, —OH, and —O—C$_{1-3}$alkyl optionally substituted by 1, 2 or 3 halogen. Suitably, when present each R$^{13}$ is —C$_{1-6}$alkyl optionally substituted by 1, 2 or 3 substituents, each substituent being independently selected from the group consisting of halogen, —OH, and —OC$_{1-3}$alkyl optionally substituted by 1, 2 or 3 halogen; and —O—C$_{1-6}$alkyl optionally substituted by 1, 2 or 3 substituents, each substituent being independently selected from the group consisting of halogen, —OH, and —O—C$_{1-3}$alkyl optionally substituted by 1, 2 or 3 halogen. Even more suitably, each R$^{13}$ is independently methyl.

When present, each $R^{14}$ may be independently selected from the group consisting of halogen; —$C_{1-6}$alkyl optionally substituted by 1, 2 or 3 substituents, each substituent being independently selected from the group consisting of halogen, —OH, and —$OC_{1-3}$alkyl optionally substituted by 1, 2 or 3 halogen; and —O—$C_{1-6}$alkyl optionally substituted by 1, 2 or 3 substituents, each substituent being independently selected from the group consisting of halogen, —OH, and —O—$C_{1-3}$alkyl optionally substituted by 1, 2 or 3 halogen.

In certain suitable embodiments, each $R^{13}$ (and/or each substituent of a $C_{4-6}$cycloalkyl group or a 4- to 6-membered non-aromatic heterocyclyl group formed from two $R^{13}$ groups, or each substituent of a 5- to 6-membered non-aromatic heterocyclyl group formed from a N—$R^{12}$ and $R^{13}$ group; or each $R^{14}$) is independently selected from the group consisting of halogen; —$C_{1-4}$ alkyl optionally substituted by 1, 2 or 3 substituents, each substituent being independently selected from the group consisting of halogen, —OH, and —$OC_{1-4}$alkyl optionally substituted by 1, 2 or 3 halogen; and —O—$C_{1-4}$alkyl optionally substituted by 1, 2 or 3 substituents, each substituent being independently selected from the group consisting of halogen, —OH, and —O—$C_{1-3}$ alkyl optionally substituted by 1, 2 or 3 halogen. More suitably, each $R^{13}$ (and/or each substituent of a $C_{4-6}$cycloalkyl group or a 4- to 6-membered non-aromatic heterocyclyl group formed from two $R^{13}$ groups, or each substituent of a 5- to 6-membered non-aromatic heterocyclyl group formed from a N—$R^{12}$ and $R^{13}$ group; or each $R^{14}$) is independently selected from the group consisting of halogen; —$C_{1-4}$alkyl optionally substituted by 1 substituent selected from the group consisting of halogen and —$OC_{1-3}$alkyl optionally substituted by 1, 2 or 3 halogen; and —O—$C_{1-4}$alkyl optionally substituted by 1 substituent selected from the group consisting of halogen and —O—$C_{1-3}$alkyl optionally substituted by 1, 2 or 3 halogen (for example, each substituent is independently —$C_{1-4}$alkyl optionally substituted by 1 substituent selected from the group consisting of halogen and —$OC_{1-3}$alkyl optionally substituted by 1, 2 or 3 halogen). Even more suitably, each $R^{13}$ (and/or each substituent of a $C_{4-6}$cycloalkyl group or a 4- to 6-membered non-aromatic heterocyclyl group formed from two $R^{13}$ groups, or each substituent of a 5- to 6-membered non-aromatic heterocyclyl group formed from a N—$R^{12}$ and $R^{13}$ group; or each $R^{14}$) is independently selected from the group consisting of halogen; —$C_{1-4}$alkyl optionally substituted by 1 substituent selected from the group consisting of F and —$OC_{1-3}$alkyl optionally substituted by 1, 2 or 3 F atoms; and —O—$C_{1-4}$alkyl optionally substituted by 1 substituent selected from the group consisting of F and —O—$C_{1-3}$alkyl optionally substituted by 1, 2 or 3 F atoms (for example, each substituent is independently —$C_{1-4}$alkyl optionally substituted by 1 substituent selected from the group consisting of F and —$OC_{1-3}$alkyl optionally substituted by 1, 2 or 3 F atoms).

Alternatively, each $R^{13}$ (and/or each substituent of a $C_{4-6}$cycloalkyl group or a 4- to 6-membered non-aromatic heterocyclyl group formed from two $R^{13}$ groups, or each substituent of a 5- to 6-membered non-aromatic heterocyclyl group formed from a N—$R^{12}$ and $R^{13}$ group; or each $R^{14}$) is independently selected from the group consisting of halogen; —$C_{1-4}$alkyl optionally substituted by 1, 2 or 3 substituents, each substituent being independently selected from the group consisting of halogen and —$OC_{1-3}$alkyl optionally substituted by 1, 2 or 3 halogen; and —O—$C_{1-4}$alkyl optionally substituted by 1, 2 or 3 substituents, each substituent being independently selected from the group consisting of halogen and —O—$C_{1-4}$alkyl optionally substituted by 1, 2 or 3 halogen (for example, each substituent is independently —$C_{1-4}$alkyl optionally substituted by 1, 2 or 3 substituents, each substituent being independently selected from the group consisting of halogen and —$OC_{1-3}$alkyl optionally substituted by 1, 2 or 3 halogen). More suitably, each $R^{13}$ (and/or each substituent of a $C_{4-6}$cycloalkyl group or a 4- to 6-membered non-aromatic heterocyclyl group formed from two $R^{13}$ groups, or each substituent of a 5- to 6-membered non-aromatic heterocyclyl group formed from a N—$R^{12}$ and $R^{13}$ group; or each $R^{14}$) is independently selected from the group consisting of halogen; —$C_{1-4}$alkyl optionally substituted by 1, 2 or 3 substituents, each substituent being independently selected from the group consisting of halogen and methoxy optionally substituted by 1, 2 or 3 halogen; and —O—$C_{1-4}$alkyl optionally substituted by 1, 2 or 3 substituents, each substituent being independently selected from the group consisting of halogen and methoxy optionally substituted by 1, 2 or 3 halogen. Even more suitably, each $R^{13}$ (and/or each substituent of a $C_{4-6}$cycloalkyl group or a 4- to 6-membered non-aromatic heterocyclyl group formed from two $R^{13}$ groups, or each substituent of a 5- to 6-membered non-aromatic heterocyclyl group formed from a N—$R^{12}$ and $R^{13}$ group; or each $R^{14}$) is independently selected from the group consisting of halogen; —$C_{1-4}$alkyl optionally substituted by 1, 2 or 3 substituents, each substituent being independently selected from the group consisting of F and methoxy optionally substituted by 1, 2 or 3 F atoms; and —O—$C_{1-4}$alkyl optionally substituted by 1, 2 or 3 substituents, each substituent being independently selected from the group consisting of F and methoxy optionally substituted by 1, 2 or 3 F atoms.

In one suitable embodiment Z is

In such an embodiment, the compound for formula (I) is a compound of formula (Id):

In another suitable embodiment Z is (and more suitably Z is wherein

〜 denotes the point of attachment;

m is 1 or 2; r is 0, 1 or 2; s is 0, 1 or 2;

$R^{12}$ is selected from the group consisting of hydrogen; —$C_{1-6}$alkyl optionally substituted by 1, 2 or 3 substituents, each substituent being independently selected from the group consisting of halogen and —$OC_{1-4}$alkyl optionally substituted by 1, 2 or 3 halogen (suitably, $R^{12}$ is selected from the group consisting of hydrogen and —$C_{1-4}$alkyl optionally substituted by 1, 2 or 3 substituents, each substituent being independently selected from the group consisting of halogen and —$OC_{1-4}$alkyl optionally substituted by 1, 2 or 3 halogen; more suitably, $R^{12}$ is selected from the group consisting of hydrogen and —$C_{1-4}$alkyl optionally substituted by 1, 2 or 3 substituents, each substituent being independently selected from the group consisting of halogen and methoxy optionally substituted by 1, 2 or 3 halogen; more suitably, $R^{12}$ is selected from the group consisting of hydrogen and —$C_{1-4}$alkyl optionally substituted by 1 substituent selected from the group consisting of halogen and methoxy optionally substituted by 1, 2 or 3 halogen (e.g. 1, 2, or 3 F atoms)); and when present, each $R^{13}$ is selected from the group consisting of independently selected from the group consisting of hydrogen; halogen; —$C_{1-6}$alkyl optionally substituted by 1, 2 or 3 substituents, each substituent being independently selected from the group consisting of halogen, —OH, and —$OC_{1-3}$alkyl optionally substituted by 1, 2 or 3 halogen; and —O—$C_{1-6}$alkyl optionally substituted by 1, 2 or 3 substituents, each substituent being independently selected from the group consisting of halogen, —OH, and —O—$C_{1-3}$alkyl optionally substituted by 1, 2 or 3 halogen; and when present, each $R^{14}$ is selected from the group consisting of independently selected from the group consisting of hydrogen; halogen; —$C_{1-6}$alkyl optionally substituted by 1, 2 or 3 substituents, each substituent being independently selected from the group consisting of halogen, —OH, and —$OC_{1-3}$alkyl optionally substituted by 1, 2 or 3 halogen; and —O—$C_{1-6}$alkyl optionally substituted by 1, 2 or 3 substituents, each substituent being independently selected from the group consisting of halogen, —OH, and —O—$C_{1-3}$alkyl optionally substituted by 1, 2 or 3 halogen.

In one suitable embodiment, Z is wherein 〜 denotes point of attachment, m is 1 or 2; r is 0, 1 or 2, when present, each $R^{13}$ is independently selected from the group consisting of halogen; —$C_{1-3}$alkyl optionally substituted by 1, 2 or 3 substituents, each substituent being independently selected from the group consisting of halogen, —OH, and —$OC_{1-4}$alkyl optionally substituted by 1, 2 or 3 halogen; —O—$C_{1-6}$alkyl optionally substituted by 1, 2 or 3 substituents, each substituent being independently selected from the group consisting of halogen, —OH, and —O—$C_{1-3}$alkyl optionally substituted by 1, 2 or 3 halogen; $NR^cR^d$ and $C_{3-6}$cycloalkyl (i.e. cyclopropyl, cyclobutyl, cyclopentyl or cyclohexyl) optionally substituted by 1, 2 or 3 substituents, each substituent being independently selected from the group consisting of halogen, —OH, and —$OC_{1-3}$alkyl optionally substituted by 1, 2 or 3 halogen.

In embodiments wherein Z may be —$NR^{10}R^{11}$, $R^{10}$ may be selected from the group consisting of hydrogen and —$C_{1-4}$alkyl. Suitably $R^{10}$ is hydrogen or methyl.

In embodiments wherein Z may be —$NR^{10}R^{11}$, $R^{11}$ may be a 5- to 10-membered non-aromatic heterocyclyl group (i.e. a 5-, 6-, 7-, 8-, 9- or 10-membered non-aromatic heterocyclyl group) comprising 1, 2 or 3 heteroatoms selected from N, O and S, wherein at least one of the heteroatoms is N, and wherein said 5- to 10-membered non-aromatic heterocyclyl group is optionally substituted with 1, 2, 3 or 4 substituents (for example 1, 2 or 3 substituents; or 1 or 2 substituents; or 1 substituent). Suitably, $R^{11}$ is a 5- or 6-membered non-aromatic heterocyclyl group comprising 1, 2 or 3 heteroatoms selected from N, O and S, wherein at least one of the heteroatoms is N, and wherein said 5- or 6-membered non-aromatic heterocyclyl group is optionally substituted with 1, 2, or 3 substituents. More suitably, $R^{11}$ is a 5- or 6-membered non-aromatic heterocyclyl group comprising 1, 2 or 3 heteroatoms selected from N and O, and wherein said 5- or 6-membered non-aromatic heterocyclyl group is optionally substituted with 1, 2, or 3 substituents.

Alternatively, $R^{11}$ is a 5- or 6-membered non-aromatic heterocyclyl group comprising 1 or 2 heteroatoms (for example, 1 heteroatom) selected from N, O and S, wherein at least one of the heteroatoms is N, and wherein said 5- or 6-membered non-aromatic heterocyclyl group is optionally substituted with 1, 2, or 3 substituents. Suitably $R^{11}$ is a 5- or 6-membered non-aromatic heterocyclyl group comprising 1 or 2 heteroatoms (for example, 1 heteroatom) selected from N and O, wherein at least one of the heteroatoms is N, and wherein said 5- or 6-membered non-aromatic heterocyclyl group is optionally substituted with 1, 2, or 3 substituents.

In one suitable embodiment, $R^{11}$ is a 5-membered non-aromatic heterocyclyl group comprising 1 or 2 N heteroatoms, wherein said 5- or 6-membered non-aromatic heterocyclyl group is optionally substituted with 1, 2, or 3 substituents.

In one suitable embodiment, $R^{11}$ is a 6-membered non-aromatic heterocyclyl group comprising 1 or 2 heteroatoms selected from N and O, wherein at least one of the heteroatoms is N, and wherein said 5- or 6-membered non-aromatic heterocyclyl group is optionally substituted with 1, 2, or 3 substituents.

In certain suitable embodiments, $R^{11}$ is a 5- or 6-membered non-aromatic heterocyclyl group comprising 1, 2 or 3 heteroatoms selected from N, O and S, wherein at least one of the heteroatoms is N, and wherein said 5- or 6-membered non-aromatic heterocyclyl group is optionally substituted with 1 or 2 (for example 1) substituents. More suitably, $R^{11}$ is a 5- or 6-membered non-aromatic heterocyclyl group comprising 1, 2 or 3 heteroatoms selected from N and O, and wherein said 5- or 6-membered non-aromatic heterocyclyl group is optionally substituted with 1 or 2 (for example 1) substituents. Alternatively, $R^{11}$ is a 5- or 6-membered non-aromatic heterocyclyl group comprising 1 or 2 heteroatoms selected from N, O and S, wherein at least one of the heteroatoms is N, and wherein said 5- or 6-membered non-aromatic heterocyclyl group is optionally substituted with 1 or 2 (for example 1) substituents. Even more $R^{11}$ is a 5- or 6-membered non-aromatic heterocyclyl group comprising 1 or 2 heteroatoms selected from N and O, wherein at least one of the heteroatoms is N, and wherein said 5- or 6-membered non-aromatic heterocyclyl group is optionally substituted with 1 or 2 (for example 1) substituents.

In one suitable embodiment, $R^{11}$ is a 5-membered non-aromatic heterocyclyl group comprising 1 or 2 N heteroatoms, wherein said 5- or 6-membered non-aromatic heterocyclyl group is optionally substituted with 1 or 2 (for example 1) substituents.

In one suitable embodiment, $R^{11}$ is a 6-membered non-aromatic heterocyclyl group comprising 1 or 2 heteroatoms selected from N and O, wherein at least one of the heteroatoms is N, and wherein said 5- or 6-membered non-aromatic heterocyclyl group is optionally substituted with 1 or 2 (for example 1) substituents.

In embodiments wherein $R^{11}$ is optionally substituted (for example, optionally substituted with 1, 2, 3, or 4 substituents; or optionally substituted with 1, 2, or 3 substituents; or optionally substituted with 1 or 2 substituents; or optionally substituted with 1 substituent), each substituent may be independently selected from the group consisting of halogen; —OH; —$C_{1-6}$alkyl optionally substituted by 1, 2 or 3 substituents, each substituent being independently selected from the group consisting of halogen, —OH, and —$OC_{1-3}$alkyl optionally substituted by 1, 2 or 3 halogen; and —O—$C_{1-6}$alkyl optionally substituted by 1, 2 or 3 substituents, each substituent being independently selected from the group consisting of halogen, —OH, and —O—$C_{1-3}$alkyl optionally substituted by 1, 2 or 3 halogen. Suitably, each substituent is independently selected from the group consisting of halogen; —OH; —$C_{1-4}$alkyl optionally substituted by 1, 2 or 3 substituents, each substituent being independently selected from the group consisting of halogen, —OH, and —$OC_{1-3}$alkyl optionally substituted by 1, 2 or 3 halogen; and —O—$C_{1-4}$alkyl optionally substituted by 1, 2 or 3 substituents, each substituent being independently selected from the group consisting of halogen, —OH, and —O—$C_{1-3}$alkyl optionally substituted by 1, 2 or 3 halogen. More suitably, each substituent is independently selected from the group consisting of halogen; —OH; —$C_{1-4}$alkyl optionally substituted by 1 substituent selected from the group consisting of halogen, —OH, and —$OC_{1-3}$alkyl optionally substituted by 1, 2 or 3 halogen; and —O—$C_{1-4}$alkyl optionally substituted by 1 substituent selected from the group consisting of halogen, —OH, and —O—$C_{1-3}$alkyl optionally substituted by 1, 2 or 3 halogen. More suitably, each substituent is independently selected from the group consisting of halogen; —$C_{1-4}$alkyl optionally substituted by 1 substituent selected from the group consisting of halogen, and —$OC_{1-3}$alkyl optionally substituted by 1, 2 or 3 halogen; and —O—$C_{1-4}$alkyl optionally substituted by 1 substituent selected from the group consisting of halogen, and —O—$C_{1-3}$alkyl optionally substituted by 1, 2 or 3 halogen (for example, each substituent is independently —$C_{1-4}$alkyl optionally substituted by 1 substituent selected from the group consisting of halogen, and —$OC_{1-3}$alkyl optionally substituted by 1, 2 or 3 halogen).

In one suitable embodiment, each substituent is independently selected from the group consisting of halogen; —$C_{1-4}$alkyl optionally substituted by 1 substituent selected from the group consisting of F and —$OC_{1-3}$alkyl optionally substituted by 1, 2 or 3 F atoms; and —O—$C_{1-4}$alkyl optionally substituted by 1 substituent selected from the group consisting of F and —O—$C_{1-3}$alkyl optionally substituted by 1, 2 or 3 F atoms (for example, each substituent is independently —$C_{1-4}$ alkyl optionally substituted by 1 substituent selected from the group consisting of F and —$OC_{1-3}$ alkyl optionally substituted by 1, 2 or 3 F atoms).

Alternatively, each substituent is independently selected from the group consisting of halogen; —$C_{1-4}$alkyl optionally substituted by 1, 2 or 3 substituents, each substituent being independently selected from the group consisting of halogen and —$OC_{1-3}$alkyl optionally substituted by 1, 2 or 3 halogen; and —O—$C_{1-4}$alkyl optionally substituted by 1, 2 or 3 substituents, each substituent being independently selected from the group consisting of halogen and —O—$C_{1-4}$alkyl optionally substituted by 1, 2 or 3 halogen (for example, each substituent is independently —$C_{1-4}$alkyl optionally substituted by 1, 2 or 3 substituents, each substituent being independently selected from the group consisting of halogen and —$OC_{1-3}$alkyl optionally substituted by 1, 2 or 3 halogen). More suitably, each substituent is independently selected from the group consisting of halogen; —$C_{1-4}$alkyl optionally substituted by 1, 2 or 3 substituents, each substituent being independently selected from the group consisting of halogen and methoxy optionally substituted by 1, 2 or 3 halogen; and —O—$C_{1-4}$alkyl optionally substituted by 1, 2 or 3 substituents, each substituent being independently selected from the group consisting of halogen and methoxy optionally substituted by 1, 2 or 3 halogen. Even more suitably, each substituent is independently selected from the group consisting of halogen; —$C_{1-4}$alkyl optionally substituted by 1, 2 or 3 substituents, each substituent being independently selected from the group consisting of F and methoxy optionally substituted by 1, 2 or 3 F atoms; and —O—$C_{1-4}$alkyl optionally substituted by 1, 2 or 3 substituents, each substituent being independently selected from the group consisting of F and methoxy optionally substituted by 1, 2 or 3 F atoms.

In one embodiment, Z is selected from the group consisting of:

50

-continued wherein ∿∿∿ denotes the point of attachment.

For example, Z is selected from the group consisting of:

52 wherein 〰〰 denotes the point of attachment.

Alternatively, Z may selected from the group consisting of:

53

-continued

54

For example, Z is selected from the group consisting of:

wherein ∿∿∿ denotes the point of attachment.

55

-continued wherein ⌇⌇⌇ denotes the point of attachment.

In one suitable embodiment, Z is selected from the group consisting of:

56

-continued

65 wherein ⌇⌇⌇ denotes the point of attachment.

For example, Z is selected from the group consisting of:

wherein ∿∿∿ denotes the point of attachment.

In one suitable embodiment, Z is selected from the group consisting of:

-continued wherein 〜〜〜 denotes the point of attachment.

In one especially suitable embodiment, Z is selected from the group consisting of:

wherein 〜〜〜 denotes the point of attachment.

In one especially suitable embodiment, Z is:

wherein 〜〜〜 denotes the point of attachment.

In one especially suitable embodiment, Z is:

wherein 〜〜〜 denotes the point of attachment.

In one especially suitable embodiment, the compound of formula (I) is a compound for formula (Ie), wherein each group may be as defined above:

(Ie)

In another especially suitable embodiment, the compound of formula (I) is a compound for formula (If), wherein each group may be as defined above:

(If)

In another especially suitable embodiment, the compound of formula (I) is a compound for formula (Ig), wherein each group may be as defined above:

(Ig)

In another especially suitable embodiment, the compound of formula (I) is a compound for formula (Ih), wherein each group may be as defined above:

(Ih)

In another especially suitable embodiment, the compound of formula (I) is a compound for formula (Ij), wherein each group may be as defined above:

(Ij)

In another especially suitable embodiment, the compound of formula (I) is a compound for formula (Ik), wherein each group may be as defined above:

(Ik)

In one especially suitable embodiment, the compound of formula (I) is a compound for formula (Im), wherein each group may be as defined above:

(Im)

In one especially suitable embodiment, the compound of formula (I) is a compound for formula (In), wherein each group may be as defined above:

(Io)

In one especially suitable embodiment, the compound of formula (I) is a compound for formula (Ip), wherein each group may be as defined above:

(In)

(Ip)

In another especially suitable embodiment, the compound of formula (I) is a compound for formula (Io), wherein each group may be as defined above:

In one especially suitable embodiment, the compound of formula (I) is a compound of formula (Iq):

(Iq)

wherein:

$R^{3a}$ is H or $C_{1-4}$alkyl optionally substituted by 1, 2 or 3 substituents, each substituent being independently selected from the group consisting of halogen, —OCH$_3$, and —OCF$_3$;

$R^{8a}$ is halogen or $C_{1-4}$alkyl optionally substituted by 1, 2 or 3 substituents, each substituent being independently selected from the group consisting of halogen, —OCH$_3$, and —OCF$_3$;

ra is 0, 1 or 2;

$m^a$ is 1 or 2;

$R^{12a}$ is H or $C_{1-4}$alkyl optionally substituted by 1, 2 or 3 substituents, each substituent being independently selected from the group consisting of halogen, —OCH$_3$, and —OCF$_3$; and when present each $R^1$ is independently selected from the group consisting of $C_{1-4}$alkyl optionally substituted by 1, 2 or 3 substituents, each substituent being independently selected from the group consisting of halogen, —OCH$_3$, and —OCF$_3$; and $C_{3-6}$cycloalkyl optionally substituted by 1, 2 or 3 substituents, each substituent being independently selected from the group consisting of halogen, —CH$_3$, —OCH$_3$, and —OCF$_3$; or when ra is 2 and two $R^{13a}$ groups are on adjacent ring positions, said two $R^{13a}$ are linked such that together with the atoms to which they are attached they form a $C_{3-6}$cycloalkyl group optionally substituted by 1 or 2 substituents, each substituent being independently selected from the group consisting of halogen; —$C_{1-6}$alkyl optionally substituted by 1, 2 or 3 substituents, each substituent being independently selected from the group consisting of halogen, —OH, and —OC$_{1-3}$alkyl optionally substituted by 1, 2 or 3 halogen.

In one embodiment, $R^{3a}$ is H. In a second embodiment, $R^{3a}$ is $C_{1-4}$alkyl such as methyl, ethyl or propyl which are suitably unsubstituted, such as methyl which is suitably unsubstituted.

In one embodiment $R^{8a}$ is halogen, such as Cl, Br or F, especially Cl. In a second embodiment, $R^{8a}$ is $C_{1-4}$alkyl optionally substituted by 1, 2 or 3 substituents, each substituent being independently selected from the group consisting of —OCH$_3$, and —OCF$_3$; especially $R^{8a}$ is CF$_3$.

In one embodiment, ra is 0. In a second embodiment, ra is 1. In a third embodiment, ra is 2.

In one embodiment, $m^a$ is 1. In a second embodiment, $m^a$ is 2.

In one embodiment, $R^{12a}$ is H. In a second embodiment, $R^{12a}$ is $C_{1-4}$alkyl, such as methyl, ethyl or propyl which are suitably unsubstituted, in particular methyl or ethyl which are suitably unsubstituted, especially methyl which is suitably unsubstituted.

In one embodiment each $R^{13a}$ is independently $C_{1-4}$alkyl, such as such as methyl, ethyl or propyl which are suitably unsubstituted, in particular methyl or ethyl which are suitably unsubstituted, especially methyl which is suitably unsubstituted. In a second embodiment each $R^{13a}$ is independently $C_{3-6}$cycloalklyl, such as cyclopropyl, cyclobutyl or cyclopentyl which are suitably unsubstituted, especially cyclopropyl which is suitably unsubstituted.

In one embodiment, ra is 2 and two $R^{13a}$ groups are on adjacent ring positions, said two $R^{13a}$ are linked such that together with the atoms to which they are attached they form a $C_{3-6}$cycloalkyl group, such as cyclopropyl, cyclobutyl or cyclopentyl which is suitably unsubstituted, especially cyclopropyl which is suitably unsubstituted.

In certain suitable embodiments, the compound is selected from the group consisting of Example Compounds 1 to 112.

In one especially suitable embodiment, the compound of formula (I) is selected from the group consisting of:

1-{5-chloro-2-[(3R)-3-methylpiperazin-1-yl]pyrimidin-4-yl}-N-(2-{imidazo[1,2-a]pyridin-3-yl}propan-2-yl)azetidine-3-carboxamide;

1-{5-chloro-2-[(2S)-2,4-dimethylpiperazin-1-yl]pyrimidin-4-yl}-N-(2-{imidazo[1,2-a]pyridin-3-yl}propan-2-yl)azetidine-3-carboxamide;

1-{5-chloro-2-[(3R)-3,4-dimethylpiperazin-1-yl]pyrimidin-4-yl}-N-(2-{imidazo[1,2-a]pyridin-3-yl}propan-2-yl)azetidine-3-carboxamide;

1-[5-fluoro-2-(4-methylpiperazin-1-yl)pyridin-4-yl]-N-(2-{imidazo[1,2-a]pyridin-3-yl}propan-2-yl)azetidine-3-carboxamide;

1-[5-chloro-2-(1,4-diazepan-1-yl)pyrimidin-4-yl]-N-{imidazo[1,2-a]pyridin-3-ylmethyl}azetidine-3-carboxamide;

1-[2-(1,4-diazepan-1-yl)-5-fluoropyrimidin-4-yl]-N-{imidazo[1,2-a]pyridin-3-ylmethyl}azetidine-3-carboxamide;

1-(5-chloro-2-{3,6-diazabicyclo[3.2.0]heptan-3-yl}pyrimidin-4-yl)-N-{imidazo[1,2-a]pyridin-3-ylmethyl}azetidine-3-carboxamide;

1-(2-{3,6-diazabicyclo[3.2.0]heptan-3-yl}-5-fluoropyrimidin-4-yl)-N-{imidazo[1,2-a]pyridin-3-ylmethyl}azetidine-3-carboxamide;

1-[2-(1,4-diazepan-1-yl)-5-fluoropyrimidin-4-yl]-N-(1-{imidazo[1,2-a]pyridin-3-yl}ethyl)azetidine-3-carboxamide;

1-[5-chloro-2-(1,4-diazepan-1-yl)pyrimidin-4-yl]-N-(1-{imidazo[1,2-a]pyridin-3-yl}ethyl)azetidine-3-carboxamide;

1-[2-(1,4-diazepan-1-yl)-5-fluoropyrimidin-4-yl]-N-(2-{imidazo[1,2-a]pyridin-3-yl}propan-2-yl)azetidine-3-carboxamide;

1-[2-(1,4-diazepan-1-yl)-5-fluoropyrimidin-4-yl]-N-({2-methylimidazo[1,2-a]pyridin-3-yl}methyl)azetidine-3-carboxamide;

1-(2-{3,6-diazabicyclo[3.2.0]heptan-3-yl}-5-fluoropyrimidin-4-yl)-N-({2-methylimidazo[1,2-a]pyridin-3-yl}methyl)azetidine-3-carboxamide;

1-{5-fluoro-2-[methyl(pyrrolidin-3-yl)amino]pyrimidin-4-yl}-N{imidazo[1,2-a]pyridin-3-ylmethyl}azetidine-3-carboxamide;

1-[5-fluoro-2-(pyrrolidin-3-ylamino)pyrimidin-4-yl]-N{imidazo[1,2-a]pyridin-3-ylmethyl}azetidine-3-carboxamide;

1-[5-fluoro-2-(piperazin-1-yl)pyrimidin-4-yl]-N-{imidazo[1,2-a]pyridin-3-ylmethyl}azetidine-3-carboxamide;

1-[5-chloro-2-(1,4-diazepan-1-yl)pyrimidin-4-yl]-N-{imidazo[1,2-a]pyridin-3-ylmethyl}-N-methylazetidine-3-carboxamide;

1-[5-chloro-2-(1,4-diazepan-1-yl)pyrimidin-4-yl]-N-({2-methylimidazo[1,2-a]pyridin-3-yl}methyl)azetidine-3-carboxamide;

1-[2-(1,4-diazepan-1-yl)-5-methoxypyrimidin-4-yl]-N-{imidazo[1,2-a]pyridin-3-ylmethyl}azetidine-3-carboxamide;

1-[2-(1,4-diazepan-1-yl)-5-methoxypyrimidin-4-yl]-N-(2{imidazo[1,2-a]pyridin-3-yl}propan-2-yl)azetidine-3-carboxamide;

1-[5-chloro-2-(1,4-diazepan-1-yl)pyrimidin-4-yl]-N-({6-fluoroimidazo[1,2-a]pyridin-3-yl}methyl)azetidine-3-carboxamide;

1-[5-chloro-2-(1,4-diazepan-1-yl)pyrimidin-4-yl]-N-({6-chloroimidazo[1,2-a]pyridin-3-yl}methyl)azetidine-3-carboxamide;

1-[2-(1,4-diazepan-1-yl)-5-methoxypyrimidin-4-yl]-N-(1-{2-methylimidazo[1,2-a]pyridin-3-yl}ethyl)azetidine-3-carboxamide;

1-[5-chloro-2-(1,4-diazepan-1-yl)pyrimidin-4-yl]-N-(1-{2-methylimidazo[1,2-a]pyridin-3-yl}ethyl)azetidine-3-carboxamide;

1-[5-chloro-2-(piperazin-1-yl)pyrimidin-4-yl]-N-{imidazo[1,2-a]pyridin-3-ylmethyl}azetidine-3-carboxamide;

1-{5-fluoro-2-[(3S)-3-methylpiperazin-1-yl]pyrimidin-4-yl}-N{imidazo[1,2-a]pyridin-3-ylmethyl}azetidine-3-carboxamide;

1-{5-chloro-2-[(3S)-3-methylpiperazin-1-yl]pyrimidin-4-yl}-N-{imidazo[1,2-a]pyridin-3-ylmethyl}azetidine-3-carboxamide;

1-{5-fluoro-2-[(3R)-3-methylpiperazin-1-yl]pyrimidin-4-yl}-N-{imidazo[1,2-a]pyridin-3-ylmethyl}azetidine-3-carboxamide;

1-{5-chloro-2-[(3R)-3-methylpiperazin-1-yl]pyrimidin-4-yl}-N-{imidazo[1,2-a]pyridin-3-ylmethyl}azetidine-3-carboxamide;

1-[5-chloro-2-(piperazin-1-yl)pyrimidin-4-yl]-N-(1-{imidazo[1,2-a]pyridin-3-yl}ethyl)azetidine-3-carboxamide;

1-[5-fluoro-2-(piperazin-1-yl)pyrimidin-4-yl]-N-(1-{imidazo[1,2-a]pyridin-3-yl}ethyl)azetidine-3-carboxamide;

1-[5-fluoro-2-(piperazin-1-yl)pyrimidin-4-yl]-N-(2-{imidazo[1,2-a]pyridin-3-yl}propan-2-yl)azetidine-3-carboxamide;

1-[5-chloro-2-(piperazin-1-yl)pyrimidin-4-yl]-N-(2-{imidazo[1,2-a]pyridin-3-yl}propan-2-yl)azetidine-3-carboxamide;

N-(2-{imidazo[1,2-a]pyridin-3-yl}propan-2-yl)-1-[5-methoxy-2-(piperazin-1-yl)pyrimidin-4-yl]azetidine-3-carboxamide;

1-{5-fluoro-2-[(3R)-3-methylpiperazin-1-yl]pyrimidin-4-yl}-N-(2-{imidazo[1,2-a]pyridin-3-yl}propan-2-yl)azetidine-3-carboxamide;

N-(2-{imidazo[1,2-a]pyridin-3-yl}propan-2-yl)-1-{5-methoxy-2-[(3R)-3-methylpiperazin-1-yl]pyrimidin-4-yl}azetidine-3-carboxamide;

1-{5-chloro-2-[(3S)-3-methylpiperazin-1-yl]pyrimidin-4-yl}-N-(2-{imidazo[1,2-a]pyridin-3-yl}propan-2-yl)azetidine-3-carboxamide;

1-{5-fluoro-2-[(3S)-3-methylpiperazin-1-yl]pyrimidin-4-yl}-N-(2-{imidazo[1,2-a]pyridin-3-yl}propan-2-yl)azetidine-3-carboxamide;

N-(2-{imidazo[1,2-a]pyridin-3-yl}propan-2-yl)-1-{5-methoxy-2-[(3S)-3-methylpiperazin-1-yl]pyrimidin-4-yl}azetidine-3-carboxamide;

1-{5-fluoro-2-[methyl(pyrrolidin-3-yl)amino]pyrimidin-4-yl}-N-(2{imidazo[1,2-a]pyridin-3-yl}propan-2-yl)azetidine-3-carboxamide;

1-{5-chloro-2-[methyl(pyrrolidin-3-yl)amino]pyrimidin-4-yl}-N-(2-{imidazo[1,2-a]pyridin-3-yl}propan-2-yl)azetidine-3-carboxamide;

1-{2-[(3R,5S)-3,5-dimethylpiperazin-1-yl]-5-methoxypyrimidin-4-yl}-N-(2-{imidazo[1,2-a]pyridin-3-yl}propan-2-yl)azetidine-3-carboxamide;

1-{2-[(3R,5S)-3,5-dimethylpiperazin-1-yl]-5-chloropyrimidin-4-yl}-N-(2-{imidazo[1,2-a]pyridin-3-yl}propan-2-yl)azetidine-3-carboxamide;

1-{2-[(3R,5S)-3,5-dimethylpiperazin-1-yl]-5-fluoropyrimidin-4-yl}-N-(2-{imidazo[1,2-a]pyridin-3-yl}propan-2-yl)azetidine-3-carboxamide 1-{2-[(3S,5S)-3,5-dimethylpiperazin-1-yl]-5-methoxypyrimidin-4-yl}-N-(2-{imidazo[1,2-a]pyridin-3-yl}propan-2-yl)azetidine-3-carboxamide;

1-{5-chloro-2-[(3R,5R)-3,5-dimethylpiperazin-1-yl]pyrimidin-4-yl}-N-(2-{imidazo[1,2-a]pyridin-3-yl}propan-2-yl)azetidine-3-carboxamide;

1-{2-[(3R,5R)-3,5-dimethylpiperazin-1-yl]-5-fluoropyrimidin-4-yl}-N-(2-{imidazo[1,2-a]pyridin-3-yl}propan-2-yl)azetidine-3-carboxamide;

1-{5-chloro-2-[(3S,5S)-3,5-dimethylpiperazin-1-yl]pyrimidin-4-yl}-N-(2-{imidazo[1,2-a]pyridin-3-yl}propan-2-yl)azetidine-3-carboxamide;

1-{5-fluoro-2-[(3S,5S)-3,4,5-trimethylpiperazin-1-yl]pyrimidin-4-yl}-N-(2-{imidazo[1,2-a]pyridin-3-yl}propan-2-yl)azetidine-3-carboxamide;

1-{5-chloro-2-[(2S)-2-methylpiperazin-1-yl]pyrimidin-4-yl}-N-(2-{imidazo[1,2-a]pyridin-3-yl}propan-2-yl)-N-methylazetidine-3-carboxamide;

1-[5-chloro-2-(1,4-diazepan-1-yl)pyrimidin-4-yl]-N-(2-{imidazo[1,2-a]pyridin-3-yl}propan-2-yl)azetidine-3-carboxamide 1-[5-fluoro-2-(4-methyl-1,4-diazepan-1-yl)pyrimidin-4-yl]-N-{imidazo[1,2-a]pyridin-3-ylmethyl}azetidine-3-carboxamide;

1-[5-chloro-2-(4-methyl-1,4-diazepan-1-yl)pyrimidin-4-yl]-N-(1-{imidazo[1,2-a]pyridin-3-yl}ethyl)azetidine-3-carboxamide;

1-[5-fluoro-2-(4-methylpiperazin-1-yl)pyrimidin-4-yl]-N-(2-{imidazo[1,2-a]pyridin-3-yl}propan-2-yl)azetidine-3-carboxamide;

1-[5-chloro-2-(4-methylpiperazin-1-yl)pyrimidin-4-yl]-N-(2-{imidazo[1,2-a]pyridin-3-yl}propan-2-yl)azetidine-3-carboxamide;

1-[5-fluoro-2-(4-methyl-1,4-diazepan-1-yl)pyrimidin-4-yl]-N-(2-{imidazo[1,2-a]pyridin-3-yl}propan-2-yl)azetidine-3-carboxamide;

1-[5-chloro-2-(4-methyl-1,4-diazepan-1-yl)pyrimidin-4-yl]-N-(2-{imidazo[1,2-a]pyridin-3-yl}propan-2-yl)azetidine-3-carboxamide;

1-{5-fluoro-2-[methyl(1-methylpyrrolidin-3-yl)amino]pyrimidin-4-yl}-N-(2-{imidazo[1,2-a]pyridin-3-yl}propan-2-yl)azetidine-3-carboxamide;

1-{5-chloro-2-[methyl(1-methylpyrrolidin-3-yl)amino]pyrimidin-4-yl}-N-(2-{imidazo[1,2-a]pyridin-3-yl}propan-2-yl)azetidine-3-carboxamide;

1-[5-fluoro-2-(4-methylpiperazin-1-yl)pyrimidin-4-yl]-N-(2-{6-methylimidazo[1,2-a]pyridin-3-yl}propan-2-yl)azetidine-3-carboxamide;

1-[5-fluoro-2-(4-methylpiperazin-1-yl)pyrimidin-4-yl]-N-(2-{8-fluoroimidazo[1,2-a]pyridin-3-yl}propan-2-yl)azetidine-3-carboxamide;

N-(2-{imidazo[1,2-a]pyridin-3-yl}propan-2-yl)-1-[5-methoxy-2-(4-methyl-1,4-diazepan-1-yl)pyrimidin-4-yl]azetidine-3-carboxamide;

N-(2-{imidazo[1,2-a]pyridin-3-yl}propan-2-yl)-1-[5-methoxy-2-(4-methylpiperazin-1-yl)pyrimidin-4-yl]azetidine-3-carboxamide;

1-[5-fluoro-2-(4-methylpiperazin-1-yl)pyrimidin-4-yl]-N-(2-{imidazo[1,2-a]pyridin-3-yl}propan-2-yl)pyrrolidine-3-carboxamide;

1-[5-fluoro-2-(4-methylpiperazin-1-yl)pyrimidin-4-yl]-N-(2-{imidazo[1,2-a]pyridin-3-yl}propan-2-yl)-3-methyl-azetidine-3-carboxamide;

N-(2-{imidazo[1,2-a]pyridin-3-yl}propan-2-yl)-1-[5-methyl-2-(4-methylpiperazin-1-yl)pyrimidin-4-yl]azetidine-3-carboxamide;

1-[5-chloro-2-(4-methylpiperazin-1-yl)pyrimidin-4-yl]-N-(2-{6-methylimidazo[1,2-a]pyridin-3-yl}propan-2-yl)azetidine-3-carboxamide;

1-{5-chloro-2-[(2R)-2,4-dimethylpiperazin-1-yl]pyrimidin-4-yl}-N-(2-{imidazo[1,2-a]pyridin-3-yl}propan-2-yl)azetidine-3-carboxamide;

1-{5-chloro-2-[3-(fluoromethyl)-4-methylpiperazin-1-yl]pyrimidin-4-yl}-N-(2-{imidazo[1,2-a]pyridin-3-yl}propan-2-yl)azetidine-3-carboxamide;

1-[5-chloro-2-(4-ethylpiperazin-1-yl)pyrimidin-4-yl]-N-(2-{imidazo[1,2-a]pyridin-3-yl}propan-2-yl)azetidine-3-carboxamide;

1-{5-chloro-2-[4-(propan-2-yl)piperazin-1-yl]pyrimidin-4-yl}-N-(2-{imidazo[1,2-a]pyridin-3-yl}propan-2-yl)azetidine-3-carboxamide;

1-{5-chloro-2-[4-(2-methoxyethyl)piperazin-1-yl]pyrimidin-4-yl}-N-(2-{imidazo[1,2-a]pyridin-3-yl}propan-2-yl)azetidine-3-carboxamide;

1-[5-chloro-2-(4-methylpiperazin-1-yl)pyrimidin-4-yl]-N-(2-{imidazo[1,2-a]pyridin-3-yl}propan-2-yl)-N-methyl-azetidine-3-carboxamide;

1-{5-chloro-2-[(3R)-3,4-dimethylpiperazin-1-yl]pyrimidin-4-yl}-N-(2-{imidazo[1,2-a]pyridin-3-yl}propan-2-yl)-N-methylazetidine-3-carboxamide;

(3R)-1-[5-chloro-2-(4-methylpiperazin-1-yl)pyrimidin-4-yl]-N-(2-{imidazo[1,2-a]pyridin-3-yl}propan-2-yl)pyrrolidine-3-carboxamide;

(3S)-1-[5-chloro-2-(4-methylpiperazin-1-yl)pyrimidin-4-yl]-N-(2-{imidazo[1,2-a]pyridin-3-yl}propan-2-yl)pyrrolidine-3-carboxamide;

1-[5-chloro-2-(4-methylpiperazin-1-yl)pyrimidin-4-yl]-N-(2-{imidazo[1,2-a]pyridin-3-yl}propan-2-yl)piperidine-4-carboxamide;

1-[5-fluoro-2-(4-methylpiperazin-1-yl)pyrimidin-4-yl]-N-(2-{imidazo[1,2-a]pyridin-3-yl}propan-2-yl)-N-methyl-azetidine-3-carboxamide;

1-{5-chloro-2-[(2S,3R)-2,3-dimethylpiperazin-1-yl]pyrimidin-4-yl}-N-(2-{imidazo[1,2-a]pyridin-3-yl}propan-2-yl)azetidine-3-carboxamide;

1-{5-chloro-2-[3-(methoxymethyl)-4-methylpiperazin-1-yl]pyrimidin-4-yl}-N-(2-{imidazo[1,2-a]pyridin-3-yl}propan-2-yl)azetidine-3-carboxamide;

1-(5-fluoro-2-{6-methyl-3,6-diazabicyclo[3.2.0]heptan-3-yl}pyrimidin-4-yl)-N-{imidazo[1,2-a]pyridin-3-ylmethyl}azetidine-3-carboxamide;

1-{2-[(3S)-3,4-dimethylpiperazin-1-yl]-5-fluoropyrimidin-4-yl}-N-(2-{imidazo[1,2-a]pyridin-3-yl}propan-2-yl)azetidine-3-carboxamide;

1-{5-chloro-2-[(3S)-3,4-dimethylpiperazin-1-yl]pyrimidin-4-yl}-N-(2-{imidazo[1,2-a]pyridin-3-yl}propan-2-yl)azetidine-3-carboxamide;

1-{2-[(3R)-3,4-dimethylpiperazin-1-yl]-5-fluoropyrimidin-4-yl}-N-(2-{imidazo[1,2-a]pyridin-3-yl}propan-2-yl)azetidine-3-carboxamide;

1-{2-[(3R)-3,4-dimethylpiperazin-1-yl]-5-methoxypyrimidin-4-yl}-N-(2-{imidazo[1,2-a]pyridin-3-yl}propan-2-yl)azetidine-3-carboxamide;

1-{2-[(3R)-3,4-dimethylpiperazin-1-yl]-5-fluoropyrimidin-4-yl}-N-(2-{imidazo[1,2-a]pyridin-3-yl}propan-2-yl)pyrrolidine-3-carboxamide;

1-{2-[(3R)-3,4-dimethylpiperazin-1-yl]-5-fluoropyrimidin-4-yl}-N-(2-{imidazo[1,2-a]pyridin-3-yl}propan-2-yl)-3-methylazetidine-3-carboxamide;

N-(2-{imidazo[1,2-a]pyridin-3-yl}propan-2-yl)-1-{5-methoxy-2-[(3R,5S)-3,4,5-trimethylpiperazin-1-yl]pyrimidin-4-yl}azetidine-3-carboxamide;

1-{5-chloro-2-[(3R,5S)-3,4,5-trimethylpiperazin-1-yl]pyrimidin-4-yl}-N-(2-{imidazo[1,2-a]pyridin-3-yl}propan-2-yl)azetidine-3-carboxamide;

1-{5-fluoro-2-[(3R,5S)-3,4,5-trimethylpiperazin-1-yl]pyrimidin-4-yl}-N-(2-{imidazo[1,2-a]pyridin-3-yl}propan-2-yl)azetidine-3-carboxamide;

N-(2-{imidazo[1,2-a]pyridin-3-yl}propan-2-yl)-1-{5-methoxy-2-[(3R,5R)-3,4,5-trimethylpiperazin-1-yl]pyrimidin-4-yl}azetidine-3-carboxamide;

1-{5-chloro-2-[(3R,5R)-3,4,5-trimethylpiperazin-1-yl]pyrimidin-4-yl}-N-(2-{imidazo[1,2-a]pyridin-3-yl}propan-2-yl)azetidine-3-carboxamide;

1-{5-fluoro-2-[(3S,5S)-3,4,5-trimethylpiperazin-1-yl]pyrimidin-4-yl}-N-(2-{imidazo[1,2-a]pyridin-3-yl}propan-2-yl)azetidine-3-carboxamide;

N-(2-{imidazo[1,2-a]pyridin-3-yl}propan-2-yl)-1-{5-methoxy-2-[(3R,5R)-3,4,5-trimethylpiperazin-1-yl]pyrimidin-4-yl}azetidine-3-carboxamide;

1-{5-chloro-2-[(3R,5R)-3,4,5-trimethylpiperazin-1-yl]pyrimidin-4-yl}-N-(2-{imidazo[1,2-a]pyridin-3-yl}propan-2-yl)azetidine-3-carboxamide;

1-{5-fluoro-2-[(3S,5S)-3,4,5-trimethylpiperazin-1-yl]pyrimidin-4-yl}-N-(2-{imidazo[1,2-a]pyridin-3-yl}propan-2-yl)azetidine-3-carboxamide;

1-{2-[(3R)-3,4-dimethylpiperazin-1-yl]-5-fluoropyrimidin-4-yl}-N-(2-{6-methylimidazo[1,2-a]pyridin-3-yl}propan-2-yl)azetidine-3-carboxamide;

1-{5-chloro-2-[(3R)-3,4-dimethylpiperazin-1-yl]pyrimidin-4-yl}-N-(2-{6-methylimidazo[1,2-a]pyridin-3-yl}propan-2-yl)azetidine-3-carboxamide;

(3R)-1-{5-chloro-2-[(3R)-3,4-dimethylpiperazin-1-yl]pyrimidin-4-yl}-N-(2-{imidazo[1,2-a]pyridin-3-yl}propan-2-yl)pyrrolidine-3-carboxamide;

(3S)-1-{5-chloro-2-[(3R)-3,4-dimethylpiperazin-1-yl]pyrimidin-4-yl}-N-(2-{imidazo[1,2-a]pyridin-3-yl}propan-2-yl)pyrrolidine-3-carboxamide;

1-{5-chloro-2-[(3R)-3,4-dimethylpiperazin-1-yl]pyrimidin-4-yl}-N-(2-{imidazo[1,2-a]pyridin-3-yl}propan-2-yl)piperidine-4-carboxamide;

1-{2-[(3R)-3,4-dimethylpiperazin-1-yl]-5-fluoropyrimidin-4-yl}-N-(2-{imidazo[1,2-a]pyridin-3-yl}propan-2-yl)-N-methylazetidine-3-carboxamide;

1-{5-chloro-2-[(3R)-3,4-dimethylpiperazin-1-yl]pyridin-4-yl}-N-(2-{imidazo[1,2-a]pyridin-3-yl}propan-2-yl)azetidine-3-carboxamide;

1-{2-[(3R)-3,4-dimethylpiperazin-1-yl]-5-fluoropyridin-4-yl}-N-(2-{imidazo[1,2-a]pyridin-3-yl}propan-2-yl)azetidine-3-carboxamide;

1-[5-chloro-2-(4-methylpiperazin-1-yl)pyridin-4-yl]-N-(2{imidazo[1,2-a]pyridin-3-yl}propan-2-yl)azetidine-3-carboxamide;

1-{5-chloro-2-[(2S)-2,4-dimethylpiperazin-1-yl]pyrimidin-4-yl}-N{imidazo[1,2-a]pyridin-3-ylmethyl}-N-methyl-azetidine-3-carboxamide;

1-{5-chloro-2-[(2S)-2,4-dimethylpiperazin-1-yl]pyrimidin-4-yl}-N-(2{imidazo[1,2-a]pyridin-3-yl}propan-2-yl)-N-methylazetidine-3-carboxamide;

1-{2-[(2S)-2,4-dimethylpiperazin-1-yl]-5-fluoropyrimidin-4-yl}-N-(2-{imidazo[1,2-a]pyridin-3-yl}propan-2-yl)-N-methylazetidine-3-carboxamide;

1-{5-chloro-2-[(2S,5R)-2,4,5-trimethylpiperazin-1-yl]pyrimidin-4-yl}-N-(2-{imidazo[1,2-a]pyridin-3-yl}propan-2-yl)azetidine-3-carboxamide;

1-{5-chloro-2-[(2R,5R)-2,4,5-trimethylpiperazin-1-yl]pyrimidin-4-yl}-N-(2{imidazo[1,2-a]pyridin-3-yl}propan-2-yl)azetidine-3-carboxamide;

1-{5-fluoro-2-[(2S,5R)-2,4,5-trimethylpiperazin-1-yl]pyrimidin-4-yl}-N-(2-{imidazo[1,2-a]pyridin-3-yl}propan-2-yl)azetidine-3-carboxamide; and 1-[5-chloro-2-(1,4-diazepan-1-yl)pyrimidin-4-yl]-N-{[1,2,4]triazolo[4,3-a]pyridin-3-ylmethyl}azetidine-3-carboxamide;

and pharmaceutically acceptable esters, amides, carbamates and salts of any one thereof, including salts of such esters, amides and carbamates.

In one especially suitable embodiment, the compound of formula (I) is selected from the group consisting of:

N-(2-(imidazo[1,2-a]pyridin-3-yl)propan-2-yl)-1-(2-(4-methyl-1,4-diazepan-1-yl)quinazolin-4-yl)azetidine-3-carboxamide;

N-(2-(imidazo[1,2-a]pyridin-3-yl)propan-2-yl)-1-(2-(4-methyl-1,4-diazepan-1-yl)thieno[2,3-d]pyrimidin-4-yl)azetidine-3-carboxamide;

N-(2-(imidazo[1,2-a]pyridin-3-yl)propan-2-yl)-1-(2-(4-methyl-1,4-diazepan-1-yl)-6,7-dihydro-5H-cyclopenta[d]pyrimidin-4-yl)azetidine-3-carboxamide;

1-(5-chloro-6-methyl-2-(4-methyl-1,4-diazepan-1-yl)pyrimidin-4-yl)-N-(2-(imidazo[1,2-a]pyridin-3-yl)propan-2-yl)azetidine-3-carboxamide;

N-(2-(imidazo[1,2-a]pyridin-3-yl)propan-2-yl)-1-(6-methyl-2-(4-methyl-1,4-diazepan-1-yl)thieno[3,2-d]pyrimidin-4-yl)azetidine-3-carboxamide;

N-(2-(imidazo[1,2-a]pyridin-3-yl)propan-2-yl)-1-(6-methyl-2-(4-methyl-1,4-diazepan-1-yl)thieno[2,3-d]pyrimidin-4-yl)azetidine-3-carboxamide;

1-(2-(1,4-diazepan-1-yl)thieno[3,2-d]pyrimidin-4-yl)-N-(2-(imidazo[1,2-a]pyridin-3-yl)propan-2-yl)azetidine-3-carboxamide;

1-(5-chloro-2-(piperazin-1-yl)pyrimidin-4-yl)-N-(2-(imidazo[1,2-a]pyridin-3-yl)propan-2-yl)-N-methylazetidine-3-carboxamide;

1-(5-chloro-2-(1,4-diazepan-1-yl)pyrimidin-4-yl)-N-(2-(imidazo[1,2-a]pyridin-3-yl)propan-2-yl)-N-methylazetidine-3-carboxamide;

1-(5-chloro-2-(4-methyl-1,4-diazepan-1-yl)pyrimidin-4-yl)-N-(2-(imidazo[1,2-a]pyridin-3-yl)propan-2-yl)-N-methylazetidine-3-carboxamide;

N-(2-(imidazo[1,2-a]pyridin-3-yl)propan-2-yl)-N-methyl-1-(2-(4-methyl-1,4-diazepan-1-yl)thieno[3,2-d]pyrimidin-4-yl)azetidine-3-carboxamide;

(R)-1-(5-chloro-2-(3-methylpiperazin-1-yl)pyrimidin-4-yl)-N-(2-(imidazo[1,2-a]pyridin-3-yl)propan-2-yl)-N-methylazetidine-3-carboxamide;

(S)—N-(2-(imidazo[1,2-a]pyridin-3-yl)propan-2-yl)-N-methyl-1-(2-(2-methylpiperazin-1-yl)thieno[3,2-d]pyrimidin-4-yl)azetidine-3-carboxamide;

(S)—N-(2-(imidazo[1,2-a]pyridin-3-yl)propan-2-yl)-1-(2-(2-methylpiperazin-1-yl)thieno[3,2-d]pyrimidin-4-yl)azetidine-3-carboxamide;

1-(5-chloro-2-(3,3-dimethylpiperazin-1-yl)pyrimidin-4-yl)-N-(2-(imidazo[1,2-a]pyridin-3-yl)propan-2-yl)-N-methylazetidine-3-carboxamide;

1-(2-(4-aminopiperidin-1-yl)-5-chloropyrimidin-4-yl)-N-(2-(imidazo[1,2-a]pyridin-3-yl)propan-2-yl)-N-methylazetidine-3-carboxamide;

1-(5-chloro-2-(4,7-diazaspiro[2.5]octan-7-yl)pyrimidin-4-yl)-N-(2-(imidazo[1,2-a]pyridin-3-yl)propan-2-yl)-N-methylazetidine-3-carboxamide;

1-(2-(4-aminoazepan-1-yl)-5-chloropyrimidin-4-yl)-N-(2-(imidazo[1,2-a]pyridin-3-yl)propan-2-yl)-N-methylazetidine-3-carboxamide;

1-(2-(2,5-diazabicyclo[2.2.1]heptan-2-yl)-5-chloropyrimidin-4-yl)-N-(2-(imidazo[1,2-a]pyridin-3-yl)propan-2-yl)-N-methylazetidine-3-carboxamide;

1-(2-(3,8-diazabicyclo[3.2.1]octan-3-yl)-5-chloropyrimidin-4-yl)-N-(2-(imidazo[1,2-a]pyridin-3-yl)propan-2-yl)-N-methylazetidine-3-carboxamide;

1-(5-chloro-2-(2,3-dimethylpiperazin-1-yl)pyrimidin-4-yl)-N-(2-(imidazo[1,2-a]pyridin-3-yl)propan-2-yl)-N-methylazetidine-3-carboxamide;

(S)—N-(2-(imidazo[1,2-a]pyridin-3-yl)propan-2-yl)-N-methyl-1-(2-(2-methylpiperazin-1-yl)-5-(trifluoromethyl)pyrimidin-4-yl)azetidine-3-carboxamide;

1-(5-chloro-2-(piperazin-1-yl)pyrimidin-4-yl)-N-ethyl-N-(2-(imidazo[1,2-a]pyridin-3-yl)propan-2-yl)azetidine-3-carboxamide;

1-(5-chloro-2-(3-ethylpiperazin-1-yl)pyrimidin-4-yl)-N-(2-(imidazo[1,2-a]pyridin-3-yl)propan-2-yl)azetidine-3-carboxamide;

(R)-1-(5-chloro-2-(2-methylpiperazin-1-yl)pyrimidin-4-yl)-N-(2-(imidazo[1,2-a]pyridin-3-yl)propan-2-yl)-N-methylazetidine-3-carboxamide;

(R)-1-(5-chloro-2-(2,4-dimethylpiperazin-1-yl)pyrimidin-4-yl)-N-(2-(imidazo[1,2-a]pyridin-3-yl)propan-2-yl)-N-methylazetidine-3-carboxamide;

(S)-1-(5-chloro-2-(3-methylpiperazin-1-yl)pyrimidin-4-yl)-N-(2-(imidazo[1,2-a]pyridin-3-yl)propan-2-yl)-N-methylazetidine-3-carboxamide;

(S)-1-(5-chloro-2-(3,4-dimethylpiperazin-1-yl)pyrimidin-4-yl)-N-(2-(imidazo[1,2-a]pyridin-3-yl)propan-2-yl)-N-methylazetidine-3-carboxamide;

(R)-1-(5-chloro-2-(2-methylpiperazin-1-yl)pyrimidin-4-yl)-N-(2-(imidazo[1,2-a]pyridin-3-yl)propan-2-yl)azetidine-3-carboxamide;

1-(5-chloro-2-(2,3-dimethylpiperazin-1-yl)pyrimidin-4-yl)-N-(2-(imidazo[1,2-a]pyridin-3-yl)propan-2-yl)azetidine-3-carboxamide;

(S)-1-(5-chloro-2-(2-methylpiperazin-1-yl)pyrimidin-4-yl)-N-ethyl-N-(2-(imidazo[1,2-a]pyridin-3-yl)propan-2-yl)azetidine-3-carboxamide;

1-(2-(3,8-diazabicyclo[3.2.1]octan-3-yl)-5-chloropyrimidin-4-yl)-N-(2-(imidazo[1,2-a]pyridin-3-yl)propan-2-yl)azetidine-3-carboxamide;

1-(2-(2,5-diazabicyclo[4.1.0]heptan-2-yl)-5-chloropyrimidin-4-yl)-N-(2-(imidazo[1,2-a]pyridin-3-yl)propan-2-yl)-N-methylazetidine-3-carboxamide;

(S)-1-(5-chloro-2-(2-methylpiperazin-1-yl)pyrimidin-4-yl)-
N-(2-(imidazo[1,2-a]pyridin-3-yl)propan-2-yl)azetidine-
3-carboxamide;

(S)-1-(5-chloro-2-(2-ethylpiperazin-1-yl)pyrimidin-4-yl)-
N-(2-(imidazo[1,2-a]pyridin-3-yl)propan-2-yl)azetidine-
3-carboxamide;

(S)-1-(5-chloro-2-(2-ethylpiperazin-1-yl)pyrimidin-4-yl)-
N-(2-(imidazo[1,2-a]pyridin-3-yl)propan-2-yl)-N-meth-
ylazetidine-3-carboxamide:

1-(5-chloro-2-(2,2-dimethylpiperazin-1-yl)pyrimidin-4-yl)-
N-(2-(imidazo[1,2-a]pyridin-3-yl)propan-2-yl)-N-meth-
ylazetidine-3-carboxamide;

1-(5-chloro-2-(4,7-diazaspiro[2.5]octan-4-yl)pyrimidin-4-
yl)-N-(2-(imidazo[1,2-a]pyridin-3-yl)propan-2-yl)-N-
methylazetidine-3-carboxamide;

1-(5-chloro-2-((2S,5S)-2,5-dimethylpiperazin-1-yl)pyrimi-
din-4-yl)-N-(2-(imidazo[1,2-a]pyridin-3-yl)propan-2-yl)
azetidine-3-carboxamide;

1-(5-chloro-2-((2S,5S)-2,4,5-trimethylpiperazin-1-yl)py-
rimidin-4-yl)-N-(2-(imidazo[1,2-a]pyridin-3-yl)propan-
2-yl)azetidine-3-carboxamide;

1-(5-chloro-2-((2S,5R)-2,5-dimethylpiperazin-1-yl)pyrimi-
din-4-yl)-N-(2-(imidazo[1,2-a]pyridin-3-yl)propan-2-yl)
azetidine-3-carboxamide; and 1-(5-chloro-2-((2S,5R)-2,4,5-trimethylpiperazin-1-yl)py-
rimidin-4-yl)-N-(2-(imidazo[1,2-a]pyridin-3-yl)propan-
2-yl)azetidine-3-carboxamide;

and pharmaceutically acceptable esters, amides, carbamates
and salts of any one thereof, including salts of such esters,
amides and carbamates.

Depending upon the substituents present in compounds of
the invention, the compounds may form esters, amides,
carbamates or salts, including salts of esters, amides, car-
bamates.

Suitably, if the compound is in the form of an ester, amide,
carbamate and/or a salt, it is a pharmaceutically acceptable
ester, amide, carbamate and/or salt.

The compound of the invention may be in the form of a
pharmaceutically acceptable salt. Salts of compounds of the
invention which are suitable for use in medicine are those
wherein a counter-ion is pharmaceutically acceptable. How-
ever, salts having non-pharmaceutically acceptable counter-
ions are within the scope of the present invention, for
example, for use as intermediates in the preparation of
compounds of the invention and their pharmaceutically
acceptable salts. In one embodiment, the compound of the
invention is not in the form of a pharmaceutically acceptable
salt.

Suitable salts according to the invention include those
formed with organic or inorganic acids or bases. In particu-
lar, suitable salts formed with acids according to the inven-
tion include those formed with mineral acids, strong organic
carboxylic acids, such as alkanecarboxylic acids of 1 to 4
carbon atoms which are unsubstituted or substituted, for
example, by halogen, such as saturated or unsaturated dicar-
boxylic acids, such as hydroxycarboxylic acids, such as
amino acids, or with organic sulfonic acids, such as $(C_1-
C_4)$-alkyl- or aryl-sulfonic acids which are unsubstituted or
substituted, for example by halogen. Pharmaceutically
acceptable acid addition salts include those formed from
hydrochloric, hydrobromic, sulphuric, nitric, citric, tartaric,
acetic, phosphoric, lactic, pyruvic, acetic, trifluoroacetic,
succinic, perchloric, fumaric, maleic, glycolic, lactic, sali-
cylic, oxaloacetic, methanesulfonic, ethanesulfonic, p-tolu-
enesulfonic, formic, benzoic, malonic, naphthalene-2-sulfo-
nic, benzenesulfonic, isethionic, ascorbic, malic, phthalic,
aspartic, and glutamic acids, lysine and arginine. Other acids, which may or may not in themselves be pharmaceu-
tically acceptable, may be useful as intermediates in obtain-
ing the compounds of the invention and their pharmaceutical
acceptable acid addition salts.

Pharmaceutically acceptable base salts include ammo-
nium salts, alkali metal salts, for example those of potassium
and sodium, alkaline earth metal salts, for example those of
calcium and magnesium, and salts with organic bases, for
example dicyclohexylamine, N-methyl-D-glucomine, mor-
pholine, thiomorpholine, piperidine, pyrrolidine, a mono-,
di- or tri-lower alkylamine, for example ethyl-, tert-butyl-,
diethyl-, diisopropyl-, triethyl-, tributyl- or dimethyl-pro-
pylamine, or a mono-, di- or trihydroxy lower alkylamine,
for example mono-, di- or triethanolamine. Corresponding
internal salts may furthermore be formed.

Compounds of the invention may have an appropriate
group converted to an ester, an amide or a carbamate. Thus
typical ester and amide groups formed from an acid group in
the compound of the invention include —$COOR^G$,
—$CONR^G_2$, —$SO_2OR^G$, or —$SO_2N(R^G)_2$, while typical
ester and amide and carbamate groups formed from an
—OH or —$NHR^G$ group in the compound of the invention
include —$OC(O)R^G$, —$NR^GC(O)R^G$, —$NR^GCO_2R^G$,
—$OSO_2R^G$, and —$NR^GSO_2R^G$, where $R^G$ is selected from
the group consisting of $C_{1-8}$alkyl, $C_{2-8}$alkenyl, $C_{2-8}$alkynyl,
$C_{3-8}$cycloalkyl and $C_{3-8}$acycoalkylC$_{1-8}$alkyl, haloC$_{1-8}$alkyl,
dihaloC$_{1-8}$alkyl, trihaloC$_{1-8}$alkyl, phenyl and phenylC$_{1-4}$al-
kyl; more suitably $R^G$ is selected from the group consisting
of $C_{1-6}$alkyl, $C_{2-6}$alkenyl, $C_{2-6}$alkynyl, $C_{3-8}$cycloalkyl and
$C_{3-8}$cycloalkylC$_{1-6}$alkyl.

Those skilled in the art of organic chemistry will appre-
ciate that many organic compounds can form complexes
with solvents in which they are reacted or from which they
are precipitated or crystallized. These complexes are known
as "solvates". For example, a complex with water is known
as a "hydrate". Solvates, such as hydrates, exist when the
drug substance incorporates solvent, such as water, in the
crystal lattice in either stoichiometric or non-stoichiometric
amounts. Drug substances are routinely screened for the
existence of hydrates since these may be encountered at any
stage of the drug manufacturing process or upon storage of
the drug substance or dosage form. Solvates are described in
S. Byrn et al., *Pharmaceutical Research,* 1995. 12(7): p.
954-954, and Water-Insoluble Drug Formulation, $2^{nd}$ ed. R.
Liu, CRC Press, page 553, which are incorporated herein by
reference. Accordingly, it will be understood by the skilled
person that the compounds of the invention may therefore be
present in the form of solvates. Solvates of compounds of
the invention which are suitable for use in medicine are
those wherein the associated solvent is pharmaceutically
acceptable. For example, a hydrate is an example of a
pharmaceutically acceptable solvate. However, solvates
having non-pharmaceutically acceptable associated solvents
may find use as intermediates in the preparation of a
compound of the invention. In one embodiment, the com-
pound of the invention is not in the form of a solvate.

Suitable pharmaceutically acceptable derivatives of the
compounds of the invention are salts.

Uses of Compounds of the Invention

Inhibition of human NMT has been suggested as a target
for treating or preventing various diseases or disorders, as
described above.

As the compounds of the present invention are NMT
inhibitors, a compound of the invention may be used in the
treatment of diseases or disorders associated with NMT
activity or may be used in the treatment of a disease or
disorder by targeting NMT activity (for example in hyperproliferative diseases (such as cancer), and viral infections (such as picornaviral infections)). Accordingly, the present invention provides a compound according to the invention, or a pharmaceutical composition comprising a compound according to the invention and a pharmaceutically acceptable carrier, for use as a medicament. There is also provided a compound according to the invention, or a pharmaceutical composition comprising a compound according to the invention and a pharmaceutically acceptable carrier, for use in the treatment or prevention of a disease or disorder in which inhibition of N-myristoyl transferase provides a therapeutic or prophylactic effect. There is also provided a compound according to the invention, or a pharmaceutical composition comprising a compound according to the invention and a pharmaceutically acceptable carrier, for use in the treatment of a disease or disorder in which inhibition of N-myristoyl transferase provides a therapeutic effect. There is also provided a compound according to the invention, or a pharmaceutical composition comprising a compound according to the invention and a pharmaceutically acceptable carrier, for use in the prevention of a disease or disorder in which inhibition of N-myristoyl transferase provides a prophylactic effect.

The invention also provides a method for the treatment or prevention of a disease or disorder in a subject in which inhibition of N-myristoyl transferase provides a therapeutic or prophylactic effect in a subject (e.g. a mammal, for example a human), which comprises administering to the subject a therapeutically effective amount of a compound according to the invention, or a pharmaceutical composition comprising compound according to the invention and a pharmaceutically acceptable carrier. The invention also provides a method for the treatment of a disease or disorder in a subject in which inhibition of N-myristoyl transferase provides a therapeutic effect in a subject (e.g. a mammal, for example a human), which comprises administering to the subject a therapeutically effective amount of a compound according to the invention, or a pharmaceutical composition comprising compound according to the invention and a pharmaceutically acceptable carrier. The invention also provides a method for the prevention of a disease or disorder in a subject in which inhibition of N-myristoyl transferase provides a prophylactic effect in a subject (e.g. a mammal, for example a human), which comprises administering to the subject a prophylatically effective amount of a compound according to the invention, or a pharmaceutical composition comprising compound according to the invention and a pharmaceutically acceptable carrier.

The invention also provides the use of a compound according to the invention for the manufacture of a medicament for the treatment or prevention of a disease or disorder in which inhibition of N-myristoyl transferase provides a therapeutic or prophylactic effect. The invention also provides the use of a compound according to the invention for the manufacture of a medicament for the treatment of a disease or disorder in which inhibition of N-myristoyl transferase provides a therapeutic effect. The invention also provides the use of a compound according to the invention for the manufacture of a medicament for the prevention of a disease or disorder in which inhibition of N-myristoyl transferase provides a prophylactic effect.

Diseases and disorders in which inhibition of N-myristoyl transferase provides a therapeutic or prophylactic effect include: hyperproliferative disorders, viral infections, neurological diseases, ischemia, osteoporosis, diabetes, autoimmune diseases and inflammatory diseases. As such, compounds of the invention find use the treatment or prevention of those disorders/diseases.

Diseases or disorders in which inhibition of N-myristoyl transferase provides a therapeutic or prophylactic effect also include microbial infections; e.g. fungal infections, and protozoan infections such as malaria, leishmaniasis, human African trypanosomiasis (sleeping sickness) and American trypanosomiasis (Chagas disease).

It is also expected that the compounds of the present invention will find particular utility in targeting diseases in particular patient populations, i.e. where the disease is expected to be particularly affected by inhibition of N-myristoyl transferase, for example human N-myristoyl transferase. Such diseases include hyperproliferative disorders, and especially cancer, for example a haematologic malignancy (such as a lymphoma, and in particular a B-cell lymphoma (e.g. high grade mantle zone lymphoma, follicular lymphoma, plasmablastic lymphoma, diffuse large B-cell lymphoma and Burkitt's lymphoma), a myeloma (e.g. multiple myeloma) or a leukaemia (e.g. chronic lymphocytic leukaemia, AML and B-acute lymphocytic leukaemia)) or a solid-tumor (such as brain, lung, breast (e.g. triple negative breast cancer or a breast invasive carcinoma), prostate, ovary, colorectal (e.g. colon), gallbladder, kidney or liver cancer, or a neuroblastoma).

Compounds which are particularly good inhibitors of human NMT may suitably be used in the treatment and/or prevention of hyperproliferative disorders (e.g. cancer) and viral infections (e.g. human immunodeficiency virus (HIV), human rhinovirus (RV, formally abbreviated as HRV)), as well as other conditions for which inhibition of human NMT has been suggested as a means of therapy.

In one suitable embodiment, the compounds of the invention are for use in the treatment of a disease or disorder selected from hyperproliferative disorders and viral infections.

Hyperproliferative Disorders

In one especially suitable embodiment, the compounds of the invention are for use in the prevention or treatment of a hyperproliferative disorder, wherein the hyperproliferative disorder is cancer. In one especially suitable embodiment, the compounds of the invention are for use in the prevention of a hyperproliferative disorder, wherein the hyperproliferative disorder is cancer.

In one especially suitable embodiment, the compounds of the invention are for use in the treatment of a hyperproliferative disorder, wherein the hyperproliferative disorder is cancer. The cancer may be selected from the group consisting of colorectal cancer, gallbladder carcinoma, brain tumors, lymphomas (such as B-cell lymphoma (for example diffuse large B-cell lymphoma)), leukaemia (such as acute myeloid leukaemia (AML)) and neuroblastoma.

The cancer may additionally, or alternatively, be a solid tumour selected from the group consisting of brain, lung, breast (e.g. triple negative breast cancer or a breast invasive carcinoma), prostate, ovary, colorectal (e.g. colon), gallbladder, kidney and liver cancer. For example, the cancer may be ovarian serous cystadenocarcinoma, esophageal carcinoma, lung squamous cell carcinoma, lung adenocarcinoma, bladder urothelial carcinoma, uterine carcinosarcoma, stomach adenocarcinoma, breast invasive carcinoma or liver hepatocellular carcinoma. In certain embodiments, the cancer is breast cancer, for example triple negative breast cancer or a breast invasive carcinoma. In certain embodiments, the cancer is brain, breast, prostate, colon, gallbladder or kidney cancer. In certain embodiments, the cancer is breast, colon or gallbladder cancer.

The cancer may additionally, or alternatively, be a haematologic malignancy selected from the group consisting of lymphoma (for example B-cell lymphoma, and in particular a lymphoma selected from the group consisting high grade mantle zone lymphoma, follicular lymphoma, plasmablastic lymphoma, diffuse large B-cell lymphoma and Burkitt's lymphoma), myeloma (for example multiple myeloma) and leukaemia (for example a leukaemia selected from the group consisting chronic lymphocytic leukaemia, AML and B-acute lymphocytic leukaemia).

The cancer may also additionally, or alternatively, be a neuronal-originating-cancer (i.e. a cancer of the nervous system), in particular the cancer may be selected from a neuroblastoma, retinoblastoma, a glioblastoma, a small cell lung carcinoma and an astrocytoma. In a particular embodiment, the cancer is a blastoma, in particular a neuroblastoma, a retinoblastoma or a glioblastoma. In certain embodiments, the cancer is a neuroblastoma.

In one embodiment, the cancer may be selected from the group consisting of diffuse large B-cell lymphoma, Burkitt's lymphoma, multiple myeloma, neuroblastoma, AML, and B-acute lymphocytic leukaemia. In one embodiment, the cancer may be selected from the group consisting of diffuse large B-cell lymphoma, Burkitt's lymphoma, neuroblastoma, AML, B-acute lymphocytic leukaemia and breast cancer. In another embodiment, the cancer may be selected from the group consisting of diffuse large B-cell lymphoma, neuroblastoma, B-acute lymphocytic leukaemia and triple negative breast cancer. In another embodiment, the cancer may be selected from the group consisting of colorectal cancer, gallbladder carcinoma, brain tumour, lymphoma (such as diffuse large B-cell lymphoma), leukemia (such as acute myeloid leukemia) and blastoma (such as neuroblastoma, retinoblastoma or glioblastoma, and suitably neuroblastoma). In another embodiment, the cancer may be selected from the group consisting of diffuse large B-cell lymphoma, Burkitt's lymphoma, multiple myeloma, neuroblastoma, AML, B-acute lymphocytic leukaemia and triple negative breast cancer. In another embodiment, the cancer may be selected from the group consisting of multiple myeloma, neuroblastoma, AML, B-acute lymphocytic leukaemia and triple negative breast cancer. In another embodiment, the cancer may be selected from the group consisting of multiple myeloma, neuroblastoma and triple negative breast cancer.

The oncogenes c-MYC and MYCN are common diagnostic markers for particularly aggressive types of malignancies and there are recent findings demonstrating that c-MYC and MYCN overexpression and/or mutation correlate strongly with some of the worst clinical outcomes (Jung et al., Tumor and Stem Cell Biology, 2016, 65(16), 7065-7070, Habermann et al., Blood, 2016, 128(22), 155, Xu et al., Genes Cancer, 2010, 1(6), 629-640). There therefore remains a need for improved treatments that are able to target cancers where one or more structural alterations of the MYC oncogene exist.

The compounds of the invention are also especially well-suited for application in the treatment of cancers which: i) are addicted to the MYC oncogene; and/or ii) have one or more structural alterations in the MYC oncogene locus.

Thus the compounds of the invention may be used in the treatment of a MYC addicted cancer. Suitably, the compounds may be used in the prevention of a MYC addicted cancer. Suitably, the compounds of the invention may be used in the prevention or treatment of a MYC addicted cancer. Suitably, the MYC addicted cancer is a cancer which is addicted to c-MYC and/or MYCN. In certain embodiments, the MYC addicted cancer is a cancer which is addicted to c-MYC, and, suitably, the MYC addicted cancer is a cancer which is transcriptionally addicted to c-MYC. In other embodiments, the MYC addicted cancer is a cancer which is addicted to MYCN, and, suitably, the MYC addicted cancer is a cancer which is transcriptionally addicted to MYCN.

In a particular embodiment, the present invention provides a compound of the invention for use in the prevention or treatment e.g. treatment of a c-MYC or MYCN addicted cancer, wherein the c-MYC or MYCN oncogene is overexpressed. Suitably, the present invention provides a compound of the invention, or a pharmaceutically acceptable salt, solvate or hydrate thereof, for use in the prevention or treatment e.g. treatment of a c-MYC or MYCN addicted cancer, wherein the c-MYC or MYCN oncogene is overexpressed such that the levels of RNA transcript and/or protein of c-MYC or MYCN are at least 25% greater than the RNA transcript and/or protein levels of c-MYC or MYCN found in a normal, healthy cell.

More suitably, the present invention provides a compound of the invention, or a pharmaceutically acceptable salt, solvate or hydrate thereof, for use in the prevention or treatment e.g. treatment of a c-MYC or MYCN addicted cancer, wherein the c-MYC or MYCN is overexpressed such that the levels of RNA transcript and/or protein of c-MYC or N-MYC are at least 50% greater than the RNA transcript and/or protein levels of c-MYC or N-MYC found in a normal, healthy cell.

The present invention also provides a compound of the invention for use in the prevention or treatment e.g. treatment of a MYC dysregulated cancer. A MYC dysregulated cancer may include, for example, cancers comprising mutations and/or structural alterations of the MYC oncogene which impart, for instance, overexpression or stabilisation of the protein and/or mRNA levels of MYC. A non-limiting list of possible mutations include: i) point mutations in the MYC coding region (Bahram et. al., Blood, 2000, 95, 2104-2110); ii) mutations of distal enhancers (Sur et al., Science, 2012, 338, 1360-1363 and Zhang et al., Nat. Genet., 2016, 48-176-182); and iii) activating mutations in the signal transduction pathways that augment MYC expression (Herranz et al., Nat. Med., 2014, 20, 1130-1137, Muncan et al., Mol. Cell Biol., 2006, 26, 8418-8426 and Weng et al., Genes Dev., 2006, 20, 2096-2109).

In one embodiment, the MYC dysregulated cancer is a MYC oncogene overexpressing cancer. Suitably, the MYC dysregulated cancer is a c-MYC or MYCN oncogene overexpressing cancer. More suitably, the MYC oncogene dysregulated cancer is a c-MYC or MYCN oncogene overexpressing cancer, wherein the c-MYC or MYCN is overexpressed such that the levels of RNA transcript and/or protein of c-MYC or MYCN are at least 25% greater than the RNA transcript and/or protein levels of c-MYC or MYCN found in a normal, healthy cell. Most suitably, the MYC dysregulated cancer is a c-MYC or MYCN oncogene overexpressing cancer, wherein the c-MYC or MYCN is overexpressed such that the levels of RNA transcript and/or protein of c-MYC or MYCN are at least 50% greater than the RNA transcript and/or protein levels of c-MYC or MYCN found in a normal, healthy cell.

The present invention further provides a compound of the invention, for use in the prevention or treatment e.g. treatment of a cancer, wherein said cancer comprises one or more structural alterations of the MYC locus. Non-limiting examples of "structural alterations" include, for example, mutations, copy-number gains and/or chromosomal rearrangements. In one embodiment, there is provided a compound of the invention for use in the prevention or treatment e.g. treatment of a cancer, wherein said cancer comprises one or more mutations of the MYC locus. Suitably, the present invention provides a compound of the invention for use in the prevention or treatment e.g. treatment of a cancer, wherein said cancer comprises one or more mutations of the MYC locus which impart overexpression of MYC. More suitably, the present invention provides a compound of the invention for use in the prevention or treatment e.g. treatment of a cancer, wherein said cancer comprises one or more mutations of the MYC locus which impart overexpression of c-MYC or MYCN. In one particular embodiment, the present invention provides a compound of the invention for use in the prevention or treatment e.g. treatment of a cancer, wherein said cancer comprises one or more mutations of c-MYC. In another particular embodiment, the invention provides compound of the invention for use in the prevention or treatment e.g. treatment of a cancer, wherein said cancer comprises one or more mutations of MYCN.

In a particular embodiment, there is provided a compound of the invention for use in the prevention or treatment e.g. treatment of a cancer, wherein said cancer comprises one or more mutations of the MYC locus which impart stabilisation of MYC.

In a particular embodiment, the MYC addicted cancer, the MYC dysregulated cancer or the cancer comprising one or more structural alterations of the MYC locus, is a cancer selected from a haematologic malignancy or a solid-tumour.

In another embodiment, the MYC addicted cancer, the MYC dysregulated cancer or the cancer comprising one or more structural alterations of the MYC locus, is a haematological malignancy. Suitably, the MYC addicted cancer, the MYC dysregulated cancer or the cancer comprising one or more structural alterations of the MYC locus, is a haematological malignancy selected from lymphoma, myeloma or leukaemia.

In another embodiment, the MYC addicted cancer, the MYC dysregulated cancer or the cancer comprising one or more structural alterations of the MYC locus, is a lymphoma. Suitably, the MYC addicted cancer, the MYC dysregulated cancer or the cancer comprising one or more structural alterations of the MYC locus, is a lymphoma selected from high grade mantle zone lymphoma, follicular lymphoma, plasmablastic lymphoma, diffuse large B-cell lymphoma and Burkitt's lymphoma. More suitably, the MYC addicted cancer, the MYC dysregulated cancer or the cancer comprising one or more structural alterations of the MYC locus, is a lymphoma selected from diffuse large B-cell lymphoma or Burkitt's lymphoma. Most suitably, the MYC addicted cancer, the MYC dysregulated cancer or the cancer comprising one or more structural alterations of the MYC locus, is a diffuse large B-cell lymphoma.

In another embodiment, the MYC addicted cancer, the MYC dysregulated cancer or the cancer comprising one or more structural alterations of the MYC locus, is a myeloma. Suitably, the MYC addicted cancer, the MYC dysregulated cancer or the cancer comprising one or more structural alterations of the MYC locus, is a multiple myeloma.

In another embodiment, the MYC addicted cancer, the MYC dysregulated cancer or the cancer comprising one or more structural alterations of the MYC locus, is a leukaemia. Suitably, the MYC addicted cancer, the MYC dysregulated cancer or the cancer comprising one or more structural alterations of the MYC locus, is a leukaemia selected from chronic lymphocytic leukaemia, acute myeloid leukemia and B-acute lymphocytic leukaemia. Most suitably, the MYC addicted cancer, the MYC dysregulated cancer or the cancer comprising one or more structural alterations of the MYC locus, is a B-acute lymphocytic leukaemia.

In another embodiment, the MYC addicted cancer, the MYC dysregulated cancer or the cancer comprising one or more structural alterations of the MYC locus, is a blastoma. Suitably, the MYC addicted cancer, the MYC dysregulated cancer or the cancer comprising one or more structural alterations of the MYC locus, is a blastoma selected from a neuroblastoma, a retinoblastoma and a glioblastoma. More suitably, the MYC addicted cancer, the MYC dysregulated cancer or the cancer comprising one or more structural alterations of the MYC locus, is a blastoma selected from a retinoblastoma and a glioblastoma. In a particular embodiment, the MYC addicted cancer, the MYC dysregulated cancer or the cancer comprising one or more structural alterations of the MYC locus, is a neuroblastoma.

In another embodiment, the MYC addicted cancer, the MYC dysregulated cancer or the cancer comprising one or more structural alterations of the MYC locus, is a neuronal-originating-cancer (i.e. a cancer of the nervous system). In a particular embodiment, the MYC addicted cancer, the MYC dysregulated cancer or the cancer comprising one or more structural alterations of the MYC locus, is selected from a neuroblastoma, retinoblastoma, a glioblastoma, a small cell lung carcinoma and an astrocytoma.

In another embodiment, the MYC addicted cancer, the MYC dysregulated cancer or the cancer comprising one or more structural alterations of the MYC locus, is a solid-tumour. In certain embodiments, the solid-tumour is a carcinoma. Suitably, the MYC addicted cancer, the MYC dysregulated cancer or the cancer comprising one or more structural alterations of the MYC locus, is a solid tumour in an organ selected from brain, lung, breast, prostate, ovary, colon, gallbladder, kidney and liver. More suitably, the MYC addicted cancer, the MYC dysregulated cancer or the cancer comprising one or more structural alterations of the MYC locus, is a solid tumour in an organ selected from brain, breast, prostate, colon, gallbladder and kidney. Yet more suitably, the MYC addicted cancer, the MYC dysregulated cancer or the cancer comprising one or more structural alterations of the MYC locus, is a solid tumour in an organ selected from breast, colon and gallbladder.

In certain embodiments, the MYC addicted cancer, the MYC dysregulated cancer or the cancer comprising one or more structural alterations of the MYC locus, is a solid tumour selected from ovarian serous cystadenocarcinoma, esophageal carcinoma, lung squamous cell carcinoma, lung adenocarcinoma, bladder urothelial carcinoma, uterine carcinosarcoma, stomach adenocarcinoma, breast invasive carcinoma and liver hepatocellular carcinoma.

In certain embodiments, the MYC addicted cancer, the MYC dysregulated cancer or the cancer comprising one or more structural alterations of the MYC locus, is breast cancer. Suitably, the MYC addicted cancer, the MYC dysregulated cancer or the cancer comprising one or more structural alterations of the MYC locus, is triple negative breast cancer or a breast invasive carcinoma. In particular embodiments, the MYC addicted cancer, the MYC dysregulated cancer or the cancer comprising one or more structural alterations of the MYC locus, is basal-like breast cancer.

In other embodiments, the MYC addicted cancer, the MYC dysregulated cancer or the cancer comprising one or more structural alterations of the MYC locus, is cancer of the gallbladder.

In other embodiments, the MYC addicted cancer, the MYC dysregulated cancer or the cancer comprising one or more structural alterations of the MYC locus, is colorectal cancer.

In other embodiments, the MYC addicted cancer, the MYC dysregulated cancer or the cancer comprising one or more structural alterations of the MYC locus, is brain cancer (e.g. an astrocytoma).

In certain embodiments, the MYC addicted cancer, the MYC dysregulated cancer or the cancer comprising one or more structural alterations of the MYC locus, is selected from diffuse large B-cell lymphoma, a Burkitt's lymphoma, multiple myeloma, blastoma (e.g. a neuroblastoma, retinoblastoma or glioblastoma), acute myeloid leukemia, B-acute lymphocytic leukaemia and a solid tumour in an organ selected from breast, colon and gallbladder. Suitably, the MYC addicted cancer, the MYC dysregulated cancer or the cancer comprising one or more structural alterations of the MYC locus, is selected from diffuse large B-cell lymphoma, Burkitt's lymphoma, neuroblastoma, retinoblastoma, glioblastoma, acute myeloid leukemia, B-acute lymphocytic leukaemia and breast cancer. More suitably, the MYC addicted cancer, the MYC dysregulated cancer or the cancer comprising one or more structural alterations of the MYC locus, is selected from diffuse large B-cell lymphoma, neuroblastoma, B-acute lymphocytic leukaemia and triple negative breast cancer.

In particular embodiments, the MYC addicted cancer, the MYC dysregulated cancer or the cancer comprising one or more structural alterations of the MYC locus, is colorectal cancer, gallbladder carcinoma, brain tumour, lymphoma (such as diffuse large B-cell lymphoma), leukemia (such as acute myeloid leukemia) or blastoma (such as neuroblastoma, retinoblastoma or glioblastoma).

In certain embodiments, the MYC addicted cancer, the MYC dysregulated cancer or the cancer comprising one or more structural alterations of the MYC locus, is diffuse large B-cell lymphoma, Burkitt's lymphoma, multiple myeloma, blastoma (such as neuroblastoma, retinoblastoma or glioblastoma), acute myeloid leukemia, B-acute lymphocytic leukaemia or triple negative breast cancer. Suitably, the MYC addicted cancer, the MYC dysregulated cancer or the cancer comprising one or more structural alterations of the MYC locus, is multiple myeloma, neuroblastoma, retinoblastoma, glioblastoma, acute myeloid leukemia, B-acute lymphocytic leukaemia or triple negative breast cancer. More suitably, the MYC addicted cancer, the MYC dysregulated cancer or the cancer comprising one or more structural alterations of the MYC locus, is multiple myeloma, neuroblastoma, retinoblastoma, glioblastoma, or triple negative breast cancer. Even more suitably, the MYC addicted cancer, the MYC dysregulated cancer or the cancer comprising one or more structural alterations of the MYC locus, is neuroblastoma or triple negative breast cancer (e.g. basal-like breast cancer).

In a particular embodiment, the invention provides a compound of the invention, or a pharmaceutically acceptable salt, solvate or hydrate thereof, for use in the prevention or treatment e.g. treatment of a blastoma, wherein said blastoma comprises one or more mutations of MYCN. Suitably, the blastoma is selected from a neuroblastoma, a retinoblastoma and a glioblastoma. Most suitably, the invention provides a compound of the invention, or a pharmaceutically acceptable salt, solvate or hydrate thereof, for use in the prevention or treatment e.g. treatment of a neuroblastoma, wherein said neuroblastoma comprises one or more mutations of MYCN.

In another particular embodiment, the invention provides a compound of the invention, for use in the prevention or treatment e.g. treatment of a c-MYC addicted cancer, wherein the c-MYC addicted cancer is a breast cancer. Suitably, the invention provides a compound of the invention for use in the prevention or treatment e.g. treatment of a c-MYC addicted cancer, wherein the c-MYC addicted cancer is a triple negative breast cancer (e.g. a basal-like breast cancer) or a breast invasive carcinoma.

The present invention also provides a method for the prevention or treatment e.g. treatment of a MYC addicted cancer in a subject in need of such treatment, said method comprising administering a therapeutically effective amount of a compound of the invention. Suitably, the MYC addicted cancer is any one of the MYC addicted cancers described hereinabove.

Further provided is a method for the prevention or treatment e.g. treatment of a MYC dysregulated cancer in a subject in need of such treatment, said method comprising administering a therapeutically effective amount of a compound of the invention. Suitably, the MYC dysregulated cancer is any one of the MYC dysregulated cancers described hereinabove.

Further provided is a method for the prevention or treatment e.g. treatment of a cancer comprising one or more structural alterations of the MYC locus in a subject in need of such treatment, said method comprising administering a therapeutically effective amount of a compound of the invention. Suitably, the cancer comprising one or more structural alterations of the MYC locus is any one of the cancers described hereinabove.

According to a further aspect of the present invention, there is provided a method for determining whether a subject with a cancer will benefit from treatment with a compound of the invention, said method comprising the steps of i) taking a sample of cancer cells taken from said subject;

ii) analysing the cancer cells of step i) to check for the presence of one or more structural alterations (e.g. chromosomal rearrangements, copy number gains and/or mutations) in the MYC locus;

iii) determining whether one or more structural alterations (e.g. chromosomal rearrangements, copy number gains and/or mutations) are present in the MYC locus of the sample of cancer cells when compared to a control; and iv) determining whether the subject will benefit from being administered a compound of the invention in order to treat said cancer, wherein if the sample of cancer cells contains one or more structural alterations (e.g. chromosomal rearrangements, copy number gains and/or mutations) in the MYC locus, then the subject will benefit from being administered a compound of the invention, and if the sample of cancer cells does not contain one or more structural alterations (e.g. chromosomal rearrangements, copy number gains and/or mutations) in the MYC locus, then the subject will not benefit from being administered a compound of the invention.

In an embodiment, the one or more structural alterations are chromosomal rearrangements. Thus, suitably, step ii) of the above method involves analysing the cancer cells of step i) to check for the presence of one or more chromosomal rearrangements in the MYC locus. The person skilled in the art will be able to readily determine suitable techniques for checking for the presence of one or more chromosomal rearrangements in the MYC locus. One, non-limiting, example of a suitable technique for checking for the presence of one or more chromosomal rearrangements in the MYC locus is fluorescence in-situ hybridisation (FISH).

In another embodiment, the one or more structural alterations are mutations. Thus, suitably, step ii) of the above method involves analysing the cancer cells of step i) to check for the presence of one or more mutations in the MYC locus. The person skilled in the art will be able to readily determine suitable techniques for checking for the presence of one or more mutations in the MYC locus. One, non-limiting, example of a suitable technique for checking for the presence of one or more mutations in the MYC locus is gene sequencing.

Suitably, the control of step iii) is the structural arrangement of the MYC locus found in a normal, healthy cell, specifically, the control of step iii) is the chromosomal arrangement and/or genetic sequence found in the MYC locus of a normal, healthy cell.

It will be understood that the sample of cancer cells taken from said subject may be obtained by any suitable method known in the art. For instance, the sample of cancer cells taken from said subject may be those taken from a biopsy or may be a sample of circulating tumour cells (CTCs) taken from the subject.

According to a further aspect of the present invention, there is provided a method for determining whether a subject with a cancer will benefit from treatment with an NMT inhibitor, said method comprising the steps of:

i) measuring the level of MYC expression in a sample of cancer cells taken from said subject;
   ii) comparing the level of MYC expression from step i) with a control;
   iii) determining whether the MYC expression in the sample of cancer cells is increased compared to the control; and
   iv) determining whether the subject will benefit from being administered a compound of the invention in order to treat said cancer, wherein if the MYC expression in the sample of cancer cells is higher than in the control, then the subject will benefit from being administered a compound of the invention, and if the MYC expression in the sample of cancer cells is not higher than in the control, then the subject will not benefit from being administered a compound of the invention.

It will be appreciated that the level of MYC expression in the sample of cancer cells may be determined by any suitable means known in the art. For example, the level of expression of MYC may be determined by measuring MYC protein levels. The MYC protein levels may be measured using any suitable technique known in the art, such as, for example, SDS-PAGE followed by Western blot using suitable antibodies raised against the target protein. In addition, or alternatively, the level of expression of MYC may be determined by measuring the level of mRNA. The level of mRNA may be measured using any suitable technique known in the art, such as, for example, northern blot or quantitative RT-PCR (qRT-PCR).

Suitably, the control of step ii) above is the MYC expression level found in a normal, healthy cell, for example, a normal, healthy cell of the same type as the cell being investigated. It will be understood that the MYC expression level found in a normal, healthy cell may also be determined using any of the techniques described above.

According to a further aspect of the present invention, there is provided a method for the prevention or treatment e.g. treatment of cancer in a subject who has been identified as benefiting from being administered a compound of the invention as determined by a method as described above, wherein said method comprises administering a therapeutically effective amount of a compound of the invention.

Viral Infections and Associated Diseases

In another suitable embodiment, the compounds of the invention are for use in the prevention or treatment e.g. treatment of a viral infection, and in particular an enteroviral infection, a retroviral infection or a poxviral infection. For example, the enteroviral infection may be a picornaviral infection (for example a rhinovirus, poliovirus, foot-and-mouth disease virus, coxsackievirus, hepatitis A virus or enterovirus 71 infection); the retroviral infection may be a lentiviral infection (for example an HIV infection)); and the poxviral infection may be a orthopoxvirus, parapoxvirus, yatapoxvirus, or molluscipoxvirus infection. Thus the viral infection may be selected from the group consisting of a rhinovirus infection (for example RV, also known as the common cold), lentivirus infection (for example HIV infection), poliovirus infection, foot-and-mouth disease virus infection, coxsackievirus infection, hepatitis A virus infection, enterovirus 71 infection, smallpox virus (variola) infection, vaccinia virus infection, cowpox virus infection, monkeypox virus infection, buffalopox virus infection, camelpox virus infection, ectromelia virus infection, rabbitpox virus infection, raccoonpox virus infection, sealpox virus infection, skunkpox virus infection, taterapox virus infection, volepox virus infection, orf virus infection, pseudocowpox infection, bovine papular stomatitis virus infection; tanapox virus infection, yaba monkey tumor virus infection and molluscum contagiosum virus (MCV) infection. It may suitably be selected from the group consisting of a rhinovirus infection (for example RV, also known as the common cold), lentivirus infection (for example HIV infection), poliovirus infection, foot-and-mouth disease virus infection, coxsackievirus infection, hepatitis A virus infection, enterovirus 71 infection, smallpox virus (variola) infection, vaccinia virus infection, cowpox virus infection, monkeypox virus infection, orf virus infection, pseudocowpox infection, bovine papular stomatitis virus infection; tanapox virus infection, yaba monkey tumor virus infection and molluscum contagiosum virus (MCV) infection. In one especially suitable embodiment, the compounds of the invention are for use in the prevention or treatment e.g. treatment of a viral infection, wherein the viral infection is a picornaviral infection, and even more especially it is a rhinovirus infection (for example RV, also known as the common cold).

The above-mentioned viral infections cause many types of diseases. For example: rhinovirus infection causes the common cold; various picornaviral infections (in particular coxsackievirus and enterovirus 71) cause hand, foot and mouth disease and polio-like syndrome; coxsackieviruses can also cause a flaccid paralysis, herpangina, acute hemorrhagic conjunctivitis, nonspecific febrile illnesses, rashes, upper respiratory tract disease, pericardial effusion, insulin-dependent diabetes (IDDM), Sjogren's syndrome, myocarditis (inflammation of the heart), pericarditis (inflammation of the sac surrounding the heart), meningitis (inflammation of the membranes that line the brain and spinal cord), and pancreatitis (inflammation of the pancreas); enterovirus 71 can also cause severe neurological diseases in children; foot-and-mouth disease virus causes foot-and-mouth disease; hepatitis A virus causes hepatitis A; HIV infection can cause acquired immunodeficiency syndrome (AIDS); smallpox virus (variola) infection causes smallpox; cowpox virus infection causes cowpox; monkeypox virus infection causes monkeypox; orf virus infection causes orf; pseudocowpox infection causes pseudocowpox; bovine papular stomatitis virus infection causes bovine papular stomatitis; tanapox virus infection can cause acute febrile illness and localized skin lesions; yaba monkey tumor virus infection can cause formation of cutaneous histiocytomas; and molluscum contagiosum virus (MCV) infection causes molluscum contagiosum. Compounds of the present invention may be used in the prevention or treatment e.g. treatment of the above-mentioned diseases caused by the viral infections mentioned above, as well as other diseases and conditions caused by an enteroviral infection or a retroviral infection or a poxviral infection.

Microbial Infections

In another embodiment, the compounds of the invention are for use in the prevention or treatment e.g. treatment of a disease or disorder that is a microbial infection; e.g. fungal infections such as Aspergillus infections, and protozoan infections such as malaria, leishmaniasis, human African trypanosomiasis (sleeping sickness) and American trypanosomiasis (Chagas disease). In certain embodiments, the compounds for the invention are for use in the prevention or treatment e.g. treatment of a disease or disorder that is selected from the group consisting of aspergillosis, malaria, leishmaniasis, human African trypanosomiasis (sleeping sickness) and American trypanosomiasis (Chagas disease), and in particular malaria, leishmaniasis, human African trypanosomiasis (sleeping sickness) and American trypanosomiasis (Chagas disease).

In one embodiment, the compounds of the invention are for use in the prevention or treatment e.g. treatment of a disease or disorder that is a protozoan infection caused by a species of *Plasmodium, Leishmania* or *Trypanosoma* (for example *Plasmodium falciparum, Plasmodium vivax, Leishmania donovani, Leishmania major, Trypanosoma brucei, Trypanosoma cruzi*).

Compounds which are particularly good inhibitors of the NMT enzyme of a particular non-human species (e.g. *Plasmodium falciparum, Plasmodium vivax, Leishmania donovani, Leishmania major, Trypanosoma brucei, Trypanosoma cruzi*); and/or compounds of the invention which are selective for the NMT enzyme of a particular species (e.g. *Plasmodium falciparum, Plasmodium vivax, Leishmania donovani, Leishmania major, Trypanosoma brucei, Trypanosoma cruzi*) over human NMT (human NMT1 and/or human NMT2) may be particularly useful in the prevention or treatment e.g. treatment of conditions associated with those species. For example, they may be particularly useful in the prevention or treatment e.g. treatment of a disease or disorder selected from malaria, leishmaniasis, and sleeping sickness.

For example, use of a selective NMT inhibitor may result in fewer side effects compared with use of a less selective compound. In one embodiment, NMT inhibitors are selective for a non-human NMT (e.g. *Plasmodium falciparum, Plasmodium vivax, Leishmania donovani, Trypanosoma brucei* and/or *Trypanosoma cruzi*) over human NMT (e.g. over human NMT1 and/or human NMT2). NMT inhibitors are considered selective if the ratio of human NMT $IC_{50}$ value to non-human NMT $IC_{50}$ value is greater than 5, suitably greater than 10, more suitably greater than 100, most suitably greater than 1000.

Other Diseases

In another embodiment, the compounds of the invention are for use in the prevention or treatment e.g. treatment of a disease or disorder that is selected from the group consisting of neurological diseases/disorders, ischemia, osteoporosis and diabetes. In a further embodiment, the compounds of the invention are for use in the prevention or treatment e.g. treatment of a disease or disorder that is selected from the group consisting of autoimmune diseases and inflammatory diseases.

Diagnosis

In one embodiment, the compound of the invention comprises an isotope atom, suitably a radioactive isotope atom. As defined herein, an isotope atom is an atom of an element that is not the most common naturally occurring isotope. Such compounds may find use as diagnostic agents for the diagnosis of a disease or disorder in which inhibition of NMT provides a therapeutic or prophylactic effect. Accordingly, the present invention also provides the use of a compound of the invention comprising an isotope atom, suitably a radioactive isotope atom, as a diagnostic agent for the diagnosis of a disease or disorder in which inhibition of NMT provides a therapeutic or prophylactic effect.

Doses and Formulations

The amount of active ingredient which is required to achieve a therapeutic effect will, of course, vary with the particular compound, the route of administration, the subject under treatment, including the type, species, age, weight, sex, and medical condition of the subject and the renal and hepatic function of the subject, and the particular disorder or disease being treated, as well as its severity. An ordinarily skilled physician, veterinarian or clinician can readily determine and prescribe the effective amount of the drug required to prevent, counter or arrest the progress of the condition.

Oral dosages of the present invention, when used for the indicated effects, will range between about 0.01 mg per kg of body weight per day (mg/kg/day) to about 500 mg/kg/day, suitably 0.01 mg per kg of body weight per day (mg/kg/day) to 100 mg/kg/day, and most suitably 0.05 to 50 mg/kg/day, for adult humans, for example 0.05, 0.1, 0.25, 0.5, 0.75, 1, 2, 3, 5, 10, 15, 20, 25, 30, 35, 40, 45 or 50 mg/kg/day. For oral administration, the compositions are suitably provided in the form of tablets or other forms of presentation provided in discrete units containing 0.01, 0.05, 0.1, 0.25 0.5, 1.0, 2.0, 2.5, 5.0, 10.0, 15.0, 25.0, 50.0, 100, 150, 200, 250 and 500 milligrams of the active ingredient for the symptomatic adjustment of the dosage to the patient to be treated. A medicament typically contains from about 0.01 mg to about 500 mg of the active ingredient, suitably from about 1 mg to about 250 mg of active ingredient, for example from about 1 mg to about 150 mg of active ingredient. Intravenously, the most suitable doses will range from about 0.1 to about 10 mg/kg/minute during a constant rate infusion. Advantageously compounds of the present invention may be administered in a single daily dose, or the total daily dosage may be administered in divided doses of two, three or four times daily.

Furthermore, compounds of the present invention can be administered in intranasal form via topical use of suitable intranasal vehicles, or via transdermal routes, using those forms of transdermal skin patches well known to those of ordinary skill in the art. To be administered in the form of a transdermal delivery system, the dosage administration will, of course, be continuous rather than intermittent throughout the dosage regimen.

While it is possible for the active ingredient to be administered alone, it is suitable for it to be present in a pharmaceutical formulation or composition. Accordingly, the invention provides a pharmaceutical formulation or composition comprising a compound of the invention, and a pharmaceutically acceptable diluent, excipient or carrier (collectively referred to herein as "carrier" materials). Pharmaceutical compositions of the invention may take the form of a pharmaceutical formulation as described below.

The pharmaceutical formulations according to the invention include those suitable for oral, parenteral (including subcutaneous, intradermal, intramuscular, intravenous [bolus or infusion], and intraarticular), intranasal (also known as nasal administration), inhalation (including fine particle dusts or mists which may be generated by means of various types of metered dose pressurized aerosols, nebulizers or insufflators) insufflation, rectal, intraperitoneal and topical (including dermal, buccal, sublingual, and intraocular) administration, although the most suitable route may depend upon, for example, the condition and disorder of the recipient.

In certain embodiments a compound of the invention is administered by intranasal, inhalation (including fine particle dusts or mists which may be generated by means of various types of metered dose pressurized aerosols, nebulizers or insufflators) or insufflation administration. Such embodiments are especially suitable for, for example, the treatment of a picornaviral infection, such as human rhinovirus infection. Such a method of administration allows for low doses of a compound of the invention to be administered, which can lead to a reduction in side-effects. For example, a daily dose of 10 to 0.01 μg, suitably 1 to 0.01 μg, and more suitably in the region of as low as 0.1 μg (100 ng) of a compound of the invention may be used.

The formulations may conveniently be presented in unit dosage form and may be prepared by any of the methods well known in the art of pharmacy. All methods include the step of bringing the active ingredient into association with the carrier which constitutes one or more accessory ingredients. In general the formulations are prepared by uniformly and intimately bringing into association the active ingredient with liquid carriers or finely divided solid carriers or both and then, if necessary, shaping the product into the desired formulation.

Formulations of the present invention suitable for oral administration may be presented as discrete units such as capsules, cachets, pills or tablets each containing a predetermined amount of the active ingredient; as a powder or granules; as a solution or a suspension in an aqueous liquid or a non-aqueous liquid, for example as elixirs, tinctures, suspensions or syrups; or as an oil-in-water liquid emulsion or a water-in-oil liquid emulsion. The active ingredient may also be presented as a bolus, electuary or paste.

A tablet may be made by compression or moulding, optionally with one or more accessory ingredients. Compressed tablets may be prepared by compressing in a suitable machine the active ingredient in a free-flowing form such as a powder or granules, optionally mixed with a binder, lubricant, inert diluent, lubricating, surface active or dispersing agent. Moulded tablets may be made by moulding in a suitable machine a mixture of the powdered compound moistened with an inert liquid diluent. The tablets may optionally be coated or scored and may be formulated so as to provide slow or controlled release of the active ingredient therein. The compounds of the invention can, for example, be administered in a form suitable for immediate release or extended release. Immediate release or extended release can be achieved by the use of suitable pharmaceutical compositions comprising the compounds of the invention, or, particularly in the case of extended release, by the use of devices such as subcutaneous implants or osmotic pumps. The compounds of the invention may also be administered liposomally.

Exemplary compositions for oral administration include suspensions which can contain, for example, microcrystalline cellulose for imparting bulk, alginic acid or sodium alginate as a suspending agent, methylcellulose as a viscosity enhancer, and sweeteners or flavoring agents such as those known in the art; and immediate release tablets which can contain, for example, microcrystalline cellulose, dicalcium phosphate, starch, magnesium stearate, calcium sulfate, sorbitol, glucose and/or lactose and/or other excipients, binders, extenders, disintegrants, diluents and lubricants such as those known in the art. Suitable binders include starch, gelatin, natural sugars such as glucose or beta-lactose, corn sweeteners, natural and synthetic gums such as acacia, tragacanth or sodium alginate, carboxymethylcellulose, polyethylene glycol, waxes and the like. Disintegrators include without limitation starch, methylcellulose, agar, bentonite, xanthan gum and the like. The compounds of the invention can also be delivered through the oral cavity by sublingual and/or buccal administration. Molded tablets, compressed tablets or freeze-dried tablets are exemplary forms which may be used. Exemplary compositions include those formulating the present compounds with fast dissolving diluents such as mannitol, lactose, sucrose and/or cyclodextrins. Also included in such formulations may be high molecular weight excipients such as celluloses (avicel) or polyethylene glycols (PEG). Such formulations can also include an excipient to aid mucosal adhesion such as hydroxy propyl cellulose (HPC), hydroxy propyl methyl cellulose (HPMC), sodium carboxy methyl cellulose (SCMC), maleic anhydride copolymer (e.g., Gantrez), and agents to control release such as polyacrylic copolymer (e.g. Carbopol 934). Lubricants, glidants, flavors, coloring agents and stabilizers may also be added for ease of fabrication and use. Lubricants used in these dosage forms include sodium oleate, sodium stearate, magnesium stearate, sodium benzoate, sodium acetate, sodium chloride and the like. For oral administration in liquid form, the oral drug components can be combined with any oral, non-toxic, pharmaceutically acceptable inert carrier such as ethanol, glycerol, water, and the like.

The compounds of the present invention can also be administered in the form of liposome delivery systems, such as small unilamellar vesicles, large unilamellar vesicles and multilamellar vesicles. Liposomes can be formed from a variety of phospholipids, 1,2-dipalmitoylphosphatidylcholine, phosphatidyl ethanolamine (cephaline), or phosphatidylcholine (lecithin).

Formulations for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents. The formulations may be presented in unit-dose or multi-dose containers, for example sealed ampoules and vials, and may be stored in a freeze-dried (lyophilised) condition requiring only the addition of the sterile liquid carrier, for example saline or water-for-injection, immediately prior to use. Extemporaneous injection solutions and suspensions may be prepared from sterile powders, granules and tablets of the kind previously described. Exemplary compositions for parenteral administration include injectable solutions or suspensions which can contain, for example, suitable non-toxic, parenterally acceptable diluents or solvents, such as mannitol, 1,3-butanediol, water, Ringer's solution, an isotonic sodium chloride solution, or other suitable dispersing or wetting and suspending agents, including synthetic mono- or diglycerides, and fatty acids, including oleic acid, or Cremaphor.

Exemplary compositions for intranasal, aerosol or inhalation administration include solutions in saline, which can contain, for example, benzyl alcohol or other suitable preservatives, absorption promoters to enhance bioavailability, and/or other solubilizing or dispersing agents such as those known in the art.

Formulations for rectal administration may be presented as a suppository with the usual carriers such as cocoa butter, synthetic glyceride esters or polyethylene glycol. Such carriers are typically solid at ordinary temperatures, but liquefy and/or dissolve in the rectal cavity to release the drug.

Formulations for topical administration in the mouth, for example buccally or sublingually, include lozenges comprising the active ingredient in a flavoured basis such as sucrose and acacia or tragacanth, and pastilles comprising the active ingredient in a basis such as gelatin and glycerine or sucrose and acacia. Exemplary compositions for topical administration include a topical carrier such as Plastibase (mineral oil gelled with polyethylene).

Suitable unit dosage formulations are those containing an effective dose, as hereinbefore recited, or an appropriate fraction thereof, of the active ingredient.

It should be understood that in addition to the ingredients particularly mentioned above, the formulations of this invention may include other agents conventional in the art having regard to the type of formulation in question, for example those suitable for oral administration may include flavouring agents.

Whilst a compound of the invention may be used as the sole active ingredient in a medicament, it is also possible for a compound of the invention to be used in combination with one or more further therapeutic agents. Accordingly, the present invention also provides a compound of the invention, together with a further therapeutic agent. The further therapeutic ingredient may be for simultaneous, sequential or separate administration. The invention also provides a kit of parts comprising: (a) a first pharmaceutical composition comprising a compound of the invention and a pharmaceutically acceptable carrier; and (b) a second pharmaceutical composition comprising a further therapeutic agent, and a pharmaceutically acceptable carrier.

Such further therapeutic agents may be further NMT inhibitors, for example a further compound according to the invention (i.e. a further compound of formula (I) (or (Ia) to (Ip)), or a pharmaceutically acceptable ester, amide or carbamate or salt thereof, including salts of such esters, amides or carbamates).

The compounds of the invention can be used in combination with one or more further therapeutic agents useful for the treatment or prevention of a disease or disorder in which inhibition of N-myristoyl transferase provides a therapeutic or prophylactic effect (for example agents useful for the treatment or prevention of hyperproliferative disorders, viral infections, microbial infections, neurological diseases, ischemia, osteoporosis, diabetes, autoimmune diseases and inflammatory diseases, and in particular hyperproliferative disorders (e.g. cancer) and viral infections (e.g. RV or HIV infection)). The individual components of such combinations can be administered separately at different times during the course of therapy or concurrently in divided or single combination forms. The present invention is therefore to be understood as embracing all such regimes of simultaneous or alternating treatment and the term "administering" is to be interpreted accordingly. It will be understood that the scope of combinations of a compound of the invention with other therapeutic agents useful for treating or prevention of a disease or disorder in which inhibition of N-myristoyl transferase provides a therapeutic or prophylactic effect includes in principle any combination with any pharmaceutical composition useful for treating or prevention of a disease or disorder in which inhibition of N-myristoyl transferase provides a therapeutic or prophylactic effect.

A further therapeutic agent, when employed in combination with the compounds of the present invention, may be used, for example, in those amounts indicated in the Physicians' Desk Reference (PDR) for that agent, or as otherwise determined by one of ordinary skill in the art. Where the compounds of the invention are utilized in combination with one or more further therapeutic agent(s), either concurrently or sequentially, the following combination ratios and dosage ranges are suitable: when combined with a further therapeutic agent, the compound of the invention may for example be employed in a weight ratio to the further therapeutic agent within the range from about 10:1 to about 1:10.

In one embodiment, where the compound of the invention is for the treatment or prevention of cancer, the compound of the invention may be utilized in combination with one or more further therapeutic agent(s), either concurrently or sequentially, for the treatment of cancer.

In one embodiment, where the compound of the invention is for the treatment or prevention of RV (also known as the common cold), the compound of the invention may be utilized in combination with one or more further therapeutic agent(s), either concurrently or sequentially, for the treatment of RV and/or for the treatment of asthma and/or for the treatment of chronic obstructive pulmonary disease (COPD).

In one embodiment, for example where the compound of the invention is for the treatment or prevention of microbial infection, and in particular a protozoan invention, the compound of the invention is administered in combination with an effective amount of a further anti-protozoan agent, for example (i) an anti-malarial agent; and/or (ii) an anti-leishmaniasis agent; and/or (iii) an anti-human African trypanosomiasis or anti-American trypanosomiasis agent. One or more of those further anti-protozoan agents may be used in combination with a compound of the invention.

The invention also provides a kit of parts comprising: (a) a first pharmaceutical composition comprising a compound of the invention and a pharmaceutically acceptable carrier; and (b) a second pharmaceutical composition comprising a further therapeutic agent, suitably a further N-myristoyl transferase inhibitor, and a pharmaceutically acceptable carrier.

Synthesis of Compounds of the Invention Numerous synthetic routes to the compounds of the present invention can be devised by any person skilled in the art and the exemplified synthetic routes described below do not limit the invention. Many methods exist in the literature for the synthesis of heterocycles, for example: Joule, J. A.; Mills, K., Heterocyclic Chemistry, 2010, 5$^{th}$ Edition, Pub. Wiley. A number of possible synthetic routes are exemplified below. Where appropriate, any initially produced compound according to the invention can be converted into another compound according to the invention by known methods. General Synthesis Schemes The following synthetic schemes detail synthetic routes to compounds of the invention and intermediates in the synthesis of such compounds. In the following schemes, reactive groups can be protected with protecting groups and deprotected according to established techniques well known to the skilled person.

Compounds may be prepared by the general methods outlined hereinafter. In the following description, and unless otherwise stated, references to all groups such as groups $R^1$, $R^2$, $R^3$, $R^{5a}$, $R^{5b}$, $R^{5c}$, $R^{5d}$, $R^6$, $R^7$, $R^8$, $R^9$, $R^{12}$, $R^{13}$, $X^1$, $X^2$, m, p, r, $n_1$, $n_2$ and Z have the meanings as previously defined for the compound of formula (I)

Scheme 1

(I)

$R^{12}CHO$
or
$CH_2O$ (I)

Compounds of formula (I) wherein $R^{12}$ is $C_{1-6}$alkyl may be prepared by reductive amination. In such a case, another compound of formula (I), wherein $R^{12}$ is H (as shown above), is reacted with an aldehyde such as formaldehyde, in the presence of a reducing agent e.g. $NaCNBH_3$.

Scheme 2

(II)

(I)

Compounds of formula (I) wherein $R^{12}$ is H may be prepared by reacting a compound of formula (11), wherein Q is a nitrogen protecting group such as tert-butyloxycarbonyl (BOC), with an acid such as trifluoroacetic acid.

Scheme 3

(V)

(IV)

-continued (II)

Compounds of formula (II) may be obtained by reacting a compound of formula (V), wherein D is halo such as chloro, with a compound of formula (IV), wherein Q is a nitrogen protecting group such as tert-butyloxycarbonyl (BOC), in the presence of an alcohol, such as n-BuOH, under microwave irradiation.

Alternatively, compounds of formula (V) and (IV) may be reacted under transition metal catalysed conditions, using a palladium catalyst such as palladium(0)bis(dibenzylide-neacetone), (Pd$_2$(dba)$_3$), a ligand such as SPhos (2-dicyclo-hexylphosphino-2',6'-dimethoxybiphenyl) and a base such as caesium carbonate.

Scheme 4

-continued (V)

Compounds of formula (V) may be prepared by reacting a compound of formula (VI) with a compound of formula (VII) in the presence of a base e.g. triethylamine and a coupling agent e.g. propylphosphonic anhydride.

Scheme 5

(IX)

(VIII)

(VII)

Compounds of formula (VII) may be prepared by reacting a compound of formula (VIII) with a compound of formula (IX), wherein D and E are each independently halo, such as chloro.

Scheme 6

(X)

(XI)

(I)

Compounds of formula (I) wherein $R^{12}$ is H may alternatively be obtained by reacting a compound of formula (X) with a compound of formula (XI), wherein T is $C_{1-6}$alkyl, such as methyl, and Q is a nitrogen protecting group such as tert-butyloxycarbonyl (BOO), in the presence of a base, such as triethylamine. Compounds of formula (I) wherein $R^{12}$ is $C_{1-6}$alkyl may be obtained using the reductive amidation method described herein.

Scheme 7

(XIV)

-continued (XIII)

(IV)

(XII)

(XI)

Compounds of formula (XI) may be obtained by reacting compounds of formula (XII), wherein T is $C_{1-6}$alkyl, such as methyl, under oxidising conditions, using an oxidant such as meta-chloroperoxybenzoic acid (m-CPBA). Compounds of formula (XII) may be obtained by reacting a compound of formula (XIII), wherein D is halo such as chloro and T is $C_{1-6}$alkyl such as methyl, with a compound of formula (IV) wherein Q is a nitrogen protecting group such as tert-butyloxycarbonyl (BOC), in the presence of an alcohol, such as n-BuOH, under microwave irradiation. Compounds of formula (XIII), wherein D is halo such as chloro and T is $C_{1-6}$alkyl such as methyl, may be prepared by reacting compounds of formula (XIV), wherein D and E are each independently halo, such as chloro, with a thiolating agent, such as sodium thiomethoxide.

Scheme 8

(XVI)

(XVII)

-continued (XV)

(X)

Compounds of formula (X) may be obtained by reacting a compound of formula (XV), wherein Q is a nitrogen protecting group, such as tert-butyloxycarbonyl (BOC) with an acid, such as trifluoroacetic acid. Compounds of formula (XV) may be obtained by reacting a compound of formula (XVI) with a compound of formula (XVII) in the presence of a base such as triethylamine, and a coupling agent such as propylphosphonic anhydride.

Compounds wherein Z is may be prepared, using analogous methods to those described above, for example:

Scheme 9

(V')

(II')

Compounds of formula (II') may be prepared by reacting a compound of formula (V') and a compound of formula (IV') under conditions described herein e.g. those of Scheme 3. Functional groups within Z may be manipulated to provide compounds of formula (I) using conditions and methods known to the person skilled in the art or described below.

Scheme 10

(X)

-continued (I)

Compounds of formula (I) may be obtained by reacting a compound of formula (X) with a compound of formula (XI') under condition described herein e.g. those of Scheme 6.

Scheme 11

(XIV)

(XIII)

(XII')  (XI')

Compounds of formula (XI') may be obtained by reacting compounds of formula (XII'), wherein T is $C_{1-6}$alkyl, such as methyl, under oxidising conditions, using an oxidant such as meta-chloroperoxybenzoic acid (m-CPBA). Compounds of formula (XII') may be obtained by reacting a compound of formula (XIII), wherein D is halo such as chloro and T is $C_{1-6}$alkyl such as methyl, with a compound of formula (IV') in the presence of an alcohol, such as n-BuOH, under microwave irradiation. Compounds of formula (XIII) may be obtained using methods described herein e.g. those of Scheme 7.

Processes of the Invention

According to further aspects of the present invention are provided processes for the preparation of compounds of formula (I) or an ester, amide, carbamate or salt thereof such as a pharmaceutically acceptable ester, amide, carbamate or salt thereof, including salts (such as pharmaceutically acceptable salts) of such esters, amides or carbamates, as well as processes for preparing intermediates or salts thereof in the synthesis of compounds of formula (I).

The processes of the invention are described above and include any individual step of a multi-step scheme.

Intermediates of the Invention

The invention also provides novel intermediates used in the synthesis of compounds of formula (I), such as the compounds of formula (II) to (XVI). Particular intermediates of interest are those of the following general formulae, wherein the variable groups and preferences are as defined previously for the compounds of formula (I), or are defined above.

Thus in one embodiment, there is a provided a compound selected from the group consisting of:

a compound of formula (II)

(II)

wherein $R^1$, $R^2$, $R^3$, $R^{5a}$, $R^{5b}$, $R^{5c}$, $R^{5d}$, $R^6$, $R^7$, $R^8$, $R^9$, $X^1$, $X^2$, m, p, r, $n_1$, $n_2$ and $R^{13}$ are as defined for the compound of formula (I), and Q is defined above;

a compound of formula (V)

(V)

wherein D is halo such as chloro and $R^1$, $R^2$, $R^3$, $R^{5a}$, $R^{5b}$, $R^{5c}$, $R^{5d}$, $R^6$, $R^7$, $R^8$, $R^9$, $X^1$, $X^2$, p, $n_1$ and $n_2$ are as defined for the compound of formula (I);

a compound of formula (VII)

(VII)

wherein D is halo such as chloro and $R^6$, $R^7$, $R^8$, $R^9$, p, $X^1$, $n_1$ and $n_2$ are as defined for the compound of formula (I);

a compound of formula (X)

(X)

wherein $R^1$, $R^2$, $R^3$, $R^{5a}$, $R^{5b}$, $R^{5c}$, $R^{5d}$, $R^6$, $R^7$, p, $X^2$, $n_1$ and $n_2$ are as defined for the compound of formula (I)

a compound of formula (XI)

(XI)

wherein Q is a nitrogen protecting group, such as such as tert-butyloxycarbonyl (BOC), T is $C_{1-3}$alkyl such as methyl, $R^8$, $R^9$, $R^{13}$, $X^1$, r and m are as defined for the compound of formula (I); and a compound of formula (XII)

(XII)

wherein Q is a nitrogen protecting group, such as such as tert-butyloxycarbonyl (BOC), T is $C_{1-6}$alkyl such as methyl, and $R^8$, $R^9$, $R^{13}$, $X^1$, r and m are as defined for the compound of formula (I).

Salts, such as pharmaceutically acceptable salts for such intermediates are also provided by the present invention.

EXAMPLES

The following compounds illustrate compounds of the invention or, where appropriate, compounds for use in the invention.

Hplc

The purity of certain examples was determined by analytical hplc using an Eclipse Extend or XDB 5 µm C18 (150×4.6 mm), Xbridge 5 µm C18 (100×4.6 mm), Zorbax Extend 5 µm C18 (150×4.6 mm), or Shimadzu L Column 2 ODS 5 µm C18 (150×4.6 mm) column using gradient elution of acetonitrile in water containing 10 mM ammonium acetate over 15 mins (HPLC B), 17 mins (B1) or 21 mins (B2). The purity certain of examples were determined by analytical hplc using a Poroshell 120 2.7 µm EC18 (100×4.6 mm), Luna Omega Polar 3 µm C18 (100×4.6 mm), Xbridge 5 µm C18 (150×4.6 mm) or Sunfire 5 µm C18 (100×4.6 mm) using gradient elution of acetonitrile in water containing 0.05% trifluoroacetic acid over 12 mins (HPLC A), 14 mins (A1) or 17 mins (A2). The purity of certain other examples was determined by analytical hplc using a Gemini NX 3 µm C18 (100×4.6 mm) column using gradient elution of acetonitrile in water containing 0.05% formic acid over 12 mins (A3). The hplc method used for each example is indicated below.

NMR $^1$H and $^{13}$C NMR spectra were recorded on 400 MHz and 101 MHz respectively Bruker AV instruments at room temperature unless specified otherwise and were referenced to residual solvent signals. Data are presented as follows: chemical shift in ppm, integration, multiplicity (br=broad, app=apparent, s=singlet, d=doublet, t=triplet, q=quartet, p=pentet, m=multiplet) and coupling constants in Hz.

Prep HPLC

Preparative HPLC was done on Waters auto purification instrument. Column name: YMC Triart Actus C18 (250×20 mm, 5p) operating at ambient temperature and flow rate of 16 mL/min. Mobile phase: A=20 mM Ammonium Bicarbonate in water, B=Acetonitrile; Gradient Profile: Mobile phase initial composition of 80% A and 20% B, then 70% A and 30% B in 3 min, then to 20% A and 80% B in 20 min, then to 5% A and 95% B in 21 min, and held at this composition up to 23 min for column washing, then returned to initial composition in 24 min and held till 26 min.

Prep TLC

Preparative TLC was carried out using TLC Silica gel 60 g F$_{254}$ Glass plates 20×20 cm (Merck).

Microwave

All microwave reactions were carried out on a CEM Discover (Model No. 908010) microwave reactor.

General Procedures

Boc Deprotection

A stirred solution of the Boc protected amine in DCM was treated with TFA (trifluoroacetic acid). The reaction mixture was stirred room temperature for 4 h. All volatiles were removed under reduced pressure and the product purified by LC-MS or preparative TLC.

Reductive Amination

A stirred solution of the secondary amine in MeOH was treated with aqueous formaldehyde solution (5 mol equiv) and the mixture was stirred at room temperature (RT) for 1 h. Sodium cyanoborohydride NaCNBH$_3$ (3 mol equiv) was added at 0° C. and the reaction mixture was stirred at RT for 16 h. The reaction mixture was quenched with NaHCO$_3$ solution and extracted with DCM. Organic layer was dried over Na$_2$SO$_4$ and concentrated under reduced pressure. The crude was purified over preparative TLC or LC-MS Diamine Displacement (Method A)

A solution of the 2-chloropyrimidine and the diamine (3 mol equiv) in n-butanol was treated with triethylamine (6 mol equiv) then heated to 160° C. for 160 minutes under microwave irradiation. The reaction mixture was evaporated under reduced pressure and the crude product was purified by LC-MS or preparative TLC.

Diamine Displacement (Method B)

A solution of the 2-chloropyridine or 2-chloropyrimidine, diamine (3 mol equiv) cesium carbonate (5 mol equiv) in DME was purged with argon for 10 mins before addition of a catalytic quantity of Pd$_2$(dba)$_3$ (0.05 equiv) and either 2-dicyclohexylphosphino-2',6'-dimethoxybiphenyl (SPhOs) or 4,5-Bis(diphenylphosphino)-9,9-dimethylxanthene (Xantphos) (1.2 equiv). After purging with argon for a further 5 mins, the mixture was heated to 120° C. overnight. The reaction mixture was extracted by EtOAc and washed by water and brine, dried over Na$_2$SO$_4$, and evaporated under vacuum. The crude product was then purified using column chromatography, LC-MS or preparative TLC.

Intermediate 1

1-(2,5-dichloropyrimidin-4-yl)-N-(2-{imidazo[1,2-a] pyridin-3-yl}propan-2-yl)azetidine-3-carboxamide Step 1

To a stirred solution of 2,4,5-trichloropyrimidine (6.0 g, 32.8 mmol) in a mixture of EtOH (20 mL) and water (50 mL) was added azetidine-3-carboxylic acid (3.31 g, 32.8 mmol) and the mixture was heated to reflux for 5 h. The reaction mixture was cooled to RT, filtered and the solid was collected. The solid was azeotroped with toluene to afford 1-(2,5-dichloropyrimidin-4-yl)azetidine-3-carboxylic acid (3.5 g, 43%) as a white solid. $^1$H NMR (DMSO-d$_6$) 12.8 (s, 1H), 8.15 (s, 1H), 4.0-4.8 (br. m 4H), 3.50 (m, 1H). LCMS m/z 248

Step 2

To a solution of 1-(2,5-dichloropyrimidin-4-yl)azetidine-3-carboxylic acid (3.5 g, 14.1 mmol) and 2-{imidazo[1,2-a]pyridin-3-yl}propan-2-amine (2.47 g, 14.1 mmol) in THF (40 mL) was added Et$_3$N (7.87 mL, 56 mmol). Propylphosphonic anhydride (T3PI, 50%, 12.4 mL, 42 mmol) was added and the reaction mixture stirred at RT for 2 days. The reaction mixture was quenched with NaHCO$_3$ solution and extracted with EtOAc. The organic layer was washed with water, dried over Na$_2$SO$_4$ and concentrated under reduced pressure to afford desired product 1-(2,5-dichloropyrimidin-4-yl)-N-(2-{imidazo[1,2-a]pyridin-3-yl}propan-2-yl)azetidine-3-carboxamide (4.0 g, 70%). $^1$H NMR (DMSO-d$_6$) 8.45 (d, 1H), 8.40 (s, 1H), 8.11 (s, 1H), 7.56 (d, 1H), 7.45 (s, 1H), 7.16-7.25 (m, 2H), 6.91 (t, 1H), 3.8-4.6 (br. m, 4H), 3.48 (m, 1H), 1.75 (s, 6H). LCMS m/z 405

Intermediate 2

1-(2-chloro-5-fluoropyridin-4-yl)-N-(2-{imidazo[1, 2-a]pyridin-3-yl}propan-2-yl)azetidine-3-carboxamide Step 1

Methyl 1-(2-chloro-5-fluoropyridin-4-yl)azetidine-3-carboxylate

A solution of 2-chloro-5-fluoro-4-iodopyridine (300 mg, 1.16 mmol), methyl azetidine-3-carboxylate. Trifluoroacetic acid (TFA) salt (267 mg, 1.16 mmol) and cesium carbonate (1.1 g, 3.5 mmol) in dioxane (5 mL) was purged with argon for 10 mins before addition of Pd$_2$(OAc)$_2$ (10.4 mg, 0.047 mmol) and XanthphOs (40.5 mg, 0.07 mmol). After purging with argon for a further 5 mins, the mixture was heated to 110° C. for 16 h. The reaction mixture was extracted by EtOAc and washed by water and brine, dried over Na$_2$SO$_4$, and evaporated under vacuum. The crude product was then purified using combiflash chromatography by elution with 3% MeOH in DCM to give methyl 1-(2-chloro-5-fluoro-pyridin-4-yl)azetidine-3-carboxylate (150 mg, 53%). LCMS MH$^+$ 245.

Step 2

1-(2-chloro-5-fluoropyridin-4-yl)azetidine-3-carboxylic acid

A solution of methyl 1-(2-chloro-5-fluoropyridin-4-yl) azetidine-3-carboxylate (300 mg, 1.22 mmol) in THF-methanol (10:1, 8.8 mL) was treated with lithium hydroxide (128 mg, 3.1 mmol) in water (1.5 mL). The resulting mixture was stirred at RT for 3 hours. The reaction mixture was cooled at 0° C., acidified with saturated citric acid solution and extracted with 5% MeOH in DCM. The organic layer dried over sodium sulphate and concentrated to afford 1-(2-chloro-5-fluoropyrimidin-4-yl)-3-methylazetidine-3-carboxylic acid (200 mg, 70%). $^1$H NMR (DMSO-d$_6$) 7.97 (d, 1H), 7.39 (br.s, 1H), 6.57 (d, 1H), 4.30 (m, 2H), 4.17 (m, 2H), 3.58 (m, 1H).

Step 3

1-(2-chloro-5-fluoropyridin-4-yl)-N-(2-{imidazo[1,2-a]pyridin-3-yl}propan-2-yl)azetidine-3-carboxamide To a solution of 1-(2-chloro-5-fluoropyridin-4-yl)azetidine-3-carboxylic acid (300 mg, 1.3 mmol) and 2-{imidazo[1,2-a]pyridin-3-yl}propan-2-amine (228 mg, 1.3 mmol) in THF (80 mL) was added Et$_3$N (0.725 mL, 5.2 mmol). T3P® (50%, 1.1 mL, 3.9 mmol) was added and stirred at RT for 1 day. The reaction mixture was quenched with NaHCO$_3$ solution and extracted with EtOAc. The organic layer was washed with water, dried over Na$_2$SO$_4$ and concentrated under reduced pressure and purified by column chromatography by elution with 2% MeOH in DCM to give 1-(2-chloro-5-fluoropyridin-4-yl)-N-(2-{imidazo[1,2-a]pyridin-3-yl}propan-2-yl)azetidine-3-carboxamide (150 mg, 30%). $^1$H NMR (DMSO-d$_6$) 8.44 (d, 1H), 8.39 (s, 1H), 7.92 (d, 1H), 7.56 (d, 1H), 7.45 (s, 1H), 7.39 (s, 1H), 7.21 (dd, 1H), 6.91 (t, 1H), 6.48 (d, 1H), 4.20 (m, 2H), 3.96 (m, 2H), 3.53 (m, 1H), 1.73 (s, 6H). LCMS m/z 388

Intermediate 3-31

All 2-chloropyrimidine intermediates were prepared from the appropriate 2,4-dichloropyrimidine, amino acid and {imidazo[1,2-a]pyridin-3-yl}methanamine using the same two-step method described above for Intermediate 1.

TABLE 1

| Intermediate | Structure | 2,4-DiCl Pyrimidine | Amino Acid | {Imidazo[1,2-a]pyridin-3-yl}methanamine or triazolo[4,3-a]pyridin-3-yl}methanamine |
|---|---|---|---|---|
| | | Starting materials | | |
| 3 | | | | |
| 4 | | | | |
| 5 | | | | |

TABLE 1-continued

| | | Starting materials | | |
|---|---|---|---|---|
| Inter-medi-ate | Structure | 2,4-DiCl Pyrimidine | Amino Acid | {Imidazo[1,2-a]pyridin-3-yl}methanamine or triazolo[4,3-a]pyridin-3-yl}methanamine |
| 6 | | | | |
| 7 | | | | |
| 8 | | | | |
| 9 | | | | |
| 10 | | | | |

TABLE 1-continued

| | | Starting materials | | |
| Inter-medi-ate | Structure | 2,4-DiCl Pyrimidine | Amino Acid | {Imidazo[1,2-a]pyridin-3-yl}methanamine or triazolo[4,3-a]pyridin-3-yl}methanamine |
|---|---|---|---|---|
| 11 | | | | |
| 12 | | | | |
| 13 | | | | |
| 14 | | | | |
| 15 | | | | |

TABLE 1-continued

| | | Starting materials | | |
|---|---|---|---|---|
| Inter-mediate | Structure | 2,4-DiCl Pyrimidine | Amino Acid | {Imidazo[1,2-a]pyridin-3-yl}methanamine or triazolo[4,3-a]pyridin-3-yl}methanamine |
| 16 | | | | |
| 17 | | | | |
| 18 | | | | |
| 19 | | | | |
| 20 | | | | |

TABLE 1-continued

| | | Starting materials | | |
|---|---|---|---|---|
| Inter-<br>medi-<br>ate | Structure | 2,4-DiCl<br>Pyrimidine | Amino Acid | {Imidazo[1,2-a]pyridin-3-<br>yl}methanamine or<br>triazolo[4,3-a]pyridin-3-<br>yl}methanamine |
| 21 | | | | |
| 22 | | | | |
| 23 | | | | |
| 24 | | | | |
| 25 | | | | |

TABLE 1-continued

| | | Starting materials | | {Imidazo[1,2-a]pyridin-3-yl}methanamine or triazolo[4,3-a]pyridin-3-yl}methanamine |
|---|---|---|---|---|
| Intermediate | Structure | 2,4-DiCl Pyrimidine | Amino Acid | |
| 26 | *(chemical structure)* | *(chemical structure)* | *(chemical structure)* | *(chemical structure)* |
| 30 | *(chemical structure)* | *(chemical structure)* | *(chemical structure)* | *(chemical structure)* |

Intermediate 20 was prepared using the conditions as Intermediate 1, step 2.

1-(2-chloro-5-fluoro pyrimidin-4-yl)-3-methylazetidine-3-carboxylic acid was prepared by the following route.

Step 1

Methyl 1-(2-chloro-5-fluoropyrimidin-4-yl)-3-methylazetidine-3-carboxylate

A stirred solution of methyl 3-methylazetidine carboxylate (491 mg, 3.0 mmol) in isopropyl alcohol (IPA, 7 mL) was treated with triethylamine (1.25 mL, 9 mmol) and 2,4-dichloro-5-fluoropyrimidine (500 mg, 3 mmol). The reaction mixture was refluxed for overnight then concentrated under reduced pressure and partitioned between ethyl acetate and aqueous $NaHCO_3$. The organic layer was concentrated under reduced pressure and was purified by column chromatography by elution with 30% EtOAC-hexane to afford methyl 1-(2-chloro-5-fluoropyrimidin-4-yl)-3-methylazetidine-3-carboxylate (300 mg, 39%) as a colourless gum. $^1H$ NMR (DMSO-$d_6$) 8.13 (d, 1H), 4.45 (m, 2H), 4.07 (m, 2H), 3.70 (s, 3H), 1.53 (s, 3H).

Step 2

1-(2-chloro-5-fluoropyrimidin-4-yl)-3-methylazetidine-3-carboxylic acid

A solution of 1-(2-chloro-5-fluoropyrimidin-4-yl)-3-methylazetidine-3-carboxylate (300 mg, 1.16 mmol) in THF-water (4:1, 15 mL) was cooled at 0° C. and treated with methanol (0.02 mL) and lithium hydroxide (121 mg, 2.9 mmol). The resulting mixture was stirred at RT for 3 h. The reaction mixture was cooled at 0° C., acidified with saturated citric acid solution and extracted with DCM. The organic layer dried over sodium sulphate and concentrated to afford 1-(2-chloro-5-fluoropyrimidin-4-yl)-3-methylazetidine-3-carboxylic acid (280 mg, 98%) as a colourless solid.

$^1H$ NMR (DMSO-$d_6$) 12.94 (s, 1H), 8.11 (d, 1H), 4.41 (m, 2H), 4.04 (m, 2H), 3.70 (s, 3H), 1.51 (s, 3H).

Intermediate 24

Step 1 tert-butyl (3R)-3-[(2-{imidazo[1,2-a]pyridin-3-yl}propan-2-yl)carbamoyl]pyrrolidine-1-carboxylate (R)-1-(t-butoxycarbonyl)pyrrolidine-3-carboxylic acid (300 mg, 1.67 mmol) and 2-{imidazo[1,2-a]pyridin-3-yl}propan-2-amine (293 mg, 1.67 mmol) were dissolved in THF (6 mL) and treated with triethylamine (0.93 mL, 6.69 mmol) followed by T3P® (50% solution, 1.46 mL, 5.0 mmol). The mixture was stirred at room temperature overnight, then quenched with $NaHCO_3$ solution and extracted with EtOAc. The organic layer was washed with water, dried over $Na_2SO_4$ and concentrated under reduced pressure to afford tert-butyl (3R)-3-[(2-{imidazo[1,2-a]pyridin-3-yl}propan-2-yl)carbamoyl]pyrrolidine-1-carboxylate (120 mg, 19%). $^1H$ NMR (DMSO-$d_6$) 8.44 (d, 1H), 8.30 (s, 1H), 7.55 (d, 1H), 7.42 (s, 1H), 7.19 (dd, 1H), 6.88 (t, 1H), 5.76 (s, 1H), 2.90-3.40 (m, 6H), 1.93 (m, 1H), 1.70 (s, 6H), 1.36 (s, 9H).

Step 2

((3R)—N-(2-{imidazo[1,2-a]pyridin-3-yl}propan-2-yl)pyrrolidine-3-carboxamide TFA Salt tert-Butyl(3R)-3-[(2-{imidazo[1,2-a]pyridin-3-yl}propan-2-yl)carbamoyl]pyrrolidine-1-carboxylate (200 mg, 0.54 mmol) was dissolved in DCM (5 mL and treated with TFA (0.4 mL). The mixture was stirred at room temperature for 4 h and evaporated under reduced pressure. The crude product ((3R)—N-(2-{imidazo[1,2-a]pyridin-3-yl}propan-2-yl)pyrrolidine-3-carboxamide TFA salt, 207 mg) was used without purification Step 3

(3R)-1-(2,5-dichloropyrimidin-4-yl)-N-(2-{imidazo[1,2-a]pyridin-3-yl}propan-2-yl)pyrrolidine-3-carboxamide The crude product from Step 2 was dissolved in isopropanol (6 mL) and treated with 2,4,5-trichloropyrimidine (150 mg, 0.8 mmol) followed by triethylamine (0.23 mL, 1.64 mmol). The reaction mixture was heated to 100° C. for 16 h, concentered and extracted with EtOAc and washed by brine. The crude was purified by column chromatography on silica 5% EtOAc-Hexane) to afford the desired product (3R)-1-(2,5-dichloropyrimidin-4-yl)-N-(2{imidazo[1,2-a]pyridin-3-yl}propan-2-yl)pyrrolidine-3-carboxamide (125 mg, 36%) $^1$H NMR (DMSO-d$_6$) 8.48 (d, 1H), 8.42 (s, 1H), 8.13 (s, 1H), 7.56 (d, 1H), 7.44 (s, 1H), 7.21 (dd, 1H), 6.90 (t, 1H), 3.87 (m, 1H), 3.65-3.75 (m, 3H), 3.06 (m, 1H), 2.09 (m, 1H), 1.86 (m, 1H), 1.72 (s, 6H).

Intermediate 23 was prepared from (S)-1-(t-butoxycarbonyl)pyrrolidine-3-carboxylic acid using the same route as Intermediate 24.

Intermediate 27 (1-(2-chloro-5-fluoropyrimidin-4-yl)-N-(2-{imidazo[1,2-a]pyridin-3-yl}propan-2-yl)-N-methylazetidine-3-carboxamide) was prepared from Intermediate 7.

Intermediate 27

(1-(2-chloro-5-fluoropyrimidin-4-yl)-N-(2-{imidazo[1,2-a]pyridin-3-yl}propan-2-yl)-N-methylazetidine-3-carboxamide Intermediate 28

1-(2,5-dichloropyrimidin-4-yl)-N-(2-{imidazo[1,2-a]pyridin-3-yl}propan-2-yl)-N-methylazetidine-3-carboxamide A solution of (1-(2-chloro-5-fluoropyrimidin-4-yl)-N-(2{imidazo[1,2-a]pyridin-3-yl}propan-2-yl)-azetidine-3-carboxamide) (Intermediate 7, 350 mg, 0.9 mmol) in THF/DME (1:1, 6 mL) was cooled to 0° C. and treated with sodium hydride (60%, 55 mg, 1.35 mmol). The mixture was maintained at 0° C. for 30 min and them treated with iodomethane (0.067 mL, 1.08 mmol), and stirred for a further hour. The reaction mixture was quenched with water and extracted with EtOAc. The organic extract was washed with brine, dried over Na$_2$SO$_4$ and concentrated under reduced pressure to give (1-(2-chloro-5-fluoropyrimidin-4-yl)-N-(2-{imidazo[1,2-a]pyridin-3-yl}propan-2-yl)-N-methylazetidine-3-carboxamide) (240 mg, 66%) $^1$H NMR (DMSO-d$_6$) 8.27 (d, 1H), 8.10 (d, 1H), 7.55 (d, 1H), 7.46 (s, 1H), 7.19 (dd, 1H), 6.87 (t, 1H), 4.2-4.4 (m, 4H), 3.90 (m, 1H), 2.75 (s, 3H), 1.80 (s, 6H).

Intermediate 28 was prepared from Intermediate 1 using the same route as Intermediate 27.

Intermediate 29 was prepared from 2,5-dichloro-4-iodopyridine using the same route as Intermediate 2.

Intermediate 2

Intermediate 29

Preparation of Building Blocks

All of the building blocks were obtained from commercial sources or using literature methods with the exception of the following building block compounds:

2-{imidazo[1,2-a]pyridin-3-yl}propan-2-amine

Step 1

A mixture of 2-aminopyridine (11 g, 117 mmol) in DMF dimethyl acetal (23.3 mL, 175 mmol) was stirred at 100° C. for 16 h. The reaction mixture was evaporated and the crude compound was dissolved in EtOH (60 mL) and treated with chloroacetone (10.6 mL, 132 mmol). The reaction mixture was stirred at RT for 16 h. The reaction mixture was quenched with saturated NaHCO$_3$ solution and extracted with EtOAc and washed with water, brine, dried over Na$_2$SO$_4$ and concentrated under reduced pressure. The crude was purified by column chromatography (100-200 mesh silica 1% MeOH-DCM) to afford 1-{imidazo[1,2-a]pyridin-3-yl}ethan-1-one (9.0 g, 48%) $^1$H NMR (CDCl$_3$) 9.63 (d, 1H), 8.33 (s, 1H), 7.74 (d, 1H), 7.48 (dd, 1H), 7.07 (t, 1H), 2.60 (s, 3H).

Step 2

To a stirred solution of 1-{imidazo[1,2-a]pyridin-3-yl}ethan-1-one (7.0 g, 43.7 mmol) in THF (250 mL) was added MeMgBr (3M in ether, 30 mL, 90 mmol) at −20° C. and the reaction was stirred at RT for 3 h. The reaction mixture was quenched with NH$_4$Cl solution and extracted with EtOAc.

The organic layer was washed with brine, dried over Na$_2$SO$_4$ and concentrated under reduced pressure. The crude was purified through column (silica gel, 100-200 mesh, 2.5% MeOH-DCM to afford 2-{imidazo[1,2-a]pyridin-3-yl}propan-2-ol (6.0 g, 78%) $^1$H NMR (DMSO-d$_6$) 8.73 (d, 1H), 7.54 (d, 1H), 7.39 (s, 1H), 7.21 (dd, 1H), 6.89 (t, 1H), 5.37 (s, 1H), 1.61 (s, 6H). LCMS m/z 177

Step 3

To a solution of 2-{imidazo[1,2-a]pyridin-3-yl}propan-2-ol (6.0 g, 34 mmol) in TFA (90 mL) was added sodium azide (11.07 g, 170 mmol) at 0° C. and the reaction mixture was stirred at RT for 16 h. The reaction mixture was basified with K$_2$CO$_3$ solution and extracted with EtOAc. The organic layer was dried over Na$_2$SO$_4$ and concentrated under reduced pressure to give 3-(2-azidopropan-2-yl)imidazo[1,2-a]pyridine (5.3 g, 77%). $^1$H NMR (CDCl$_3$) 8.46 (d, 1H), 7.63 (d, 1H), 7.52 (s, 1H), 7.22 (dd, 1H), 6.85 (t, 1H), 1.78 (s, 6H). LCMS m/z 191.

Step 4

A solution of 3-(2-azidopropan-2-yl)imidazo[1,2-a]pyridine (5.5 g, 27.3 mmol) in MeOH (110 mL) was degassed with argon for 15 min. Then Pd—C (200 mg) was added and the reaction was stirred under H$_2$ balloon for 30 min. The reaction mixture was filtered through Celite™ and the filtrate was concentrated under reduced pressure to afford 2-{imidazo[1,2-a]pyridin-3-yl}propan-2-amine (4.75 g, 99%) $^1$H NMR (CDCl$_3$) 8.96 (d, 1H), 7.56 (d, 1H), 7.41 (s, 1H), 7.12 (dd, 1H), 6.74 (t, 1H), 1.64 (s, 6H), 1.50 (br, s, 2H). LCMS m/z 176

2-{6-Methylimidazo[1,2-a]pyridin-3-yl}propan-2-amine and 2-{8-fluoroimidazo[1,2-a]pyridin-3-yl}propan-2-amine were prepared from (5-methylpyridin-2-yl)amine and (3-fluoropyridin-2-yl)amine, respectively, by the same 4-step method as was used to prepare 2-{imidazo[1,2-a]pyridin-3-yl}propan-2-amine.

Preparation of Examples 1-112

Example 1

1-{5-chloro-2-[(3R)-3-methylpiperazin-1-yl]pyrimidin-4-yl}-N-(2-{imidazo[1,2-a]pyridin-3-yl}propan-2-yl)azetidine-3-carboxamide Step 1

A stirred solution of 1-(2,5-dichloropyrimidin-4-yl)-N-(2-{imidazo[1,2-a]pyridin-3-yl}propan-2-yl)azetidine-3-carboxamide (Intermediate 1, 60 mg, 0.148 mmol) and ((R)-1-N-Boc-2-methylpiperazine (148 mg, 0.74 mmol) in n-BuOH (0.8 mL) was heated under microwave irradiation at 120° C. for 30 min. The reaction mixture was cooled to RT and concentrated under reduced pressure. The crude was then purified over prep TLC (3% MeOH in EtOAc) to give tert-butyl (2R)-4-(5-chloro-4-{3-[(2-{imidazo[1,2-a]pyridin-3-yl}propan-2-yl)carbamoyl]azetidin-1-yl}pyrimidin-2-yl)-2-methylpiperazine-1-carboxylate as a white solid (42 mg, 50%). LCMS MH$^+$ 569.

Step 2

A stirred solution of tert-butyl (2R)-4-(5-chloro-4-{3-[(2-{imidazo[1,2-a]pyridin-3-yl}propan-2-yl)carbamoyl]azetidin-1-yl}pyrimidin-2-yl)-2-methylpiperazine-1-carboxylate (42 mg, 0.074 mmol) in DCM (1 mL) was treated with TFA (0.057 mL, 0.74 mmol). The reaction mixture was stirred room temperature for 4 h. The crude was dissolved in MeOH and loaded on an Isolute® SCX column. The column was washed with MeOH. Then compound was then eluted with NH$_3$-MeOH and the collected fractions were concentrated under reduced pressure to give (2R)-4-(-{5-chloro-2-[(3R)-3-methylpiperazin-1-yl]pyrimidin-4-yl}-N-(2-{imidazo[1,2-a]pyridin-3-yl}propan-2-yl)azetidine-3-carboxamide as off white solid (33 mg, 95.35%). $^1$H NMR (400 MHz, DMSO-d$_6$) δ 8.44 (d, 1H), 8.37 (s, 1H), 7.79 (s, 1H), 7.56 (d, 1H), 7.44 (s, 1H), 7.18 (t, 1H), 6.88 (t, 1H), 4.32-4.22 (m, 4H), 4.05-4.01 (m, 2H), 3.47-3.40 (m, 1H), 2.91 (d, 1H), 2.74-2.66 (m, 1H), 2.62-2.54 (m, 2H), 2.40-2.32 (m, 1H), 1.72 (s, 6H), 0.99 (d, 3H). HPLC RT (B2) 7.23 min; LCMS MH$^+$ 469.

Example 2

1-(5-chloro-2-[(2S)-2,4-dimethylpiperazin-1-yl]pyrimidin-4-yl)-N-(2-{imidazo[1,2-a]pyridin-3-yl}propan-2-yl)azetidine-3-carboxamide A solution of 1-(2,5-dichloropyrimidin-4-yl)-N-(2-{imidazo[1,2-a]pyridin-3-yl}propan-2-yl)azetidine-3-carboxamide (Intermediate 1, 50 mg, 0.12 mmol) and [(3S)-1,3-dimethylpiperazine bis-TFA salt (211 mg, 0.61 mmol) in n-butanol (0.7 mL) was treated with triethylamine (0.17 mL, 1.23 mmol) then heated to 160° C. for 160 minutes under microwave irradiation. The reaction mixture was evaporated under reduced pressure and the crude product was purified by preparative TLC by elution with 9% MeOH in DCM to give the 1-{5-chloro-2-[(2S)-2,4-dimethylpiperazin-1-yl]pyrimidin-4-yl}-N-(2-{imidazo[1,2-a]pyridin-3-yl}propan-2-yl)azetidine-3-carboxamide as a light yellow solid (27 mg, 45%). $^1$H NMR (400 MHz, DMSO-d$_6$) δ 8.41 (d, 1H), 8.33

(s, 1H), 7.77 (s, 1H), 7.53 (d, 1H), 7.41 (s, 1H), 7.16 (dd, 1H), 6.85 (t, 1H), 4.58 (m, 1H), 4.15-4.20 (m, 3H), 4.05 (m 2H), 3.41 (t, 1H), 2.93 (t, 1H), 2.73 (m, 1H), 2.60 (m, 1H), 2.14 (s, 3H), 1.95 (m, 1H), 1.74 (m, 1H), 1.69 (s, 6H), 1.09 (d, 3H). HPLC RT (B1) 7.16 min; LCMS MH$^+$ 483. HRMS obs. 483.2384, calc. 483.288 ($C_{24}H_{32}ClN_8O$)

Example 2A

1-{5-chloro-2-[(2R)-2,4-dimethylpiperazin-1-yl]
pyrimidin-4-yl}-N-(2-{imidazo[1,2-a]pyridin-3-yl)
propan-2-yl)azetidine-3-carboxamide Example 2A may be prepared using the method as Example 2 from the appropriate chloropyrimidine intermediate and Boc-protected diamine.

Example 3

1-(5-chloro-2-[(3R)-3,4-dimethylpiperazin-1-yl]
pyrimidin-4-yl}-N-(2-{imidazo[1,2-a]pyridin-3-
yl}propan-2-yl)azetidine-3-carboxamide To a stirred solution of 1-{5-chloro-2-[(3R)-3-methylpiperazin-1-yl]pyrimidin-4-yl}-N-(2-{imidazo[1,2-a]pyridin-3-yl}propan-2-yl)azetidine-3-carboxamide.bis-TFA salt (Example 1, 800 mg, 1.15 mmol) in MeOH (6 mL) was added HCHO solution (37% in $H_2O$, 172 μL, 5.7 mmol) and the mixture was stirred at RT for 1 h. Then, NaCNBH$_3$ (214 mg, 3.5 mmol) was added at 0° C. and the reaction mixture was stirred at RT for 16 h.

The reaction mixture was quenched with NaHCO$_3$ solution and extracted with DCM. Organic layer was dried over Na$_2$SO$_4$ and concentrated under reduced pressure. The crude was purified over prep TLC (6% MeOH in DCM) to afford 1-{5-chloro-2-[(3R)-3,4-dimethylpiperazin-1-yl]pyrimidin-4-yl}-N-(2-{imidazo[1,2-a]pyridin-3-yl}propan-2-yl)azetidine-3-carboxamide as an off-white solid (320 mg, 58%). $^1$H NMR (DMSO-d$_6$) 8.44 (d, 1H), 8.36 (s, 1H), 7.79 (s, 1H), 7.56 (d, 1H), 7.44 (s, 1H), 7.19 (dd, 1H), 4.15-4.25 (m, 4H), 4.00-4.05 (p, 2H), 3.46 (7, 1H), 2.92 (t, 1H), 2.73 (t, 1H), 2.50-2.55 (m, 1H), 2.17 (s, 3H), 1.90-2.00 (m, 2H), 1.73 (s, 6H), 0.99 (d, 3H). HPLC RT (A1) 4.89 min; LCMS MH$^+$ 483. HRMS obs. 483.2387, calc. 483.288 ($C_{24}H_{32}ClN_8O$).

Example 4

1-[5-fluoro-2-(4-methylpiperazin-1-yl)pyridin-4-yl]-
N-(2-{imidazo[1,2-a]pyridin-3-yl}propan-2-yl)azeti-
dine-3-carboxamide A solution of 1-(2-chloro-5-fluoropyridin-4-yl)-N-(2-{imidazo[1,2-a]pyridin-3-yl}propan-2-yl)azetidine-3-carboxamide (Intermediate 2, 90 mg, 0.23 mmol), 1-methylpiperazine (69 mg, 0.69 mmol) and cesium carbonate (377 mg, 1.16 mmol) in dimethoxyethane (DME, 3 mL) was purged with argon for 10 mins before addition of Pd$_2$(dba)$_3$ (42.6 mg, 0.046 mmol) and SPhOs (49.5 mg, 0.12 mmol). After purging with argon for a further 5 mins, the mixture was heated to 120° C. for 16 h. The reaction mixture was extracted by EtOAc and washed by water and brine, dried over Na$_2$SO$_4$, and evaporated under vacuum. The crude product was then purified using combiflash chromatography by elution with 3% MeOH in DCM to give 1-[5-fluoro-2-(4-methylpiperazin-1-yl)pyridin-4-yl]-N-(2-{imidazo[1,2-a]pyridin-3-yl}propan-2-yl)azetidine-3-carboxamide as an off-white solid (30 mg, 29%).

$^1$H NMR (400 MHz, DMSO-d$_6$) δ 8.40 (d, 1H), 8.32 (s, 1H), 7.65 (d, 1H), 7.53 (d, 1H), 7.41 (s, 1H), 7.17 (dd, 1H), 6.86 (t, 1H), 5.65 (d, 1H), 4.04 (t, 2H), 3.48 (t, 1H), 3.28 (s, 4H), 2.31 (m, 4H), 2.16 (s, 3H), 1.70 (s, 6H). HPLC RT (A2) 5.58 min; LCMS MH$^+$ 452.

Examples 5-51 and 112 were prepared by the same methods as Example 1 from the appropriate chloropyrimidine intermediate and Boc-protected diamine.

TABLE 2

| Ex. No. | Structure | Int | Yield | HPLC/MS | NMR (400 MHz, DMSO-d$_6$) |
|---|---|---|---|---|---|
| 5 | 1-[5-chloro-2-(1,4-diazepan-1-yl)pyrimidin-4-yl]-N-{imidazo[1,2-a]pyridin-3-ylmethyl}azetidine-3-carboxamide | 3 | 26 mg, 64% | HPLC RT (method B1) 4.59 min MH$^+$ 441 | 8.52 (t, 1H), 8.35 (d, 1H), 7.82 (s, 1H), 7.57 (d, 1H), 7.52 (s, 1H), 7.26 (dd, 1H), 6.96 (t, 1H), 4.67 (d, 2H), 4.22 (m, 4H), 3.65 (m, 4H), 3.40 (m, 1H), 2.81 (m, 2H), 2.67 (m, 2H), 1.71 (m, 2H). |
| 6 | 1-[2-(1,4-diazepan-1-yl)-5-fluoropyrimidin-4-yl]-N-{imidazo[1,2-a]pyridin-3-ylmethyl}azetidine-3-carboxamide | 4 | 18 mg, 64% | HPLC RT (method A) 3.38 min MH$^+$ 425 | 8.52 (t, 1H), 8.35 (d, 1H), 7.82 (d, 1H), 7.59 (d, 1H), 7.52 (s, 1H), 7.26 (dd, 1H), 6.97 (t, 1H), 5.76 (s, 1H), 4.67 (d, 2H), 4.10-4.20 (m, 4H), 3.65 (m, 3H), 3.47 (m, 1H), 2.84 (m, 2H), 2.71 (m, 2H), 1.73 (m, 2H) |
| 7 | 1-(5-chloro-2-{3,6-diazabicyclo[3.2.0]heptan-3-yl}pyrimidin-4-yl)-N-{imidazo[1,2-a]pyridin-3-ylmethyl}azetidine-3-carboxamide | 3 | 25 mg, 68% | HPLC RT (method A) 3.46 min MH$^+$ 438 | 8.53 (t, 1H), 8.36 (d, 1H), 7.86 (s, 1H), 7.57 (d, 1H), 7.52 (s, 1H), 7.25 (dd, 1H), 6.97 (t, 1H), 5.76 (s, 1H), 4.67 (d, 2H), 4.20-4.70 (m, 5H), 3.86 (dd, 3H), 3.65 (m, 1H), 3.41 (m, 1H), 3.09-3.25 (m, 4H) |

TABLE 2-continued

| Ex. No. | Structure | Int | Yield | HPLC/MS | NMR (400 MHz, DMSO-d$_6$) |
|---|---|---|---|---|---|
| 8 |  1-(2-{3,6-diazabicyclo[3.2.0]heptan-3-yl}-5-fluoropyrimidin-4-yl)-N-{imidazo[1,2-a]pyridin-3-ylmethyl}azetidine-3-carboxamide | 4 | 62 mg, 64% | HPLC RT (method A) 4.73 min MH$^+$ 423 | 8.53 (t, 1H), 8.35 (d, 1H), 7.85 (d, 1H), 7.57 (d, 1H), 7.52 (s, 1H), 7.26 (dd, 1H), 6.97 (t, 1H), 5.76 (s, 1H), 4.68 (d, 1H), 4.10-4.70 (m, 5H), 3.81 (dd, 2H), 3.62 (m, 1H), 3.49 (m, 1H), 3.09-3.25 (m, 4H) |
| 9 |  1-[2-(1,4-diazepan-1-yl)-5-fluoropyrimidin-4-yl]-N-(1-{imidazo[1,2-a]pyridin-3-yl}ethyl)azetidine-3-carboxamide | 5 | 30 mg, 74% | HPLC RT (method A) 3.63 min MH$^+$ 439 | 8.43 (d, 1H), 8.19 (d, 1H), 7.81 (d, 1H), 7.58 (m, 2H), 7.25 (dd, 1H), 6.95 (t, 1H), 5.43 (m, 1H), 4.18 (m, 3H), 4.09 (m, 1H), 3.65 (m, 4H), 3.47 (m, 1H), 2.84 (m, 2H), 2.70 (m, 2H), 1.73 (m, 2H), 1.60 (d, 3H). |
| 10 |  1-[5-chloro-2-(1,4-diazepan-1-yl)pyrimidin-4-yl]-N-(1-{imidazo[1,2-a]pyridin-3-yl}ethyl)azetidine-3-carboxamide | 6 | 40 mg, 98% | HPLC RT (method A) 3.97 min MH$^+$ 455 | 8.42 (d, 1H), 8.19 (d, 1H), 7.82 (s, 1H), 7.58 (m, 2H), 7.25 (dd, 1H), 6.94 (t, 1H), 5.76 (s, 2H), 5.44 (m, 1H), 4.15-4.30 (m, 3H), 3.65 (m, 4H), 2.81 (m, 2H), 2.68 (m, 2H), 1.71 (m, 2H), 1.60 (d, 3H). |

TABLE 2-continued

| Ex. No. | Structure | Int | Yield | HPLC/MS | NMR (400 MHz, DMSO-d$_6$) |
|---|---|---|---|---|---|
| 11 | 1-[2-(1,4-diazepan-1-yl)-5-fluoropyrimidin-4-yl]-N-(2-{imidazo[1,2-a]pyridin-3-yl}propan-2-yl)azetidine-3-carboxamide | 7 | 28 mg, 98% | HPLC RT (method B1) 6.49 min MH$^+$ 453 | 8.43 (d, 1H), 8.36 (s, 1H), 7.78 (d, 1H), 7.55 (d, 1H), 7.44 (s, 1H), 7.19 (dd, 1H), 6.87 (t, 1H), 4.15 (m, 2H), 3.94 (m, 2H), 3.52 (m, 3H), 3.52 (m, 1H), 2.83 (m, 2H), 2.71 (m, 2H), 1.73 (s, 6H). |
| 12 | 1-[2-(1,4-diazepan-1-yl)-5-fluoropyrimidin-4-yl]-N-({2-methylimidazo[1,2-a]pyridin-3-yl}methyl)azetidine-3-carboxamide | 8 | 14 mg, 57% | HPLC RT (method B1) 4.35 min MH$^+$ 439 | 8.47 (t, 1H), 8.30 (d, 1H), 7.81 (d, 1H), 7.45 (d, 1H), 7.19 (dd, 1H), 6.89 (t, 1H), 4.62 (d, 2H), 4.17 (m, 2H), 4.10 (m, 1H), 3.65 (m, 4H), 3.46 (m, 1H), 2.82 (m, 2H), 2.69 (m, 2H), 2.37 (s, 3H), 1.72 (m, 2H). |
| 13 | 1-(2-{3,6-diazabicyclo[3.2.0]heptan-3-yl}-5-fluoropyrimidin-4-yl)-N-({2-methylimidazo[1,2-a]pyridin-3-yl}methyl)azetidine-3-carboxamide | 8 | 30 mg, 82% | HPLC RT (method B) 3.99 min MH$^+$ 437 | 8.48 (t, 1H), 8.30 (d, 1H), 7.85 (d, 1H), 7.45 (d, 1H), 7.20 (dd, 1H), 6.90 (t, 1H), 5.75 (s, 1H), 4.63 (d, 1H), 4.32 (m, 1H), 4.21 (m, 2H), 4.13 (m, 2H), 3.81 (dd, 2H), 3.63 (t, 1H), 3.47 (m, 1H), 3.09-3.25 (m, 5H), 2.37 )s, 3H) |

TABLE 2-continued

| Ex. No. | Structure | Int | Yield | HPLC/MS | NMR (400 MHz, DMSO-d$_6$) |
|---|---|---|---|---|---|
| 14 | 1-{5-fluoro-2-[methyl(pyrrolidin-3-yl)amino]pyrimidin-4-yl}-N-{imidazo[1,2-a]pyridin-3-ylmethyl}azetidine-3-carboxamide | 4 | 17 mg, 21% | HPLC RT (method B1) 6.21 min MH$^+$ 425 | 8.53 (t, 1H), 8.35 (d, 1H), 7.82 (d, 1H), 7.57 (d, 1H), 7.52 (s, 1H), 7.26 (dd, 1H), 6.97 (t, 1H), 5.10 (m, 1H), 4.67 (d, 2H), 4.21 (m, 2H), 4.14 (m, 2H), 3.49 (m, 1H), 2.91 (m, 1H), 2.88 (s, 3H), 2.78 (m, 1H), 2.67 (m, 1H), 1.86 (m, 1H), 1.63 (m, 1H) |
| 15 | 1-[5-fluoro-2-(pyrrolidin-3-ylamino)pyrimidin-4-yl]-N-{imidazo[1,2-a]pyridin-3-ylmethyl}azetidine-3-carboxamide | 4 | 5 mg, 37% | HPLC RT (method B1) 5.57 min MH$^+$ 411 | 8.51 (t, 1H), 8.32 (d, 1H), 7.77 (d, 1H), 7.55 (d, 1H), 7.49 (s, 1H), 7.23 (dd, 1H), 6.94 (t, 1H), 6.81 (d, 1H), 4.64 (d, 2H), 4.19 (m, 2H), 4.10 (m, 2H), 3.45 (m, 1H), 3.14 (m, 2H), 3.01 (m, 1H), 2.90 (m, 1H), 2.01 (m, 1H), 1.78 (m, 1H) |
| 16 | 1-[5-fluoro-2-(piperazin-1-yl)pyrimidin-4-yl]-N-{imidazo[1,2-a]pyridin-3-ylmethyl}azetidine-3-carboxamide | 4 | 30 mg, 58% | HPLC RT (method A) 5.83 min MH$^+$ 411 | 8.52 (t, 1H), 8.35 (d, 1H), 7.82 (s, 1H), 7.57 (d, 1H), 7.52 (s, 1H), 7.25 (dd, 1H), 6.97 (t, 1H), 4.68 (d, 2H), 4.21 (m, 2H), 4.17 (m, 2H), 3.44-3.52 (m, 5H), 2.71 (m, 4H). |

TABLE 2-continued

| Ex. No. | Structure | Int | Yield | HPLC/MS | NMR (400 MHz, DMSO-d$_6$) |
|---|---|---|---|---|---|
| 17 | 1-[5-chloro-2-(1,4-diazepan-1-yl)pyrimidin-4-yl]-N-{imidazo[1,2-a]pyridin-3-ylmethyl}-N-methylazetidine-3-carboxamide | 9 | 25 mg, 87% | HPLC RT (method B1) 7.06 min MH⁺ 455 | 8.43 (d, 1H), 7.84 (s, 1H), 7.64 (s, 1H), 7.59 (d, 2H), 7.25 (dd, 1H), 6.95 (t, 1H), 4.90 (s, 2H), 4.38 (m, 2H), 4.28 (m, 2H), 3.83 (m, 1H), 3.68 (m, 4H), 2.89 (m, 2H), 2.83 (s, 3H), 2.70 (m, 2H), 1.76 (m, 2H). |
| 18 | 1-[5-chloro-2-(1,4-diazepan-1-yl)pyrimidin-4-yl]-N-({2-methylimidazo[1,2-a]pyridin-3-yl}methyl)azetidine-3-carboxamide | 10 | 40 mg, 97% | HPLC RT (method A) 3.85 min MH⁺ 455 | 8.47 (t, 1H), 8.30 (d, 1H), 7.81 (s, 1H), 7.57 (d, 1H), 7.45 (d, 1H), 7.20 (dd, 1H), 6.90 (t, 1H), 5.76 (s, 1H), 4.63 (d, 2H), 4.27 (m, 2H), 4.19 (m, 2H), 3.66 (m, 4H), 3.37 (m, 1H), 2.80 (m, 2H), 2.67 (m, 2H), 2.37 (s, 3H), 1.70 (m, 2H). |
| 19 | 1-[2-(1,4-diazepan-1-yl)-5-methoxypyrimidin-4-yl]-N-{imidazo[1,2-a]pyridin-3-ylmethyl}azetidine-3-carboxamide | 11 | 20 mg, 70% | HPLC RT (method B2) 8.50 min MH⁺ 437 | 8.49 (t, 1H), 8.35 (d, 1H), 7.61 (s, 1H), 7.57 (d, 1H), 7.51 (s, 1H), 7.26 (dd, 1H), 6.96 (t, 1H), 5.76 (s, 1H), 4.66 (d, 2H), 4.00-4.20 (m, 4H), 3.64 (m, 4H), 3.61 (s, 3H), 3.39 (m, 1H), 2.83 (m, 2H), 2.70 (m, 2H), 1.72 (m, 8H). |

US 12,637,458 B2

133

134

TABLE 2-continued

| Ex. No. | Structure | Int | Yield | HPLC/MS | NMR (400 MHz, DMSO-d$_6$) |
|---|---|---|---|---|---|
| 20 |  1-[2-(1,4-diazepan-1-yl)-5-methoxypyrimidin-4-yl]-N-(2-{imidazo[1,2-a]pyridin-3-yl}propan-2-yl)azetidine-3-carboxamide | 12 | 22 mg, 89% | HPLC RT (method B2) 10.38 min MH$^+$ 465 | 8.43 (t, 1H), 8.33 (s, 1H), 7.57 (s, 1H), 7.54 (d, 1H), 7.44 (s, 1H), 7.19 (dd, 1H), 6.88 (t, 1H), 4.10 (m, 2H), 3.92 (m, 2H), 3.67 (m, 4H), 3.62 (s, 3H), 3.44 (m, 1H), 2.88 (m, 2H), 2.76 (m, 2H), 2.37 (s, 3H), 2.07 (s, 2H), 1.74 (m, 2H). |
| 21 |  1-[5-chloro-2-(1,4-diazepan-1-yl)pyrimidin-4-yl]-N-({6-fluoroimidazo[1,2-a]pyridin-3-yl}methyl)azetidine-3-carboxamide | 13 | 30 mg, 91% | HPLC RT (method B1) 6.98 min MH$^+$ 459 | 8.57 (m, 2H), 7.82 (s, 1H), 7.65 (dd, 1H), 7.58 (s, 1H), 7.35 (d, 1H), 4.64 (d, 2H), 4.29 (m, 2H), 4.20 (m, 2H), 3.65 (m, 4H), 3.41 (m, 1H), 2.83 (m, 2H), 2.69 (m, 2H), 1.72 (m, 2H). |
| 22 |  1-[5-chloro-2-(1,4-diazepan-1-yl)pyrimidin-4-yl]-N-({6-chloroimidazo[1,2-a]pyridin-3-yl}methyl)azetidine-3-carboxamide | 14 | 30 mg, 81% | HPLC RT (method B1) 7.58 min MH$^+$ 475 | 8.58-8.62 (m, 2H), 7.83 (s, 1H), 7.62 (d, 1H), 7.56 (s, 1H), 7.31 (d, 1H), 4.67 (d, 2H), 4.30 (m, 2H), 4.21 (m, 2H), 3.68 (m, 4H), 3.41 (m, 1H), 2.90 (m, 2H), 2.78 (m, 2H), 1.75 (m, 2H). |

TABLE 2-continued

| Ex. No. | Structure | Int | Yield | HPLC/MS | NMR (400 MHz, DMSO-d$_6$) |
|---|---|---|---|---|---|
| 23 |  1-[2-(1,4-diazepan-1-yl)-5-methoxypyrimidin-4-yl]-N-(1-{2-methylimidazo[1,2-a]pyridin-3-yl}ethyl)azetidine-3-carboxamide | 15 | 15 mg, 93% | HPLC RT (method B1) 3.38 min MH+ 465 | 8.60 (t, 1H), 8.34 (d, 1H), 7.59 (s, 1H), 7.43 (d, 1H), 7.16 (dd, 1H), 6.87 (t, 1H), 5.40 (m, 1H), 4.17 (m, 1H), 4.10 (m, 2H), 3.96 (m, 1H), 3.63 (m, 3H), 3.61 (s, 3H), 3.41 (m, 1H), 2.83 (m, 2H), 2.69 (m, 2H), 2.40 (s, 3H), 1.72 (m, 8H), 1.56 (d, 3H). |
| 24 |  1-[5-chloro-2-(1,4-diazepan-1-yl)pyrimidin-4-yl]-N-(1-{2-methylimidazo[1,2-a]pyridin-3-yl}ethyl)azetidine-3-carboxamide | 16 | 30 mg, 82% | HPLC RT (method B1) 7.17 min MH+ 469 | 8.64 (d, 1H), 8.34 (d, 1H), 7.80 (s, 1H), 7.43 (d, 1H), 7.16 (dd, 1H), 6.87 (t, 1H), 5.76 (s, 1H), 5.41 (m, 1H), 4.31 (m, 1H), 4.21 (m, 2H), 4.06 (m, 1H), 3.64 (m, 4H), 3.41 (m, 1H), 2.82 (m, 2H), 2.69 (m, 2H), 2.40 (s, 3H), 1.75 (m, 2H), 1.57 (d, 3H). |
| 25 |  1-[5-chloro-2-(piperazin-1-yl)pyrimidin-4-yl]-N-{imidazo[1,2-a]pyridin-3-ylmethyl}azetidine-3-carboxamide | 3 | 25 mg, 62% | HPLC RT method (A) 3.81 min MH$^+$ 427 | 8.53 (t, 1H), 8.35 (d, 1H), 7.83 (s, 1H), 7.57 (d, 1H), 7.52 (s, 1H), 7.26 (dd, 1H), 6.96 (t, 1H), 5.75 (s, 1H), 4.67 (d, 2H), 4.29 (m, 2H), 4.22 (m, 2H), 3.56 (m, 4H), 3.41 (m, 1H), 2.70 (m, 4H). |

TABLE 2-continued

| Ex. No. | Structure | Int | Yield | HPLC/MS | NMR (400 MHz, DMSO-d$_6$) |
|---|---|---|---|---|---|
| 26 | <br><br>1-{5-fluoro-2-[(3S)-3-methylpiperazin-1-yl]pyrimidin-4-yl}-N-{imidazo[1,2-a]pyridin-3-ylmethyl}azetidine-3-carboxamide | 4 | 20 mg, 82% | HPLC RT (method B1) 6.02 min MH$^+$ 425 | 8.53 (t, 1H), 8.35 (s, 1H), 7.84 (d, 1H), 7.56 (d, 1H), 7.52 (s, 1H), 7.25 (dd, 1H), 6.96 (t, 1H), 4.67 (d, 2H), 4.34 (m, 2H), 4.21 (m, 2H), 4.14 (m, 2H), 3.49 (m, 1H), 2.98 (d, 1H), 2.75 (m, 1H), 2.67 (m, 1H), 2.43 (m, 1H), 1.03 (d, 3H) |
| 27 | <br><br>1-{5-chloro-2-[(3S)-3-methylpiperazin-1-yl]pyrimidin-4-yl}-N-{imidazo[1,2-a]pyridin-3-ylmethyl}azetidine-3-carboxamide | 6 | 40 mg, 98% | HPLC RT (method B1) 6.50 min MH$^+$ 441 | 8.52 (t, 1H), 8.35 (s, 1H), 7.82 (s, 1H), 7.57 (d, 1H), 7.52 (s, 1H), 7.26 (dd, 1H), 6.96 (t, 1H), 5.76 (s, 1H), 4.67 (d, 2H), 4.20-4.40 (m, 6H), 3.40 (m, 1H), 2.87 (d, 1H), 2.72 (m, 1H), 2.67 (m, 2H), 2.37 (m, 1H), 0.98 (d, 3H) |
| 28 | <br><br>1-{5-fluoro-2-[(3R)-3-methylpiperazin-1-yl]pyrimidin-4-yl}-N-{imidazo[1,2-a]pyridin-3-ylmethyl}azetidine-3-carboxamide | 4 | 20 mg, 99% | HPLC RT (method B1) 6.01 min MH+ 425 | 8.53 (t, 1H), 8.35 (s, 1H), 7.84 (d, 1H), 7.56 (d, 1H), 7.52 (s, 1H), 7.26 (dd, 1H), 6.96 (t, 1H), 4.67 (d, 2H), 4.34 (m, 2H), 4.20 (m, 2H), 4.14 (m, 2H), 3.49 (m, 1H), 2.98 (d, 1H), 2.75 (m, 2H), 2.43 (m, 1H), 1.03 (d, 3H) |

TABLE 2-continued

| Ex. No. | Structure | Int | Yield | HPLC/MS | NMR (400 MHz, DMSO-d$_6$) |
|---|---|---|---|---|---|
| 29 | <br>1-{5-chloro-2-[(3R)-3-methylpiperazin-1-yl]pyrimidin-4-yl}-N-{imidazo[1,2-a]pyridin-3-ylmethyl}azetidine-3-carboxamide | 6 | 35 mg, 86% | HPLC RT (method B1) 6.50 min MH⁺ 441 | 8.52 (t, 1H), 8.35 (s, 1H), 7.83 (s, 1H), 7.57 (d, 1H), 7.52 (s, 1H), 7.26 (dd, 1H), 6.96 (t, 1H), 5.76 (s, 1H), 4.67 (d, 2H), 4.20-4.40 (m, 6H), 3.40 (m, 1H), 2.87 (d, 1H), 2.72 (m, 1H), 2.67 (m, 2H), 2.37 (m, 1H), 0.98 (d, 3H). |
| 30 | <br>1-[5-chloro-2-(piperazin-1-yl)pyrimidin-4-yl]-N-(1-{imidazo[1,2-a]pyridin-3-yl}ethyl)azetidine-3-carboxamide | 6 | 25 mg, 87% | HPLC RT (method B2) 6.07 min MH⁺ 441 | 8.44 (d, 1H), 8.19 (d, 1H), 7.84 (d, 1H), 7.60 (s, 1H), 7.58 (s, 1H), 7.25 (dd, 1H), 6.96 (t, 1H), 5.44 (m, 1H), 4.19-4.27 (m, 4H), 3.64 (m, 4H), 3.40 (m, 1H), 2.87 (m, 4H), 1.59 (d, 3H). |
| 31 | <br>1-[5-fluoro-2-(piperazin-1-yl)pyrimidin-4-yl]-N-(1-{imidazo[1,2-a]pyridin-3-yl}ethyl)azetidine-3-carboxamide | 5 | 25 mg, 88% | HPLC RT (method B2) 5.43 min MH+ 425 | 8.44 (d, 1H), 8.19 (d, 1H), 7.59 (d, 1H), 7.58 (s, 1H), 7.25 (dd, 1H), 6.96 (t, 1H), 5.45 (m, 1H), 4.10-4.22 (m, 4H), 3.56 (m, 4H), 3.45 (m, 1H), 2.76 (m, 4H), 1.60 (d, 3H). |

TABLE 2-continued

| Ex. No. | Structure | Int | Yield | HPLC/MS | NMR (400 MHz, DMSO-d$_6$) |
|---|---|---|---|---|---|
| 32 | 1-[5-fluoro-2-(piperazin-1-yl)pyrimidin-4-yl]-N-(2-{imidazo[1,2-a]pyridin-3-yl}propan-2-yl)azetidine-3-carboxamide | 7 | 35 mg, 96% | HPLC RT (method B) 5.00 min MH+ 439 | 8.44 (d, 1H), 8.38 (s, 1H), 7.84 (d, 1H), 7.57 (d, 1H), 7.45 (s, 1H), 7.20 (dd, 1H), 6.89 (t, 1H), 4.18 (m, 2H), 4.00 (m, 2H), 3.66 (m, 4H), 3.53 (m, 1H), 2.96 (m, 4H), 1.73 (d, 6H). |
| 33 | 1-[5-chloro-2-(piperazin-1-yl)pyrimidin-4-yl]-N-(2-{imidazo[1,2-a]pyridin-3-yl}propan-2-yl)azetidine-3-carboxamide | 1 | 30 mg, 81% | HPLC RT (method B2) 7.03 min MH+ 455 | 8.44 (d, 1H), 8.37 (s, 1H), 7.80 (d, 1H), 7.56 (d, 1H), 7.44 (s, 1H), 7.19 (dd, 1H), 6.89 (t, 1H), 4.24 (m, 2H), 4.03 (m, 2H), 3.53 (m, 4H), 3.45 (m, 1H), 2.70 (m, 4H), 1.74 (d, 6H). |
| 34 | N-(2-{imidazo[1,2-a]pyridin-3-yl}propan-2-yl)-1-[5-methoxy-2-(piperazin-1-yl)pyrimidin-4-yl]azetidine-3-carboxamide | 12 | 36 mg, 96% | HPLC RT (method B) 4.87 min MH+ 451 | 8.43 (d, 1H), 8.32 (s, 1H), 7.80 (d, 1H), 7.57 (s, 1H), 7.44 (d, 1H), 7.43 (s, 1H), 7.18 (dd, 1H), 6.89 (t, 1H), 4.09 (m, 2H), 3.93 (m, 2H), 3.67 (s, 3H), 3.58 (m, 4H), 3.17 (s, 2H), 2.71 (m, 4H), 1.72 (d, 6H). |

TABLE 2-continued

| Ex. No. | Structure | Int | Yield | HPLC/MS | NMR (400 MHz, DMSO-d$_6$) |
|---|---|---|---|---|---|
| 35 | <br>1-{5-fluoro-2-[(3R)-3-methylpiperazin-1-yl]pyrimidin-4-yl}-N-(2-{imidazo[1,2-a]pyridin-3-yl}propan-2-yl)azetidine-3-carboxamide | 7 | 30 mg, 92% | HPLC RT (method B) 5.15 min MH+ 453 | 8.44 (d, 1H), 8.36 (s, 1H), 7.79 (d, 1H), 7.55 (d, 1H), 7.44 (s, 1H), 7.19 (dd, 1H), 6.88 (t, 1H), 4.27 (m, 2H), 4.17 (m, 2H), 3.95 (m, 2H), 3.51 (m, 1H), 2.89 (m, 1H), 2.73 (t, 1H), 2.60-2.70 (m, 3H), 2.35 (m, 1H), 1.73 (s, 6H), 0.99 (d, 3H) |
| 36 | <br>N-(2-{imidazo[1,2-a]pyridin-3-yl}propan-2-yl)-1-{5-methoxy-2-[(3R)-3-methylpiperazin-1-yl]pyrimidin-4-yl}azetidine-3-carboxamide | 12 | 16 mg, 85% | HPLC RT (method B1) 6.48 min MH+ 465 | 8.44 (d, 1H), 8.33 (s, 1H), 7.57 (s, 1H), 7.55 (d, 1H), 7.44 (s, 1H), 7.19 (dd, 1H), 6.89 (t, 1H), 4.29 (m, 2H), 4.26 (m, 2H), 3.93 (m, 2H), 3.58 (s, 3H), 3.44 (m, 1H), 2.97 (m, 1H), 2.65-2.70 (m, 3H), 2.40 (m, 1H), 1.72 (s, 6H), 1.02 (d, 3H) |
| 37 | <br>1-{5-chloro-2-[(3S)-3-methylpiperazin-1-yl]pyrimidin-4-yl}-N-(2-{imidazo[1,2-a]pyridin-3-yl}propan-2-yl)azetidine-3-carboxamide | 1 | 30 mg, 91% | HPLC RT (method B2) 7.21 min MH+ 469 | 8.44 (d, 1H), 8.37 (s, 1H), 7.79 (s, 1H), 7.55 (d, 1H), 7.44 (s, 1H), 7.19 (dd, 1H), 6.88 (t, 1H), 4.30 (m, 2H), 4.25 (m, 2H), 4.03 (m, 2H), 3.44 (m, 1H), 2.89 (d, 1H), 2.71 (t, 1H), 2.61 (m, 2H), 2.38 (m, 1H), 1.73 (s, 6H), 0.99 (d, 3H) |

TABLE 2-continued

| Ex. No. | Structure | Int | Yield | HPLC/MS | NMR (400 MHz, DMSO-d$_6$) |
|---|---|---|---|---|---|
| 38 | <br>1-{5-fluoro-2-[(3S)-3-methylpiperazin-1-yl]pyrimidin-4-yl}-N-(2-{imidazo[1,2-a]pyridin-3-yl}propan-2-yl)azetidine-3-carboxamide | 7 | 34 mg, 83% | HPLC RT (method B) 5.15 min MH⁺ 453 | 8.44 (d, 1H), 8.36 (s, 1H), 7.79 (d, 1H), 7.56 (d, 1H), 7.44 (s, 1H), 7.19 (dd, 1H), 6.88 (t, 1H), 4.27 (m, 2H), 4.16 (m, 2H), 3.95 (m, 2H), 3.51 (m, 1H), 3.16 (s, 2H), 2.89 (m, 1H), 2.60-2.70 (m, 3H), 2.35 (m, 1H), 1.73 (s, 6H), 1.00 (d, 3H) |
| 39 | <br>N-(2-{imidazo[1,2-a]pyridin-3-yl}propan-2-yl)-1-{5-methoxy-2-[(3S)-3-methylpiperazin-1-yl]pyrimidin-4-yl}azetidine-3-carboxamide | 12 | 16 mg, 97% | HPLC RT (method B1) 6.49 min MH⁺ 465 | 8.44 (d, 1H), 8.33 (s, 1H), 7.57 (s, 1H), 7.55 (d, 1H), 7.44 (s, 1H), 7.17 (dd, 1H), 6.89 (t, 1H), 4.25 (m, 2H), 4.10 (m, 2H), 3.93 (m, 2H), 3.58 (s, 3H), 3.44 (m, 1H), 3.17 (d, 2H), 2.92 (m, 1H), 2.65 (m, 3H), 2.32 (m, 1H), 1.72 (s, 6H), 1.01 (d, 3H) |
| 40 | <br>1-{5-fluoro-2-[methyl(pyrrolidin-3-yl)amino]pyrimidin-4-yl}-N-(2-{imidazo[1,2-a]pyridin-3-yl}propan-2-yl)azetidine-3-carboxamide | 7 | 27 mg, 94% | HPLC RT (method B1) 6.90 min MH⁺ 453 | 8.44 (t, 1H), 8.33 (d, 1H), 7.80 (d, 1H), 7.56 (d, 1H), 7.44 (s, 1H), 7.19 (dd, 1H), 6.89 (t, 1H), 5.07 (m, 1H), 4.17 (m, 2H), 4.09 (m, 1H), 3.96 (m, 2H), 3.52 (m, 1H), 3.00-3.20 (m, 3H), 2.96 (m, 1H), 2.95 (s, 3H), 1.96 (m, 1H), 1.73 (s, 6H) |

TABLE 2-continued

| Ex. No. | Structure | Int | Yield | HPLC/MS | NMR (400 MHz, DMSO-d$_6$) |
|---|---|---|---|---|---|
| 41 | <br><br>1-{5-chloro-2-[methyl(pyrrolidin-3-yl)amino]pyrimidin-4-yl}-N-(2-{imidazo[1,2-a]pyridin-3-yl}propan-2-yl)azetidine-3-carboxamide | 1 | 20 mg, 97% | HPLC RT (method B1) 5.66 min MH$^+$ 469 | 8.44 (t, 1H), 8.38 (d, 1H), 7.79 (d, 1H), 7.57 (d, 1H), 7.44 (s, 1H), 7.19 (dd, 1H), 6.89 (t, 1H), 5.09 (m, 1H), 4.28 (m, 2H), 4.05 (m, 1H), 3.45 (m, 1H), 3.00-3.20 (m, 2H), 2.89 (s, 3H), 2.85 (m, 1H), 1.94 (m, 1H), 1.73 (s, 6H) |
| 42 | <br><br>1-{2-[(3R,5S)-3,5-dimethylpiperazin-1-yl]-5-methoxypyrimidin-4-yl}-N-(2-{imidazo[1,2-a]pyridin-3-yl}propan-2-yl)azetidine-3-carboxamide | 12 | 37 mg, 64% | HPLC RT (method A2) 7.17 min MH$^+$ 479 | 8.44 (d, 1H), 8.35 (s, 1H), 7.58 (s, 1H), 7.56 (d, 1H), 7.44 (s, 1H), 7.19 (dd, 1H), 6.87 (t, 1H), 4.47 (m, 2H), 4.13 (m, 2H), 3.94 (m, 2H), 3.60 (s, 3H), 3.47 (m, 1H), 3.00 (m, 2H), 1.72 (s, 6H), 1.13 (d, 6H) |
| 43 | <br><br>1-{2-[(3R,5S)-3,5-dimethylpiperazin-1-yl]-5-chloropyrimidin-4-yl}-N-(2-{imidazo[1,2-a]pyridin-3-yl}propan-2-yl)azetidine-3-carboxamide | 1 | 30 mg, 94% | HPLC RT (method A1) 5.29 min MH$^+$ 483 | 8.44 (d, 1H), 8.37 (s, 1H), 7.79 (s, 1H), 7.56 (d, 1H), 7.45 (s, 1H), 7.18 (dd, 1H), 6.88 (t, 1H), 5.57 (s, 1H), 4.39 (m, 2H), 4.25 (m, 2H), 4.03 (m, 2H), 3.44 (m, 1H), 2.67 (m, 1H), 2.29 (m, 1H), 1.72 (s, 6H), 1.02 (d, 6H) |

TABLE 2-continued

| Ex. No. | Structure | Int | Yield | HPLC/MS | NMR (400 MHz, DMSO-d$_6$) |
|---|---|---|---|---|---|
| 44 |  1-{2-[(3R,5S)-3,5-dimethylpiperazin-1-yl]-5-fluoropyrimidin-4-yl}-N-(2-{imidazo[1,2-a]pyridin-3-yl}propan-2-yl)azetidine-3-carboxamide | 6 | 70 mg, 94% | HPLC RT (method A) 6.28 min MH$^+$ 467 | 8.44 (d, 1H), 8.37 (s, 1H), 7.79 (s, 1H), 7.56 (d, 1H), 7.45 (s, 1H), 7.18 (dd, 1H), 6.88 (t, 1H), 5.57 (s, 1H), 4.39 (m, 2H), 4.25 (m, 2H), 4.03 (m, 2H), 3.44 (m, 1H), 2.26 (m, 2H), 1.74 (s, 6H), 1.02 (d, 6H) |
| 45 |  1-{2-[(3S,5S)-3,5-dimethylpiperazin-1-yl]-5-methoxypyrimidin-4-yl}-N-(2-{imidazo[1,2-a]pyridin-3-yl}propan-2-yl)azetidine-3-carboxamide | 12 | 20 mg, 54% | HPLC RT (method A) 6.00 min MH$^+$ 479 | 8.43 (d, 1H), 8.34 (s, 1H), 7.57 (s, 1H), 7.56 (d, 1H), 7.44 (s, 1H), 7.19 (dd, 1H), 6.89 (t, 1H), 5.76 (s, 1H), 4.11 (m, 2H), 3.94 (m, 2H), 3.70 (m, 2H), 3.68 (s, 3H), 3.45 (m, 2H), 1.72 (s, 6H), 1.09 (d, 6H) |

TABLE 2-continued

| Ex. No. | Structure | Int | Yield | HPLC/MS | NMR (400 MHz, DMSO-d$_6$) |
|---|---|---|---|---|---|
| 46 |  1-{5-chloro-2-[(3R,5R)-3,5-dimethylpiperazin-1-yl]pyrimidin-4-yl}-N-(2-{imidazo[1,2-a]pyridin-3-yl}propan-2-yl)azetidine-3-carboxamide | 1 | 20 mg, 54% | HPLC RT (method A) 3.27 min MH⁺ 483 | 8.44 (d, 1H), 8.37 (s, 1H), 7.77 (s, 1H), 7.56 (d, 1H), 7.44 (s, 1H), 7.19 (dd, 1H), 6.88 (t, 1H), 4.25 (m, 2H), 4.09 (m, 2H), 3.65 (m, 2H), 3.42 (m, 1H), 3.07 (m, 2H), 1.73 (s, 6H), 0.97 (d, 6H) |
| 46a | 1-{5-chloro-2-[(3S,5S)-3,5-dimethylpiperazin-1-yl]pyrimidin-4-yl}-N-(2-{imidazo[1,2-a]pyridin-3-yl}propan-2-yl)azetidine-3-carboxamide | | | | May be prepared using the method of Example 46, from the appropriate chloropyrimidine intermediate and Boc-protected diamine |
| 47 |  1-{2-[(3R,5R)-3,5-dimethylpiperazin-1-yl]-5-fluoropyrimidin-4-yl}-N-(2-{imidazo[1,2-a]pyridin-3-yl}propan-2-yl)azetidine-3-carboxamide | 7 | 20 mg, 54% | HPLC RT (method A1) 3.00 min MH⁺ 467 | 8.45 (d, 1H), 8.36 (s, 1H), 7.77 (d, 1H), 7.56 (d, 1H), 7.44 (s, 1H), 7.19 (dd, 1H), 6.88 (t, 1H), 4.15 (m, 2H), 3.96 (m, 2H), 3.62 (m, 2H), 3.51 (m, 1H), 3.10-3.30 (m, 3H), 3.06 (m, 2H), 1.73 (s, 6H), 0.97 (d, 6H) |
| 47a | 1-{2-[(3S,5S)-3,5-dimethylpiperazin-1-yl]-5-fluoropyrimidine-4-yl}-N-(2-{imidazo[1,2-a]pyridin-3-yl}propan-2-yl)azetidine-3-carboxamide | | | | May be prepared using the method of Example 47, from the appropriate chloropyrimidine intermediate and Boc-protected diamine |

TABLE 2-continued

| Ex. No. | Structure | Int | Yield | HPLC/MS | NMR (400 MHz, DMSO-d$_6$) |
|---|---|---|---|---|---|
| 48 |  1-{5-chloro-2-[(3S,5S)-3,5-dimethylpiperazin-1-yl]pyrimidin-4-yl}-N-(2-{imidazo[1,2-a]pyridin-3-yl}propan-2-yl)azetidine-3-carboxamide |  | 20 mg, 60% | HPLC RT (method A1) 5.42 min MH⁺ 483 | 8.44 (d, 1H), 8.36 (s, 1H), 7.76 (s, 1H), 7.56 (d, 1H), 7.44 (s, 1H), 7.19 (dd, 1H), 6.88 (t, 1H), 5.76 (s, 1H), 4.24 (m, 2H), 4.02 (m, 2H), 3.62 (m, 2H), 3.42 (m, 1H), 3.22 (m, 2H), 3.02 )m, 2H), 1.73 (s, 6H), 0.95 (d, 6H) |
| 48a | 1-{5-chloro-2-[(3R,5R)-3,5-dimethylpiperazin-1-yl]pyrimidin-4-yl}-N-(2-{imidazo[1,2-a]pyridin-3 yl}propan-2-yl)azetidine-3-carboxamide |  |  | May be prepared using the method of Example 48, from the appropriate chloropyrimidine intermediate and Boc-protected diamine | |
| 49 |  1-{5-fluoro-2-[(3S,5S)-3,4,5-dimethylpiperazin-1-yl]pyrimidin-4-yl}-N-(2-{imidazo[1,2-a]pyridin-3-yl}propan-2-yl)azetidine-3-carboxamide | 7 | 16 mg, 39% | HPLC RT (method A1) 4.89 min MH⁺ 467 | 8.44 (d, 1H), 8.36 (s, 1H), 7.77 (d, 1H), 7.56 (d, 1H), 7.44 (s, 1H), 7.19 (dd, 1H), 6.88 (t, 1H), 4.16 (m, 2H), 3.95 (m, 2H), 3.63 (m, 2H), 3.51 (m, 1H), 3.10-3.30 (m, 2H), 3.07 (m, 2H), 1.73 (s, 6H), 0.97 (d, 6H) |
| 49a | 1-{5-fluoro-2-[(3R,5R)-3,4,5-dimethylpiperazin-1-yl]pyrimidin-4-yl}-N-(2-{imidazo[1,2-a]pyridin-3-yl}propan-2-yl)azetidine-3-carboxamide |  |  | May be prepared using the method of Example 49, from the appropriate chloropyrimidine intermediate and Boc-protected diamine | |
| 49b | 1-{5-fluoro-2-[(3R,5R)-3,4,5-trimethylpiperazin-1-yl]pyrimidin-4-yl}-N-(2-{imidazo[1,2-a]pyridin-3 yl}propan-2-yl)azetidine-3-carboxamide |  |  | May be prepared using the method of Example 49, from the appropriate chloropyrimidine intermediate and Boc-protected diamine | |

TABLE 2-continued

| Ex. No. | Structure | Int | Yield | HPLC/MS | NMR (400 MHz, DMSO-d$_6$) |
|---|---|---|---|---|---|
| 50 | <br><br>1-{5-chloro-2-[(2S)-2-methylpiperazin-1-yl]pyrimidin-4-yl}-N-(2-{imidazo[1,2-a]pyridin-3-yl}propan-2-yl)-N-methylazetidine-3-carboxamide | 13 | 10 mg, 48% | HPLC RT (method A2) 5.01 min MH$^+$ 483 | 8.23 (d, 1H), 7.81 (s, 1H), 7.55 (d, 1H), 7.45 (s, 1H), 7.18 (dd, 1H), 6.84 (t, 1H), 4.56 (m, 1H), 4.00-4.30 (m, 5H), 3.77 (m, 1H), 3.30 (s, 3H), 2.70-3.00 (m, 7H), 1.78 (s, 6H), 1.11 (d, 3H). |
| 50a | 1-{5-chloro-2-[(2R)-2-methylpiperazin-1-yl]pyrimidin-4-yl}-N-(2-{imidazo[1,2-a]pyridin-3-yl}propan-2-yl)-N-methylazetidine-3-carboxamide | | | May be prepared using the method of Example 50, from the appropriate chloropyrimidine intermediate and Boc-protected diamine | |
| 51 | <br><br>1-[5-chloro-2-(1,4-diazepan-1-yl)pyrimidin-4-yl]-N-(2-{imidazo[1,2-a]pyridin-3-yl}propan-2-yl)azetidine-3-carboxamide | 1 | 85 mg, 86% | HPLC RT (method B1) 7.26 min MH$^+$ 469 | 8.44 (d, 1H), 8.37 (s, 1H), 7.77 (s, 1H), 7.55 (d, 1H), 7.44 (s, 1H), 7.19 (dd, 1H), 6.88 (t, 1H), 4.23 (m, 2H), 4.02 (m, 2H), 3.84 (m, 4H), 3.44 (m, 1H), 2.77 (m, 2H), 2.64 (m, 2H), 1.75 (s, 6H), 1.68 (m, 2H). |

TABLE 2-continued

| Ex. No. | Structure | Int | Yield | HPLC/MS | NMR (400 MHz, DMSO-$d_6$) |
|---|---|---|---|---|---|
| 112 |  1-[5-chloro-2-(1,4-diazepan-1-yl)pyrimidin-4-yl]-N-{[1,2,4]triazolo[4,3-a]pyridin-3-ylmethyl}azetidine-3-carboxamide | 30 | 23 mg, 63% | HPLC RT (method B1) 5.87 min MH⁺ 442 | 8.82 (t, 1H), 8.46 (d, 1H), 7.83 (s, 1H), 7.76 (d, 1H), 7.38 (t, 1H), 7.01 (t, 1H), 4.85 (d, 2H), 4.30 (m, 2H), 4.21 (m, 2H), 3.68 (m, 4H), 3.44 (m, 1H), 2.92 (m, 2H), 2.81 (m, 2H), 1.73 (m, 2H). |

Examples 52-80 were prepared by the same methods as Example 2 from the appropriate chloropyrimidine intermediate and diamine.

TABLE 3

| Ex | Structure | Int | Yield | HPLC/MS | NMR (400 MHz, DMSO-$d_6$) |
|---|---|---|---|---|---|
| 52 |  1-[5-fluoro-2-(4-methyl-1,4-diazepan-1-yl)pyrimidin-4-yl]-N-{imidazo[1,2-a]pyridin-3-ylmethyl}azetidine-3-carboxamide | 4 | 13 mg, 21% | HPLC RT (method B1) 6.48 min MH⁺ 439 | 8.52 (t, 1H), 8.35 (d, 1H), 7.82 (d, 1H), 7.57 (d, 1H), 7.52 (s, 1H), 7.26 (dd, 1H), 6.96 (t, 1H), 4.67 (d, 2H), 4.10-4.20 (m, 4H), 3.70 (m, 2H), 3.61 (m, 2H), 3.48 (m, 1H), 2.50-2.70 (m, 4H), 2.25 (s, 3H), 1.81 (m, 2H) |

TABLE 3-continued

| Ex | Structure | Int | Yield | HPLC/MS | NMR (400 MHz, DMSO-d<sub>6</sub>) |
|---|---|---|---|---|---|
| 53 | 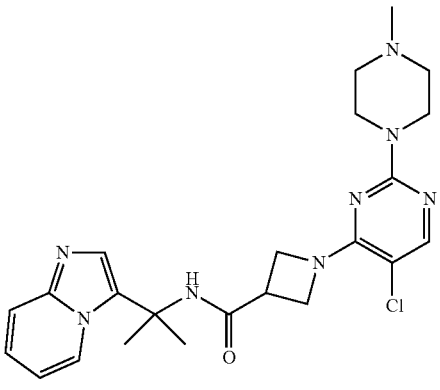 [SMILES: CN1CCN(c2cc(N3CC(C(=O)NC(C)(C)c4cnc5ccccn45)C3)c(Cl)cn2)CC1]1-[5-chloro-2-(4-methyl-1,4-diazepan-1-yl)pyrimidin-4-yl]-N-(1-{imidazo[1,2-a]pyridin-3-yl}ethyl)azetidine-3-carboxamide | 3 | 52 mg, 47% | HPLC RT (method A1) 8.63 min MH<sup>+</sup> 455 | 8.53 (t, 1H), 8.36 (d, 1H), 7.82 (s, 1H), 7.57 (d, 1H), 7.52 (s, 1H), 7.26 (dd, 1H), 6.96 (t, 1H), 4.67 (d, 2H), 4.28 (m, 2H), 4.20 (m, 2H), 3.70 (m, 2H), 3.63 (m, 2H), 3.42 (m, 1H), 2.54 (m, 2H), 2.43 (m, 2H), 2.23 (s, 3H), 1.80 (m, 2H). |
| 54 | 1-[5-fluoro-2-(4-methylpiperazin-1-yl)pyrimidin-4-yl]-N-(2-{imidazo[1,2-a]pyridin-3-yl}propan-2-yl)azetidine-3-carboxamide | 7 | 25 mg, 43% | HPLC RT (method B1) 5.89 min MH<sup>+</sup> 453 | 8.43 (d, 1H), 8.36 (s, 1H), 7.78 (d, 1H), 7.55 (d, 1H), 7.44 (s, 1H), 7.19 (dd, 1H), 6.89 (t, 1H), 4.17 (m, 2H), 3.95 (m, 2H), 3.53 (m, 4H), 2.27 (m, 4H), 2.17 (s, 3H), 1.73 (s, 6H). |
| 55 | 1-[5-chloro-2-(4-methylpiperazin-1-yl)pyrimidin-4-yl]-N-(2-{imidazo[1,2-a]pyridin-3-yl}propan-2-yl)azetidine-3-carboxamide | 1 | 39 mg, 67% | HPLC RT (method B1) 6.48 min MH<sup>+</sup> 469 | 8.44 (d, 1H), 8.36 (s, 1H), 7.80 (s, 1H), 7.56 (d, 1H), 7.44 (s, 1H), 7.19 (dd, 1H), 6.89 (t, 1H), 4.25 (m, 2H), 4.04 (m, 2H), 3.58 (m, 4H), 3.44 (m, 1H), 2.29 (m, 4H), 2.19 (s, 3H), 1.73 (s, 6H). |

TABLE 3-continued

| Ex | Structure | Int | Yield | HPLC/MS | NMR (400 MHz, DMSO-d$_6$) |
|---|---|---|---|---|---|
| 56 | <br>1-[5-fluoro-2-(4-methyl-1,4-diazepan-1-yl)pyrimidin-4-yl]-N-(2-{imidazo[1,2-a]pyridin-3-yl}propan-2-yl)azetidine-3-carboxamide | 7 | 26 mg, 60% | HPLC RT (method B1) 5.54 min MH$^+$ 467 | 8.44 (d, 1H), 8.36 (s, 1H), 7.77 (d, 1H), 7.54 (d, 1H), 7.44 (s, 1H), 7.19 (dd, 1H), 6.88 (t, 1H), 4.15 (m, 2H), 3.94 (m, 2H), 3.60 (m, 2H), 3.53 (m, 2H), 3.50 (m, 1H), 2.50 (m, 2H), 2.23 (s, 3H), 1.79 (m, 2H), 1.73 (s, 6H) |
| 57 | <br>1-[5-chloro-2-(4-methyl-1,4-diazepan-1-yl)pyrimidin-4-yl]-N-(2-{imidazo[1,2-a]pyridin-3-yl}propan-2-yl)azetidine-3-carboxamide | 1 | 35 mg, 59% | HPLC RT (method B1) 6.00 min MH$^+$ 483 | 8.41 (d, 1H), 8.33 (s, 1H), 7.74 (s, 1H), 7.52 (d, 1H), 7.41 (s, 1H), 7.16 (dd, 1H), 6.85 (t, 1H), 4.21 (m, 2H), 4.00 (m, 2H), 3.65 (m, 2H), 3.57 (m, 2H), 3.41 (m, 1H), 2.47 (m, 2H), 2.39 (m, 2H), 2.20 (s, 3H), 1.76 (m, 2H), 1.70 (s, 6H) |
| 58 | <br>1-{5-fluoro-2-[methyl(1-methylpyrrolidin-3-yl)amino]pyrimidin-4-yl}-N-(2-{imidazo[1,2-a]pyridin-3-yl}propan-2-yl)azetidine-3-carboxamide | 7 | 10 mg, 17% | HPLC RT (method B) 5.74 min MH$^+$ 467 | 8.53 (t, 1H), 8.37 (d, 1H), 7.78 (d, 1H), 7.57 (d, 1H), 7.44 (s, 1H), 7.19 (dd, 1H), 6.88 (t, 1H), 5.21 (m, 1H), 4.17 (m, 2H), 3.94 (m, 2H), 3.50 (m, 1H), 2.89 (s, 3H), 2.67 (m, 1H), 2.58 (m, 1H), 2.31 (m, 4H), 1.72 (s, 6H) |

TABLE 3-continued

| Ex | Structure | Int | Yield | HPLC/MS | NMR (400 MHz, DMSO-$d_6$) |
|---|---|---|---|---|---|
| 59 | 1-{5-chloro-2-[methyl(1-methylpyrrolidin-3-yl)amino]pyrimidin-4-yl}-N-(2-{imidazo[1,2-a]pyridin-3-yl}propan-2-yl)azetidine-3-carboxamide | 1 | 14 mg, 23% | HPLC RT (method A2) 3.67 min MH$^+$ 483 | 8.53 (t, 1H), 8.37 (s, 1H), 7.79 (d, 1H), 7.56 (d, 1H), 7.45 (s, 1H), 7.19 (dd, 1H), 6.88 (t, 1H), 5.22 (m, 1H), 4.26 (m, 2H), 4.04 (m, 2H), 3.44 (m, 1H), 2.91 (s, 3H), 2.75 (m, 1H), 2.67 (m, 1H), 2.28 (m, 3H), 2.03 (m, 1H), 1.73 (s, 6H) |
| 60 | 1-[5-fluoro-2-(4-methylpiperazin-1-yl)pyrimidin-4-yl]-N-(2-{6-methylimidazo[1,2-a]pyridin-3-yl}propan-2-yl)azetidine-3-carboxamide | 17 | 30 mg, 43% | HPLC RT (method A) 6.00 min MH$^+$ 467 | 8.34 (s, 1H), 8.27 (s, 1H), 7.80 (d, 1H), 7.46 (d, 1H), 7.38 (s, 1H), 7.06 (d, 1H), 4.18 (m, 2H), 3.94 (m, 2H), 3.54 (m, 4H), 2.10-2.35 (m, 7H), 1.78 (s, 6H). |
| 61 | 1-[5-fluoro-2-(4-methylpiperazin-1-yl)pyrimidin-4-yl]-N-(2-{8-fluoroimidazo[1,2-a]pyridin-3-yl}propan-2-yl)azetidine-3-carboxamide | 18 | 35 mg, 50% | HPLC RT (A1) 5.03 min MH$^+$ 471 | 8.44 (d, 1H), 8.32 (s, 1H), 7.78 (d, 1H), 7.57 (s, 1H), 7.56 (d, 1H), 7.19 (dd, 1H), 6.88 (t, 1H), 4.12 (m, 2H), 4.09 (m, 2H), 3.58 (s, 3H), 3.47 (m, 5H), 2.28 (m, 4H), 2.19 (s, 3H), 1.72 (s, 6H). |

TABLE 3-continued

| Ex | Structure | Int | Yield | HPLC/MS | NMR (400 MHz, DMSO-d₆) |
|---|---|---|---|---|---|
| 62 | <br><br>N-(2-{imidazo[1,2-a]pyridin-3-yl}propan-2-yl)-1-[5-methoxy-2-(4-methyl-1,4-diazepan-1-yl)pyrimidin-4-yl]azetidine-3-carboxamide | 12 | 30 mg, 42% | HPLC RT (method A1) 4.72 min MH⁺ 479 | 8.44 (d, 1H), 8.32 (s, 1H), 7.56 (d, 1H), 7.55 (s, 1H), 7.43 (s, 1H), 7.19 (dd, 1H), 6.88 (t, 1H), 4.13 (m, 2H), 3.93 (m, 2H), 3.67 (m, 2H), 3.59 (m, 2H), 3.56 (s, 3H), 3.53 (m, 2H), 2.30-2.50 (m, 2H), 2.26 (s, 3H), 1.80 (m, 2H), 1.72 (s, 6H) |
| 63 | <br><br>N-(2-{imidazo[1,2-a]pyridin-3-yl}propan-2-yl)-1-[5-methoxy-2-(4-methylpiperazin-1-yl)pyrimidin-4-yl]azetidine-3-carboxamide | 12 | 27 mg, 39% | HPLC RT (method A1) 4.69 min MH⁺ 465 | 8.38 (s, 1H), 8.29 (d, 1H), 7.79 (d, 1H), 7.50 (s, 1H), 7.10 (dt, 1H), 6.88 (t, 1H), 5.75 (s, 1H), 4.17 (m, 2H), 3.94 (m, 2H), 3.52 (m, 5H), 2.27 (m, 4H), 2.18 (s, 3H), 1.73 (s, 6H) |
| 64 | <br><br>1-[5-fluoro-2-(4-methylpiperazin-1-yl)pyrimidin-4-yl]-N-(2-{imidazo[1,2-a]pyridin-3-yl}propan-2-yl)pyrrolidine-3-carboxamide | 19 | 42 mg, 58% | HPLC RT (method A2) 7.88 min MH⁺ 467 | 8.47 (d, 1H), 8.39 (s, 1H), 7.79 (d, 1H), 7.55 (d, 1H), 7.42 (s, 1H), 7.19 (dd, 1H), 6.86 (t, 1H), 3.71 (t, 1H), 3.39-3.57 (m, 6H), 3.31 (t, 1H), 3.05 (p, 1H), 2.33 (m, 4H), 2.21 (s, 3H), 2.06 (m, 1H), 1.87 (m, 1H), 1.73 (s, 3H), 1.71 (s, 3H). |

TABLE 3-continued

| Ex | Structure | Int | Yield | HPLC/MS | NMR (400 MHz, DMSO-$d_6$) |
|---|---|---|---|---|---|
| 65 | <br><br>1-[5-fluoro-2-(4-methylpiperazin-1-yl)pyrimidin-4-yl]-N-(2-{imidazo[1,2-a]pyridin-3-yl}propan-2-yl)-3-methylazetidine-3-carboxamide | 20 | 25 mg, 36% | HPLC RT (method A) 5.04 min MH$^+$ 467 | 8.48 (d, 1H), 8.12 (s, 1H), 7.80 (d, 1H), 7.55 (d, 1H), 7.43 (s, 1H), 7.18 (dd, 1H), 6.85 (t, 1H), 4.22 (d, 2H), 2.01 (d, 2H), 3.56 (m, 4H), 2.32 (m, 4H), 2.18 (s, 3H), 1.75 (s, 6H), 1.48 (s, 3H) |
| 66 | <br><br>N-(2-{imidazo[1,2-a]pyridin-3-yl}propan-2-yl)-1-[5-methyl-2-(4-methylpiperazin-1-yl)pyrimidin-4-yl]azetidine-3-carboxamide | 21 | 42 mg, 72% | HPLC RT (method A1) 4.53 min MH$^+$ 449 | 8.44 (d, 1H), 8.34 (s, 1H), 7.57 (s, 1H), 7.55 (d, 1H), 7.44 (s, 1H), 7.19 (dd, 1H), 6.89 (t, 1H), 4.14 (m, 2H), 3.97 (m, 2H), 3.54 (m, 4H), 3.44 (m, 1H), 2.32 (m, 4H), 2.27 (s, 3H), 1.90 (s, 3H), 1.73 (s, 6H) |
| 67 | <br><br>1-[5-chloro-2-(4-methylpiperazin-1-yl)pyrimidin-4-yl]-N-(2-{6-methylimidazo[1,2-a]pyridin-3-yl}propan-2-yl)azetidine-3-carboxamide | 22 | 50 mg, 72% | HPLC RT (method A2) 5.19 min MH$^+$ 483 | 8.33 (s, 1H), 8.27 (s, 1H), 7.79 (s, 1H), 7.46 (d, 1H), 7.38 (s, 1H), 7.06 (d, 1H), 4.25 (m, 2H), 4.02 (m, 2H), 3.57 (m, 4H), 3.45 (m, 1H), 2.32 (m, 7H), 2.19 (s, 3H), 1.71 (s, 6H) |

TABLE 3-continued

| Ex | Structure | Int | Yield | HPLC/MS | NMR (400 MHz, DMSO-d₆) |
|---|---|---|---|---|---|
| 68 | <br><br>1-{5-chloro-2-[(2R)-2,4-dimethylpiperazin-1-yl]pyrimidin-4-yl}-N-(2-{imidazo[1,2-a]pyridin-3-yl}propan-2-yl)azetidine-3-carboxamide | 1 | 14 mg, 24% | HPLC RT (method A2) 5.37 min MH⁺ 483 | 8.44 (d, 1H), 8.36 (s, 1H), 7.80 (s, 1H), 7.55 (d, 1H), 7.44 (s, 1H), 7.19 (dd, 1H), 6.87 (t, 1H), 4.60 (m, 1H), 4.15-4.25 (m, 3H), 4.03 (m 2H), 3.44 (m, 1H), 3.16 (d, 1H), 2.96 (t, 1H), 2.76 (m, 1H), 2.63 (m, 1H), 2.16 (s, 3H), 1.99 (m, 1H), 1.74 (m, 1H), 1.73 (s, 6H), 1.11 (d, 3H). |
| 68a | 1-{5-chloro-2-[(2S)-2,4-dimethylpiperazin-1-yl]pyrimidin-4-yl}-N-(2-{imidazo[1,2-a]pyridin-3-yl}propan-2-yl)azetidine-3-carboxamide | | | | May be prepared using the method of Example 68, from the appropriate chloropyrimidin intermediate and diamine |
| 69 | <br><br>1-{5-chloro-2-[3-(fluoromethyl)-4-methylpiperazin-1-yl]pyrimidin-4-yl}-N-(2-{imidazo[1,2-a]pyridin-3-yl}propan-2-yl)azetidine-3-carboxamide | 1 | 20 mg, 23% | HPLC RT (method B1) 7.55 min MH⁺ 501 | 8.44 (d, 1H), 8.37 (s, 1H), 7.81 (s, 1H), 7.56 (d, 1H), 7.44 (s, 1H), 7.19 (dd 1H), 6.88 (t, 1H), 4.32 (m, 1H), 4.29 (m, 2H), 4.20 (m, 1H), 4.16 (m, 4H), 4.04 (m, 2H), 3.45 (m, 1H), 2.97 (t, 1H), 2.75 (m, 2H), 2.32 (s, 3H), 2.26 (m, 2H), 1.72 (s, 6H) |

TABLE 3-continued

| Ex | Structure | Int | Yield | HPLC/MS | NMR (400 MHz, DMSO-$d_6$) |
|---|---|---|---|---|---|
| 70 | 1-[5-chloro-2-(4-ethylpiperazin-1-yl)pyrimidin-4-yl]-N-(2-{imidazo[1,2-a]pyridin-3-yl}propan-2-yl)azetidine-3-carboxamide | 1 | 40 mg, 66% | HPLC RT (method A1) 5.43 min MH+ 483 | 8.44 (d, 1H), 8.36 (s, 1H), 7.80 (s, 1H), 7.56 (d, 1H), 7.44 (s, 1H), 7.19 (dd, 1H), 6.89 (t, 1H), 4.25 (m, 2H), 4.04 (m, 2H), 3.57 (m, 4H), 3.45 (m, 1H), 2.33 (m, 6H), 1.73 (s, 6H), 1.01 (t, 3H). |
| 71 | 1-{5-chloro-2-[4-(propan-2-yl)piperazin-1-yl]pyrimidin-4-yl}-N-(2-{imidazo[1,2-a]pyridin-3-yl}propan-2-yl)azetidine-3-carboxamide | 1 | 38 mg, 52% | HPLC RT (method A1) 4.92 min MH+ 497 | 8.44 (d, 1H), 8.36 (s, 1H), 7.79 (s, 1H), 7.56 (d, 1H), 7.44 (s, 1H), 7.19 (dd, 1H), 6.89 (t, 1H), 4.24 (m, 2H), 4.03 (m, 2H), 3.56 (m, 4H), 3.44 (m, 1H), 2.68 (m, 1H), 2.40 (m, 4H), 1.73 (s, 6H), 0.97 (d, 6H). |

TABLE 3-continued

| Ex | Structure | Int | Yield | HPLC/MS | NMR (400 MHz, DMSO-$d_6$) |
|---|---|---|---|---|---|
| 72 | <br><br>1-{5-chloro-2-[4-(2-methoxyethyl)piperazin-1-yl]pyrimidin-4-yl}-N-(2-{imidazo[1,2-a]pyridin-3-yl}propan-2-yl)azetidine-3-carboxamide | 1 | 40 mg, 53% | HPLC RT (method A1) 5.53 min MH⁺ 513 | 8.44 (d, 1H), 8.36 (s, 1H), 7.79 (s, 1H), 7.56 (d, 1H), 7.44 (s, 1H), 7.19 (dd, 1H), 6.89 (t, 1H), 4.25 (m, 2H), 4.03 (m, 2H), 3.56 (m, 4H), 3.45 (t, 2H), 3.41 (m, 1H), 3.23 (s, 3H), 2.52 (m, 2H), 2.45 (m, 4H), 1.73 (s, 6H). |
| 73 | <br><br>1-[5-chloro-2-(4-methylpiperazin-1-yl)pyrimidin-4-yl]-N-(2-{imidazo[1,2-a]pyridin-3-yl}propan-2-yl)-N-methylazetidine-3-carboxamide | 28 | 45 mg, 75% | HPLC RT (method A3) 4.33 min MH⁺ 4.83 | 8.22 (d, 1H), 7.81 (s, 1H), 7.55 (d, 1H), 7.45 (s, 1H), 7.18 (dd, 1H), 6.84 (t, 1H), 4.31 (m, 1H), 4.17 (m, 1H), 3.79 (s, 1H), 3.59 (m, 4H), 2.80 (s, 3H), 2.29 (m, 4H), 2.18 (s, 3H), 1.78 (s, 6H) |

TABLE 3-continued

| Ex | Structure | Int | Yield | HPLC/MS | NMR (400 MHz, DMSO-d<sub>6</sub>) |
|----|-----------|-----|-------|---------|--------------------------------------|
| 74 | <br>1-{5-chloro-2-[(3R)-3,4-dimethylpiperazin-1-yl]pyrimidin-4-yl}-N-(2-{imidazo[1,2-a]pyridin-3-yl}propan-2-yl)-N-methylazetidine-3-carboxamide | 28 | 110 mg, 66% | HPLC RT (method A1) 5.05 min MH⁺ 497 | 8.23 (d, 1H), 7.81 (s, 1H), 7.55 (d, 1H), 7.46 (s, 1H), 7.19 (dd, 1H), 6.85 (t, 1H), 4.10-4.25 (m, 7H), 3.78 (m, 2H), 2.94 (t, 2H), 2.60-2.90 (m, 4H), 2.32 (s, 3H), 2.00-2.20 (m, 2H), 1.77 (s, 6H), 1.00 (d, 3H) |
| 75 | <br>(3R)-1-[5-chloro-2-(4-methylpiperazin-1-yl)pyrimidin-4-yl]-N-(2-{imidazo[1,2-a]pyridin-3-yl}propan-2-yl)pyrrolidine-3-carboxamide | 23 | 45 mg, 65% | HPLC RT (method A) 3.55 min MH⁺ 483 | 8.46 (d, 1H), 8.38 (s, 1H), 7.81 (s, 1H), 7.55 (d, 1H), 7.42 (s, 1H), 7.19 (dd, 1H), 6.86 (t, 1H), 3.79 (m, 1H), 3.68 (m, 1H), 3.62 (m, 4H), 3.51 (m, 1H), 3.03 (m, 1H), 2.30 (m, 4H), 2.19 (s, 3H), 2.06 (m 1H), 1.85 (m, 1H), 1.73 (d, 6H). |
| 76 | <br>(3S)-1-[5-chloro-2-(4-methylpiperazin-1-yl)pyrimidin-4-yl]-N-(2-{imidazo[1,2-a]pyridin-3-yl}propan-2-yl)pyrrolidine-3-carboxamide | 24 | 42 mg, 73% | HPLC RT (method A2) 4.88 min MH⁺ 483 | 8.46 (d, 1H), 8.39 (s, 1H), 7.81 (s, 1H), 7.55 (d, 1H), 7.42 (s, 1H), 7.19 (dd, 1H), 6.86 (t, 1H), 3.79 (m, 1H), 3.68 (m, 1H), 3.62 (m, 4H), 3.51 (m, 1H), 3.03 (m, 1H), 2.30 (m, 4H), 2.19 (s, 3H), 2.06 (m, 1H), 1.85 (m, 1H), 1.72 (d, 6H). |

TABLE 3-continued

| Ex | Structure | Int | Yield | HPLC/MS | NMR (400 MHz, DMSO-$d_6$) |
|---|---|---|---|---|---|
| 77 | <br><br>1-[5-chloro-2-(4-methylpiperazin-1-yl)pyrimidin-4-yl]-N-(2-{imidazo[1,2-a]pyridin-3-yl}propan-2-yl)piperidine-4-carboxamide | 25 | 35 mg, 68% | HPLC RT (method A3) 4.09 min MH+ 497 | 8.46 (d, 1H), 8.19 (s, 1H), 7.93 (s, 1H), 7.54 (d, 1H), 7.40 (s, 1H), 7.18 (dd, 1H), 6.89 (t, 1H), 4.18 (m, 2H), 3.60 (m, 4H), 2.85 (t, 2H), 2.30 (m, 4H), 2.18 (s, 3H), 1.69 (m, 8H), 1.45 (m, 2H). |
| 78 | <br><br>1-[5-fluoro-2-(4-methylpiperazin-1-yl)pyrimidin-4-yl]-N-(2-{imidazo[1,2-a]pyridin-3-yl}propan-2-yl)-N-methylazetidine-3-carboxamide | 27 | 40 mg, 57% | HPLC RT (method A) 4.70 min MH+ 467 | 8.24 (d, 1H), 7.82 (s, 1H), 7.55 (d, 1H), 7.45 (s, 1H), 7.18 (dd, 1H), 6.84 (t, 1H), 4.22 (m, 1H), 4.10 (m, 1H), 3.86 (s, 1H), 3.56 (m, 4H), 2.78 (s, 3H), 2.29 (m, 4H), 2.19 (s, 3H), 1.78 (s, 6H) |

TABLE 3-continued

| Ex | Structure | Int | Yield | HPLC/MS | NMR (400 MHz, DMSO-d$_6$) |
|---|---|---|---|---|---|
| 79 |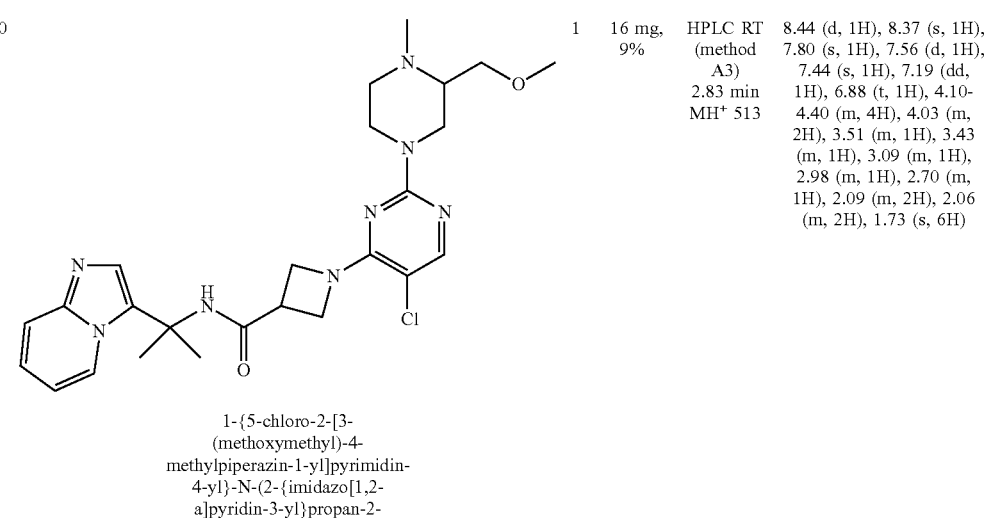

1-{5-chloro-2-[(2S,3R)-2,3-dimethylpiperazin-1-yl]pyrimidin-4-yl}-N-(2-{imidazo[1,2-a]pyridin-3-yl}propan-2-yl)azetidine-3-carboxamide | 1 | 10 mg, 28% | HPLC RT (method A1) 6.09 min MH⁺ 483 | 8.44 (d, 1H), 8.36 (s, 1H), 7.79 (s, 1H), 7.56 (d, 1H), 7.44 (s, 1H), 7.19 (dd, 1H), 6.88 (t, 1H), 4.41 (m, 2H), 4.15-4.25 (m, 3H), 4.03 (m, 2H), 3.43 (m, 1H), 2.88 (d, 1H), 2.73 (m, 2H), 2.67 (m, 2H), 2.37 (m, 1H), 2.50-2.60 (m, 2H), 1.72 (s, 6H), 0.94 (d, 3H) |
| 80 | 1-{5-chloro-2-[3-(methoxymethyl)-4-methylpiperazin-1-yl]pyrimidin-4-yl}-N-(2-{imidazo[1,2-a]pyridin-3-yl}propan-2-yl)azetidine-3-carboxamide | 1 | 16 mg, 9% | HPLC RT (method A3) 2.83 min MH⁺ 513 | 8.44 (d, 1H), 8.37 (s, 1H), 7.80 (s, 1H), 7.56 (d, 1H), 7.44 (s, 1H), 7.19 (dd, 1H), 6.88 (t, 1H), 4.10-4.40 (m, 4H), 4.03 (m, 2H), 3.51 (m, 1H), 3.43 (m, 1H), 3.09 (m, 1H), 2.98 (m, 1H), 2.70 (m, 1H), 2.09 (m, 2H), 2.06 (m, 2H), 1.73 (s, 6H) |

Examples 81-102 were prepared by the same methods as Example 3 from the appropriate secondary amine intermediate and formaldehyde. Examples 103 and 104 were prepared by the method of Example 4 (Buchwald amine displacement on a chloropyrindine), followed by Boc deprotection (Example 1), followed by the reductive amination method of Example 3.

TABLE 4

| Ex | Structure | Int | Yield | HPLC/MS | NMR (400 MHz, (DMSO-d$_6$) |
|---|---|---|---|---|---|
| 81 | <br><br>1-(5-fluoro-2-{6-methyl-3,6-diazabicyclo[3.2.0]heptan-3-yl}pyrimidin-4-yl)-N-{imidazo[1,2-a]pyridin-3-ylmethyl}azetidine-3-carboxamide | Ex 3 | 20 mg, 65% | HPLC RT (method B1) 6.00 min MH$^+$ 437 | 8.53 (t, 1H), 8.35 (d, 1H), 7.84 (d, 1H), 7.58 (d, 1H), 7.52 (s, 1H), 7.26 (dd, 1H), 6.97 (t, 1H), 5.76 (s, 1H), 4.68 (d, 2H), 4.15-4.24 (m, 4H), 3.75-3.80 (m, 3H), 3.30-3.70 (m, 3H), 3.49 (m, 1H), 2.97-3.1- (m, 4H), 2.23 (s, 3H) |
| 82 | <br><br>1-{2-[(3S)-3,4-dimethylpiperazin-1-yl]-5-fluoropyrimidin-4-yl}-N-(2-{imidazo[1,2-a]pyridin-3-yl}propan-2-yl)azetidine-3-carboxamide | Ex 35 | 32 mg, 43% | HPLC RT (method A) 3.54 min MH$^+$ 467 | 8.44 (d, 1H), 8.36 (s, 1H), 7.79 (d, 1H), 7.56 (d, 1H), 7.44 (s, 1H), 7.19 (dd, 1H), 6.89 (t, 1H), 4.15-4.25 (m, 4H), 3.95 (m, 2H), 3.51 (m, 1H), 2.89 (t, 1H), 2.68 (t, 1H), 2.50-2.55 (m, 1H), 2.17 (s, 3H), 1.90-2.00 (m, 2H), 1.73 (s, 6H), 0.99 (d, 3H) |
| 83 | <br><br>1-{5-chloro-2-[(3S)-3,4-dimethylpiperazin-1-yl]pyrimidin-4-yl}-N-(2-{imidazo[1,2-a]pyridin-3-yl}propan-2-yl)azetidine-3-carboxamide | Ex 37 | 39 mg, 52% | HPLC RT (method B1) 6.75 min MH$^+$ 483 | 8.44 (d, 1H), 8.37 (s, 1H), 7.79 (s, 1H), 7.56 (d, 1H), 7.44 (s, 1H), 7.19 (dd, 1H), 6.88 (t, 1H) 4.15-4.25 (m, 4H), 3.95 (m, 2H), 3.52 (m, 1H), 2.89 (t, 1H), 2.68 (m, 1H), 2.17 (s, 3H), 1.90-2.00 (m, 2H), 1.73 (s, 6H), 0.99 (d, 3H) |

TABLE 4-continued

| Ex | Structure | Int | Yield | HPLC/MS | NMR (400 MHz, (DMSO-d$_6$) |
|---|---|---|---|---|---|
| 84 | <br><br>1-{2-[(3R)-3,4-dimethylpiperazin-1-yl]-5-fluoropyrimidin-4-yl}-N-(2-{imidazo[1,2-a]pyridin-3-yl}propan-2-yl)azetidine-3-carboxamide | Ex 38 | 23 mg, 31% | HPLC RT (method A) 3.61 min MH$^+$ 467 | 8.44 (d, 1H), 8.36 (s, 1H), 7.79 (d, 1H), 7.56 (d, 1H), 7.44 (s, 1H), 7.19 (dd, 1H), 6.89 (t, 1H), 4.15-4.25 (m, 4H), 3.95 (m, 2H), 3.51 (m, 1H), 2.89 (t, 1H), 2.68 (t, 1H), 2.50-2.55 (m, 1H), 2.18 (s, 3H), 1.90-2.00 (m, 2H), 1.73 (s, 6H), 0.99 (d, 3H) |
| 85 | <br><br>1-{2-[(3S)-3,4-dimethylpiperazin-1-yl]-5-methoxypyrimidin-4-yl}-N-(2-{imidazo[1,2-a]pyridin-3-yl}propan-2-yl)azetidine-3-carboxamide | Ex 36 | 28 mg, 54% | HPLC RT (method A1) 5.75 min MH$^+$ 479 | 8.44 (d, 1H), 8.33 (s, 1H), 7.56 (s, 1H), 7.55 (d, 1H), 7.44 (s, 1H), 7.18 (dd, 1H), 6.89 (t, 1H), 4.10-4.20 (m, 4H), 3.93 (m, 2H), 3.58 (s, 3H), 3.44 (m, 1H), 2.60-2.85 (m, 2H), 2.17 (s, 3H), 1.90-2.10 (m, 2H), 1.73 (s, 6H), 0.99 (d, 3H) |
| 85a | 1-{2-[(3R)-3,4-dimethylpiperazin-1-yl]-5-methoxypyrimidin-4-yl}-N-(2-{imidazo[1,2-a]pyridin-3-yl}propan-2-yl)azetidine-3-carboxamide | | | | May be prepared using the method of Example 85. from the appropriate secondary amine intermediate and formaldehyde |

TABLE 4-continued

| Ex | Structure | Int | Yield | HPLC/MS | NMR (400 MHz, (DMSO-d$_6$) |
|---|---|---|---|---|---|
| 86 | <br><br>1-{2-[(3R)-3,4-dimethylpiperazin-1-yl]-5-fluoropyrimidin-4-yl}-N-(2-{imidazo[1,2-a]pyridin-3-yl}propan-2-yl)pyrrolidine-3-carboxamide | 26 | 75 mg, 89% | HPLC RT (method A1) 7.44 min MH$^+$ 481 | 8.48 (d, 1H), 8.13 (s, 1H), 7.80 (d, 1H), 7.55 (d, 1H), 7.43 (s, 1H), 7.17 (dd, 1H), 6.85 (t, 1H), 4.15-4.25 (m, 4H), 3.79 (m, 2H), 2.89 (t, 1H), 2.73 (t, 1H), 2.33 (s, 3H), 1.90-2.20 (m, 2H), 1.75 (s, 6H), 1.48 (s, 3H), 0.99 (d, 3H) |
| 87 | <br><br>1-{2-[(3R)-3,4-dimethylpiperazin-1-yl]-5-fluoropyrimidin-4-yl}-N-(2-{imidazo[1,2-a]pyridin-3-yl}propan-2-yl)-3-methylazetidine-3-carboxamide | 20 | 14 mg, 47% | HPLC RT (method A1) 5.92 min MH$^+$ 481 | 8.44 (d, 1H), 8.33 (s, 1H), 7.56 (s, 1H), 7.56 (d, 1H), 7.44 (s, 1H), 7.18 (dd, 1H), 6.88 (t, 1H), 4.21 (m, 2H), 4.12 (m, 2H), 3.93 (m, 2H), 3.58 (s, 3H), 3.44 (m, 1H), 2.50 (m, 2H), 2.15 (s, 3H), 1.99 (m, 2H), 1.72 (s, 6H), 1.02 (d, 6H) |
| 87a | 1-{2-[(3S)-3,4-dimethylpiperazin-1-yl]-5-fluoropyrimidin-4-yl}-N-(2-{imidazo[1,2-a]pyridin-3-yl}propan-2-yl)-3-methylazetidine-3-carboxamide | | | | May be prepared using the method of Example 87. from the appropriate secondary amine intermediate and formaldehyde |

TABLE 4-continued

| Ex | Structure | Int | Yield | HPLC/MS | NMR (400 MHz, (DMSO-d$_6$) |
|---|---|---|---|---|---|
| 88 | <br><br>N-(2-{imidazo[1,2-a]pyridin-3-yl}propan-2-yl)-1-{5-methoxy-2-[(3R,5S)-3,4,5-trimethylpiperazin-1-yl]pyrimidin-4-yl}azetidine-3-carboxamide | Ex 42 | 22 mg, 53% | HPLC RT (method B1) 6.07 min MH$^+$ 493 | 8.44 (d, 1H), 8.37 (s, 1H), 7.79 (s, 1H), 7.56 (d, 1H), 7.45 (s, 1H), 7.19 (dd, 1H), 6.88 (t, 1H), 4.20-4.35 (m, 4H), 4.03 (m, 2H), 3.44 (m, 1H), 2.15 (s, 3H), 2.00 (m, 2H), 1.72 (s, 6H), 1.02 (d, 6H) |
| 89 | <br><br>1-{5-chloro-2-[(3R,5S)-3,4,5-trimethylpiperazin-1-yl]pyrimidin-4-yl}-N-(2-{imidazo[1,2-a]pyridin-3-yl}propan-2-yl)azetidine-3-carboxamide | Ex 43 | 40 mg, 65% | HPLC RT (method A1) 5.56 min MH$^+$ 497 | 8.44 (d, 1H), 8.37 (s, 1H), 7.79 (d, 1H), 7.57 (d, 1H), 7.45 (s, 1H), 7.19 (dd, 1H), 6.88 (t, 1H), 4.24 (d, 2H), 4.17 (m, 2H), 3.94 (m, 2H), 3.52 (m, 1H), 2.70 (m, 1H), 2.15 (m, 4H), 2.00 (m, 2H), 1.73 (s, 6H), 1.02 (d, 6H) |
| 90 | <br><br>1-{5-fluoro-2-[(3R,5S)-3,4,5-trimethylpiperazin-1-yl]pyrimidin-4-yl}-N-(2-{imidazo[1,2-a]pyridin-3-yl}propan-2-yl)azetidine-3-carboxamide | Ex 44 | 15 mg, 21% | HPLC RT (method A1) 6.92 min MH$^+$ 481 | 8.43 (d, 1H), 8.33 (s, 1H), 7.55 (m, 2H), 7.44 (s, 1H), 7.19 (dd, 1H), 6.88 (t, 1H), 4.12 (m, 2H), 3.94 (m, 2H), 3.57 (m, 5H), 3.44 (m, 1H), 2.67 (m, 2H), 2.19 (s, 3H), 1.72 (s, 6H), 0.88 (d, 6H) |

TABLE 4-continued

| Ex | Structure | Int | Yield | HPLC/MS | NMR (400 MHz, (DMSO-d$_6$) |
|---|---|---|---|---|---|
| 91 | <br><br>N-(2-{imidazo[1,2-a]pyridin-3-yl}propan-2-yl)-1-{5-methoxy-2-[(3R,5R)-3,4,5-trimethylpiperazin-1-yl]pyrimidin-4-yl}azetidine-3-carboxamide | Ex 45 | 20 mg, 34% | HPLC RT (method A) 6.00 min MH$^+$ 493 | 8.44 (d, 1H), 8.37 (s, 1H), 7.77 (s, 2H), 7.56 (d, 1H), 7.44 (s, 1H), 7.19 (dd, 1H), 6.87 (t, 1H), 4.25 (m, 2H), 4.03 (m, 2H), 3.66 (m, 2H), 3.44 (m, 1H), 2.67 (m, 2H), 2.19 (s, 3H), 1.73 (s, 6H), 0.87 (d, 6H) |
| 91a | N-(2-{imidazo[1,2-a]pyridin-3-yl}propan-2-yl)-1-[5-methoxy-2-[(3S,5S)-3,4,5-trimethylpiperazin-1-yl]pyrimidin-4-yl}azetidine-3-carboxamide | | | May be prepared using the method of Example 91. from the appropriate secondary amine intermediate and formaldehyde | |
| 92 | <br><br>1-{5-chloro-2-[(3R,5R)-3,4,5-trimethylpiperazin-1-yl]pyrimidin-4-yl}-N-(2-{imidazo[1,2-a]pyridin-3-yl}propan-2-yl)azetidine-3-carboxamide | Ex 46 | 30 mg, 45% | HPLC RT (method A1) 6.29 min MH$^+$ 497 | 8.44 (d, 1H), 8.36 (s, 1H), 7.77 (d, 2H), 7.56 (d, 1H), 7.44 (s, 1H), 7.20 (dd, 1H), 6.87 (t, 1H), 4.16 (m, 2H), 3.94 (m, 2H), 3.59 (m, 2H), 3.51 (m, 1H), 2.67 (m, 2H), 2.20 (s, 3H), 1.73 (s, 6H), 0.88 (d, 6H) |
| 92a | 1-{5-chloro-2-[(3S,5S)-3,4,5-trimethylpiperazin-1-yl]pyrimidin-4-yl}-N-(2-{imidazo[1,2-a]pyridin-3-yl}propan-2-yl)azetidine-3-carboxamide | | | May be prepared using the method of Example 92. from the appropriate secondary amine intermediate and formaldehyde | |

TABLE 4-continued

| Ex | Structure | Int | Yield | HPLC/MS | NMR (400 MHz, (DMSO-d$_6$) |
|---|---|---|---|---|---|
| 93 | <br><br>1-{5-fluoro-2-[(3R,5R)-3,4,5-trimethylpiperazin-1-yl]pyrimidin-4-yl}-N-(2-{imidazo[1,2-a]pyridin-3-yl}propan-2-yl)azetidine-3-carboxamide | Ex 47 | 30 mg, 51% | HPLC RT (method A1) 5.68 min MH$^+$ 481 | 8.44 (d, 1H), 8.33 (s, 1H), 7.55 (m, 2H), 7.44 (s, 1H), 7.17 (dd, 1H), 6.88 (t, 1H), 4.11 (m, 2H), 3.92 (m, 2H), 3.64 (m, 5H), 3.44 (m, 1H), 2.67 (m, 2H), 2.23 (s, 3H), 1.72 (s, 6H), 0.90 (d, 6H) |
| 93a | 1-{5-fluoro-2-[(3S,5S)-3,4,5-trimethylpiperazin-1-yl]pyrimidin-4-yl}-N-(2-{imidazo[1,2-a]pyridin-3-yl}propan-2-yl)azetidine-3-carboxamide | | | May be prepared using the method of Example 93, from the appropriate secondary amine intermediate and formaldehyde | |
| 94 | <br><br>N-(2-{imidazo[1,2-a]pyridin-3-yl}propan-2-yl)-1-{5-methoxy-2-[(3S,5S)-3,4,5-trimethylpiperazin-1-yl]pyrimidin-4-yl}azetidine-3-carboxamide | 12 | 10 mg, 24% | HPLC RT (method A) 4.72 min MH$^+$ 493 | 8.44 (d, 1H), 8.37 (s, 1H), 7.77 (s, 2H), 7.56 (d, 1H), 7.44 (s, 1H), 7.19 (dd, 1H), 6.88 (t, 1H), 4.25 (m, 2H), 4.02 (m, 2H), 3.63 (m, 2H), 3.44 (m, 1H), 2.67 (m, 2H), 2.20 (s, 3H), 2.07 (s, 2H), 1.72 (s, 6H), 0.87 (d, 6H) |
| 94a | N-(2-{imidazo[1,2-a]pyridin-3-yl}propan-2-yl)-1-{5-methoxy-2-[(3R,5R)-3,4,5-trimethylpiperazin-1-yl]pyrimidin-4-yl}azetidine-3-carboxamide | | | May be prepared using the method of Example 94, from the appropriate secondary amine intermedaite and formaldehyde | |

TABLE 4-continued

| Ex | Structure | Int | Yield | HPLC/MS | NMR (400 MHz, (DMSO-d$_6$) |
|---|---|---|---|---|---|
| 95 | <br><br>1-{5-chloro-2-[(3S,5S)-3,4,5-trimethylpiperazin-1-yl]pyrimidin-4-yl}-N-(2-{imidazo[1,2-a]pyridin-3-yl}propan-2-yl)azetidine-3-carboxamide | Ex 48 | 16 mg, 38% | HPLC RT (method A2) 7.44 min MH$^+$ 497 | 8.48 (d, 1H), 8.40 (s, 1H), 7.80 (d, 1H) ,7.55 (d, 1H), 7.43 (s, 1H), 7.19 (dd, 1H), 6.87 (t, 1H), 4.20-4.30 (m, 2H), 3.70 (m, 1H), 3.57 (m, 1H), 3.48 (m, 1H), 3.40 (m, 1H), 3.05 (m, 1H), 2.95 (m, 1H), 2.24 (m, 2H), 2.07 (s, 3H), 2.06 (m, 1H), 1.85 (m, 1H), 1.73 (d, 6H), 1.04 (d, 3H). |
| 95a | 1-{5-chloro-2-[(3R,5R)-3,4,5-trimethylpiperazin-1-yl]pyrimidin-4-yl}-N-(2-{imidazo[1,2-a]pyridin-3-yl}propan-2-yl)azetidine-3-carboxamide | May be prepared using the method of Example 95, from the appropriate secondary amine intermediate and formaldehyde | | | |
| 96 | <br><br>1-{5-fluoro-2-[(3S,5S)S-3,4,5-trimethylpiperazin-1-yl]pyrimidin-4-yl}-N-(2-{imidazo[1,2-a]pyridin-3-yl}propan-2-yl)azetidine-3-carboxamide | Ex 49 | 16 mg, 39% | HPLC RT (method A2) 6.45 min MH$^+$ 481 | 8.44 (d, 1H), 8.36 (s, 1H), 7.77 (d, 2H), 7.56 (d, 1H), 7.44 (s, 1H), 7.19 (dd, 1H), 6.89 (t, 1H), 4.16 (m, 2H), 3.94 (m, 2H), 3.59 (m, 2H), 3.51 (m, 1H), 2.67 (m, 2H), 2.19 (s, 3H), 1.73 (s, 6H), 0.87 (d, 6H) |
| 96a | 1-{5-fluoro-2-[(3R,5R)-3,4,5-trimethylpiperazin-1-yl]pyrimidin-4-yl}-N-(2-{imidazo[1,2-a]pyridin-3-yl}propan-2-yl)azetidine-3-carboxamide | May be prepared using the method of Example 96, from the appropriate secondary amine intermediate and formaldehyde | | | |

TABLE 4-continued

| Ex | Structure | Int | Yield | HPLC/MS | NMR (400 MHz, (DMSO-d₆) |
|---|---|---|---|---|---|
| 97 |  1-{2-[(3R)-3,4-dimethylpiperazin-1-yl}-5-fluoropyrimidin-4-yl}-N-(2-{6-methylimidazo[1,2-a]pyridin-3-yl}propan-2-yl)azetidine-3-carboxamide | 17 | 35 mg, 56% | HPLC RT (method A3) 3.68 min MH⁺ 481 | 8.34 (s, 1H), 8.30 (s, 1H), 7.79 (d, 1H), 7.46 (d, 1H), 7.38 (s, 1H), 7.06 (d, 1H), 4.15-4.25 (m, 4H), 3.94 (m, 2H), 3.52 (m, 1H), 2.88 (t, 1H), 2.73 (t, 1H), 2.28 (s, 3H), 2.18 (s, 3H), 1.90-2.00 (m, 2H), 1.71 (s, 6H), 0.99 (d, 3H) |
| 98 |  1-{5-chloro-2-[(3R)-3,4-dimethylpiperazin-1-yl]pyrimidin-4-yl}-N-(2-{6-methylimidazo[1,2-a]pyridin-3-yl}propan-2-yl)azetidine-3-carboxamide | 22 | 20 mg, 22% | HPLC RT (method A) 6.54 min MH⁺497 | 8.34 (s, 1H), 8.27 (s, 1H), 7.79 (s, 1H), 7.46 (d, 1H), 7.38 (s, 1H), 7.05 (d, 1H), 4.15-4.25 (m, 4H), 4.01 (m, 2H), 3.46 (m, 1H), 2.92 (t, 1H), 2.70 (t, 1H), 2.55 (m, 1H), 2.29 (s, 3H), 2.17 (s, 3H), 2.00 (t, 1H), 1.90 (m, 1H), 1.71 (s, 6H), 0.99 (d, 3H) |

TABLE 4-continued

| Ex | Structure | Int | Yield | HPLC/MS | NMR (400 MHz, (DMSO-d$_6$) |
|---|---|---|---|---|---|
| 99 | (3R)-1-{5-chloro-2-[(3R)-3,4-dimethylpiperazin-1-yl]pyrimidin-4-yl}-N-(2-{imidazo[1,2-a]pyridin-3-yl}propan-2-yl)pyrrolidine-3-carboxamide | 23 | 45 mg, 68% | HPLC RT (method A) 3.61 min MH$^+$ 497 | 8.47 (d, 1H), 8.39 (s, 1H), 7.82 (s, 1H), 7.55 (d, 1H), 7.43 (s, 1H), 7.19 (dd, 1H), 6.87 (t, 1H), 4.23 (m, 2H), 3.80 (t, 1H), 3.66 (m, 1H), 3.59 (t, 1H), 3.54 (t, 1H), 3.04 (t, 1H), 3.00 (m, 1H), 2.74 (m, 1H), 2.67 (m, 1H), 2.21 (m, 2H), 2.06 (m, 2H), 1.83 (m, 1H), 1.73 (s, 3H), 1.71 (s, 3H), 1.01 (d, 3H) |
| 100 | (3S)-1-{5-chloro-2-[(3R)-3,4-dimethylpiperazin-1-yl]pyrimidin-4-yl}-N-(2-{imidazo[1,2-a]pyridin-3-yl}propan-2-yl)pyrrolidine-3-carboxamide | 24 | 40 mg, 49% | HPLC RT (method A3) 3.91 min MH$^+$ 497 | 8.47 (d, 1H), 8.39 (s, 1H), 7.81 (s, 1H), 7.56 (d, 1H), 7.43 (s, 1H), 7.19 (dd, 1H), 6.86 (t, 1H), 4.22 (m, 2H), 3.80 (t, 1H), 3.66 (m, 1H), 3.63 (t, 1H), 3.59 (t, 1H), 3.04 (t, 1H), 2.98 (m, 1H), 2.76 (m, 1H), 2.56 (m, 1H), 2.21 (s, 3H), 2.04 (m, 2H), 1.87 (m, 1H), 1.73 (s, 3H), 1.71 (s, 3H), 1.00 (d, 3H) |
| 101 | 1-{5-chloro-2-[(3S)-3,4-dimethylpiperazin-1-yl]pyrimidin-4-yl}-N-(2-{imidazo[1,2-a]pyridin-3-yl}propan-2-yl)piperidine-4-carboxamide | 25 | 36 mg, 63% | HPLC RT (method A3) 4.14 min MH$^+$ 511 | 8.46 (d, 1H), 8.18 (s, 1H), 7.93 (s, 1H), 7.54 (d, 1H), 7.40 (s, 1H), 7.18 (dd, 1H), 6.89 (t, 1H), 4.16-4.27 (m, 4H), 2.99 (t, 1H), 2.86 (t, 2H), 2.75 (m, 1H), 2.59 (m, 1H), 2.30 (m, 4H), 1.90-2.03 (m, 2H), 1.69 (m, 8H), 1.45 (m, 2H), 1.00 (d, 3H). |

TABLE 4-continued

| Ex | Structure | Int | Yield | HPLC/MS | NMR (400 MHz, (DMSO-d$_6$) |
|---|---|---|---|---|---|
| 101a | 1-{5-chloro-2-[(3S)-3,4-dimethylpiperazin-1-yl]pyrimidin-4-yl}-N-(2-{imidazo[1,2-a]pyridin-3-yl}propan-2-yl)piperidine-4-carboxamide | | | May be prepared using the method of Example 101, from the appropriate secondary amine intermediate and formaldehyde | |
| 102 | 1-{2-[(3R)-3,4-dimethylpiperazin-1-yl]-5-fluoropyrimidin-4-yl}-N-(2-{imidazo[1,2-a]pyridin-3-yl}propan-2-yl)-N-methylazetidine-3-carboxamide | 27 | 18 mg, 43% | HPLC RT (method B1) 7.83 min MH$^+$ 481 | 8.24 (d, 1H), 7.81 (d, 1H), 7.56 (d, 1H), 7.45 (s, 1H), 7.18 (dd, 1H), 6.85 (t, 1H), 4.00-4.25 (m, 4H), 3.86 (m, 1H), 2.90 (t, 1H), 2.70-2.85 (m, 3H), 2.18 (s, 3H), 1.90-2.10 (m, 2H), 1.79 (s, 6H), 1.00 (d, 3H) |
| 103 | 1-{5-chloro-2-[(3R)-3,4-dimethylpiperazin-1-yl]pyridin-4-yl}-N-(2-{imidazo[1,2-a]pyridin-3-yl}propan-2-yl)azetidine-3-carboxamide | 29 (3 steps) | 20 mg, 29% | HPLC RT (method A2) 4.73 min MH$^+$ 482 | 8.43 (d, 1H), 8.37 (s, 1H), 7.68 (s, 1H), 7.56 (d, 1H), 7.44 (s, 1H), 7.19 (dd, 1H), 6.90 (t, 1H), 4.17 (t, 2H), 3.92 (m, 4H), 3.46 (m, 1H), 2.77 (m, 1H), 2.50 (m, 1H), 2.18 (s, 3H), 1.90-2.00 (m, 2H), 1.73 (s, 6H), 1.01 (d, 3H) |
| 103a | 1-{5-chloro-2-[(3S)-3,4-dimethylpiperazin-1-yl]pyridin-4-yl}-N-(2-{imidazo[1,2-a]pyridin-3-yl}propan-2-yl)azetidine-3-carboxamide | | | May be prepared using the method of 103a, using the appropriate amine, chloropyridine and aldehyde | |

TABLE 4-continued

| Ex | Structure | Int | Yield | HPLC/MS | NMR (400 MHz, (DMSO-d$_6$) |
|---|---|---|---|---|---|
| 104 | <br><br>1-{2-[(3R)-3,4-dimethylpiperazin-1-yl]-5-fluoropyridin-4-yl}-N-(2-{imidazo[1,2-a]pyridin-3-yl}propan-2-yl)azetidine-3-carboxamide | 2 (3 steps) | 12 mg, 28% | HPLC RT (method B1) 6.05 min MH$^+$ 466 | 8.43 (d, 1H), 8.35 (s, 1H), 7.67 (d, 1H), 7.56 (d, 1H), 7.44 (s, 1H), 7.20 (dd, 1H), 6.90 (t, 1H), 5.68 (d, 1H), 4.08 (t, 2H), 3.87 (m, 4H), 3.51 (m, 1H), 2.73 (m, 1H), 2.35 (m, 1H), 2.18 (s, 3H), 1.90-2.00 (m, 2H), 1.73 (s, 6H), 1.01 (d, 3H) |
| 104a | 1-{2-[(3S)-3,4-dimethylpiperazin-1-yl]-5-fluoropyridin-4-yl}-N-(2-{imidazo[1,2-a]pyridin-3-yl}propan-2-yl)azetidine-3-carboxamide | | | May be prepared using the method of 103a, using the appropriate amine, chloropyridine and aldehyde | |

Examples 105-111 were prepared by the same method as Example 4 from the appropriate chloropyridine or chloro-pyrimidine intermediate and diamine.

TABLE 5

| Ex | Structure | Int. | Yield | HPLC/MS | NMR (400 MHz, DMSO-d$_6$) |
|---|---|---|---|---|---|
| 105 | <br><br>1-[5-chloro-2-(4-methylpiperazin-1-yl)pyridin-4-yl]-N-(2-{imidazo[1,2-a]pyridin-3-yl}propan-2-yl)azetidine-3-carboxamide | 29 | 30 mg, 17% | HPLC RT (method B1) 6.29 min MH$^+$ 468 | 8.43 (d, 1H), 7.85 (s, 1H), 7.64 (s, 1H), 7.58 (d, 1H), 7.25 (dd, 1H), 6.95 (t, 1H), 4.89 (s, 2H), 4.64 (m, 1H), 4.20-4.40 (m, 3H), 3.83 (t, 1H), 2.99 (t, 1H), 2.73 (m, 1H), 2.60 (m, 1H), 2.16 (s, 3H), 1.99 (m, 1H), 1.80 (m, 1H), 1.13 (d, 3H). |

TABLE 5-continued

| Ex | Structure | Int. | Yield | HPLC/MS | NMR (400 MHz, DMSO-d₆) |
|---|---|---|---|---|---|
| 106 |  1-{5-chloro-2-[(2S)-2,4-dimethylpiperazin-1-yl]pyrimidin-4-yl}-N-{imidazo[1,2-a]pyridin-3-ylmethyl}-N-methylazetidine-3-carboxamide | 9 | 6 mg, 5% | HPLC RT (method A2) 6.39 min MH⁺ 469 | 8.23 (d, 1H), 7.82 (s, 1H), 7.55 (d, 1H), 7.44 (s, 1H), 7.18 (dd, 1H), 6.85 (t, 1H), 4.63 (m, 1H), 4.20-4.40 (m, 3H), 3.78 (m, 1H), 2.97 (t, 1H), 2.80 (m, 2H), 2.67 (m, 1H), 2.16 (s, 3H), 2.00 (m, 1H), 1.78 (s, 6H), 1.19 (s, 3H). |
| 107 |  1-{5-chloro-2-[(2S)-2,4-dimethylpiperazin-1-yl]pyrimidin-4-yl}-N-(2-{imidazo[1,2-a]pyridin-3-yl}propan-2-yl)-N-methylazetidine-3-carboxamide | 28 | 8 mg, 6% | HPLC RT (method A1) 5.07 min MH⁺ 497 | 8.24 (d, 1H), 7.82 (s, 1H), 7.55 (d, 1H), 7.45 (s, 1H), 7.18 (dd, 1H), 6.84 (t, 1H), 4.59 (m, 1H), 4.20-4.40 (m, 3H), 3.86 (m, 1H), 2.95 (t, 1H), 2.78 (m, 3H), 2.65 (m, 1H), 2.16 (s, 3H), 2.00 (m, 1H), 1.78 (s, 6H), 1.11 (d, 3H). |

TABLE 5-continued

| Ex | Structure | Int. | Yield | HPLC/MS | NMR (400 MHz, DMSO-d<sub>6</sub>) |
|---|---|---|---|---|---|
| 108 | <br><br>1-{2-[(2S)-2,4-dimethylpiperazin-1-yl]-5-fluoropyrimidin-4-yl}-N-(2-{imidazo[1,2-a]pyridin-3-yl}propan-2-yl)-N-methylazetidine-3-carboxamide | 27 | 15 mg, 21% | HPLC RT (method A1) 4.79 min MH$^+$ 481 | 8.41 (d, 1H), 8.33 (s, 1H), 7.75 (s, 1H), 7.53 (d, 1H), 7.41 (s, 1H), 7.16 (dd, 1H), 6.85 (t, 1H), 4.57 (m, 1H), 4.21 (m, 2H), 4.13 (d, 1H), 4.01 (m, 2H), 3.42 (m, 1H), 3.13 (d, 1H), 2.84 (m, 1H), 2.57 (m, 1H), 2.22 (m, 1H), 2.17 (s, 3H), 1.70 (s, 6H), 1.09 (d, 3H), 0.76 (d, 3H). |
| 109 | <br><br>1-{5-chloro-2-[(2S,5R)-2,4,5-trimethylpiperazin-1-yl]pyrimidin-4-yl}-N-(2-{imidazo[1,2-a]pyridin-3-yl}propan-2-yl)azetidine-3-carboxamide | 1 | 21 mg, 9% | HPLC RT (method A2) 6.36 min MH$^+$ 497 | 8.43 (d, 1H), 8.37 (s, 1H), 7.69 (s, 1H), 7.56 (d, 1H), 7.44 (s, 1H), 7.20 (dd, 1H), 6.90 (t, 1H), 5.63 (s, 1H), 4.17 (t, 2H), 3.93 (t, 2H), 3.46 (m, 1H), 3.35 (m, 4H), 2.35 (m, 4H), 2.20 (s, 3H), 1.73 (s, 6H). |

TABLE 5-continued

| Ex | Structure | Int. | Yield | HPLC/MS | NMR (400 MHz, DMSO-$d_6$) |
|---|---|---|---|---|---|
| 110 | | 1 | 20 mg, 11% | HPLC RT (method A) 6.06 min MH$^+$ 497 | 8.45 (d, 1H), 8.39 (s, 1H), 7.80 (s, 1H), 7.55 (d, 1H), 7.44 (s, 1H), 7.19 (dd, 1H), 6.88 (t, 1H), 4.57 (m, 1H), 4.25 (m, 2H), 4.13 (d, 1H), 4.03 (m, 2H), 3.42 (m, 1H), 2.58 (m, 1H), 2.47 (m, 1H), 2.14 (s, 3H), 1.78 (m, 1H), 1.70 (s, 6H), 1.12 (d, 3H), 1.02 (d, 3H). |
| | 1-{5-chloro-2-[(2R,5R)-2,4,5-trimethylpiperazin-1-yl]pyrimidin-4-yl}-N-(2-{imidazo[1,2-a]pyridin-3-yl}propan-2-yl)azetidine-3-carboxamide | | | | |
| 110a | 1-{5-chloro-2-[(2S,5S)-2,4,5-trimethylpiperazin-1-yl]pyrimidin-4-yl}-N-(2-{imidazo[1,2-a]pyridin-3-yl}propan-2-yl)azetidine-3-carboxamide | | May be prepared using the method of Example 110, from the appropriate chloropyrimidine intermediate and diamine. | | |
| 111 | | 7 | 70 mg, 28% | HPLC RT (method A2) 4.71 min MH$^+$ 481 | 8.44 (d, 1H), 8.36 (s, 1H), 7.77 (d, 1H), 7.56 (d, 1H), 7.44 (s, 1H), 7.19 (dd, 1H), 6.88 (t, 1H), 4.56 (m, 1H), 4.16 (m, 2H), 4.09 (d, 1H), 3.94 (m, 2H), 3.51 (m, 1H), 3.14 (d, 1H), 2.85 (m, 1H), 2.60 (m, 1H), 2.24 (m, 1H), 2.20 (s, 3H), 1.73 (s, 6H), 1.09 (d, 3H), 0.80 (d, 3H). |
| | 1-{5-fluoro-2-[(2S,5R)-2,4,5-trimethylpiperazin-1-yl]pyrimidin-4-yl}-N-(2-{imidazo[1,2-a]pyridin-3-yl}propan-2-yl)azetidine-3-carboxamide | | | | |

HPLC Methods for Examples 113 to 158:

Eclipse Extend or XDB 5 μm C18 (150×4.6 mm), Xbridge 5 μm C18 (100×4.6 mm), Zorbax Extend μm C18 (150×4.6 mm), or Shimadzu L Column 2 ODS 5 μm C18 (150×4.6 mm) column using gradient elution of acetonitrile (ACN) in water containing 10 mM ammonium acetate over 15 mins (HPLC B), 17 mins (B1) or 21 mins (B2) and 18 mins (B3). The purity certain of examples were determined by analytical hplc using a Poroshell 120 2.7 μm EC18 (100×4.6 mm), Luna Omega Polar 3 μm C18 (100×4.6 mm), Xbridge 5 μm C18 (150×4.6 mm) or Sunfire 5 μm C18 (100×4.6 mm) using gradient elution of acetonitrile (ACN) in water containing 0.05% trifluoroacetic acid over 12 mins (HPLC A), 14 mins (A1) or 17 mins (A2) and 16 mins (A4). The purity of certain other examples was determined by analytical hplc using a Gemini NX 3 μm C18 (100×4.6 mm) column using gradient elution of acetonitrile in water containing 0.05% formic acid over 12 mins (A3) and 14 mins (A5) 16 mins (A6).

Synthesis of Example: 113, N-(2-(imidazo[1,2-a]pyridin-3-yl)propan-2-yl)-1-(2-(4-methyl-1,4-diazepan-1-yl)thieno[2,3-d]pyrimidin-4-yl)azetidine-3-carboxamide Step 1

To a solution of N-(2-(imidazo[1,2-a]pyridin-3-yl)pro-pan-2-yl)azetidine-3-carboxamide (TFA salt, 300 mg, 0.62 mmol) (product of step 2 in example 118) in 2-propanol (5 ml) was added Et3N (0.864 ml, 6.198 mmol) at 0° C. Then 2,4-dichlorothieno[2,3-d]pyrimidine (190.6 mg, 0.93 mmol) was added and the reaction mixture was stirred at RT for 2 h. Reaction mixture was evaporated under reduce pressure, diluted with ethyl acetate and washed with water. Organic layer was separated, dried over Na2SO4 and evaporated under reduce pressure to get crude compound. Crude was purified by combiflash (12 g silica column) using 3% MeOH in DCM to afford 1-(2-chlorothieno[2,3-d]pyrimidin-4-yl)-N-(2-(imidazo[1,2-a]pyridin-3-yl)propan-2-yl)azetidine-3-carboxamide (200 mg, 75.58%). ¹H NMR (400 MHz, DMSO-d₆) δ 8.48-8.45 (m, 2H), 7.59-7.54 (m, 2H), 7.45 (s, 1H), 7.34 (d, 1H), 7.22-7.18 (m, 1H), 6.95-6.91 (m, 1H), 4.65-4.60 (m, 1H), 4.45-4.29 (m, 2H), 4.05-4.00 (m, 1H), 3.60-3.57 (m, 1H), 1.75 (s, 6H); LCMS (HCOOH:ACN): M+H=427, R$_t$=1.41 min in 3 mins run.

Step 2

-continued

A stirred solution of 1-(2-chlorothieno[2,3-d]pyrimidin-4-yl)-N-(2-(imidazo[1,2-a]pyridin-3-yl)propan-2-yl)azeti-dine-3-carboxamide (100 mg, 0.235 mmol) and 1-methyl-1,4-diazepane (0.146 ml, 1.174 mmol) in n-BuOH (0.75 ml) was irradiated in microwave at 115° C. for 1 h. Reaction mixture was cooled to RT and concentrated under reduced pressure. The crude was purified over Prep TLC (6% MeOH-DCM) to afforded N-(2-(imidazo[1,2-a]pyridin-3-yl)propan-2-yl)-1-(2-(4-methyl-1,4-diazepan-1-yl)thieno[2,3-d]pyrimidin-4-yl)azetidine-3-carboxamide (example 113) (50 mg, 42.21%) as white solid.

¹H NMR (400 MHz, MeOD) δ 8.44 (d, 1H), 7.55 (d, 1H), 7.49 (s, 1H), 7.30-7.26 (m, 1H), 7.03 (d, 1H), 6.95-6.92 (m, 1H), 6.83 (d, 1H), 4.42-4.37 (m, 2H), 4.23-4.20 (m, 2H), 3.87-3.85 (m, 2H), 3.79-3.76 (m, 2H), 3.62-3.60 (m, 11H), 2.74-2.72 (m, 2H), 2.62-2.59 (m, 2H), 2.37 (s, 3H), 1.99-1.96 (m, 2H), 1.84 (s, 6H); HPLC RT (method A6) 3.80 min; LCMS (NH₄OAc:ACN): M+H=505, Rt=2.59 min in 5 mins run.

Synthesis of Example 114: N-(2-(imidazo[1,2-a]pyridin-3-yl)propan-2-yl)-1-(2-(4-methyl-1,4-diazepan-1-yl)-6,7-dihydro-5H-cyclopenta[d]pyrimidin-4-yl)azetidine-3-carboxamide Step 1

211

To a solution of N-(2-(imidazo[1,2-a]pyridin-3-yl)pro-pan-2-yl)azetidine-3-carboxamide (TFA salt, 300 mg, 0.62 mmol) (product of step 2 in example 118) in 2-propanol (5 ml) was added Et3N (0.864 ml, 6.198 mmol) at 0° C. Then 2,4-dichloro-6,7-dihydro-5H-cyclopenta[d]pyrimidine (175.723 mg, 0.93 mmol) was added and the reaction mixture was stirred at RT for 2 h.

Reaction mixture was evaporated under reduce pressure, diluted with ethyl acetate and washed with water. Organic layer was separated, dried over Na2SO4 and evaporated under reduce pressure to get crude compound. Crude was purified combiflash (12 g silica column) using 3% MeOH in DCM to afford 1-(2-chloro-6,7-dihydro-5H-cyclopenta[d] pyrimidin-4-yl)-N-(2-(imidazo[1,2-a]pyridin-3-yl)propan-2-yl)azetidine-3-carboxamide (170 mg, 66.75%); H NMR (400 MHz, DMSO-d$_6$) δ 8.44 (d, 1H), 8.37 (s, 1H), 7.56 (d, 1H), 7.45 (s, 1H), 7.21 (t, 1H), 6.91 (t, 1H), 4.26-4.20 (m, 2H), 4.07-4.01 (m, 2H), 3.50-3.45 (m, 1H), 2.79 (t, 2H), 2.65 (t, 2H), 1.98-1.92 (m, 2H), 1.73 (s, 6H); LCMS (HCOOH: ACN): M+H=411, R$_t$=1.34 min in 3 mins run.

Step 2

A stirred solution of 1-(2-chloro-6,7-dihydro-5H-cyclo-penta[d]pyrimidin-4-yl)-N-(2-(imidazo[1,2-a]pyridin-3-yl) propan-2-yl)azetidine-3-carboxamide (11) (100 mg, 0.244 mmol) and 1-methyl-1,4-diazepane (0.15 ml, 1.22 mmol) in n-BuOH (0.75 ml) was irradiated in microwave at 115° C. for 1 h. Reaction mixture was cooled to RT and concentrated under reduced pressure. The crude was purified over Prep TLC (6% MeOH-DCM) to afforded N-(2-(imidazo[1,2-a] pyridin-3-yl)propan-2-yl)-1-(2-(4-methyl-1,4-diazepan-1-yl)-6,7-dihydro-5H-cyclopenta[d]pyrimidin-4-yl)azetidine-3-carboxamide (example 114) (45 mg, 37.76%) as white solid; $^1$H NMR (400 MHz, MeOD) δ 8.42 (d, 1H), 7.55 (d, 1H), 7.49 (s, 1H), 7.28 (t, 1H), 6.93 (t, 1H), 4.23-4.06 (m, 2H), 4.05-4.03 (m, 2H), 3.84-3.80 (m, 2H), 3.74-3.71 (m, 2H), 3.52-3.49 (m, 1H), 2.92-2.88 (m, 2H), 2.81-2.78 (m, 2H), 2.74-2.70 (m, 2H), 2.63-2.61 (m, 2H), 2.51 (s, 3H), 2.00-1.94 (m, 4H), 1.82 (s, 6H); HPLC RT (method B3) 7.39 min; LCMS (NH$_4$OAc:ACN): M+H=489, Rt=2.06 min in 5 mins run.

Synthesis of Example 115: 1-(5-chloro-6-methyl-2-(4-methyl-1,4-diazepan-1-yl)pyrimidin-4-yl)-N-(2-(imidazo[1,2-a]pyridin-3-yl)propan-2-yl)azetidine-3-carboxamide Step 1

To a solution of N-(2-(imidazo[1,2-a]pyridin-3-yl)pro-pan-2-yl)azetidine-3-carboxamide (TFA salt, 300 mg, 0.62 mmol) (product of step 2 in example 118) in 2-propanol (5 ml) was added Et3N (0.864 ml, 6.198 mmol) at 0° C. Then 2,4,5-trichloro-6-methylpyrimidine (183.161 mg, 0.93 mmol) was added and the reaction mixture was stirred at RT for 2 h. Reaction mixture was evaporated under reduce pressure, diluted with ethyl acetate and washed with water. Organic layer was separated, dried over Na2SO4 and evaporated under reduce pressure to get crude compound. Crude was purified combiflash (12 g silica column) using 3% MeOH in DCM to afford 1-(2,5-dichloro-6-methylpyrimi-din-4-yl)-N-(2-(imidazo[1,2-a]pyridin-3-yl)propan-2-yl) azetidine-3-carboxamide (200 mg, 76.95%). $^1$H NMR (400 MHz, DMSO-d$_6$) δ 8.44 (d, 1H), 8.38 (s, 1H), 7.56 (d, 1H), 7.45 (s, 1H), 7.20 (t, 1H), 6.90 (t, 1H), 4.50-4.10 (m, 4H), 3.48-3.42 (m, 1H), 2.28 (s, 3H), 1.73 (s, 6H); LCMS (HCOOH:ACN): M+H=419, R$_t$=1.67 min in 3 mins run.

Step 2

-continued

A stirred solution of 1-(2,5-dichloro-6-methylpyrimidin-4-yl)-N-(2-(imidazo[1,2-a]pyridin-3-yl)propan-2-yl)azeti-dine-3-carboxamide (100 mg, 0.239 mmol) and 1-methyl-1,4-diazepane (7) (0.15 ml, 1.196 mmol) in n-BuOH (0.75 ml) was irradiated in microwave at 115° C. for 1 h. Reaction mixture was cooled to RT and concentrated under reduced pressure. The crude was purified over Prep TLC (6% MeOH-DCM) to afforded 1-(5-chloro-6-methyl-2-(4-methyl-1,4-diazepan-1-yl)pyrimidin-4-yl)-N-(2-(imidazo[1,2-a]pyridin-3-yl)propan-2-yl)azetidine-3-carboxamide (example 115) (60 mg, 50.46%) as white solid. $^1$H NMR (400 MHz, MeOD) δ 8.42 (d, 1H), 7.55 (d, 1H), 7.48 (s, 1H), 7.27 (t, 1H), 6.92 (t, 1H), 4.29 (t, 2H), 4.14 (t, 2H), 3.76-3.73 (m, 2H), 3.68 (t, 2H), 3.44-3.39 (m, 1H), 2.66-2.62 (m, 2H), 2.59-2.51 (m, 2H), 2.35 (s, 3H), 2.21 (s, 3H), 1.92-1.89 (m, 2H), 1.80 (s, 6H); HPLC RT (method B3) 7.41 min; LCMS (NH$_4$OAc:ACN): M+H=497, Rt=2.95 min in 5 mins run.

Synthesis of Example 116: 1-(2-chloro-6-methylth-ieno[3,2-d]pyrimidin-4-yl)-N-(2-(Imidazo[1,2-a]pyridin-3-yl)propan-2-yl)azetidine-3-carboxamide Step 1

To a solution of N-(2-(imidazo[1,2-a]pyridin-3-yl)pro-pan-2-yl)azetidine-3-carboxamide (TFA salt, 300 mg, 0.62 mmol) (product of step 2 in example 118) in 2-propanol (5 ml) was added Et3N (0.864 ml, 6.198 mmol) at 0° C. Then 2,4-dichloro-6-methylthieno[3,2-d]pyrimidine (203.616 mg, 0.93 mmol) was added and the reaction mixture was stirred at RT for 2 h.

Reaction mixture was evaporated under reduce pressure, diluted with ethyl acetate and washed with water. Organic layer was separated, dried over Na2SO4 and evaporated under reduce pressure to get crude compound. Crude was purified combiflash (12 g silica column) using 3% MeOH in DCM to afford 1-(2-chloro-6-methylthieno[3,2-d]pyrimi-din-4-yl)-N-(2-(imidazo[1,2-a]pyridin-3-yl)propan-2-yl) azetidine-3-carboxamide (200 mg, 73.18%). $^1$H NMR (400 MHz, DMSO-d$_6$) δ 8.49-8.47 (m, 2H), 7.56 (d, 1H), 7.45 (s, 1H), 7.21 (t, 1H), 7.08 (s, 1H), 6.93 (t, 1H), 4.42-4.38 (m, 2H), 4.17-4.13 (m, 2H), 3.59-3.57 (m, 1H), 2.59 (s, 3H), 1.74 (s, 6H).

LCMS (HCOOH:ACN): M+H=441, R$_t$=1.42 min in 3 mins run.

Step 2

A stirred solution of 1-(2-chloro-6-methylthieno[3,2-d] pyrimidin-4-yl)-N-(2-(imidazo[1,2-a]pyridin-3-yl)propan-2-yl)azetidine-3-carboxamide (100 mg, 0.227 mmol) and 1-methyl-1,4-diazepane ((0.141 ml, 1.136 mmol) in n-BuOH (0.75 ml) was irradiated in microwave at 115° C. for 1 h. Reaction mixture was cooled to RT and concentrated under reduced pressure. The crude was purified over Prep TLC (6% MeOH-DCM) to afforded N-(2-(imidazo[1,2-a] pyridin-3-yl)propan-2-yl)-1-(6-methyl-2-(4-methyl-1,4-di-azepan-1-yl)thieno[3,2-d]pyrimidin-4-yl)azetidine-3-car-boxamide (example 116) (50 mg, 42.42%) as off white solid. $^1$H NMR (400 MHz, DMSO-d$_6$) δ 8.46 (d, 1H), 8.39 (s, 1H), 7.55 (d, 1H), 7.44 (s, 1H), 7.19 (t, 1H), 6.89 (t, 1H), 6.78 (s, 1H), 4.25-4.20 (m, 2H), 4.04-4.01 (m, 2H), 3.76-3.72 (m, 2H), 3.67-3.64 (m, 2H), 3.56-3.52 (m, 1H), 2.50-2.48 (m, 4H), 2.41 (s, 3H), 2.23 (s, 3H), 1.84-1.80 (m, 2H), 1.73 (s, 6H); HPLC RT (method A4) 5.04 min; LCMS (NH$_4$OAc: ACN): M+H=519, Rt=2.62 min in 5 mins run.

Synthesis of Example 117: N-(2-(imidazo[1,2-a]
pyridin-3-yl)propan-2-yl)-1-(6-methyl-2-(4-methyl-
1,4-diazepan-1-yl)thieno[2,3-d]pyrimidin-4-yl)azeti-
dine-3-carboxamide Step 1

To a solution of N-(2-(imidazo[1,2-a]pyridin-3-yl)pro-
pan-2-yl)azetidine-3-carboxamide (TFA salt, 300 mg, 0.62
mmol) (product of step 2 in example 118) in 2-propanol (5
ml) was added Et3N (0.864 ml, 6.198 mmol) at 0° C. Then
2,4-dichloro-6-methylthieno[2,3-d]pyrimidine (203.616
mg, 0.93 mmol) was added and the reaction mixture was
stirred at RT for 2 h.

Reaction mixture was evaporated under reduce pressure,
diluted with ethyl acetate and washed with water. Organic
layer was separated, dried over Na2SO4 and evaporated
under reduce pressure to get crude compound. Crude was
purified combiflash (12 g silica column) using 3% MeOH in
DCM to afford 1-(2-chloro-6-methylthieno[2,3-d]pyrimi-
din-4-yl)-N-(2-(imidazo[1,2-a]pyridin-3-yl)propan-2-yl)
azetidine-3-carboxamide (180 mg, 65.86%). $^1$H NMR (400
MHz, DMSO-d$_6$) δ 8.48-8.44 (m, 2H), 7.56 (d, 1H), 7.45 (s,
1H), 7.20 (t, 1H), 7.07 (s, 1H), 6.93 (t, 1H), 4.59-4.52 (m,
1H), 4.4-4.26 (m, 2H), 4.02-3.98 (m, 1H), 3.58-3.56 (m,
1H), 1.75 (s, 6H). (Methyl 3H merged in DMSO peak at 2.5
ppm); LCMS (HCOOH:ACN): M+H=441, R$_t$=1.41 min in 3
mins run.

Step 2

-continued

A stirred solution of 1-(2-chloro-6-methylthieno[2,3-d]
pyrimidin-4-yl)-N-(2-(imidazo[1,2-a]pyridin-3-yl)propan-
2-yl)azetidine-3-carboxamide (100 mg, 0.227 mmol) and
1-methyl-1,4-diazepane (0.141 ml, 1.136 mmol) in n-BuOH
(0.75 ml) was irradiated in microwave at 115° C. for 1 h.
Reaction mixture was cooled to RT and concentrated under
reduced pressure. The crude was purified over Prep TLC
(6% MeOH-DCM) to afforded N-(2-(imidazo[1,2-a]pyridin-
3-yl)propan-2-yl)-1-(6-methyl-2-(4-methyl-1,4-diazepan-1-
yl)thieno[2,3-d]pyrimidin-4-yl)azetidine-3-carboxamide
(example 117) (40 mg, 33.93%) as off white solid. $^1$H NMR
(400 MHz, DMSO-d$_6$) δ 8.46 (d, 1H), 8.39 (s, 1H), 7.55 (d,
1H), 7.44 (s, 1H), 7.18 (t, 1H), 6.90 (t, 1H), 6.74 (s, 1H),
4.27 (brs, 2H), 4.05 (brs, 2H), 3.75-3.72 (m, 2H), 3.66-3.63
(m, 2H), 3.55-3.51 (m, 1H), 2.54-2.50 (m, 2H), 2.44-2.40
(m, 2H), 2.36 (s, 3H), 2.23 (s, 3H), 1.83-1.79 (m, 2H), 1.73
(s, 6H); HPLC RT (method A6) 3.92 min; LCMS (NH$_4$OAc:
ACN): M+H=519, Rt=2.71 min in 5 mins run.

Synthesis of Example 118: N-(2-(Imidazo[1,2-a]
pyridin-3-yl)propan-2-yl)-1-(2-(4-methyl-1,4-diaz-
epan-1-yl)quinazolin-4-yl)azetidine-3-carboxamide Step 1

To a solution of 2-(imidazo[1,2-a]pyridin-3-yl)propan-2-
amine (0.87 g, 4.975 mmol) and 1-(tert-butoxycarbonyl)
azetidine-3-carboxylic acid (1 g, 4.975 mmol) in THF (30
mL) was added Et$_3$N (3.47 mL, 24.876 mmol). Then T3P®
(50%, 8.9 mL, 14.925 mmol) was added and stirred at RT for
16 h. The reaction mixture was quenched with NaHCO$_3$
solution and extracted with EtOAc. The organic layer was washed with water, dried over $Na_2SO_4$ and concentrated under reduced pressure and purified by column chromatography by elution with 6% MeOH in DCM to give tert-butyl 3-((2-(imidazo[1,2-a]pyridin-3-yl)propan-2-yl)carbamoyl) azetidine-1-carboxylate (1.4 g, 78.51%) as off white solid. LCMS (HCOOH:ACN): M+H=359, $R_t$=1.33 min in 3 mins run.

Step 2

To a solution of tert-butyl 3-((2-(imidazo[1,2-a]pyridin-3-yl)propan-2-yl)carbamoyl)azetidine-1-carboxylate (1.95 g, 5.44 mmol) in DCM (30 ml) was added trifluoroacetic acid (4.16 ml, 54.404 mmol) at 0° C. Reaction mixture was stirred at RT for 4 h. Reaction mixture was concentrated under reduced pressure to afford N-(2-(imidazo[1,2-a]pyridin-3-yl)propan-2-yl)azetidine-3-carboxamide (2.6 g, 98.74%) as TFA salt. $^1$H NMR (400 MHz, DMSO-$d_6$) δ 8.86 (d, 1H), 8.82 (brs, 1H), 8.73 (s, 1H), 8.59 (brs, 1H), 8.20 (s, 1H), 8.03 (d, 1H), 7.96 (t, 1H), 7.50 (t, 1H), 3.99-3.94 (m, 2H), 3.81-3.73 (m, 2H), 3.64-3.58 (m, 1H), 1.74 (s, 6H); LCMS (HCOOH:ACN): M+H=259, $R_t$=0.2 min in 3 mins run.

Step 3

218

-continued

To a solution of N-(2-(imidazo[1,2-a]pyridin-3-yl)propan-2-yl)azetidine-3-carboxamide (TFA salt, 300 mg, 0.62 mmol) in 2-propanol (5 ml) was added Et3N (0.864 ml, 6.198 mmol) at 0° C. Then 2,4-dichloroquinazoline (185 mg, 0.93 mmol) was added and the reaction mixture was stirred at RT for 2 h. Reaction mixture was evaporated under reduce pressure, diluted with ethyl acetate and washed with water. Organic layer was separated, dried over Na2SO4 and evaporated under reduce pressure to get crude compound. Crude was purified over prep TLC plate using 3% MeOH in DCM to afford 1-(2-chloroquinazolin-4-yl)-N-(2-(imidazo [1,2-a]pyridin-3-yl)propan-2-yl)azetidine-3-carboxamide (100 mg, 38.33%). $^1$H NMR (400 MHz, DMSO-$d_6$) δ 8.50-8.48 (m, 2H), 7.89 (d, 1H), 7.78 (t, 1H), 7.62-7.55 (m, 2H), 7.48-7.45 (m, 2H), 7.21 (t, 1H), 6.93 (t, 1H), 4.90-4.10 (m, 4H), 3.63-3.60 (m, 1H), 1.76 (s, 6H).

LCMS (HCOOH:ACN): M+H=421, $R_t$=1.45 min in 3 mins run.

Step 4

A stirred solution of 1-(2-chloroquinazolin-4-yl)-N-(2-(imidazo[1,2-a]pyridin-3-yl)propan-2-yl)azetidine-3-carboxamide (75 mg, 0.179 mmol) and 1-methyl-1,4-diazepane (0.111 ml, 0.893 mmol) in n-BuOH (0.75 ml) was irradiated in microwave at 115° C. for 1 h. Reaction mixture was cooled to RT and concentrated under reduced pressure. The crude was purified over Prep TLC (6% MeOH-DCM) to afforded N-(2-(imidazo[1,2-a]pyridin-3-yl)propan-2-yl)-1-(2-(4-methyl-1,4-diazepan-1-yl)quinazolin-4-yl)azetidine- 3-carboxamide (example 118) (30 mg, 33.7%) as white solid. ¹H NMR (400 MHz DMSO-d₆) δ 8.47 (d, 1H), 8.41 (s, 1H), 7.61 (d, 1H), 7.55 (d, 1H), 7.47 (d, 1H), 7.44 (s, 1H), 7.25 (d, 1H), 7.21-7.17 (m, 1H), 6.97 (t, 1H), 6.90 (t, 1H), 4.50-4.46 (m, 2H), 4.24-4.20 (m, 2H), 3.82-3.79 (m, 2H), 3.75-3.72 (m, 2H), 3.60-3.55 (m, 1H), 2.62-2.60 (m, 2H), 2.28 (s, 3H), 1.87-1.86 (m, 2H), 1.74 (s, 6H). (2H merged in DMSO peak at 2.50 ppm); HPLC RT (method A4) 4.86 min; LCMS (ACN:HCOOH): M+H=499, Rt=1.63 min in 5 mins run.

Synthesis of Example 119: 1-(5-chloro-2-(piper-
azin-1-yl)pyrimidin-4-yl)-N-(2-(imidazo[1,2-a]pyri-
din-3-yl)propan-2-yl)-N-methylazetidine-3-carbox-
amide Step 1

A stirred solution of 1-(2,5-dichloropyrimidin-4-yl)-N-(2-(imidazo[1,2-a]pyridin-3-yl)propan-2-yl)-N-methylazeti-dine-3-carboxamide (intermediate 28) (100 mg, 0.235 mmol) and tert-butyl piperazine-1-carboxylate (245 mg, 1.315 mmol) in n-BuOH (1 ml) was irradiated in microwave at 130° C. for 1 h. Reaction mixture was cooled to RT and concentrated under reduced pressure. The crude was purified over Prep TLC (4% MeOH-DCM) to afforded tert-butyl 4-(5-chloro-4-(3-((2-(imidazo[1,2-a]pyridin-3-yl)propan-2-yl)(methyl)carbamoyl)azetidin-1-yl)pyrimidin-2-yl)pipera-zine-1-carboxylate (90 mg, 60.11%). ¹H NMR (400 MHz, DMSO-d₆) δ 8.23 (d, 1H), 7.83 (s, 1H), 7.54 (d, 1H), 7.45 (s, 1H), 7.18 (t, 1H), 6.85 (t, 1H), 4.45-4.28 (m, 2H), 4.27-4.10 (m, 2H), 3.83-3.77 (m, 1H), 3.60-3.58 (m, 4H), 3.35-3.31 (m, 4H), 2.80 (s, 3H), 1.78 (s, 6H), 1.41 (s, 9H).

Step 2

A stirred solution of tert-butyl 4-(5-chloro-4-(3-((2-(imi-dazo[1,2-a]pyridin-3-yl)propan-2-yl)(methyl)carbamoyl)azetidin-1-yl)pyrimidin-2-yl)piperazine-1-carboxylate (110 mg, 0.194 mmol) in DCM (2 mL) was treated with TFA (0.221 mL, 1.936 mmol). The reaction mixture was stirred room temperature for 4 h. The crude was dissolved in MeOH and loaded on an Isolute® SCX column. The column was washed with MeOH. Then compound was then eluted with NH₃-MeOH and the collected fractions were concentrated under reduced pressure to give 1-(5-chloro-2-(piperazin-1-yl)pyrimidin-4-yl)-N-(2-(imidazo[1,2-a]pyridin-3-yl)pro-pan-2-yl)-N-methylazetidine-3-carboxamide (example 119) as off white sticky solid (46 mg, 50.67%). ¹H NMR (400 MHz, MeOD) δ 8.23 (d, 1H), 7.71 (s, 1H), 7.55 (d, 1H), 7.48 (s, 1H), 7.27 (t, 1H), 6.92 (t, 1H), 4.40 (brs, 2H), 4.27 (brs, 2H), 3.85-3.82 (m, 1H), 3.66-3.64 (m, 4H), 2.94 (s, 3H), 2.83-2.81 (m, 4H), 1.88 (s, 6H); HPLC RT (method B3) 7.54 min; LCMS (NH₄OAc:ACN): M+H=469, Rt=2.13 min in 5 mins run.

Synthesis of Example 120: 1-(5-chloro-2-(1,4-diaz-
epan-1-yl)pyrimidin-4-yl)-N-(2-(Imidazo[1,2-a]pyri-
din-3-yl)propan-2-yl)-N-methylazetidine-3-carbox-
amide Step 1

-continued

A stirred solution of 1-(2,5-dichloropyrimidin-4-yl)-N-(2-(imidazo[1,2-a]pyridin-3-yl)propan-2-yl)-N-methylazetidine-3-carboxamide (Intermediate 28)

(125 mg, 0.299 mmol) and tert-butyl 1,4-diazepane-1-carboxylate (178 mg, 1.495 mmol) in n-BuOH (2 ml) was irradiated in microwave at 130° C. for 1 h. Reaction mixture was cooled to RT and concentrated under reduced pressure. The crude was purified over Prep TLC (4% MeOH-DCM) to afforded tert-butyl 4-(5-chloro-4-(3-((2-(imidazo[1,2-a]pyridin-3-yl)propan-2-yl)(methyl)carbamoyl)azetidin-1-yl)pyrimidin-2-yl)-1,4-diazepane-1-carboxylate (80 mg, 45.89%). $^1$H NMR (400 MHz, DMSO-d$_6$) δ 8.22 (brs, 1H), 7.80 (s, 1H), 7.55 (d, 1H), 7.45 (s, 1H), 7.18 (t, 1H), 6.85 (t, 1H), 4.40-4.25 (m, 2H), 4.24-4.10 (m, 2H), 3.81-3.79 (m, 1H), 3.70-3.68 (m, 2H), 3.60-3.57 (m, 2H), 3.48-3.35 (m, 2H), 3.25-3.20 (m, 2H), 2.80 (brs, 3H), 1.78-1.59 (m, 8H), 1.33-1.26 (m, 9H).

Step 2

A stirred solution of tert-butyl 4-(5-chloro-4-(3-((2-(imidazo[1,2-a]pyridin-3-yl)propan-2-yl)(methyl)carbamoyl)azetidin-1-yl)pyrimidin-2-yl)-1,4-diazepane-1-carboxylate (85 mg, 0.146 mmol) in DCM (2 mL) was treated with TFA (0.166 mL, 1.457 mmol). The reaction mixture was stirred room temperature for 4 h. The crude was dissolved in MeOH and loaded on an Isolute® SCX column. The column was washed with MeOH. Then compound was then eluted with NH$_3$-MeOH and the collected fractions were concentrated under reduced pressure to give 1-(5-chloro-2-(1,4-diazepan-1-yl)pyrimidin-4-yl)-N-(2-(imidazo[1,2-a]pyridin-3-yl)propan-2-yl)-N-methylazetidine-3-carboxamide (example 120) as off white sticky solid (30 mg, 42.62%).

$^1$H NMR (400 MHz, MeOD) δ 8.23 (d, 1H), 7.69 (s, 1H), 7.56 (d, 1H), 7.49 (s, 1H), 7.27 (t, 1H), 6.92 (t, 1H), 4.39 (brs, 2H), 4.26-4.20 (m, 2H), 3.84-3.80 (m, 1H), 3.73-3.69 (m, 4H), 2.97-2.93 (m, 5H), 2.82-2.79 (m, 2H), 1.88 (m, 8H); HPLC RT (method B3) 7.59 min; LCMS (NH$_4$OAc: ACN): M+H=483, Rt=2.17 min in 5 mins run.

Synthesis of Example 121: 1-(5-chloro-2-(4-methyl-1,4-diazepan-1-yl)pyrimidin-4-yl)-N-(2-(Imidazo[1,2-a]pyridin-3-yl)propan-2-yl)-N-methylazetidine-3-carboxamide A stirred solution of 1-(2,5-dichloropyrimidin-4-yl)-N-(2-(imidazo[1,2-a]pyridin-3-yl)propan-2-yl)-N-methylazetidine-3-carboxamide (intermediate 28) (60 mg, 0.144 mmol) and 1-methyl-1,4-diazepane (82 mg, 0.718 mmol) in n-BuOH (1 ml) was irradiated in microwave at 130° C. for 1 h. Reaction mixture was cooled to RT and concentrated under reduced pressure. The crude was purified over Prep TLC (4% MeOH-DCM) to afforded 1-(5-chloro-2-(4-methyl-1,4-diazepan-1-yl)pyrimidin-4-yl)-N-(2-(imidazo[1,2-a]pyridin-3-yl)propan-2-yl)-N-methylazetidine-3-carboxamide (example 121) (32 mg, 44.88%). $^1$H NMR (400 MHz, MeOD) δ 8.23 (d, 1H), 7.69 (s, 1H), 7.55 (d, 1H), 7.49 (s, 1H), 7.27 (t, 1H), 6.93 (t, 1H), 4.39 (brs, 2H), 4.26-4.25 (m, 2H), 3.80-3.77 (m, 3H), 3.72-3.69 (m, 2H), 2.95 (s, 3H), 2.68-2.64 (m, 2H), 2.56-2.53 (m, 2H), 2.34 (s, 3H), 1.94-1.92 (m, 2H), 1.88 (s, 6H); HPLC RT (method A4) 4.70 min; LCMS (NH$_4$OAc:ACN): M+H=497, Rt=2.65 min in 5 mins run.

Synthesis of Example 122: N-(2-(imidazo[1,2-a]pyridin-3-yl)propan-2-yl)-N-methyl-1-(2-(4-methyl-1,4-diazepan-1-yl)thieno[3,2-d]pyrimidin-4-yl)azetidine-3-carboxamide Step 1

To a stirred solution of 1-(2-chlorothieno[3,2-d]pyrimidin-4-yl)-N-(2-(imidazo[1,2-a]pyridin-3-yl)propan-2-yl) azetidine-3-carboxamide (500 mg, 1.235 mmol) (product of step 1 in example 123) in DMF (5 ml) was added NaH (60%, 74 mg, 1.852 mmol) at 0° C. and stirred for 30 min. Then Methyl iodide (210 mg, 1.481 mmol) was added to the reaction mixture and stirred the reaction at RT for 3 hr. Then reaction mixture was quenched with ice-water and extracted with EtOAc. Organic layer was dried over Na2SO4, filtered and concentrated to afford crude product. Crude product was purified by combiflash column chromatography (12 g silica column) using MeOH in DCM to afford 1-(2-chlorothieno [3,2-d]pyrimidin-4-yl)-N-(2-(imidazo[1,2-a]pyridin-3-yl) propan-2-yl)-N-methylazetidine-3-carboxamide (400 mg, 73.31%). $^1$H NMR (400 MHz, DMSO-d6) δ 8.30-8.27 (m, 2H), 7.55 (d, 1H), 7.46 (s, 1H), 7.36 (d, 1H), 7.18 (t, 1H), 6.86 (t, 1H), 4.51-4.10 (m, 4H), 3.96-3.94 (m, 1H), 2.79 (s, 3H), 1.80 (s, 6H); LCMS (HCOOH:ACN): M+H=441, Rt=1.42 min in 3 mins run.

Step 2

-continued

A stirred solution of 1-(2-chlorothieno[3,2-d]pyrimidin-4-yl)-N-(2-(imidazo[1,2-a]pyridin-3-yl)propan-2-yl)-N-methylazetidine-3-carboxamide (100 mg, 0.227 mmol) and 1-methyl-1,4-diazepane (0.128 ml, 1.136 mmol) in n-BuOH (1 ml) was irradiated in microwave at 130° C. for 1 h. Reaction mixture was cooled to RT and concentrated under reduced pressure. The crude was purified over Prep TLC (4% MeOH-DCM) to afforded N-(2-(imidazo[1,2-a]pyridin-3-yl)propan-2-yl)-N-methyl-1-(2-(4-methyl-1,4-diazepan-1-yl)thieno[3,2-d]pyrimidin-4-yl)azetidine-3-carboxamide (example 122) (52 mg, 44.15%). $^1$H NMR (400 MHz, DMSO-d$_6$) δ 8.25 (d, 1H), 7.93 (d, 1H), 7.54 (d, 1H), 7.45 (s, 1H), 7.17 (t, 1H), 7.06 (d, 1H), 6.84 (t, 1H), 4.34 (brs, 2H), 4.17 (brs, 2H), 3.91 (brs, 1H), 3.80-3.76 (m, 2H), 3.72-3.68 (m, 2H), 2.83 (s, 3H), 2.58-2.56 (m, 2H), 2.45-2.43 (m, 2H), 2.24 (s, 3H), 1.86-1.82 (m, 2H), 1.79 (s, 6H); HPLC RT (method B3) 7.59 min; LCMS (NH$_4$OAc:ACN): M+H=519, Rt=2.57 min in 5 mins run.

Synthesis of Example 123: 1-(2-(1,4-diazepan-1-yl)thieno[3,2-d]pyrimidin-4-yl)-N-(2-(Imidazo[1,2-a]pyridin-3-yl)propan-2-yl)azetidine-3-carboxamide Step 1

To a solution of N-(2-(imidazo[1,2-a]pyridin-3-yl)propan-2-yl)azetidine-3-carboxamide (TFA salt, 800 mg, 2.151 mmol) (product of step 2 in example 118) in 2-propanol (10 ml) was added Et3N (3 ml, 21.505 mmol) at 0° C. Then 2,4-dichlorothieno[3,2-d]pyrimidine (658 mg, 3.226 mmol) was added and the reaction mixture was stirred at RT for 2 h. Reaction mixture was evaporated under reduce pressure, diluted with ethyl acetate and washed with water. Organic layer was separated, dried over Na2SO4 and evaporated under reduce pressure to get crude compound. Crude was purified combiflash (12 g silica column) using 3% MeOH in DCM to afford 1-(2-chlorothieno[3,2-d]pyrimidin-4-yl)-N-(2-(imidazo[1,2-a]pyridin-3-yl)propan-2-yl)azetidine-3-carboxamide (400 mg, 43.57%). ¹H NMR (400 MHz, DMSO-d₆) δ 8.54 (d, 1H), 8.51 (s, 1H), 8.26 (d, 1H), 7.62 (d, 1H), 7.55 (s, 1H), 7.35 (d, 1H), 7.30 (t, 1H), 7.00 (t, 1H), 4.55-4.05 (m, 4H), 3.62-3.58 (m, 1H), 1.75 (s, 6H); LCMS (HCOOH:ACN): M+H=427, R$_f$=1.37 min in 3 mins run.

Step 2

A stirred solution of 1-(2-chlorothieno[3,2-d]pyrimidin-4-yl)-N-(2-(imidazo[1,2-a]pyridin-3-yl)propan-2-yl)azetidine-3-carboxamide (100 mg, 0.235 mmol) and tert-butyl 1,4-diazepane-1-carboxylate (0.231 ml, 1.174 mmol) in n-BuOH (1 ml) was irradiated in microwave at 130° C. for 1 h. Reaction mixture was cooled to RT and concentrated under reduced pressure. The crude was purified over Prep TLC (4% MeOH-DCM) to afforded tert-butyl 4-(4-(3-((2-(imidazo[1,2-a]pyridin-3-yl)propan-2-yl)carbamoyl)azetidin-1-yl)thieno[3,2-d]pyrimidin-2-yl)-1,4-diazepane-1-carboxylate (60 mg, 43.27%). LCMS (HCOOH:ACN): M+H=591, R$_f$=1.43 min in 3 mins run.

Step 3

A stirred solution of tert-butyl 4-(4-(3-((2-(imidazo[1,2-a]pyridin-3-yl)propan-2-yl)carbamoyl)azetidin-1-yl)thieno[3,2-d]pyrimidin-2-yl)-1,4-diazepane-1-carboxylate (90 mg, 0.152 mmol) in DCM (1 mL) was treated with TFA (0.117 mL, 1.525 mmol). The reaction mixture was stirred room temperature for 4 h. The crude was dissolved in MeOH and loaded on an Isolute® SCX column. The column was washed with MeOH. Then compound was then eluted with NH₃-MeOH and the collected fractions were concentrated under reduced pressure to give 1-(2-(1,4-diazepan-1-yl)thieno[3,2-d]pyrimidin-4-yl)-N-(2-(imidazo[1,2-a]pyridin-3-yl)propan-2-yl)azetidine-3-carboxamide (Example 123) as off white solid (20 mg, 26.74%). ¹H NMR (400 MHz, MeOD) δ 8.45 (d, 1H), 7.76 (d, 1H), 7.55 (d, 1H), 7.49 (s, 1H), 7.28 (t, 1H), 7.07 (d, 1H), 6.94 (t, 1H), 4.39 (t, 2H), 4.22 (t, 2H), 3.90-3.80 (m, 4H), 3.65-3.60 (m, 1H), 3.02 (t, 2H), 2.84 (t, 2H), 1.92-1.88 (m, 2H), 1.83 (s, 6H); HPLC RT (method A4) 4.68 min; LCMS (CF3COOH:ACN): M+H=491, R$_f$=4.06 min in 10 mins run.

Synthesis of Example 124: (R)-1-(5-chloro-2-(3-methylpiperazin-1-yl)pyrimidin-4-yl)-N-(2-(Imidazo[1,2-a]pyridin-3-yl)propan-2-yl)-N-methylazetidine-3-carboxamide Step 1

-continued

A stirred solution of 1-(2,5-dichloropyrimidin-4-yl)-N-(2-(imidazo[1,2-a]pyridin-3-yl)propan-2-yl)-N-methylazetidine-3-carboxamide (150 mg, 0.358 mmol) (intermediate 28) and tert-butyl (R)-2-methylpiperazine-1-carboxylate (357.995 mg, 1.79 mmol) in n-BuOH (2 ml) was irradiated in microwave at 130° C. for 1 h. Reaction mixture was cooled to RT and concentrated under reduced pressure. The crude was purified by Prep TLC using 4% MeOH in DCM to afford tert-butyl (R)-4-(5-chloro-4-(3-((2-(imidazo[1,2-a]pyridin-3-yl)propan-2-yl)(methyl)carbamoyl)azetidin-1-yl)pyrimidin-2-yl)-2-methylpiperazine-1-carboxylate (60 mg, 28.74%) white solid. LCMS (HCOOH:ACN): M+H=583, Rt=1.57 min in 3 mins run.

Step 2

TFA, DCM

To a solution of tert-butyl (R)-4-(5-chloro-4-(3-((2-(imidazo[1,2-a]pyridin-3-yl)propan-2-yl)(methyl)carbamoyl)azetidin-1-yl)pyrimidin-2-yl)-2-methylpiperazine-1-carboxylate (90 mg, 0.155 mmol) in DCM (2 ml) was added trifluoroacetic acid (0.118 ml, 1.546 mmol) at 0° C. and stirred at RT for 4 h. Reaction mixture was concentrated under reduced pressure. The crude was dissolved in MeOH and loaded on an Isolute® SCX column. The column was washed with MeOH. Then compound was then eluted with NH₃-MeOH and the collected fractions were concentrated under reduced pressure to get (R)-1-(5-chloro-2-(3-methylpiperazin-1-yl)pyrimidin-4-yl)-N-(2-(imidazo[1,2-a]pyridin-3-yl)propan-2-yl)-N-methylazetidine-3-carboxamide (example 124) (35 mg, 46.88%) as white solid. ¹H NMR (400 MHz, DMSO-d₆) δ 8.20 (bs, 1H), 7.77 (s, 1H), 7.52 (d, 1H), 7.42 (s, 1H), 7.16 (t, 1H), 6.82 (t, 1H), 4.38-4.08 (m, 6H), 3.79-3.71 (m, 1H), 2.88-2.52 (m, 7H), 2.36-2.32 (m, 1H), 1.76 (s, 6H), 0.95 (d, 3H); HPLC RT (method A6) 3.90 min; LCMS (HCOOH:ACN): M+H=483, Rt=1.61 min in 12 mins run.

Synthesis of Example 125: (S)—N-(2-(imidazo[1,2-a]pyridin-3-yl)propan-2-yl)-N-methyl-1-(2-(2-methylpiperazin-1-yl)thieno[3,2-d]pyrimidin-4-yl)azetidine-3-carboxamide Step 1

To a stirred solution of 1-(2-chlorothieno[3,2-d]pyrimidin-4-yl)-N-(2-(imidazo[1,2-a]pyridin-3-yl)propan-2-yl)-N-methylazetidine-3-carboxamide, (product of step 1 in example 122) (150 mg, 0.341 mmol) and tert-butyl (S)-3-methylpiperazine-1-carboxylate (340.909 mg, 1.705 mmol) in DME (2 ml) was added Cs2CO3 (553.977 mg, 1.705 mmol). The reaction mixture was degassed with argon for 10 min. Then Pd2(dba)3 (62.436 mg, 0.068 mmol) and S-Phos (62.436 mg, 0.17 mmol) were added and degassed again for about 5 min. Reaction mixture was irradiated in microwave at 120° C. for 1 h. Reaction mixture was cooled to RT and concentrated under reduced pressure. The crude was purified by Prep TLC using 4% MeOH in DCM to afforded tert-butyl (S)-4-(4-(3-((2-(imidazo[1,2-a]pyridin-3-yl)propan-2-yl)(methyl)carbamoyl)azetidin-1-yl)thieno[3,2-d]pyrimidin-2-yl)-3-methylpiperazine-1-carboxylate ((80 mg, 38.8%) white solid. LCMS (NH₄OAc:ACN): M+H=605, Rt=3.44 min in 5 mins run.

Step 2

TFA, DCM

-continued

A stirred solution of 1-(2-chlorothieno[3,2-d]pyrimidin-4-yl)-N-(2-(imidazo[1,2-a]pyridin-3-yl)propan-2-yl)-N-methylazetidine-3-carboxamide, (product of step 1, example 123), (300 mg, 0.704 mmol) and tert-butyl (S)-3-methylpiperazine-1-carboxylate (424 mg, 2.112 mmol) in n-BuOH (4 ml) was irradiated in microwave at 130° C. for 2 h. Reaction mixture was cooled to RT and concentrated under reduced pressure. The crude was purified by Prep TLC using 4% MeOH in DCM to afforded tert-butyl (S)-4-(4-(3-((2-(imidazo[1,2-a]pyridin-3-yl)propan-2-yl)(methyl)carbamoyl)azetidin-1-yl)thieno[3,2-d]pyrimidin-2-yl)-3-methylpiperazine-1-carboxylate (80 mg, 19.23%) white solid. LCMS (HCOOH:ACN): M+H=591, Rt=1.48 min in 3 mins run.

Step 2

To a solution of tert-butyl (S)-4-(4-(3-((2-(imidazo[1,2-a]pyridin-3-yl)propan-2-yl)(methyl)carbamoyl)azetidin-1-yl)thieno[3,2-d]pyrimidin-2-yl)-3-methylpiperazine-1-carboxylate (80 mg, 0.132 mmol) in DCM (2 ml) was added trifluoroacetic acid (0.101 ml, 1.325 mmol) at 0° C. and stirred at RT for 4 h. Reaction mixture was concentrated under reduced pressure. The crude was dissolved in MeOH and loaded on an Isolute® SCX column. The column was washed with MeOH. Then compound was then eluted with NH₃-MeOH and the collected fractions were concentrated under reduced pressure to get (S)—N-(2-(imidazo[1,2-a]pyridin-3-yl)propan-2-yl)-N-methyl-1-(2-(2-methylpiperazin-1-yl)thieno[3,2-d]pyrimidin-4-yl)azetidine-3-carboxamide (Example 125) (35 mg, 52.36%) as white solid. ¹H NMR (400 MHz, DMSO-d₆) δ 8.26 (d, 1H), 7.95 (d, 1H), 7.55 (d, 1H), 7.46 (s, 1H), 7.18 (t, 1H), 7.06 (d, 1H), 6.84 (t, 1H), 4.73-4.68 (m, 1H), 4.41-4.15 (m, 5H), 3.95-3.89 (m, 1H), 2.95-2.67 (m, 8H), 1.80 (s, 6H), 1.13 (d, 3H); HPLC RT (method B3) 7.49 min; LCMS (NH₄OAc:ACN): M+H=505, Rt=1.81 min in 5 mins run.

Synthesis of Example 126: (S)—N-(2-(Imidazo[1,2-a]pyridin-3-yl)propan-2-yl)-1-(2-(2-methylpiperazin-1-yl)thieno[3,2-d]pyrimidin-4-yl)azetidine-3-carboxamide Step 1 n-BuOH, MW

TFA, DCM

To a solution of tert-butyl (S)-4-(4-(3-((2-(imidazo[1,2-a]pyridin-3-yl)propan-2-yl)(methyl)carbamoyl)azetidin-1-yl)thieno[3,2-d]pyrimidin-2-yl)-3-methylpiperazine-1-carboxylate (80 mg, 0.13 mmol) in DCM (2 ml) was added trifluoroacetic acid (0.104 ml, 1.353 mmol) at 0° C. and stirred at RT for 4 h. Reaction mixture was concentrated under reduced pressure. The crude was dissolved in MeOH and loaded on an Isolute® SCX column. The column was washed with MeOH. Then compound was then eluted with NH₃-MeOH and the collected fractions were concentrated under reduced pressure to get (S)—N-(2-(imidazo[1,2-a]

pyridin-3-yl)propan-2-yl)-1-(2-(2-methylpiperazin-1-yl) thieno[3,2-d]pyrimidin-4-yl)azetidine-3-carboxamide (example 126) (20 mg, 30.13%) as white solid. $^1$H NMR (400 MHz, DMSO-d$_6$) δ 8.47 (d, 1H), 8.42 (s, 1H), 7.94 (d, 1H), 7.55 (d, 1H), 7.45 (s, 1H), 7.19 (t, 1H), 7.05 (d, 1H), 6.90 (t, 1H), 4.71-4.66 (m, 1H), 4.32-4.24 (m, 3H), 4.11-4.04 (m, 2H), 3.60-3.54 (m, 1H), 2.94-2.86 (m, 2H), 2.78-2.74 (m, 2H), 2.57-2.53 (m, 1H), 1.74 (s, 6H), 1.11 (d, 3H); HPLC RT (method A4) 4.70 min; LCMS (NH4OAc:ACN): M+H=491, Rt=2.22 min in 5 mins run.

Synthesis of Example 127: 1-(5-chloro-2-(3,3-dimethylpiperazin-1-yl)pyrimidin-4-yl)-N-(2-(Imidazo [1,2-a]pyridin-3-yl)propan-2-yl)-N-methylazetidine-3-carboxamide Step 1

A stirred solution of 1-(2,5-dichloropyrimidin-4-yl)-N-(2-(imidazo[1,2-a]pyridin-3-yl)propan-2-yl)-N-methylazetidine-3-carboxamide (intermediate 28) (150 mg, 0.353 mmol) and tert-butyl 2,2-dimethylpiperazine-1-carboxylate (13) (383 mg, 1.79 mmol) in n-BuOH (2 ml) was irradiated in microwave at 120° C. for 1 h. Reaction mixture was cooled to RT and concentrated under reduced pressure. The crude was purified by Prep TLC using 4% MeOH in DCM to afforded tert-butyl 4-(5-chloro-4-(3-((2-(imidazo[1,2-a] pyridin-3-yl)propan-2-yl)(methyl)carbamoyl)azetidin-1-yl) pyrimidin-2-yl)-2,2-dimethylpiperazine-1-carboxylate (150 mg, 70.17%) white solid. LCMS (HCOOH:ACN): M+H=597. Rt=1.53 min in 3 mins run.

Step 2

To a solution of tert-butyl 4-(5-chloro-4-(3-((2-(imidazo [1,2-a]pyridin-3-yl)propan-2-yl)(methyl)carbamoyl)azetidin-1-yl)pyrimidin-2-yl)-2,2-dimethylpiperazine-1-carboxylate (150 mg, 0.251 mmol) in DCM (4 ml) was added trifluoroacetic acid (0.192 ml, 2.512 mmol) at 0° C. and stirred at RT for 3 h. Reaction mixture was concentrated under reduced pressure. The crude was dissolved in MeOH and loaded on an Isolute® SCX column. The column was washed with MeOH. Then compound was then eluted with NH$_3$-MeOH and the collected fractions were concentrated under reduced pressure to get 1-(5-chloro-2-(3,3-dimethylpiperazin-1-yl)pyrimidin-4-yl)-N-(2-(imidazo[1,2-a]pyridin-3-yl)propan-2-yl)-N-methylazetidine-3-carboxamide (example 127) (55 mg, 44.05%) as white solid. $^1$H NMR (400 MHz, MeOD) δ 8.23 (d, 1H), 7.69 (s, 1H), 7.55 (d, 1H), 7.49 (s, 1H), 7.27 (t, 1H), 6.92 (t, 1H), 4.39 (brs, 2H), 4.26 (brs, 2H), 3.84-3.81 (m, 1H), 3.66-3.63 (m, 2H), 3.47 (s, 2H), 2.95 (s, 3H), 2.88-2.85 (m, 2H), 1.88 (s, 6H), 1.10 (s, 6H); HPLC RT (method B3) 7.70 min; LCMS (NH4OAc: ACN): M+H=497. Rt=2.17 min in 5 mins run.

Synthesis of Example 128: 1-(2-(4-aminopiperidin-1-yl)-5-chloropyrimidin-4-yl)-N-(2-(Imidazo[1,2-a] pyridin-3-yl)propan-2-yl)-N-methylazetidine-3-carboxamide Step 1

-continued

A stirred solution of 1-(2,5-dichloropyrimidin-4-yl)-N-(2-(imidazo[1,2-a]pyridin-3-yl)propan-2-yl)-N-methylazeti-dine-3-carboxamide (intermediate 28), (115 mg, 0.274 mmol) and tert-butyl piperidin-4-ylcarbamate (13) (274 mg, 1.371 mmol) in n-BuOH (1 ml) was irradiated in microwave at 120° C. for 1 h. Reaction mixture was cooled to RT and concentrated under reduced pressure. The crude was purified by Prep TLC using 4% MeOH in DCM to afforded tert-butyl (1-(5-chloro-4-(3-((2-(imidazo[1,2-a]pyridin-3-yl)propan-2-yl)(methyl) carbamoyl) azetidin-1-yl)pyrimidin-2-yl)pip-eridin-4-yl)carbamate (80 mg, 50.02%) as light brown sticky gum. LCMS (HCOOH:ACN): M+H=583.7. Rt=1.77 min in 3 mins run.

Step 2

To a solution of tert-butyl (1-(5-chloro-4-(3-((2-(imidazo[1,2-a]pyridin-3-yl)propan-2-yl)(methyl) carbamoyl) azeti-din-1-yl)pyrimidin-2-yl)piperidin-4-yl)carbamate ((120 mg, 0.206 mmol) in DCM (2 ml) was added trifluoroacetic acid (0.158 ml, 2.061 mmol) at 0° C. and stirred at RT for 4 h. Reaction mixture was concentrated under reduced pressure. The crude was dissolved in MeOH and loaded on an Isolute® SCX column. The column was washed with MeOH. Then compound was then eluted with NH₃-MeOH and the collected fractions were concentrated under reduced pressure to get 1-(2-(4-aminopiperidin-1-yl)-5-chloropy-rimidin-4-yl)-N-(2-(imidazo[1,2-a]pyridin-3-yl)propan-2-yl)-N-methylazetidine-3-carboxamide (example 128) (36 mg, 36.85%) as white solid. $^1$H NMR (400 MHz, DMSO-d$_6$) δ 8.22 (d, 1H), 7.79 (s, 1H), 7.55 (d, 1H), 7.45 (s, 1H), 7.18 (t, 1H), 6.85 (t, 1H), 4.38-4.34 (m, 4H), 4.14 (brs, 2H), 3.78 (brs, 1H), 2.91-2.73 (m, 6H), 1.78 (s, 6H), 1.73-1.65 (m, 2H), 1.18-1.04 (m, 2H). HPLC RT (method A4) 4.67 min; LCMS (NH₄OAc:ACN): M+H=483, Rt=2.29 min in 5 mins run.

Synthesis of Example 129: (S)-1-(5-chloro-2-(2-methylpiperazin-1-yl)pyrimidin-4-yl)-N-(2-(imidazo[1,2-a]pyridin-3-yl)propan-2-yl)azetidine-3-carbox-amide Step 1

A solution of 2,4,5-trichloropyrimidine (10 g, 54.969 mmol) in THF (110 ml) was cooled to 0° C. and then sodium thiomethoxide (4.623 g, 65.963 mmol) was added. The temperature was slowly increased to RT and the reaction mixture was stirred overnight at RT. After the end of the reaction the reaction mixture was concentrated by rotary evaporation, mixed with water and extracted twice with DCM. The organic phases are separated, dried over MgSO4, filtered and concentrated by rotary evaporation to afford 2,5-dichloro-4-(methylthio)pyrimidine (9 g, 83%). $^1$H NMR (400 MHz, CDCl₃) δ 8.20 (s, 1H), 2.59 (s, 3H); LCMS (HCOOH:ACN): M+H=195, R$_t$=1.91 min in 3 mins run.

Step 2

A stirred solution of 2,5-dichloro-4-(methylthio)pyrimi-dine (2 g, 10.312 mmol) and tert-butyl (S)-3-methylpipera-zine-1-carboxylate (6.192 g, 30.936 mmol) in n-BuOH (5 ml) was irradiated in microwave at 130° C. for 1 h. Reaction mixture was cooled to RT and concentrated under reduced pressure to get crude product which was purified by column chromatography (silica gel, 100-200 mesh) using 4% EtOAc in Hexane to afford tert-butyl (S)-4-(5-chloro-4-(methylthio)pyrimidin-2-yl)-3-methylpiperazine-1-carboxylate (2 g, 54%) as colorless sticky gum.

$^{1}$H NMR (400 MHz, CDCl$_3$) δ 7.93 (s, 1H), 4.89-4.78 (m, 1H), 4.41 (d, 1H), 4.23-3.85 (m, 2H), 3.22-3.08 (m, 2H), 3.04-2.83 (m, 1H), 2.48 (s, 3H), 1.48 (s, 9H), 1.17 (d, 3H); LCMS (HCOOH:ACN): M+H=359, R$_t$=2.24 min in 3 mins run.

Step 3

To a stirred solution of tert-butyl (S)-4-(5-chloro-4-(methylthio)pyrimidin-2-yl)-3-methylpiperazine-1-carboxylate (7 g, 19.547 mmol) in DCM (110 ml) was added m-CPBA (6.746 g, 39.093 mmol) at ice cool condition and the mixture was stirred for 40 hrs with slow warming to RT. The mixture was filtered, and the filtrate was washed with aq. NaHCO3. The organic layer was dried over Na2SO4 and concentrated under reduced pressure to afford tert-butyl (S)-4-(5-chloro-4-(methylsulfonyl)pyrimidin-2-yl)-3-methylpiperazine-1-carboxylate (6.5 g, 85%) as solid. $^{1}$H NMR (400 MHz, DMSO-d$_6$) δ 8.72 (s, 1H), 4.79-4.65 (m, 1H), 4.30 (d, 1H), 4.06-3.74 (m, 2H), 3.43 (s, 3H), 3.27-2.80 (m, 3H), 1.42 (s, 9H), 1.12 (d, 3H); LCMS (HCOOH:ACN): M+H=391, R$_t$=1.95 min in 3 mins run.

Step 4

-continued

To a stirred solution of N-(2-(imidazo[1,2-a]pyridin-3-yl)propan-2-yl)azetidine-3-carboxamide (product of step 2 in example 118) (TFA salt, 8 g, 16.461 mmol) in isoprapanol (50 ml) were added Et3N (22.943 ml, 164.609 mmol) and tert-butyl (S)-4-(5-chloro-4-(methylsulfonyl)pyrimidin-2-yl)-3-methylpiperazine-1-carboxylate (7.726 g, 19.753 mmol) at 0° C. Reaction mixture was stirred at RT for 3 hr. Then reaction mass was concentrated under reduced pressure which was diluted with DCM and washed with NaHCO3 solution. Organic layer was dried over Na2SO4, filtered and concentrated under reduced pressure to get crude product which was purified by combi flash column chromatography (40 g silica column) using 4% MeOH in DCM to afford tert-butyl (S)-4-(5-chloro-4-(3-((2-(imidazo[1,2-a]pyridin-3-yl)propan-2-yl)carbamoyl)azetidin-1-yl)pyrimidin-2-yl)-3-methylpiperazine-1-carboxylate (6.2 g, 66.18%) as solid. $^{1}$H NMR (400 MHz, DMSO-d$_6$) δ 8.44 (d, 1H), 8.35 (s, 1H), 7.82 (s, 1H), 7.56 (d, 1H), 7.44 (s, 1H), 7.19 (t, 1H), 6.89 (t, 1H), 4.67-4.58 (m, 1H), 4.32-4.18 (m, 3H), 4.09-3.99 (m, 2H), 3.96-3.72 (m, 2H), 3.49-3.41 (m, 1H), 3.04-2.72 (m, 3H), 1.73 (s, 6H), 1.42 (s, 9H), 1.01 (d, 3H); LCMS (HCOOH:ACN): M+H=569, R$_t$=1.95 min in 3 mins run.

Step 5

237

-continued

238

-continued

A stirred solution of tert-butyl (S)-4-(5-chloro-4-(3-((2-(imidazo[1,2-a]pyridin-3-yl)propan-2-yl)carbamoyl)azetidin-1-yl)pyrimidin-2-yl)-3-methylpiperazine-1-carboxylate (6.5 g, 11.438 mmol) in DCM (55 mL) was treated with TFA (8.751 mL, 114.382 mmol) at 0° C. The reaction mixture was stirred at room temperature for 4 h. The crude was dissolved in MeOH and loaded on an Isolute® SCX column. The column was washed with MeOH. Then compound was eluted with NH₃-MeOH and the collected fractions were concentrated under reduced pressure to give product which was purified by column chromatography (silica gel, 100-200 mesh) using 3% MeOH in DCM to afford (S)-1-(5-chloro-2-(2-methylpiperazin-1-yl)pyrimidin-4-yl)-N-(2-(imidazo[1,2-a]pyridin-3-yl)propan-2-yl)azetidine-3-carboxamide (example 129) as white solid (2.8 g, 52.2%). ¹H NMR (400 MHz, DMSO-d₆) δ 8.45 (d, 1H), 8.39 (s, 1H), 7.81 (s, 1H), 7.56 (d, 1H), 7.44 (s, 1H), 7.19 (t, 1H), 6.88 (t, 1H), 4.62-4.54 (m, 1H), 4.28-4.17 (m, 3H), 4.08-3.99 (m, 2H), 3.49-3.41 (m, 1H), 3.02-2.68 (m, 4H), 2.59-2.54 (m, 1H), 1.73 (s, 6H), 1.11 (d, 3H); HPLC RT (method B1) 9.97 min; LCMS (HCOOH:ACN): M+H=469, R$_t$=1.47 min in 3 mins run.

Synthesis of Example 130: 1-(5-chloro-2-(4,7-diazaspiro[2.5]octan-7-yl)pyrimidin-4-yl)-N-(2-(imidazo[1,2-a]pyridin-3-yl)propan-2-yl)-N-methylazetidine-3-carboxamide Step 1

To the stirred solution of 1-(2,5-dichloropyrimidin-4-yl)-N-(2-(imidazo[1,2-a]pyridin-3-yl)propan-2-yl)-N-methyl-azetidine-3-carboxamide, (intermediate 28)), (150 mg, 0.358 mmol) and tert-butyl 4,7-diazaspiro[2.5]octane-4-carboxylate ((379 mg, 1.79 mmol) in DME (2 ml) was added Cs2CO3 (583 mg, 1.79 mmol) and degassed with argon for 10 min. Then Pd₂(dba)₃ (65 mg, 0.072 mmol) and S-Phos (73 mg, 0.179 mmol) were added and degassed again for about 5 min. Then the reaction mixture was allowed to stirred at 120° C. for about 1 hrs under microwave radiation. Reaction mixture was cooled to RT and concentrated under reduced pressure. The crude was purified by Prep TLC using 4% MeOH in DCM to afforded tert-butyl 7-(5-chloro-4-(3-((2-(imidazo[1,2-a]pyridin-3-yl)propan-2-yl)(methyl)carbamoyl)azetidin-1-yl)pyrimidin-2-yl)-4,7-diazaspiro[2.5]octane-4-carboxylate (100 mg, 46.94%) as white solid.

LCMS (HCOOH:ACN): M+H=595.2. Rt=1.54 min in 3 mins run.

Step 2

To a solution of tert-butyl 7-(5-chloro-4-(3-((2-(imidazo[1,2-a]pyridin-3-yl)propan-2-yl)(methyl)carbamoyl)azetidin-1-yl)pyrimidin-2-yl)-4,7-diazaspiro[2.5]octane-4-carboxylate (100 mg, 0.168 mmol) in DCM (2 ml) was added trifluoroacetic acid (0.129 ml, 1.681 mmol) at 0° C. and stirred at RT for 4 h. Reaction mixture was concentrated under reduced pressure. The crude was dissolved in MeOH and loaded on an Isolute® SCX column. The column was washed with MeOH. Then compound was then eluted with NH₃-MeOH and the collected fractions were concentrated under reduced pressure to get 1-(5-chloro-2-(4,7-diazaspiro[2.5]octan-7-yl)pyrimidin-4-yl)-N-(2-(imidazo[1,2-a]pyridin-3-yl)propan-2-yl)-N-methylazetidine-3-carboxamide (example 130) (35 mg, 42.07%) as white solid. ¹H NMR (400 MHz, DMSO-d₆) δ 8.22 (d, 1H), 7.78 (s, 1H), 7.55 (d, 1H), 7.46 (s, 1H), 7.18 (t, 1H), 6.85 (t, 1H), 4.28 (brs, 2H), 4.13 (brs, 2H), 3.77 (brs, 1H), 3.60-3.58 (m, 2H), 3.47 (s, 2H), 2.80 (s, 3H), 2.76-2.72 (m, 2H), 1.78 (s, 6H), 0.43 (s, 4H); HPLC RT (method A6) 3.97 min; LCMS (HCOOH:ACN): M+H=495, Rt=1.71 min in 3 mins run.

Synthesis of Example 131: 1-(2-(4-aminoazepan-1-yl)-5-chloropyrimidin-4-yl)-N-(2-(imidazo[1,2-a]pyridin-3-yl)propan-2-yl)-N-methylazetidine-3-carboxamide Step 1

To a stirred solution of 1-(2,5-dichloropyrimidin-4-yl)-N-(2-(imidazo[1,2-a]pyridin-3-yl)propan-2-yl)-N-methylazetidine-3-carboxamide (intermediate 28)(120 mg, 0.286 mmol) and tert-butyl azepan-4-ylcarbamate(13) (358 mg, 1.431 mmol) in n-BuOH (1 ml) was added (0.24 ml 1.431 mmol) DIPEA and the reaction was irradiated in microwave at 130° C. for 1 h. Reaction mixture was cooled to RT and concentrated under reduced pressure. The crude was purified by Prep TLC using 4% MeOH in DCM to afforded tert-butyl (1-(5-chloro-4-(3-((2-(imidazo[1,2-a]pyridin-3-yl)propan-2-yl)(methyl)carbamoyl)azetidin-1-yl)pyrimidin-2-yl)azepan-4-yl)carbamate ((90 mg, 52.66%) as light brown solid. LCMS (HCOOH:ACN): M+H=597.3. Rt=1.49 min in 3 mins run Step 2

To a solution of tert-butyl (1-(5-chloro-4-(3-((2-(imidazo[1,2-a]pyridin-3-yl)propan-2-yl)(methyl)carbamoyl)azetidin-1-yl)pyrimidin-2-yl)azepan-4-yl)carbamate (120 mg, 0.206 mmol) in DCM (2 ml) was added trifluoroacetic acid (0.158 ml, 2.061 mmol) at 0° C. and stirred at RT for 4 h. Reaction mixture was concentrated under reduced pressure. The crude was dissolved in MeOH and loaded on an Isolute® SCX column. The column was washed with MeOH. Then compound was then eluted with NH₃-MeOH and the collected fractions were concentrated under reduced pressure to get 1-(2-(4-aminoazepan-1-yl)-5-chloropyrimidin-4-yl)-N-(2-(imidazo[1,2-a]pyridin-3-yl)propan-2-yl)-N-methylazetidine-3-carboxamide (example 131) (36 mg, 35.77%) as white solid. ¹H NMR (400 MHz, DMSO-d₆, 100° C.) δ 8.20 (d, 1H), 7.77 (s, 1H), 7.53 (d, 1H), 7.47 (s, 1H), 7.18 (t, 1H), 6.85 (t, 1H), 4.24 (t, 21H), 4.16 (t, 21H), 3.81-3.74 (m, 21H), 3.68-3.57 (m, 21H), 3.51-3.44 (m, 11H), 2.88-2.83 (m, 21H), 2.81 (s, 31H), 1.93-1.74 (m, 7H), 1.70-1.57 (m, 21H), 1.51-1.42 (in, 1H), 1.38-1.24 (in, 2H); HPLC RT (method B33) 7.48 min; LCMS (NH₄OAc:ACN): M+H=497, Rt=2.29 min in 5 mins run.

Synthesis of Example 132: 1-(2-(2,5-diazabicyclo[2.2.1]heptan-2-yl)-5-chloropyrimidin-4-yl)-N-(2-(imidazo[1,2-a]pyridin-3-yl)propan-2-yl)-N-methylazetidine-3-carboxamide -continued To a stirred solution of 1-(2,5-dichloropyrimidin-4-yl)-N-(2-(imidazo[1,2-a]pyridin-3-yl)propan-2-yl)-N-methylazetidine-3-carboxamide (intermediate 28) (50 mg, 0.12 mmol) and 2,5-diazabicyclo[2.2.1]heptane dihydrochloride (102 mg, 0.598 mmol) in n-BuOH (1 ml) was added (0.20 ml 1.196 mmol) DIPEA and the reaction was irradiated in microwave at 130° C. for 1 h. Reaction mixture was cooled to RT and concentrated under reduced pressure. The crude was purified by Prep TLC using 4% MeOH in DCM to 1-(2-(2,5-diazabicyclo[2.2.1]heptan-2-yl)-5-chloropyrimidin-4-yl)-N-(2-(imidazo[1,2-a]pyridin-3-yl)propan-2-yl)-N-methylazetidine-3-carboxamide (example 132) (23 mg, 41.46%) as off-white solid. $^1$H NMR (400 MHz, DMSO-d$_6$, 100° C.) δ 8.19 (d, 1H), 7.76 (s, 1H), 7.53 (d, 1H), 7.46 (s, 1H), 7.18 (t, 1H), 6.86 (t, 1H), 4.68 (s, 1H), 4.28-4.14 (m, 4H), 3.82-3.74 (m, 2H), 3.39 (d, 1H), 3.30 (d, 1H), 2.89-2.84 (m, 2H), 2.80 (s, 3H), 1.84 (s, 6H), 1.76 (d, 1H), 1.67 (d, 1H); HPLC RT (method B3) 7.23 min; LCMS (NH$_4$OAc: ACN): M+H=481, Rt=2.50 min in 5 mins run Synthesis of Example 133: 1-(2-(3,8-diazabicyclo[3.2.1]octan-3-yl)-5-chloropyrimidin-4-yl)-N-(2-(imidazo[1,2-a]pyridin-3-yl)propan-2-yl)-N-methyl-azetidine-3-carboxamide To a stirred solution of 1-(2,5-dichloropyrimidin-4-yl)-N-(2-(imidazo[1,2-a]pyridin-3-yl)propan-2-yl)-N-methylazetidine-3-carboxamide (intermediate 28) (60 mg, 0.144 mmol) 3,8-diazabicyclo[3.2.1]octane dihydrochloride (132 mg, 0.718 mmol) in n-BuOH (1 ml) was added (0.25 ml, 1.435 mmol) DIPEA and the reaction was irradiated in microwave at 130° C. for 1 h. Reaction mixture was cooled to RT and concentrated under reduced pressure. The crude was purified by Prep TLC using 4% MeOH in DCM to afford 1-(2-(3,8-diazabicyclo[3.2.1]octan-3-yl)-5-chloropyrimidin-4-yl)-N-(2-(imidazo[1,2-a]pyridin-3-yl)propan-2-yl)-N-methylazetidine-3-carboxamide (example 133) (27 mg, 38.35%) as white solid. $^1$H NMR (400 MHz, DMSO-d$_6$) δ 8.23 (d, 1H), 7.79 (s, 1H), 7.55 (d, 1H), 7.45 (s, 1H), 7.18 (t, 1H), 6.84 (t, 1H), 4.30-4.28 (m, 2H), 4.16-4.05 (m, 4H), 3.81-3.74 (m, 1H), 3.46-3.42 (m, 2H), 2.88-2.74 (m, 5H), 1.78 (s, 6H), 1.66-1.58 (m, 2H), 1.51-1.45 (m, 2H); HPLC RT (method A5) 3.96 min; LCMS (NH$_4$OAc:ACN): M+H=495, Rt=2.30 min in 5 mins run.

Synthesis of Example 134: 1-(5-chloro-2-(2,3-dimethylpiperazin-1-yl)pyrimidin-4-yl)-N-(2-(Imidazo[1,2-a]pyridin-3-yl)propan-2-yl)-N-methylazetidine-3-carboxamide To a stirred solution of 1-(2,5-dichloropyrimidin-4-yl)-N-(2-(imidazo[1,2-a]pyridin-3-yl)propan-2-yl)-N-methylazetidine-3-carboxamide (intermediate 28) (120 mg, 0.287 mmol) and 2,3-dimethylpiperazine (163 mg, 1.435 mmol) in n-BuOH (1 ml) was added (0.25 ml 1.435 mmol) DIPEA and the reaction was irradiated in microwave at 150° C. for 1 h. Reaction mixture was cooled to RT and concentrated under reduced pressure. The crude was purified by Prep TLC using 4% MeOH in DCM to afford 1-(5-chloro-2-(2,3-dimethylpiperazin-1-yl)pyrimidin-4-yl)-N-(2-(imidazo[1,2-a]pyridin-3-yl)propan-2-yl)-N-methylazetidine-3-carboxamide (example 134) (16 mg, 11.72%) as white solid. $^1$H NMR (400 MHz, DMSO-d$_6$, 100° C.) δ 8.20 (d, 1H), 7.80 (s, 1H), 7.53 (d, 1H), 7.47 (s, 1H), 7.18 (t, 1H), 6.85 (t, 1H), 4.49-4.44 (m, 1H), 4.39-4.34 (m, 1H), 4.25-4.23 (m, 2H), 4.17-4.15 (m, 2H), 3.83-3.76 (m, 1H), 3.18-3.12 (m, 1H), 3.08-3.02 (m, 2H), 2.91-2.85 (m, 1H), 2.82 (s, 3H), 1.84 (s, 6H), 1.21-1.19 (m, 6H); HPLC RT (method A6) 4.11 min; LCMS (NH$_4$OAc:ACN): M+H=497, Rt=2.40 min in 5 mins run.

Synthesis of Example 135: (S)—N-(2-(imidazo[1,2-a]pyridin-3-yl)propan-2-yl)-N-methyl-1-(2-(2-methylpiperazin-1-yl)-5-(trifluoromethyl)pyrimidin-4-yl)azetidine-3-carboxamide Step 1

To a stirred solution of tert-butyl 3-((2-(imidazo[1,2-a]pyridin-3-yl)propan-2-yl)(methyl)carbamoyl)azetidine-1-carboxylate (750 mg, 2.094 mmol) in DMF (6 ml) was added NaH (125.64 mg, 3.141 mmol) at ice cool condition. The mixture was stirred for 30 min. Then MeI (0.156 ml, 2.513 mmol) was added to the reaction mixture and the reaction was stirred at RT for 3 hr. Then reaction mixture was quenched with ice water and extracted with EtOAc. Organic layer was dried over Na2SO4, filtered and concentrated to afford crude product. Crude product was purified by combiflash column chromatography (12 g silica column) using MeOH in DCM to afford tert-butyl 3-((2-(imidazo[1,2-a]pyridin-3-yl)propan-2-yl)(methyl)carbamoyl)azetidine-1-carboxylate. (450 mg, 57.7%); $^1$H NMR (400 MHz, DMSO-d$_6$) δ 8.20 (d, 1H), 7.55 (d, 1H), 7.44 (s, 1H), 7.19 (t, 1H), 6.86 (t, 1H), 3.93-3.71 (m, 4H), 3.65-3.61 (m, 1H), 2.75 (s, 3H), 1.76 (s, 6H), 1.34 (s, 9H); LCMS (NH4OAc:ACN): M+H=373, R$_t$=2.91 min in 5 mins run.

Step 2

TFA, DCM

To a solution of tert-butyl 3-((2-(imidazo[1,2-a]pyridin-3-yl)propan-2-yl)(methyl)carbamoyl)azetidine-1-carboxylate (600 mg, 1.612 mmol) in DCM (5 ml) was added trifluoroacetic acid (1.23 ml, 16.119 mmol) at 0° C. Reaction mixture was stirred at RT for 4 h. Reaction mixture was concentrated under reduced pressure to afford N-(2-(imidazo[1,2-a]pyridin-3-yl)propan-2-yl)-N-methylazetidine-3-carboxamide (600 mg, 74.72%) as TFA salt.

$^1$H NMR (400 MHz, DMSO-d$_6$) δ 8.81 (brs, 1H), 8.61 (d, 1H), 8.58 (brs, 1H), 8.12 (s, 1H), 8.00 (d, 1H), 7.93 (t, 1H), 7.43 (t, 1H), 4.04-3.94 (m, 3H), 3.87-3.81 (m, 2H), 2.96 (s, 3H), 1.74 (s, 6H).

Step 3 i-PrOH, TEA
0 to rt, 3 h

To a solution of N-(2-(imidazo[1,2-a]pyridin-3-yl)propan-2-yl)-N-methylazetidine-3-carboxamide (product step 3 example 119) (TFA salt, 323 mg, 0.667 mmol) in isopropanol (5 ml) were added Et$_3$N (0.93 ml, 6.674 mmol) and 2,4-dichloro-5-(trifluoromethyl)pyrimidine (3) (172 mg, 0.801 mmol) at 0° C. and stirred at RT for 3 h. Reaction mixture was concentrated under reduced pressure which was diluted with DCM and washed with sat NaHCO$_3$ solution. Organic layer was dried over Na$_2$SO$_4$, concentrated under reduced pressure to get crude which was purified by combiflash column chromatography (12 g silica column) using 2% MeOH in DCM to afford 1-(2-chloro-5-(trifluoromethyl)pyrimidin-4-yl)-N-(2-(imidazo[1,2-a]pyridin-3-yl)propan-2-yl)-N-methylazetidine-3-carboxamide (50 mg, 16.54%) as a solid. LCMS (NH$_4$OAc:ACN): M+H=453, R$_t$=3.08 min in 5 mins run.

Step 4 nBuOH,
MW 120° C.

-continued

A stirred solution of 1-(2-chloro-5-(trifluoromethyl)py-rimidin-4-yl)-N-(2-(imidazo[1,2-a]pyridin-3-yl)propan-2-yl)-N-methylazetidine-3-carboxamide (105 mg, 0.232 mmol) and tert-butyl (S)-3-methylpiperazine-1-carboxylate (5) (232 mg, 1.161 mmol) in n-BuOH (2 ml) was added (0.20 ml 1.161 mmol) DIPEA and irradiated in microwave at 120° C. for 1 h. Reaction mixture was cooled to RT and concentrated under reduced pressure. The crude was purified by Prep TLC using 4% MeOH in DCM to afforded tert-butyl (S)-4-(4-(3-((2-(imidazo[1,2-a]pyridin-3-yl)propan-2-yl)(methyl)carbamoyl)azetidin-1-yl)-5-(trifluoromethyl)py-rimidin-2-yl)-3-methylpiperazine-1-carboxylate (80 mg, 55.86%) white solid. LCMS (NH₄OAc:ACN): M+H=617, R$_t$=2.06 min in 3 mins run.

Step 5

To a solution of tert-butyl (S)-4-(4-(3-((2-(imidazo[1,2-a]pyridin-3-yl)propan-2-yl)(methyl)carbamoyl)azetidin-1-yl)-5-(trifluoromethyl)pyrimidin-2-yl)-3-methylpiperazine-1-carboxylate (80 mg, 0.13 mmol) in DCM (2 ml) was added trifluoroacetic acid (0.09 ml, 1.298 mmol) at 0° C. and stirred at RT for 4 h. Reaction mixture was concentrated under reduced pressure. The crude was dissolved in MeOH and loaded on an Isolute® SCX column. The column was washed with MeOH. Then compound was then eluted with NH₃-MeOH and the collected fractions were concentrated under reduced pressure to get (S)—N-(2-(imidazo[1,2-a]pyridin-3-yl)propan-2-yl)-N-methyl-1-(2-(2-methylpiper-azin-1-yl)-5-(trifluoromethyl)pyrimidin-4-yl)azetidine-3-carboxamide (example 135) (34 mg, 51.62%) as white solid; ¹H NMR (400 MHz, DMSO-d₆, 100° C.) δ 8.19 (d, 1H), 8.12 (s, 1H), 7.53 (d, 1H), 7.41 (s, 1H), 7.18 (t, 1H), 6.84 (t, 1H), 4.71-4.69 (m, 1H), 4.36-4.30 (m, 1H), 4.16-4.08 (m, 4H), 3.84-3.78 (m, 1H), 2.99-2.94 (m, 2H), 2.82 (s, 3H), 2.76 (d, 2H), 2.58-2.56 (m, 1H), 1.84 (s, 6H), 1.18 (d, 3H); HPLC RT (method A4) 5.99 min; LCMS (NH₄OAc:ACN): M+H=517, R$_t$=1.74 min in 3 mins run.

Synthesis of Example 136: 1-(5-chloro-2-(piper-azin-1-yl)pyrimidin-4-yl)-N-ethyl-N-(2-(imidazo[1,2-a]pyridin-3-yl)propan-2-yl)azetidine-3-carboxam-ide Step 1

To a stirred solution of 1-(2,5-dichloropyrimidin-4-yl)-N-(2-(imidazo[1,2-a]pyridin-3-yl)propan-2-yl)azetidine-3-car-boxamide (intermediate 1) (404 mg, 1 mmol) in (5 ml) DMF was added NaH (60% in oil) (37 mg, 1.5 mmol) in ice cool condition and continue for 30 min. Then (185 mg, 1.87 mmol) Ethyl-iodide (0.093 ml, 1.157 mmol) was added to reaction mixture and continue the reaction at RT for 3 hr. Then reaction mixture was quenched with ice water and extracted with EtOAc. Organic layer was dried over $Na_2SO_4$, concentrated to afford crude product which was purified by combiflash column chromatography (12 g silica column) using 1% MeOH in DCM to afford 1-(2,5-dichloropyrimidin-4-yl)-N-ethyl-N-(2-(imidazo[1,2-a]pyridin-3-yl)propan-2-yl)azetidine-3-carboxamide (200 mg, 47.87%) as a solid. LCMS ($NH_4OAc$:ACN): M+H=433, $R_t$=1.48 min in 3 mins run.

Step 2

A stirred solution of 1-(2,5-dichloropyrimidin-4-yl)-N-ethyl-N-(2-(imidazo[1,2-a]pyridin-3-yl)propan-2-yl)azetidine-3-carboxamide (75 mg, 0.173 mmol) and Piperazine (0.07 ml, 0.866 mmol) in n-BuOH (1 ml) was irradiated in microwave at 130° C. for 1 h. Reaction mixture was cooled to RT and concentrated under reduced pressure. The crude was purified by Prep TLC using 6% MeOH in DCM to afforded 1-(5-chloro-2-(piperazin-1-yl)pyrimidin-4-yl)-N-ethyl-N-(2-(imidazo[1,2-a]pyridin-3-yl)propan-2-yl)azetidine-3-carboxamide (example 136) (60 mg, 71.72%) as white solid. $^1H$ NMR (400 MHz, DMSO-$d_6$, 100° C.) δ 8.10 (d, 1H), 7.76 (s, 1H), 7.53 (d, 1H), 7.48 (s, 1H), 7.17 (t, 1H), 6.86 (t, 1H), 4.20-4.10 (m, 2H), 4.08-4.06 (m, 2H), 3.82-3.74 (m, 1H), 3.57-3.54 (m, 4H), 3.44-3.39 (m, 2H), 2.75-2.66 (m, 4H), 1.86 (s, 6H), 1.18 (t, 3H); HPLC RT (method A7) 4.81 min; LCMS (HCOOH:ACN): M+H=483, $R_t$=1.67 min in 3 mins run.

Synthesis of Example 137: 1-(5-chloro-2-(3-eth-ylpiperazin-1-yl)pyrimidin-4-yl)-N-(2-(imidazo[1,2-a]pyridin-3-yl)propan-2-yl)azetidine-3-carboxamide Step 1

A stirred solution of 1-(2,5-dichloropyrimidin-4-yl)-N-(2-(imidazo[1,2-a]pyridin-3-yl)propan-2-yl)azetidine-3-car-boxamide (intermediate 1) (100 mg, 0.248 mmol) and tert-butyl 2-ethylpiperazine-1-carboxylate (159 mg, 0.743 mmol) in n-BuOH (1 ml) was added (0.21 ml 1.238 mmol) DIPEA and irradiated in microwave at 130° C. for 1 h. Reaction mixture was cooled to RT and concentrated under reduced pressure. The crude was purified by Prep TLC using 2% MeOH in DCM to afforded tert-butyl 4-(5-chloro-4-(3-((2-(imidazo[1,2-a]pyridin-3-yl)propan-2-yl)carbamoyl)azetidin-1-yl)pyrimidin-2-yl)-2-ethylpiperazine-1-carboxy-late (85 mg, 58.89%) white solid; LCMS (NH4OAc:ACN): M+H=583, Rt=1.57 min in 3 mins run.

Step 2

-continued

-continued

A stirred solution of tert-butyl 4-(5-chloro-4-(3-((2-(imidazo[1,2-a]pyridin-3-yl)propan-2-yl)carbamoyl)azetidin-1-yl)pyrimidin-2-yl)-2-ethylpiperazine-1-carboxylate (85 mg, 0.146 mmol) in DCM (2 mL) was treated with trifluoroacetic acid (0.112 mL, 1.463 mmol). The reaction mixture was stirred room temperature for 4 h. The crude was dissolved in MeOH and loaded on an Isolute® SCX column. The column was washed with MeOH. Then compound was eluted with NH₃-MeOH and the collected fractions were concentrated under reduced pressure to give 1-(5-chloro-2-(3-ethylpiperazin-1-yl)pyrimidin-4-yl)-N-(2-(imidazo[1,2-a]pyridin-3-yl)propan-2-yl)azetidine-3-carboxamide (example 137) (25 mg, 35.46%) as white solid. ¹H NMR (400 MHz, DMSO-d₆) δ 8.43 (d, 1H), 8.36 (s, 1H), 7.79 (s, 1H), 7.55 (d, 1H), 7.44 (s, 1H), 7.18 (t, 1H), 6.87 (t, 1H), 4.37-4.35 (m, 1H), 4.32-4.24 (m, 3H), 4.04-4.00 (m, 2H), 3.46-3.42 (m, 1H), 2.93-2.86 (m, 1H), 2.77-2.71 (m, 1H), 2.51-2.47 (m, 1H), 2.42-2.30 (m, 2H), 1.72 (s, 6H), 1.35-1.32 (m, 1H), 0.88 (t, 3H); HPLC RT (method A6) 3.97 min; LCMS (NH₄OAc: ACN): M+H=483, R_t=1.54 min in 3 mins run.

Synthesis of Example 138: (R)-1-(5-chloro-2-(2-methylpiperazin-1-yl)pyrimidin-4-yl)-N-(2-(Imidazo[1,2-a]pyridin-3-yl)propan-2-yl)-N-methylazetidine-3-carboxamide Step 1

To a stirred solution of 1-(2,5-dichloropyrimidin-4-yl)-N-(2-(imidazo[1,2-a]pyridin-3-yl)propan-2-yl)-N-methylazetidine-3-carboxamide (intermediate 28) (100 mg, 0.239 mmol) and tert-butyl (R)-3-methylpiperazine-1-carboxylate (2) (239 mg, 1.196 mmol) in n-BuOH (1 ml) was added (0.20 ml 1.196 mmol) DIPEA and irradiated in microwave at 150° C. for 4 h. Reaction mixture was cooled to RT and concentrated under reduced pressure. The crude was purified by Prep TLC using 4% MeOH in DCM to afford tert-butyl (R)-4-(5-chloro-4-(3-((2-(imidazo[1,2-a]pyridin-3-yl)propan-2-yl)(methyl)carbamoyl)azetidin-1-yl)pyrimidin-2-yl)-3-methylpiperazine-1-carboxylate (60 mg, 43.02%) as off white solid. LCMS (NH₄OAc:ACN): M+H=584, R_t=1.58 min in 3 mins run.

Step 2

TFA, DCM

A stirred solution of tert-butyl (R)-4-(5-chloro-4-(3-((2-(imidazo[1,2-a]pyridin-3-yl)propan-2-yl)(methyl)carbamoyl)azetidin-1-yl)pyrimidin-2-yl)-3-methylpiperazine-1-carboxylate (60 mg, 0.103 mmol) in DCM (2 mL) was treated with trifluoroacetic acid (0.07 mL, 1.03 mmol). The reaction mixture was stirred room temperature for 4 h. The crude was dissolved in MeOH and loaded on an Isolute® SCX column. The column was washed with MeOH. Then compound was eluted with NH₃-MeOH and the collected fractions were concentrated under reduced pressure to give (R)-1-(5-chloro-2-(2-methylpiperazin-1-yl)pyrimidin-4-yl)-N-(2-(imidazo[1,2-a]pyridin-3-yl)propan-2-yl)-N-methyl-azetidine-3-carboxamide (example 138) (29 mg, 58.97%) as white solid. $^1$H NMR (400 MHz, DMSO-d$_6$, 100° C.) δ 8.19 (d, 1H), 7.78 (s, 1H), 7.53 (d, 1H), 7.46 (s, 1H), 7.18 (t, 1H), 6.85 (t, 1H), 4.60-4.56 (m, 1H), 4.26-4.16 (m, 5H), 3.79-3.72 (m, 1H), 2.94-2.87 (m, 2H), 2.82-2.75 (m, 5H), 2.56-2.53 (m, 1H), 1.84 (s, 6H), 1.10 (d, 3H); HPLC RT (method A4) 4.70 min; LCMS (NH4OAc:ACN): M+H=483, Rt=1.49 min in 3 mins run.

Synthesis of Example 139: (S)-1-(5-chloro-2-(3-methylpiperazin-1-yl)pyrimidin-4-yl)-N-(2-(Imidazo[1,2-a]pyridin-3-yl)propan-2-yl)-N-methylazetidine-3-carboxamide

Step 1

To a stirred solution of 1-(2,5-dichloropyrimidin-4-yl)-N-(2-(imidazo[1,2-a]pyridin-3-yl)propan-2-yl)-N-methylazetidine-3-carboxamide (intermediate 28)(100 mg, 0.239 mmol) and tert-butyl (S)-2-methylpiperazine-1-carboxylate (239 mg, 1.196 mmol) in n-BuOH (1 ml) was added (0.20 ml 1.196 mmol) DIPEA and the reaction mixture was irradiated in microwave at 130° C. for 1 h. Reaction mixture was cooled to RT and concentrated under reduced pressure.

The crude was purified by Prep TLC using 4% MeOH in DCM to afforded tert-butyl(S)-4-(5-chloro-4-(3-((2-(imidazo[1,2-a]pyridin-3-yl)propan-2-yl)(methyl)carbamoyl)azetidin-1-yl)pyrimidin-2-yl)-2-methylpiperazine-1-carboxylate (110 mg, 79.04%) as off white solid.

$^1$H NMR (400 MHz, DMSO-d$_6$) δ 8.22 (d, 1H), 7.82 (s, 1H), 7.53 (d, 1H), 7.45 (s, 1H), 7.18 (t, 1H), 6.85 (t, 1H), 4.37-4.27 (m, 4H), 4.18-4.14 (m, 3H), 3.80-3.71 (m, 2H), 3.07-2.97 (m, 2H), 2.88-2.81 (m, 4H), 1.78 (s, 6H), 1.41 (s, 9H), 1.10 (d, 3H); LCMS (NH₄OAc:ACN): M+H=583, R$_t$=1.57 min in 3 mins run.

Step 2

A stirred solution of tert-butyl (S)-4-(5-chloro-4-(3-((2-(imidazo[1,2-a]pyridin-3-yl)propan-2-yl)(methyl)carbamoyl)azetidin-1-yl)pyrimidin-2-yl)-2-methylpiperazine-1-carboxylate (110 mg, 0.189 mmol) in DCM (4 mL) was treated with TFA (0.144 mL, 1.89 mmol). The reaction mixture was stirred room temperature for 3 h. The reaction mixture was evaporated to get crude which was dissolved in MeOH and loaded on an Isolute® SCX column. The column was washed with MeOH. Then compound was eluted with NH₃-MeOH and the collected fractions were concentrated under reduced pressure to get (S)-1-(5-chloro-2-(3-methylpiperazin-1-yl)pyrimidin-4-yl)-N-(2-(imidazo[1,2-a]pyridin-3-yl)propan-2-yl)-N-methylazetidine-3-carboxamide (example 139) (47 mg, 41.80%) as white solid. $^1$H NMR (400 MHz, DMSO-d$_6$) δ 8.22 (d, 1H), 7.79 (s, 1H), 7.54 (d, 1H), 7.45 (s, 1H), 7.18 (t, 1H), 6.84 (t, 1H), 4.33-4.31 (m, 4H), 4.14 (brs, 2H), 3.78 (brs, 1H), 2.88-2.80 (m, 4H), 2.72-2.66 (m, 1H), 2.61-2.53 (m, 2H), 2.35-2.30 (m, 1H), 1.78 (s, 6H), 0.97 (d, 3H); HPLC RT (method A7) 4.77 min; LCMS (NH₄OAc:ACN): M+H=483, Rt=1.67 min in 3 mins run.

Synthesis of Example 140: (S)-1-(5-chloro-2-(3,4-dimethylpiperazin-1-yl)pyrimidin-4-yl)-N-(2-(imidazo[1,2-a]pyridin-3-yl)propan-2-yl)-N-methylazetidine-3-carboxamide

254

Synthesis of Example 141: (R)-1-(5-chloro-2-(2-methylpiperazin-1-yl)pyrimidin-4-yl)-N-(2-(Imidazo[1,2-a]pyridin-3-yl)propan-2-yl)azetidine-3-carboxamide Step 1

To a solution of (R)-1-(5-chloro-2-(2-methylpiperazin-1-yl)pyrimidin-4-yl)-N-(2-(imidazo[1,2-a]pyridin-3-yl)propan-2-yl)-N-methylazetidine-3-carboxamide (example 139) (TFA salt, 90 mg, 0.151 mmol) in methanol (2 ml) was added HCHO (37% solution 0.05 ml, 1.5 mmol) and stirred at RT for 1 hrs. Then NaCNBH₃ (28.24 mg, 0.453 mmol) was added at 0° C. and stirred the reaction mixture at RT for 16 hours. The reaction mixture was quenched with sat NaHCO₃ solution and extracted with DCM. The organic layer was washed with water, brine, dried over Na₂SO₄ and concentrated under reduced pressure to get crude compound which was purified by prep TLC plate using 5% MeOH in DCM with 1% 7M Ammonia in methanol to get (R)-1-(5-chloro-2-(2,4-dimethylpiperazin-1-yl)pyrimidin-4-yl)-N-(2-(imidazo[1,2-a]pyridin-3-yl)propan-2-yl)-N-methylazetidine-3-carboxamide (example 140) (45 mg, 74.80%) as a white solid.

¹H NMR (400 MHz, DMSO-d₆) δ 8.22 (d, 1H), 7.81 (s, 1H), 7.53 (d, 1H), 7.45 (s, 1H), 7.18 (t, 1H), 6.84 (t, 1H), 4.63-4.59 (m, 1H), 4.30-4.15 (m, 5H), 3.80-3.76 (m, 1H), 2.97 (t, 1H), 2.80-2.92 (m, 4H), 2.62 (d, 1H), 2.16 (s, 3H), 2.02-1.96 (m, 1H), 1.79-1.78 (m, 7H), 1.12 (d, 3H). HPLC RT (method A7) 4.83 min; LCMS (NH4OAc:ACN): M+H=497, Rt=1.71 min in 3 mins run.

To a stirred solution of 1-(2,5-dichloropyrimidin-4-yl)-N-(2-(imidazo[1,2-a]pyridin-3-yl)propan-2-yl)azetidine-3-carboxamide, intermediate 1, (120 mg, 0.297 mmol) and tert-butyl (R)-3-methylpiperazine-1-carboxylate (297 mg, 1.485 mmol) in n-BuOH (1 ml) was added (0.25 ml 1.485 mmol) DIPEA and the reaction mixture was irradiated in microwave at 135° C. for 3 h. Reaction mixture was cooled to RT and concentrated under reduced pressure. The crude was purified by Prep TLC using 4% MeOH in DCM to tert-butyl (R)-4-(5-chloro-4-(3-((2-(imidazo[1,2-a]pyridin-3-yl)propan-2-yl)carbamoyl)azetidin-1-yl)pyrimidin-2-yl)-3-methylpiperazine-1-carboxylate (70 mg, 41.42%) as white solid. LCMS (NH4OAc:ACN): M+H=569, Rt=1.86 min in 3 mins run.

Step 2

-continued

-continued

A stirred solution of tert-butyl (R)-4-(5-chloro-4-(3-((2-(imidazo[1,2-a]pyridin-3-yl)propan-2-yl)carbamoyl)azeti-din-1-yl)pyrimidin-2-yl)-3-methylpiperazine-1-carboxylate (60 mg, 0.106 mmol) in DCM (2 mL) was treated with trifluoroacetic acid (0.08 mL, 1.05 mmol). The reaction mixture was stirred room temperature for 3 h. The reaction mixture was evaporated to get crude which was dissolved in MeOH and loaded on an Isolute® SCX column. The column was washed with MeOH. Then compound was eluted with NH₃-MeOH and the collected fractions were concentrated under reduced pressure to get (R)-1-(5-chloro-2-(2-meth-ylpiperazin-1-yl)pyrimidin-4-yl)-N-(2-(imidazo[1,2-a]pyri-din-3-yl)propan-2-yl)azetidine-3-carboxamide (example 141) (15 mg, 30.29%) as white solid. $^1$H NMR (400 MHz, DMSO-d6) δ 8.43 (d, 1H), 8.35 (s, 1H), 7.79 (s, 1H), 7.54 (d, 1H), 7.44 (s, 1H), 7.18 (t, 1H), 6.88 (t, 1H), 4.52-4.50 (m, 1H), 4.25-4.21 (m, 2H), 4.18-4.16 (m, 1H), 4.04-4.01 (m, 2H), 3.44-3.43 (m, 1H), 2.88-2.84 (m, 2H), 2.72-2.70 (m, 2H), 2.49-2.47 (m, 1H) 1.72 (s, 6H), 1.10 (d, 3H); HPLC RT (method B3) 8.00 min LCMS (NH4OAc:ACN): M+H=469, Rt=1.55 min in 3 mins run.

Synthesis of Example 142: (R)-1-(5-chloro-2-(2,4-dimethylpiperazin-1-yl)pyrimidin-4-yl)-N-(2-(imi-dazo[1,2-a]pyridin-3-yl)propan-2-yl)-N-methylazeti-dine-3-carboxamide To a solution of (R)-1-(5-chloro-2-(2-methylpiperazin-1-yl)pyrimidin-4-yl)-N-(2-(imidazo[1,2-a]pyridin-3-yl)pro-pan-2-yl)-N-methylazetidine-3-carboxamide (example 138) (TFA salt, 90 mg, 0.151 mmol) in methanol (2 ml) was added HCHO (37% solution 0.05 ml, 1.5 mmol) and stirred at RT for 1 hrs. Then NaCNBH₃ (28.24 mg, 0.453 mmol) was added at 0° C. and stirred the reaction mixture at RT for 16 hours. The reaction mixture was quenched with sat NaHCO₃ solution and extracted with DCM. The organic layer was washed with water, brine, dried over Na₂SO₄ and concentrated under reduced pressure to get crude compound which was purified by prep TLC plate using 5% MeOH in DCM with 1% 7M Ammonia in methanol to get (R)-1-(5-chloro-2-(2,4-dimethylpiperazin-1-yl)pyrimidin-4-yl)-N-(2-(imidazo[1,2-a]pyridin-3-yl)propan-2-yl)-N-methylazeti-dine-3-carboxamide (example 142) (45 mg, 74.80%) as a white solid. $^1$H NMR (400 MHz, DMSO-d₆) δ 8.22 (d, 1H), 7.81 (s, 1H), 7.53 (d, 1H), 7.45 (s, 1H), 7.18 (t, 1H), 6.84 (t, 1H), 4.63-4.59 (m, 1H), 4.30-4.15 (m, 5H), 3.80-3.76 (m, 1H), 2.97 (t, 1H), 2.80-2.92 (m, 4H), 2.62 (d, 1H), 2.16 (s, 3H), 2.02-1.96 (m, 1H), 1.79-1.78 (m, 7H), 1.12 (d, 3H).

HPLC RT (method A7) 4.83 min; LCMS (NH4OAc:ACN): M+H=497, Rt=1.71 min in 3 mins run.

Synthesis of Example 143: 1-(5-chloro-2-(2,3-dim-ethylpiperazin-1-yl)pyrimidin-4-yl)-N-(2-(Imidazo[1,2-a]pyridin-3-yl)propan-2-yl)azetidine-3-carbox-amide

HCHO, NaCNBH3
MeOH, 0° C.-RT

60 nBuOH, MW

-continued

To a stirred solution of 1-(2,5-dichloropyrimidin-4-yl)-N-(2-(imidazo[1,2-a]pyridin-3-yl)propan-2-yl)azetidine-3-carboxamide (intermediate 1) (100 mg, 0.247 mmol) and 2,3-dimethylpiperazine (141 mg, 1.237 mmol) in n-BuOH (1 ml) was added (0.20 ml 1.237 mmol) DIPEA and the reaction mixture was irradiated in microwave at 150° C. for 3 h. Reaction mixture was cooled to RT and concentrated under reduced pressure. The crude was purified by Prep TLC using 4% MeOH in DCM to 1-(5-chloro-2-(2,3-dimethylpiperazin-1-yl)pyrimidin-4-yl)-N-(2-(imidazo[1,2-a]pyridin-3-yl)propan-2-yl)azetidine-3-carboxamide (example 143) (15 mg, 12.66%) as off white solid. $^1$H NMR (400 MHz, DMSO-d6, 100° C.) δ 8.46 (d, 1H), 8.05 (s, 1H), 7.76 (s, 1H), 7.52 (d, 1H), 7.43 (s, 1H), 7.17 (t, 1H), 6.84 (t, 1H), 4.49-4.37 (m, 1H), 4.29-4.21 (m, 3H), 4.12-4.10 (m, 2H), 3.48-3.46 (m, 1H), 2.84-2.76 (m, 3H), 2.66-2.60 (m, 1H), 1.77 (s, 6H), 1.18-1.10 (m, 3H), 0.88 (t, 3H). HPLC RT (method A4) 4.93 min; LCMS (NH4OAc:ACN): M+H=483, Rt=1.65 min in 3 mins run.

Synthesis of Example 144: 1-(2-(3,8-diazabicyclo[3.2.1]octan-3-yl)-5-chloropyrimidin-4-yl)-N-(2-(imidazo[1,2-a]pyridin-3-yl)propan-2-yl)azetidine-3-carboxamide Step 1

To a stirred solution of 1-(2,5-dichloropyrimidin-4-yl)-N-(2-(imidazo[1,2-a]pyridin-3-yl)propan-2-yl)azetidine-3-carboxamide, (intermediate 1), (120 mg, 0.297 mmol) and tert-butyl 3,8-diazabicyclo[3.2.1]octane-8-carboxylate (315 mg, 1.485 mmol) in (1 ml) n-BuOH was added (0.25 ml 1.485 mmol) DIPEA and the reaction mixture was irradiated in microwave at 150° C. for 1 h. Reaction mixture was cooled to RT and concentrated under reduced pressure. The crude was purified by Prep TLC using 4% MeOH in DCM to afforded tert-butyl 3-(5-chloro-4-(3-((2-(imidazo[1,2-a]pyridin-3-yl)propan-2-yl)carbamoyl)azetidin-1-yl)pyrimidin-2-yl)-3,8-diazabicyclo[3.2.1]octane-8-carboxylate (70 mg, 40.56%) as solid. LCMS (NH4OAc:ACN): M+H=582, Rt=1.50 min in 3 mins run.

Step 2

To a solution of tert-butyl 3-(5-chloro-4-(3-((2-(imidazo[1,2-a]pyridin-3-yl)propan-2-yl)carbamoyl)azetidin-1-yl)pyrimidin-2-yl)-3,8-diazabicyclo[3.2.1]octane-8-carboxylate (80 mg, 0.138 mmol) in (5 ml) DCM was added Trifluoruacetic acid (0.105 ml, 1.379 mmol) at 0° C. Reaction mixture was stirred at RT for 4 h. Reaction mixture was concentrated under reduced pressure which was passed through SCX column followed by prep TLC using 5% MeOH in DCM afford desired 1-(2-(3,8-diazabicyclo[3.2.1]octan-3-yl)-5-chloropyrimidin-4-yl)-N-(2-(imidazo[1,2-a]pyridin-3-yl)propan-2-yl)azetidine-3-carboxamide (Example 144) (40 mg, 60.32%) as a white solid. $^1$H NMR (400 MHz, DMSO-d6) δ 8.44 (d, 1H), 8.34 (s, 1H), 7.76 (s, 1H), 7.55 (d, 1H), 7.44 (s, 1H), 7.20 (t, 1H), 6.88 (t, 1H), 4.24-4.22 (m, 2H), 4.06-4.00 (m, 4H), 3.43-3.40 (m, 3H), 2.82 (d, 2H), 1.72 (s, 6H), 1.59-1.57 (m, 2H), 1.46 (d, 2H); HPLC RT (method A4) 4.84 min; LCMS (HCOOH:ACN): M+H=481, Rt=1.64 min in 3 mins run.

Synthesis of Example 145: (S)-1-(5-chloro-2-(2-methylpiperazin-1-yl)pyrimidin-4-yl)-N-ethyl-N-(2-(imidazo[1,2-a]pyridin-3-yl)propan-2-yl)azetidine-3-carboxamide Step 1

To a stirred solution of 1-(2,5-dichloropyrimidin-4-yl)-N-(2-(imidazo[1,2-a]pyridin-3-yl)propan-2-yl)azetidine-3-carboxamide, (intermediate 1) (400 mg, 0.99 mmol) in (5 ml) DMF was added (60%, 59.4 mg, 1.485 mmol) NaH in ice cool condition and stirred for 30 min. Then (185 mg, 1.188 mmol) Ethyl-iodide was added to reaction mixture and continued the reaction at RT for 3 hr. Then reaction mixture was quenched with ice-water and extracted with EtOAc. Organic layer was dried over Na2SO4, concentrated to afford crude product which was purified by combiflash column chromatography (12 g silica column) using 1% MeOH in DCM to afford 1-(2,5-dichloropyrimidin-4-yl)-N-ethyl-N-(2-(imidazo[1,2-a]pyridin-3-yl)propan-2-yl)azetidine-3-carboxamide (200 mg, 46.63%) as a solid; 1H NMR (400 MHz, DMSO-d6) δ 8.17-8.10 (m, 2H), 7.61-7.47 (m, 2H), 7.18 (t, 1H), 6.90 (t, 1H), 4.75-4.40 (m, 4H), 3.84-3.78 (m, 1H), 3.42-3.38 (m, 2H), 1.82 (s, 6H), 1.17 (t, 3H); LCMS (NH$_4$OAc:ACN): M+H=433, R$_t$=1.71 min in 3 mins run.

Step 2

260

-continued

To a stirred solution of 1-(2,5-dichloropyrimidin-4-yl)-N-ethyl-N-(2-(imidazo[1,2-a]pyridin-3-yl)propan-2-yl)azetidine-3-carboxamide (125 mg, 0.289 mmol) and tert-butyl (S)-3-methylpiperazine-1-carboxylate (289 mg, 1.446 mmol) in (1 ml) n-BuOH was added (0.25 ml 1.446 mmol) DI PEA and the reaction mixture was irradiated in microwave at 150° C. for 3 h. Reaction mixture was cooled to RT and concentrated under reduced pressure. The crude was purified by Prep TLC using 4% MeOH in DCM to afforded tert-butyl (S)-4-(5-chloro-4-(3-(ethyl(2-(imidazo[1,2-a]pyridin-3-yl)propan-2-yl)carbamoyl)azetidin-1-yl)pyrimidin-2-yl)-3-methylpiperazine-1-carboxylate (80 mg, 46.32%) white solid. LCMS (NH4OAc:ACN): M+H=597, Rt=1.67 min in 3 mins run.

Step 3

To a solution of tert-butyl (S)-4-(5-chloro-4-(3-(ethyl(2-(imidazo[1,2-a]pyridin-3-yl)propan-2-yl)carbamoyl)azetidin-1-yl)pyrimidin-2-yl)-3-methylpiperazine-1-carboxylate (100 mg, 0.168 mmol) in (4 ml) DCM, (0.12 ml, 1.677 mmol) was added trifluoroacetic acid (0.128 ml, 1.677 mmol) at 0° C. Reaction mixture was stirred at RT for 4 h. Reaction mixture was concentrated under reduced pressure which was dissolved in MeOH and loaded on an Isolute® SCX column. The column was washed with MeOH. Then compound was eluted with NH₃-MeOH and the collected fractions were concentrated under reduced pressure followed by prep TLC using 5% MeOH in DCM and lyophilization afforded (S)-1-(5-chloro-2-(2-methylpiperazin-1-yl)pyrimidin-4-yl)-N-ethyl-N-(2-(imidazo[1,2-a]pyridin-3-yl)propan-2-yl)azetidine-3-carboxamide (Example 145) (20 mg, 23.99%) as a white solid. ¹H NMR (400 MHz, DMSO-d6, 100° C.) δ 8.10 (d, 1H), 7.78 (s, 1H), 7.51 (d, 1H), 7.48 (s, 1H), 7.18 (t, 1H), 6.86 (t, 1H), 4.66-4.64 (m, 1H), 4.28-4.26 (m, 1H), 4.14-4.11 (m, 2H), 4.09-4.06 (m, 2H), 3.81-3.79 (m, 1H), 3.45-3.40 (m, 2H), 3.05-2.88 (m, 4H), 2.68-2.65 (m, 1H), 1.86 (s, 6H), 1.21-1.16 (m, 6H). HPLC RT (method B4) 12.63 min; LCMS (NH4OAc:ACN): M+H=497, Rt=2.78 min in 5 mins run.

Synthesis of Example 146: 1-(2-(2,5-diazabicyclo [4.1.0]heptan-2-yl)-5-chloropyrimidin-4-yl)-N-(2-(imidazo[1,2-a]pyridin-3-yl)propan-2-yl)-N-methyl-azetidine-3-carboxamide To a stirred solution of 2,5-diazabicyclo[4.1.0]heptanes (85 mg, 0.502 mmol) in (2 ml) THF was added NaH (67 mg, 1.674 mmol) in ice cool condition and stirred at that temperature for 30 min. Then 1-(2,5-dichloropyrimidin-4-yl)-N-(2-(imidazo[1,2-a]pyridin-3-yl)propan-2-yl)-N-methyl-azetidine-3-carboxamide, (intermediate 28) (140 mg, 0.33 mmol) was added into reaction mixture and stirred at 80° C. for 16 hr. Then reaction mixture was quenched with ice water and extracted with EtOAc, dried over Na2SO4 and concentrated under reduced pressure to get crude compound which was purified by reverse phase prep HPLC (NH4HCO3:ACN) to afford 1-(2-(2,5-diazabicyclo[4.1.0] heptan-2-yl)-5-chloropyrimidin-4-yl)-N-(2-(imidazo[1,2-a] pyridin-3-yl)propan-2-yl)-N-methylazetidine-3-carboxamide (example 146) (3 mg, 1.91%) as a white solid. ¹H NMR (400 MHz, DMSO-d6 at 100° C.) δ 8.19 (d, 1H), 7.82 (s, 1H), 7.52 (d, 1H), 7.46 (s, 1H), 7.18 (t, 1H), 6.85 (t, 1H), 4.28-4.23 (m, 2H), 4.20-4.17 (m, 2H), 3.80-3.77 (m, 1H), 3.61-3.55 (m, 1H), 3.08-3.04 (m, 1H) 2.88-2.85 (m, 1H), 2.80 (s, 3H), 2.76-2.72 (m, 2H), 2.67-2.62 (m, 1H), 1.84 (s, 6H), 0.71-0.72 (m, 1H), 0.31 (d, 1H); HPLC RT (method A4) 4.77 min; LCMS (NH4OAc:ACN): M+H=481, Rt=1.53 min in 3 mins run.

Synthesis of Example 147: (S)-1-(5-chloro-2-(2-ethylpiperazin-1-yl)pyrimidin-4-yl)-N-(2-(imidazo [1,2-a]pyridin-3-yl)propan-2-yl)azetidine-3-carbox-amide Step 1

To a stirred solution of 2,5-dichloro-4-(methylthio)pyrimidine (product of step 1 in example 129) (500 mg, 2.578 mmol) and tert-butyl (S)-3-ethylpiperazine-1-carboxylate (1.655 g, 7.734 mmol) in n-BuOH (2 ml) was added DIPEA (1.345 ml, 7.734 mmol) and the reaction was irradiated in microwave at 150° C. for 1 h. Reaction mixture was cooled to RT and concentrated under reduced pressure to get crude product which was purified by combiflash column (12 g silica column) using 10% EtOAc in Hexane to afford tert-butyl (S)-4-(5-chloro-4-(methylthio)pyrimidin-2-yl)-3-eth-ylpiperazine-1-carboxylate (600 mg, 62%) as colorless sticky gum. ¹H NMR (400 MHz, CDCl₃) δ 7.91 (s, 1H), 4.69-4.56 (m, 1H), 4.48 (d, 1H), 4.19-3.92 (m, 2H), 3.18-3.06 (m, 1H), 3.05-2.78 (m, 2H), 2.47 (s, 3H), 1.69-1.58 (m, 2H), 1.48 (s, 9H), 0.91 (t, 3H); LCMS (NH4OAc:ACN): M+H=373, Rt=4.68 min in 5 mins run.

Step 2

To a stirred solution of tert-butyl (S)-4-(5-chloro-4-(meth-ylthio)pyrimidin-2-yl)-3-ethylpiperazine-1-carboxylate (600 mg, 1.608 mmol) in DCM (8 ml) was added mCPBA (554.962 mg, 3.216 mmol) at ice cool condition and the mixture was stirred for 18 h with slow warming to RT. Reaction mixture was quenched with NaHCO3 solution and extracted with DCM. Organic layer was washed with water, brine, dried over Na2SO4 and evaporated under reduce pressure to get crude. Crude was purified by combiflash (12 g silica column) using 10% EtOAc in hexane to afford tert-butyl (S)-4-(5-chloro-4-(methylsulfonyl)pyrimidin-2-yl)-3-ethylpiperazine-1-carboxylate (500 mg, 76.8%) as solid. ¹H NMR (400 MHz, DMSO-d₆) δ 8.71 (s, 1H), 4.61-4.47 (m, 1H), 4.42-4.27 (m, 1H), 4.06-3.83 (m, 2H), 3.43 (s, 3H), 3.18-2.84 (m, 3H), 1.66-1.51 (m, 2H), 1.42 (s, 9H), 0.91-0.78 (m, 3H); LCMS (NH4OAc:ACN): M+H=405.2, R$_f$=3.64 min in 5 mins run.

Step 3

To a stirred solution of N-(2-(imidazo[1,2-a]pyridin-3-yl) propan-2-yl)azetidine-3-carboxamide (TFA salt, 150 mg, 0.309 mmol) in isoprapanol (2 ml) were added Et3N (0.429 ml, 3.086 mmol) and tert-butyl (S)-4-(5-chloro-4-(methyl-sulfonyl)pyrimidin-2-yl)-3-ethylpiperazine-1-carboxylate (product of step 1 in example 149) (149.63 mg, 0.37 mmol) at 0° C. Reaction mixture was stirred at RT for 3 hr. Then reaction mass was concentrated under reduced pressure which was diluted with DCM and washed with bicarbonate. Organic layer was dried over Na2SO4, filtered and concentrated under reduced pressure to get crude product which was purified by combi flash column chromatography (12 g silica column) using 2% MeOH in DCM to afford tert-butyl (S)-4-(5-chloro-4-(3-((2-(imidazo[1,2-a]pyridin-3-yl)pro-pan-2-yl)carbamoyl)azetidin-1-yl)pyrimidin-2-yl)-3-eth-ylpiperazine-1-carboxylate (150 mg, 83.34%) as solid. LCMS (NH4OAc:ACN): M+H=583, R$_f$=3.48 min in 5 mins run.

Step 4

A stirred solution of tert-butyl (S)-4-(5-chloro-4-(3-((2-(imidazo[1,2-a]pyridin-3-yl)propan-2-yl)carbamoyl)azeti-din-1-yl)pyrimidin-2-yl)-3-ethylpiperazine-1-carboxylate (150 mg, 0.257 mmol) in DCM (3 mL) was treated with TFA (0.197 mL, 2.572 mmol). The reaction mixture was stirred at room temperature for 4 h. The volatiles was evaporated and crude was dissolved in MeOH and loaded on an Iso-lute® SCX column. The column was washed with MeOH. Then compound was then eluted with NH$_3$-MeOH and the collected fractions were concentrated under reduced pressure which was again purified by prep TLC Plate using 5% MeOH in DCM with 1% 7(N) ammonia in Methanol to give (S)-1-(5-chloro-2-(2-ethylpiperazin-1-yl)pyrimidin-4-yl)-N-(2-(imidazo[1,2-a]pyridin-3-yl)propan-2-yl)azetidine-3-carboxamide (example 147) as white solid (45 mg, 36.23%). $^1$H NMR (400 MHz, DMSO-d$_6$) δ 8.44 (d, 1H), 8.36 (s, 1H), 7.77 (s, 1H), 7.56 (d, 1H), 7.44 (s, 1H), 7.19 (t, 1H), 6.87 (t, 1H), 4.36-4.17 (m, 4H), 4.08-3.96 (m, 2H), 3.47-3.41 (m, 1H), 2.86-2.75 (m, 3H), 2.63-2.54 (m, 1H), 2.47-2.39 (m, 1H), 1.83-1.61 (m, 7H), 1.59-1.49 (m, 1H), 0.76 (t, 3H); HPLC RT (method A4) 4.96 min; LCMS (NH4OAc:ACN): M+H=483.3, R$_f$=1.49 min in 3 mins run.

Synthesis of Example 148: (S)-1-(5-chloro-2-(2-ethylpiperazin-1-yl)pyrimidin-4-yl)-N-(2-(Imidazo[1,2-a]pyridin-3-yl)propan-2-yl)-N-methylazetidine-3-carboxamide Step 1

-continued

To a stirred solution of N-(2-(imidazo[1,2-a]pyridin-3-yl) propan-2-yl)-N-methylazetidine-3-carboxamide (product of example 118 step 2) (TFA salt, 80 mg, 0.207 mmol) in isoprapanol (2 ml) were added Et3N (0.288 ml, 2.073 mmol) and tert-butyl (S)-4-(5-chloro-4-(methylsulfonyl)pyrimidin-2-yl)-3-ethylpiperazine-1-carboxylate (product of step 1 in example 149) (100.477 mg, 0.249 mmol) at 0° C. Reaction mixture was stirred at RT for 3 hr. Then reaction mass was concentrated under reduced pressure which was diluted with DCM and washed with NaHCO3 solution. Organic layer was dried over Na2SO4, filtered and concentrated under reduced pressure to get crude product which was purified by combi flash column chromatography (4 g silica column) using 2% MeOH in DCM to afford tert-butyl (S)-4-(5-chloro-4-(3-((2-(imidazo[1,2-a]pyridin-3-yl)propan-2-yl)(methyl)carbamoyl)azetidin-1-yl)pyrimidin-2-yl)-3-eth-ylpiperazine-1-carboxylate (100 mg, 80.8%) as solid. LCMS (NH4OAc:ACN): M+H=597, R$_f$=2.12 min in 3 mins run.

Step 2

TFA, DCM

A stirred solution of tert-butyl (S)-4-(5-chloro-4-(3-((2-(imidazo[1,2-a]pyridin-3-yl)propan-2-yl)carbamoyl)azetidin-1-yl)pyrimidin-2-yl)-3-ethylpiperazine-1-carboxylate (100 mg, 0.167 mmol) in DCM (2 mL) was treated with TFA (0.128 mL, 1.675 mmol). The reaction mixture was stirred at room temperature for 4 h. The volatiles were evaporated and crude was dissolved in MeOH and loaded on an Iso-lute® SCX column. The column was washed with MeOH. Then compound was then eluted with $NH_3$-MeOH and the collected fractions were concentrated under reduced pressure which was again purified by prep TLC Plate using 5% MeOH in DCM with 1% 7(N) ammonia in Methanol to give (S)-1-(5-chloro-2-(2-ethylpiperazin-1-yl)pyrimidin-4-yl)-N-(2-(imidazo[1,2-a]pyridin-3-yl)propan-2-yl)-N-methyl-azetidine-3-carboxamide (example 148) as white solid (38 mg, 45.65%). $^1$H NMR (400 MHz, DMSO-$d_6$) δ 8.22 (d, 1H), 7.79 (s, 1H), 7.55 (d, 1H), 7.46 (s, 1H), 7.18 (t, 1H), 6.85 (t, 1H), 4.40-4.24 (m, 4H), 4.16-4.13 (m, 2H), 3.79-3.77 (m, 1H), 2.87-2.80 (m, 6H), 2.67-2.58 (m, 1H), 2.47-2.43 (m, 1H), 1.78 (s, 6H), 1.73-1.67 (m, 1H), 1.61-1.54 (m, 1H), 0.76 (t, 3H); HPLC RT (method A4) 5.14 min; LCMS (NH4OAc:ACN): M+H=497, $R_t$=1.54 min in 3 mins run.

Synthesis of Example 149: 1-(5-chloro-2-(2,2-dim-ethylpiperazin-1-yl)pyrimidin-4-yl)-N-(2-(Imidazo[1,2-a]pyridin-3-yl)propan-2-yl)-N-methylazetidine-3-carboxamide Step 1

To a stirred solution of 2,5-dichloro-4-(methylthio)py-rimidine (product of step one, example 129) (150 mg, 0.773 mmol) and tert-butyl 3,3-dimethylpiperazine-1-carboxylate (0.508 ml, 2.32 mmol) in n-BuOH (1 ml) was added DIPEA (0.404 ml, 2.32 mmol) and the reaction was irradiated in microwave at 170° C. for 1 h. Reaction mixture was cooled to RT and concentrated under reduced pressure to get crude product which was purified by combiflash column (4 g silica column) using EtOAc in Hexane to afford tert-butyl 4-(5-chloro-4-(methylthio)pyrimidin-2-yl)-3,3-dimethylpipera-zine-1-carboxylate (70 mg, 24.27%) as colorless sticky gum. $^1$H NMR (400 MHz, DMSO-$d_6$) δ 8.13 (s, 1H), 4.10-4.03 (m, 2H), 3.51 (s, 2H), 3.45-3.38 (m, 2H), 1.48 (s, 6H), 1.41 (s, 9H). (S—CH$_3$ merged with DMSO); LCMS (NH4OAc: ACN): M+H=373, $R_t$=4.03 min in 5 mins run.

Step 2

To a stirred solution of tert-butyl 4-(5-chloro-4-(methyl-thio)pyrimidin-2-yl)-3,3-dimethylpiperazine-1-carboxylate (120 mg, 0.322 mmol) in DCM (1.5 ml) was added mCPBA (111.294 mg, 0.645 mmol) at ice cool condition and the mixture was stirred for 18 h with slow warming to RT. Reaction mixture was quenched with NaHCO3 solution and extracted with DCM. Organic layer was washed with water, brine, dried over Na2SO4 and evaporated under reduce pressure to get crude which was purified by combiflash column chromatography (4 g silica column) using EtOAc in hexane to afford tert-butyl 4-(5-chloro-4-(methylsulfonyl) pyrimidin-2-yl)-3,3-dimethylpiperazine-1-carboxylate (105 mg, 80.42%) as solid. $^1$H NMR (400 MHz, DMSO-$d_6$) δ 8.70 (s, 1H), 4.11-4.05 (m, 2H), 3.55 (s, 2H), 3.48-3.38 (m, 5H), 1.46 (s, 6H), 1.42 (s, 9H); LCMS (NH4OAc:ACN): M+H=405, $R_t$=2.00 min in 3 mins run.

Step 3

To a stirred solution of N-(2-(imidazo[1,2-a]pyridin-3-yl) propan-2-yl)-N-methylazetidine-3-carboxamide (TFA salt, 100 mg, 0.2 mmol) in isoprapanol were added Et3N (0.279 ml, 2 mmol) and tert-butyl 4-(5-chloro-4-(methylsulfonyl)

pyrimidin-2-yl)-3,3-dimethylpiperazine-1-carboxylate (96.991 mg, 0.24 mmol) at 0° C. Reaction mixture was stirred at RT for 3 hr. Then reaction mass was concentrated under reduced pressure which was diluted with DCM and washed with NaHCO3 solution. Organic layer was dried over Na2SO4, filtered and concentrated under reduced pressure to get crude product which was purified by combi flash column chromatography using 4% MeOH in DCM to afford tert-butyl 4-(5-chloro-4-(3-((2-(imidazo[1,2-a]pyridin-3-yl)propan-2-yl)(methyl)carbamoyl)azetidin-1-yl)pyrimidin-2-yl)-3,3-dimethylpiperazine-1-carboxylate (85 mg, 71.17%) as solid. $^1$H NMR (400 MHz, DMSO-d$_6$) S 8.22 (bs, 1H), 7.81 (s, 1H), 7.55 (d, 1H), 7.46 (s, 1H), 7.18 (t, 1H), 6.83 (t, 1H), 4.37-4.12 (m, 4H), 3.95-3.93 (m, 2H), 3.88-3.73 (m, 1H), 3.44 (s, 2H), 3.38-3.33 (m, 2H), 2.80 (s, 3H), 1.79 (s, 6H), 1.41 (s, 15H); LCMS (NH4OAc:ACN): M+H=597.5, R$_t$=2.09 min in 3 mins run.

Step 4 the collected fractions were concentrated under reduced pressure to give 1-(5-chloro-2-(2,2-dimethylpiperazin-1-yl)pyrimidin-4-yl)-N-(2-(imidazo[1,2-a]pyridin-3-yl)propan-2-yl)-N-methylazetidine-3-carboxamide (example 149) as white solid (40.72 mg, 48.85%). $^1$H NMR (400 MHz, DMSO-d$_6$, 100° C.) δ 8.20 (d, 1H), 7.81 (s, 1H), 7.53 (d, 1H), 7.47 (s, 1H), 7.19 (t, 1H), 6.84 (t, 1H), 4.30-4.15 (m, 4H), 3.83-3.78 (m, 1H), 3.63-3.61 (m, 2H), 2.88-2.86 (m, 2H), 2.81 (s, 3H), 2.65 (s, 2H), 1.84 (s, 6H), 1.44 (s, 6H). HPLC RT (method A6) 3.99 min; LCMS (NH4OAc:ACN): M+H=497, R$_t$=1.54 min in 3 mins run.

Synthesis of Example 150: 1-(5-chloro-2-(4,7-diaz-aspiro[2.5]octan-4-yl)pyrimidin-4-yl)-N-(2-(imidazo[1,2-a]pyridin-3-yl)propan-2-yl)-N-methylazetidine-3-carboxamide A stirred solution of tert-butyl 4-(5-chloro-4-(3-((2-(imidazo[1,2-a]pyridin-3-yl)propan-2-yl)(methyl)carbamoyl)azetidin-1-yl)pyrimidin-2-yl)-3,3-dimethylpiperazine-1-carboxylate (100 mg, 0.168 mmol) in DCM (2 mL) was treated with TFA (0.128 mL, 1.677 mmol). The reaction mixture was stirred room temperature for 4 h. The volatiles were evaporated and crude was dissolved in MeOH and loaded on an Isolute® SCX column. The column was washed with MeOH. Then compound was eluted with NH$_3$-MeOH and Example 150 was prepared using the same procedure as example 149, starting with tert-butyl 4,7-diazaspiro[2.5]octane-7-carboxylate and 2,5-dichloro-4-(methylthio)pyrimidine (product of step one, example 129 to produce 1-(5-chloro-2-(4,7-diazaspiro[2.5]octan-4-yl)pyrimidin-4-yl)-N-(2-(imidazo[1,2-a]pyridin-3-yl)propan-2-yl)-N-methylazetidine-3-carboxamide (example 150) as white solid (50 mg, 60.03%). $^1$H NMR (400 MHz, DMSO-d$_6$) δ 8.22 (brs, 1H), 7.88 (s, 1H), 7.55 (d, 1H), 7.46 (s, 1H), 7.18 (t, 1H), 6.85 (t, 1H), 4.49-4.01 (m, 4H), 3.83-3.80 (m, 3H), 3.06-2.69 (m, 7H), 1.79 (s, 6H), 1.01-0.70 (m, 4H); HPLC RT (method A3) 3.96 min; LCMS (NH4OAc:ACN): M+H=495, R$_t$=1.48 min in 3 mins run.

Synthesis of Example 151: 1-(5-chloro-2-((2S,5S)-2,5-dimethylpiperazin-1-yl)pyrimidin-4-yl)-N-(2-(imidazo[1,2-a]pyridin-3-yl)propan-2-yl)azetidine-3-carboxamide Example 151 was prepared using the same procedure as example 149, starting with tert-butyl (2S,5S)-2,5-dimethylpiperazine-1-carboxylate and 2,5-dichloro-4-(methylthio) pyrimidine (product of step one in example 131) to produce, 1-(5-chloro-2-((2S,5S)-2,5-dimethylpiperazin-1-yl)pyrimidin-4-yl)-N-(2-(imidazo[1,2-a]pyridin-3-yl)propan-2-yl) azetidine-3-carboxamide, example 151 as white solid (40 mg, 68.89%); ${}^{1}$H NMR (400 MHz, MeOD) δ 8.43 (d, 1H), 7.69 (s, 1H), 7.55 (d, 1H), 7.49 (s, 1H), 7.28 (t, 1H), 6.93 (t, 1H), 4.63-4.58 (m, 1H), 4.42-4.14 (m, 5H), 3.51-3.46 (m, 1H), 2.92-2.82 (m, 2H), 2.68-2.50 (m, 2H), 1.83 (s, 6H), 1.17-1.08 (m, 6H); HPLC RT (method A4) 4.91 min; LCMS (NH4OAc:ACN): M+H=483.27, R$_t$=1.38 min in 3 mins run.

Synthesis of Example 152: 1-(5-chloro-2-((2S,5S)-2,4,5-trimethylpiperazin-1-yl)pyrimidin-4-yl)-N-(2-(imidazo[1,2-a]pyridin-3-yl)propan-2-yl)azetidine-3-carboxamide HCHO,
MeOH
NaCNBH₃,
RT -continued To a stirred solution of 1-(5-chloro-2-((2S,5S)-2,5-dimethylpiperazin-1-yl)pyrimidin-4-yl)-N-(2-(imidazo[1,2-a] pyridin-3-yl)propan-2-yl)azetidine-3-carboxamide (example 151) (TFA salt, 100 mg, 0.207 mmol) in MeOH (2 ml) was added HCHO solution (0.076 ml, 2.073 mmol) and the mixture was stirred for 1 hr. Then NaCNBH3 (38.774 mg, 0.622 mmol) was added at 0° C. and the reaction was stirred at RT for 16 hrs. The reaction mixture was quenched with NaHCO3 and extracted with DCM. The organic layer was dried over Na2SO4 and concentrated under reduced pressure to get crude which was purified by prep TLC using 3% MeOH in DCM to afford 1-(5-chloro-2-((2S,5S)-2,4,5-trimethylpiperazin-1-yl)pyrimidin-4-yl)-N-(2-(imidazo[1,2-a] pyridin-3-yl)propan-2-yl)azetidine-3-carboxamide (example 152) as a white solid (50 mg, 48.52%). ${}^{1}$H NMR (400 MHz, MeOD) δ 8.43 (d, 1H), 7.68 (s, 1H), 7.55 (d, 1H), 7.49 (s, 1H), 7.28 (t, 1H), 6.93 (t, 1H), 4.61-4.51 (m, 1H), 4.41-4.31 (m, 2H), 4.26-4.13 (m, 3H), 3.52-3.46 (m, 1H), 2.78-2.63 (m, 2H), 2.33-2.22 (4H), 1.99-1.89 (m, 1H), 1.83 (s, 6H), 1.19 (d, 3H), 1.11 (d, 3H); HPLC RT (method B3) 7.78 min; LCMS (NH4OAc:ACN): M+H=497.4, R$_t$=2.76 min in 5 mins run.

Synthesis of Example 153: 1-(5-chloro-2-((2S,5R)-2,5-dimethylpiperazin-1-yl)pyrimidin-4-yl)-N-(2-(imidazo[1,2-a]pyridin-3-yl)propan-2-yl)azetidine-3-carboxamide Example 153 was prepared using the same procedure as example 149, starting with and tert-butyl (2R,5S)-2,5-dimethylpiperazine-1-carboxylate and 2,5-dichloro-4-(methylthio)pyrimidine product of step one in example 129) to produce, 1-(5-chloro-2-((2S,5R)-2,5-dimethylpiperazin-1-yl)pyrimidin-4-yl)-N-(2-(imidazo[1,2-a]pyridin-3-yl)propan-2-yl)azetidine-3-carboxamide (example 153) as white solid (55 mg, 66.3%). ¹H NMR (400 MHz, DMSO-d₆) δ 8.44 (d, 1H), 8.35 (s, 1H), 7.77 (s, 1H), 7.56 (d, 1H), 7.44 (s, 1H), 7.18 (t, 1H), 6.88 (t, 1H), 4.51-4.43 (m, 1H), 4.29-4.19 (m, 2H), 4.09-3.94 (m, 3H), 3.49-3.41 (m, 1H), 3.13-3.01 (m, 3H), 2.46-2.39 (m, 1H), 1.72 (s, 6H), 1.09 (d, 3H), 0.99 (d, 3H). HPLC RT (method B3) 7.46 min; LCMS (NH4OAc:ACN): M+H=483.4, R$_t$=1.37 min in 3 mins run.

Synthesis of Example 154: 1-(5-chloro-2-((2S,5R)-2,4,5-trimethylpiperazin-1-yl)pyrimidin-4-yl)-N-(2-(imidazo[1,2-a]pyridin-3-yl)propan-2-yl)azetidine-3-carboxamide To a stirred solution of 1-(5-chloro-2-((2S,5R)-2,5-dimethylpiperazin-1-yl)pyrimidin-4-yl)-N-(2-(imidazo[1,2-a]pyridin-3-yl)propan-2-yl)azetidine-3-carboxamide (example 153) (TFA salt, 150 mg, 0.311 mmol) in MeOH (2 ml) was added HCHO solution (0.115 ml, 3.11 mmol) and the mixture was stirred RT for 1 hr. Then NaCNBH3 (58.161 mg, 0.933 mmol) was added at 0° C. and the reaction was stirred at RT for 16 hrs. The reaction mixture was quenched with NaHCO3 and extracted with DCM. The organic layer was dried over Na2SO4 and concentrated under reduced pressure to get crude which was purified by prep TLC using MeOH in DCM to afford 1-(5-chloro-2-((2S,5R)-2,4,5-trimethylpiperazin-1-yl)pyrimidin-4-yl)-N-(2-(imidazo[1,2-a]pyridin-3-yl)propan-2-yl)azetidine-3-carboxamide (example 154) as a white solid (93 mg, 60.17%).

¹H NMR (400 MHz, DMSO-d₆) δ 8.44 (d, 1H), 8.35 (s, 1H), 7.78 (s, 1H), 7.56 (d, 1H), 7.44 (s, 1H), 7.19 (t, 1H), 6.88 (t, 1H), 4.63-4.57 (m, 1H), 4.30-3.97 (m, 5H), 349-3.41

(m, 1H), 3.19-3.12 (m, 1H), 2.89-2.83 (m, 1H), 2.63-2.58 (m, 1H), 2.30-2.10 (m, 4H), 1.72 (s, 6H), 1.12 (d, 3H), 0.79 (d, 3H).

HPLC RT (method A1) 4.96 min

LCMS (HCOOH:ACN): M+H=497.34, R$_t$=1.72 min in 3 mins run.

Synthesis of Example 155: (S)-1-(5-chloro-2-(2-methylpiperazin-1-yl)pyrimidin-4-yl)-N-(2-(imidazo[1,2-a]pyridin-3-yl)propan-2-yl)-N-propylazetidine-3-carboxamide Step 1

To a solution of tert-butyl 3-((2-(imidazo[1,2-a]pyridin-3-yl)propan-2-yl)carbamoyl)azetidine-1-carboxylate (product step 1 example 118) (1.0 g, 2.793 mmol) and DMF (10 ml) was added NaH (60% in Oil) (167.59 mg, 4.19 mmol) at 0° C. Reaction mixture was stirred at RT for 30 min. After 30 min 1-Iodopropane (0.542 g, 5.587 mmol) was added at 0° C. and reaction mixture was stirred at RT for 2 h. The reaction mixture was quenched ice cold water and extracted with ethyl acetate. Organic layer was separated, dried over anhydrous Na2SO4 and concentrated under reduce pressure. Crude was purified by column chromatography by silica gel (100-200 mess) using 3% MeOH in DCM to afford tert-butyl 3-((2-(imidazo[1,2-a]pyridin-3-yl)propan-2-yl)(propyl)carbamoyl)azetidine-1-carboxylate (80 mg, 7.15%) as light yellow sticky liquid.

¹H NMR (400 MHz, DMSO-d₆) δ 8.04 (d, 1H), 7.54 (d, 1H), 7.44 (s, 1H), 7.17 (t, 1H), 6.86 (t, 1H), 4.00-3.80 (m, 2H), 3.74-3.56 (m, 3H), 3.25-3.15 (brs, 2H) 1.78 (s, 6H), 1.62-1.50 (m, 2H), 1.30 (s, 9H), 0.83 (t, 3H).

LCMS (NH₄OAc:ACN): M+H=401.25, R$_t$=3.53 min in 5 mins run.

Step 2

To a solution of tert-butyl 3-((2-(imidazo[1,2-a]pyridin-3-yl)propan-2-yl)(propyl)carbamoyl)azetidine-1-carboxylate (90 mg, 0.225 mmol) in DCM (2.0 ml) was added Trifluoroacetic acid (0.172 ml, 2.25 mmol) at 0° C. Reaction mixture was stirred at RT for 3 h. After complete consumption of starting material, reaction mixture was evaporated to get N-(2-(imidazo[1,2-a]pyridin-3-yl)propan-2-yl)-N-propylazetidine-3-carboxamide (7) (90 mg, 96.53%) as TFA Salt ¹H NMR (400 MHz, DMSO-d₆) δ 8.72 (brs, 1H), 8.52 (brs, 1H), 8.37 (d, 1H), 8.11 (s, 1H), 7.98 (d, 1H), 7.91 (t, 1H), 7.43 (t, 1H), 4.10-4.01 (m, 2H) 3.97-3.91 (m, 1H), 3.78-3.70 (m, 2H), 3.36 (m, 2H), 1.80 (s, 6H), 1.74-1.64 (m, 2H), 0.94 (t, 3H).

LCMS (HCOOH:ACN): M+H=301.2, R$_t$=1.10 min in 3 mins run.

Step 3

To a solution of N-(2-(imidazo[1,2-a]pyridin-3-yl)propan-2-yl)-N-propylazetidine-3-carboxamide (7) (TFA salt, 90 mg, 0.217 mmol) in iso-propanol (2.0 ml) were added Et3N (0.303 ml, 2.174 mmol) and tert-butyl (S)-4-(5-chloro-4-(methylsulfonyl)pyrimidin-2-yl)-3-methylpiperazine-1-carboxylate (101.76 mg, 0.261 mmol) at 0° C. Reaction mixture was stirred at RT for 3 hr. Then reaction mass was concentrated under reduced pressure which was diluted with DCM and washed with bicarbonate. Organic layer was dried over Na2SO4, filtered and concentrated under reduced pressure to get crude product which was purified by combi flash column chromatography (4 g silica column) using 4% MeOH in DCM to afford tert-butyl (S)-4-(5-chloro-4-(3-((2-(imidazo[1,2-a]pyridin-3-yl)propan-2-yl)(propyl)carbamoyl)azetidin-1-yl)pyrimidin-2-yl)-3-methylpiperazine-1- carboxylate (90 mg, 67.74%) as solid; LCMS (HCOOH: ACN): M+H=612.32, R$_t$=1.64 min in 3 mins run.

Step 4

To a solution of tert-butyl (S)-4-(5-chloro-4-(3-((2-(imidazo[1,2-a]pyridin-3-yl)propan-2-yl)(propyl)carbamoyl)azetidin-1-yl)pyrimidin-2-yl)-3-methylpiperazine-1-carboxylate (90 mg, 0. 0.147 mmol) in DCM (3 ml) was added trifluoroacetic acid (0.113 ml, 1.473 mmol) at 0° C. and stirred at RT for 4 h. Reaction mixture was concentrated under reduced pressure. The crude was dissolved in MeOH and loaded on an Isolute® SCX column. The column was washed with MeOH. Then compound was then eluted with NH₃-MeOH and the collected fractions were concentrated under reduced pressure to get (S)-1-(5-chloro-2-(2-methylpiperazin-1-yl)pyrimidin-4-yl)-N-(2-(imidazo[1,2-a]pyridin-3-yl)propan-2-yl)-N-propylazetidine-3-carboxamide (example 155) (25.0 mg, 33.21%) as white solid. ¹H NMR (400 MHz, MeOD) δ 8.10 (d, 1H), 7.67 (s, 1H), 7.54 (d, 1H), 7.49 (brs, 1H), 7.26 (t, 1H), 6.93 (t, 1H), 4.60 (brs, 1H), 4.40-4.25 (m, 2H), 4.22 (d, 1H), 4.16-4.05 (m, 2H), 3.88-3.80 (m, 1H), 3.47-3.38 (m, 2H), 2.99-2.92 (m, 2H), 2.87-2.84 (m, 2H), 2.66-2.58 (m, 1H), 1.90 (s, 6H), 1.77-1.71 (m, 2H), 1.16 (d, 3H), 0.97 (t, 3H); HPLC RT (A1) 4.95 min; LCMS (HCOOH:ACN): M+H=511.26, R$_t$=1.92 min in 5 mins run.

Synthesis of Example 156: (S)-1-(5-chloro-2-(2,4-dimethylpiperazin-1-yl)pyrimidin-4-yl)-N-ethyl-N-(2-(imidazo[1,2-a]pyridin-3-yl)propan-2-yl)azetidin-3-carboxamide To a stirred solution of (S)-1-(5-chloro-2-(2-methylpiperazin-1-yl)pyrimidin-4-yl)-N-ethyl-N-(2-(imidazo[1,2-a]pyridin-3-yl)propan-2-yl)azetidine-3-carboxamide (example 145) (TFA salt, 140 mg, 0.229 mmol) in MeOH (5 ml) was added 37% aq. HCHO solution (0.32 ml, 2.294 mmol) and the mixture was stirred for 1 hr. Then NaCNBH₃ (42.906 mg, 0.688 mmol) was added at 0° C. and the reaction was stirred at RT for 16 hrs. The reaction mixture was quenched with NaHCO3 and extracted with DCM. The organic layer was dried over Na2SO4 and concentrated under reduced pressure to get crude which was purified by prep TLC using 3% MeOH in DCM to afford (S)-1-(5-chloro-2-(2,4-dimethylpiperazin-1-yl)pyrimidin-4-yl)-N-ethyl-N-(2-(imidazo[1,2-a]pyridin-3-yl)propan-2-yl)azetidine-3-carboxamide (example 156) as a white solid (60 mg, 51.17%). ¹H NMR (400 MHz, DMSO-d₆, 100° C.) δ 8.11 (d, 1H), 7.76 (s, 1H), 7.53 (d, 1H), 7.48 (s, 1H), 7.17 (t, 1H), 6.86 (t, 1H), 4.68-4.60 (m, 1H), 4.29-4.03 (m, 5H), 3.82-3.74 (m, 1H), 3.47-3.37 (m, 2H), 3.04-2.99 (m, 1H), 2.76 (d, 1H), 2.64 (d, 1H), 2.20 (s, 3H), 2.07-2.01 (m, 1H), 1.87-1.83 (m, 7H), 1.21-1.13 (m, 6H); HPLC RT (A1) 4.82 min; LCMS (NH4OAc:ACN): M+H=511.3, R$_t$=1.65 min in 3 mins run.

Synthesis of Examples 157 and 158: Individual diastereomers of 1-(5-chloro-2-((S)-2-methylpiperazin-1-yl)pyrimidin-4-yl)-N-(-2-(imidazo[1,2-a]pyridin-3-yl)butan-2-yl)azetidine-3-carboxamide Step 1

Procedure: A stirred solution of 1-(imidazo[1,2-a]pyridin-3-yl)ethan-1-one (500 mg, 3.12 mmol) in (4 ml) THF was cooled to −20° C., then Ethylmagnesium bromide (3M in diethyl ether 1.5 ml, 4.6 mmol) was added and stirred the reaction mixture at RT for 8 h. After that, reaction mixture was quenched with saturated solution of NH₄Cl and extracted with EtOAc. Organic layer was washed with water, brine dried over Na₂SO₄ and concentrated under reduced pressure. Crude was purified by column chromatography (silica gel, 100-200 mesh) using 3% MeOH in DCM to afford 2-(imidazo[1,2-a]pyridin-3-yl)butan-2-ol (350 mg, 58.87%) as white solid.

¹H NMR (400 MHz, DMSO-d₆) δ 8.76 (d, 1H), 7.52 (d, 1H), 7.37 (s, 1H), 7.19 (t, 1H), 6.86 (t, 1H), 5.32 (s, 1H), 1.98-1.83 (m, 2H), 1.56 (s, 3H), 0.75 (t, 3H).

LCMS (NH₄OAc:ACN): M+H=190.8, R$_t$=2.12 min in 5 mins run.

Step 2

To a A stirred solution of 2-(imidazo[1,2-a]pyridin-3-yl)butan-2-ol (350 mg, 1.8 mmol) in (5 ml) trifluoroacetic acid cooled to 0° C. Then NaN₃ (598 mg, 9.2 mmol) was added portion wise and stirred the reaction mixture for 16 h at RT. After completion, reaction mixture was cooled to 0° C., basified with K₂CO₃ solution and extracted with EtOAc. Organic layer was washed with brine, dried over Na₂SO₄ and concentrated under reduced pressure to afford 3-(2-azidobutan-2-yl)imidazo[1,2-a]pyridine (4) (350 mg, 88.27%) as brown solid, used for next step without purification; ¹H NMR (400 MHz, DMSO-d₆) δ 8.59 (d, 1H), 7.64-7.61 (m, 2H), 7.31 (t, 1H), 6.98 (t, 1H), 2.16-1.98 (m, 2H), 1.77 (s, 3H), 0.78 (t, 3H); LCMS (NH$_4$OAc:ACN): M+H=216, R$_t$=3.14 min in 5 mins run.

Step 3

To a stirred solution of 3-(2-azidobutan-2-yl)imidazo[1,2-a]pyridine (350 mg, 1.74 mmol) in (10 ml) MeOH was degassed with argon for 15 mins. Then Pd/C (277.9 mg) was added and reaction mixture was allowed to stirred at RT for 2 h under H$_2$ atmosphere (balloon pressure). After completion, the reaction mixture was filtered through celite bed, filtrate was evaporated under reduced pressure to afford product 2-(imidazo[1,2-a]pyridin-3-yl)butan-2-amine (300 mg, 91%) as pale white solid.

$^1$H NMR (400 MHz, DMSO-d$_6$) δ 9.07 (d, 1H), 7.50 (d, 1H), 7.35 (s, 1H), 7.17 (t, 1H), 6.83 (t, 1H), 1.94-1.89 (m, 1H), 1.80-1.75 (m, 1H), 1.49 (s, 3H), 0.70 (t, 3H).

LCMS (NH$_4$OAc:ACN): M+H=190, Rt=1.74 min in 3 mins run.

Step 4

To a stirred solution of 2-(imidazo[1,2-a]pyridin-3-yl)butan-2-amine (5) (300 mg, 1.5 mmol) and 1-(tert-butoxycarbonyl)azetidine-3-carboxylic acid (318 mg, 1.5 mmol) in (4 ml) THF was added Et3N (1.10 ml, 7.9 mmol) and the reaction mixture was cooled to 0° C. Propylphosphonic acid anhydride 50% in Ethyl acetate solution (2.82 ml, 4.7 mmol) was added at 0° C. and the reaction mixture was allowed to stirred at RT for 16 h. Reaction mixture was diluted with water, extracted with Ethyl acetate, organic part was washed with sat NaHCO$_3$ solution, water and brine dried over Na$_2$SO$_4$. The crude was purified by column chromatography (silica gel, 100-200 mesh) eluted with 6% MeOH in DCM to afford tert-butyl 3-((2-(imidazo[1,2-a]pyridin-3-yl)butan-2-yl)carbamoyl)azetidine-1-carboxylate (400 mg, 67.70%) as pale white solid.

$^1$H NMR (400 MHz, DMSO-d$_6$) δ 8.40 (d, 1H), 8.19 (s, 1H), 7.55 (d, 1H), 7.42 (s, 1H), 7.20-7.16 (m, 1H), 6.88-6.84 (m, 1H), 3.87-3.85 (m, 2H), 3.68-3.60 (m, 2H), 3.36-3.30 (m, 1H), 2.24-2.19 (m, 1H), 2.04-1.98 (m, 1H), 1.64 (s, 3H), 1.32 (s 9H), 0.71 (t, 3H).

LCMS (NH$_4$OAc:ACN): M–H=371, R$_t$=3.22 min in 6 mins run.

Step 5

To a solution of tert-butyl 3-((2-(imidazo[1,2-a]pyridin-3-yl)butan-2-yl)carbamoyl)azetidine-1-carboxylate (300 mg, 0.80 mmol) in DCM (4 ml) was added trifluoroacetic acid (0.61 ml, 8.065 mmol) at 0° C. and the reaction mixture was stirred at RT for 3 h. Reaction mixture was concentrated under reduced pressure to get N-(2-(imidazo[1,2-a]pyridin-3-yl)butan-2-yl)azetidine-3-carboxamide (311 mg, 99.91%) which was used for next step.

LCMS (NH$_4$OAc:ACN): M+H=273, R$_t$=1.13 min in 3 mins run.

Step 6 i) DIPEA, EtOH reflux
ii) Diastereomers Separation

-continued

To a solution of N-(2-(imidazo[1,2-a]pyridin-3-yl)butan-2-yl)azetidine-3-carboxamide (TFA salt, 333 mg, 0.862 mmol) in isopropanol (2 ml) were added Et₃N (1.2 ml, 8.6 mmol) and tert-butyl (S)-4-(5-chloro-4-(methylsulfonyl)pyrimidin-2-yl)-3-methylpiperazine-1-carboxylat (504 mg, 1.2 mmol) at 0° C. and stirred at RT for 3 h. Reaction mixture was concentrated under reduced pressure which was diluted with DCM and washed with sat NaHCO₃ solution. Organic layer was dried over Na₂SO₄, concentrated under reduced pressure to get crude which was purified by combiflash column chromatography (4 g silica column) using 4% MeOH in DCM to afford mixture of diastereomers as a solid. Two diastereomers were separated by normal phase chiral prep HPLC (METHOD: Column—CHIRALPAK IC (250× 20 mm) 5 u, Flow rate—18 ml/min, Mobile phase—HEXANE/DCM/ETOH/IP AMINE—60/20/20/0.1, Solubility—MEOH+DCM, Wave length—232 nm, Run time—24 min, Loading per injection—15.0 mg) to afford tert-butyl (S)-4-(5-chloro-4-(3-((-2-(imidazo[1,2-a]pyridin-3-yl)butan-2-yl)carbamoyl)azetidin-1-yl)pyrimidin-2-yl)-3-methylpiperazine-1-carboxylate (10_Diastereomer-1) (70 mg, 13.93%) and tert-butyl (S)-4-(5-chloro-4-(3-((-2-(imidazo[1,2-a]pyridin-3-yl)butan-2-yl)carbamoyl)azetidin-1-yl)pyrimidin-2-yl)-3-methylpiperazine-1-carboxylate (10_Diastereomer-2) (69 mg, 13.73%).

Diastereomer-1

¹H NMR (400 MHz, DMSO-d₆) δ 8.44 (d, 1H), 8.26 (s, 1H), 7.82 (s, 1H), 7.55 (d, 1H), 7.43 (s, 1H), 7.19-7.17 (m, 1H), 6.88-6.86 (m, 1H), 4.63-4.61 (m, 1H), 4.30-4.19 (m, 3H), 4.07-3.98 (m, 2H), 3.95-3.73 (m, 2H), 3.50-3.48 (m, 1H), 2.98-2.94 (m, 2H), 2.85-2.80 (m, 1H), 2.24-2.19 (m, 1H), 2.04-2.01 (m, 1H), 1.66 (s, 3H), 1.41 (s, 9H), 0.99-0.98 (m, 3H), 0.74-0.73 (m, 3H).

LCMS (NH₄OAc:ACN): M+H=583, R$_t$=1.98 min in 3 mins run.

Diastereomer-2

¹H NMR (400 MHz, DMSO-d₆) δ 8.44 (d, 1H), 8.25 (s, 1H), 7.82 (s, 1H), 7.55 (d, 1H), 7.43 (s, 1H), 7.17 (t, 1H), 6.87 (t, 1H), 4.63-4.61 (m, 1H), 4.27-4.19 (m, 3H), 4.07-3.98 (m, 2H), 3.95-3.73 (m, 2H), 3.49-3.47 (m, 1H), 2.98-2.94 (m, 2H), 2.85-2.80 (m, 1H), 2.24-2.20 (m, 1H), 2.06-2.01 (m, 1H), 1.66 (s, 3H), 1.41 (s, 9H), 0.99-0.98 (d, 3H), 0.73 (t, 3H).

LCMS (NH₄OAc:ACN): M+H=583, R$_t$=1.98 min in 3 mins run.

Step 7

TFA, DCM

To a stirred solution of tert-butyl (S)-4-(5-chloro-4-(3-((-2-(imidazo[1,2-a]pyridin-3-yl)butan-2-yl)carbamoyl)azetidin-1-yl)pyrimidin-2-yl)-3-methylpiperazine-1-carboxylate (Diastereomer-1) (70 mg, 0.12 mmol) in DCM (2 mL) was treated with TFA (0.09 mL, 1.2 mmol). The reaction mixture was stirred room temperature for 4 h. The volatiles were evaporated, crude was dissolved in MeOH and loaded on an Isolute® SCX column. The column was washed with MeOH. Then compound was eluted with NH₃-MeOH and the collected fractions were concentrated under reduced pressure to give 1-(5-chloro-2-((S)-2-methylpiperazin-1-yl)pyrimidin-4-yl)-N-(-2-(imidazo[1,2-a]pyridin-3-yl)butan-2-yl)azetidine-3-carboxamide (example 157) (40 mg, 68.89%) as white solid. ¹H NMR (400 MHz, DMSO-d₆) δ 8.44 (d, 1H), 8.23 (s, 1H), 7.78 (s, 1H), 7.54 (d, 1H), 7.43 (s, 1H), 7.19-7.15 (m, 1H), 6.86 (t, 1H), 4.51-4.49 (m, 1H), 4.26-4.19 (m, 2H), 4.15-4.11 (m, 2H), 4.08-4.05 (m, 1H), 3.98-3.95 (m, 1H), 3.50-3.46 (m, 1H), 2.88-2.79 (m, 2H), 2.72-2.67 (m, 2H), 2.44-2.42 (m, 1H), 2.25-2.20 (m, 1), 2.06-2.00 (m, 1H), 1.66 (s, 3H), 1.07 (d, 3H), 0.73 (t, 3H).

HPLC RT (A1) 4.71 min; LCMS (NH₄OAc:ACN): M+H=483, R$_t$=2.11 min in 5 mins run.

Step 8

Comparative Example 1

PF-03531814

Comparative Example 2

PF-03531549

To a stirred solution of tert-butyl (S)-4-(5-chloro-4-(3-((-2-(imidazo[1,2-a]pyridin-3-yl)butan-2-yl)carbamoyl)azeti-din-1-yl)pyrimidin-2-yl)-3-methylpiperazine-1-carboxylate (10_Diastereomer-2) (70 mg, 0.12 mmol) in DCM (2 mL) was treated with TFA (0.09 mL, 1.2 mmol). The reaction mixture was stirred room temperature for 4 h. The volatiles were evaporated, crude was dissolved in MeOH and loaded on an Isolute® SCX column. The column was washed with MeOH. Then compound was eluted with $NH_3$-MeOH and the collected fractions were concentrated under reduced pressure to give 1-(5-chloro-2-((S)-2-methylpiperazin-1-yl)pyrimidin-4-yl)-N-(-2-(imidazo[1,2-a]pyridin-3-yl)butan-2-yl)azetidine-3-carboxamide (example 158) (40 mg, 68.89%) as white solid. $^1$H NMR (400 MHz, DMSO-$d_6$) δ 8.44 (d, 1H), 8.23 (s, 1H), 7.78 (s, 1H), 7.55 (d, 1H), 7.43 (s, 1H), 7.17 (t, 1H), 6.87 (t, 1H), 4.51-4.49 (m, 1H), 4.26-4.19 (m, 2H), 4.15-4.12 (m, 1H), 4.04-3.99 (m, 2H), 3.50-3.45 (m, 1H), 2.88-2.80 (m, 2H), 2.72-2.67 (m, 2H), 2.46-2.42 (m, 1H), 2.27-2.21 (m, 1), 2.06-2.00 (m, 1H), 1.66 (s, 3H), 1.07 (d, 3H), 0.75 (t, 3H); HPLC RT (A1) 4.71 min; LCMS (NH₄OAc:ACN): M+H=483, R$_t$=2.11 min in 5 mins run.

Comparative Example Compounds

The structure of Comparative Examples 1 and 2 are as follows:

Comparative Examples 1 and 2 were disclosed in PLoS Neglected Tropical Diseases, 2012, 6, e1625 without any synthetic details. For comparison, the compounds were prepared by a similar route to Example 2 using the product of Intermediate 1 step 1 and either (5-methylpyrazine-2-yl) methylamine (Comparative Example 1) or 2,4-difluoro-benzylamine (Comparative Example 2), followed by N,N-dimethylethylenediamine.

Details of Biological Assays and Results

Assay (a): HsNMT1 and *Plasmodium vivax* (Pv) NMT IC$_{50}$

The IC$_{50}$ values of certain Example Compounds of the invention, and for Comparative Examples 1 and 2, for Human NMT1 (HsNMT1) and *Plasmodium vivax* (Pv) NMT were measured using a sensitive fluorescence-based assay based on detection of CoA by 7-diethylamino-3-(4-maleimido-phenyl)-4-methylcoumarin, as described in Goncalves, V., et al., *Analytical Biochemisty*, 2012, 421, 342-344 and Goncalves, V., et al., *J. Med. Chem*, 2012, 55, 3578.

HsNMT1 and *Plasmodium vivax* (Pv) NMT IC$_{50}$ values for the Example Compounds of the invention are shown in Table 6 below:

TABLE 6

| HsNMT1 and Plasmodium vivax (Pv) NMT IC$_{50}$ values for Example Compounds | | |
| --- | --- | --- |
| Example No. | HsNMT1 IC$_{50}$ (μM) | PvNMT IC$_{50}$ (μM) |
| Comparative Example 1 | 46 | 8.4 |
| Comparative Example 2 | 7.7 | 2 |

TABLE 6-continued

| HsNMT1 and Plasmodium vivax (Pv) NMT IC$_{50}$ values for Example Compounds | | |
|---|---|---|
| Example No. | HsNMT1 IC$_{50}$ (μM) | PvNMT IC$_{50}$ (μM) |
| 1 | 0.003 | 0.0066 |
| 2 | 0.0027 | 0.0041 |
| 3 | 0.0068 | 0.0034 |
| 5 | 0.024 | 0.014 |
| 6 | 0.24 | 0.13 |
| 7 | 0.11 | 0.04 |
| 8 | 1.02 | 0.47 |
| 9 | 0.079 | 0.041 |
| 10 | 0.0079 | 0.0063 |
| 11 | 0.028 | 0.014 |
| 12 | 0.13 | 0.2 |
| 13 | 0.38 | 0.66 |
| 16 | 0.43 | 0.068 |
| 17 | 0.36 | 0.14 |
| 18 | 0.02 | 0.0088 |
| 19 | NT | 0.059 |
| 20 | 0.016 | 0.016 |
| 21 | 0.05 | 0.017 |
| 22 | 0.017 | 0.0038 |
| 23 | 0.027 | 0.03 |
| 24 | 0.0063 | 0.012 |
| 25 | 0.1 | 0.015 |
| 26 | 0.53 | 0.24 |
| 27 | NT | 0.037 |
| 28 | 0.31 | 0.095 |
| 29 | 0.079 | 0.018 |
| 30 | 0.026 | 0.0085 |
| 31 | 0.18 | 0.019 |
| 32 | 0.039 | 0.0091 |
| 33 | 0.0035 | 0.0066 |
| 34 | 0.021 | 0.0091 |
| 35 | 0.016 | 0.0083 |
| 36 | 0.022 | 0.0062 |
| 37 | 0.0079 | 0.0084 |
| 38 | 0.052 | 0.014 |
| Comparative Example 1 | 46 | 8.4 |
| Comparative Example 2 | 7.7 | 2 |
| 39 | 0.014 | 0.012 |
| 40 | 0.16 | 0.018 |
| 41 | 0.019 | 0.0072 |
| 42 | 0.04 | 0.019 |
| 43 | 0.0072 | 0.0066 |
| 44 | 0.12 | 0.032 |
| 45 | 0.037 | 0.032 |
| 46 | 0.012 | 0.013 |
| 47 | 0.043 | 0.0122 |
| 48 | 0.0042 | 0.006 |
| 49 | 0.014 | 0.0084 |
| 51 | 0.0061 | 0.0053 |
| 52 | 0.11 | 0.047 |
| 53 | 0.0039 | 0.0058 |
| 54 | 0.11 | 0.0062 |
| 55 | 0.018 | 0.0044 |
| 56 | 0.0079 | 0.0032 |
| 57 | 0.0035 | 0.0022 |
| 58 | 0.037 | 0.013 |
| 59 | 0.014 | 0.0042 |
| 60 | 0.0094 | 0.11 |
| 61 | 0.21 | 0.013 |
| 62 | 0.005 | 0.006 |
| 63 | 0.011 | 0.071 |
| 64 | 0.19 | 0.02 |
| 65 | 0.63 | 0.09 |
| 66 | 0.18 | 0.029 |
| 67 | 0.026 | 0.0056 |
| 68 | 0.088 | 0.032 |
| 69 | 0.1 | 0.012 |
| 70 | 0.049 | 0.0086 |
| 71 | 0.072 | 0.011 |
| 72 | 0.082 | 0.0077 |
| 75 | 0.25 | 0.035 |
| Comparative Example 1 | 46 | 8.4 |
| Comparative Example 2 | 7.7 | 2 |
| 76 | 0.056 | 0.0052 |
| 77 | 1.15 | 0.074 |

TABLE 6-continued

| HsNMT1 and Plasmodium vivax (Pv) NMT IC$_{50}$ values for Example Compounds | | |
|---|---|---|
| Example No. | HsNMT1 IC$_{50}$ (μM) | PvNMT IC$_{50}$ (μM) |
| 78 | 0.4 | 0.12 |
| 80 | 0.023 | 0.0079 |
| 82 | 0.1 | 0.043 |
| 83 | 0.0051 | 0.01 |
| 84 | 0.033 | 0.0046 |
| 85 | 0.0063 | 0.008 |
| 86 | 0.039 | 0.007 |
| 87 | 0.15 | 0.038 |
| 88 | 0.021 | 0.011 |
| 89 | 0.027 | 0.012 |
| 90 | 0.094 | 0.019 |
| 91 | 0.11 | 0.13 |
| 92 | 0.055 | 0.041 |
| 93 | 0.25 | 0.059 |
| 94 | 0.032 | 0.04 |
| 95 | 0.017 | 0.034 |
| 96 | 0.031 | 0.13 |
| 97 | 0.0257 | 0.0049 |
| 98 | 0.0054 | 0.0058 |
| 99 | 0.028 | 0.015 |
| 100 | 0.019 | 0.0054 |
| 101 | 0.31 | 0.033 |
| 102 | 0.072 | 0.024 |
| 112 | 0.319 | NT |
| 113 | 0.005 | NT |
| 114 | 0.004 | NT |
| 115 | 0.005 | NT |
| 116 | 0.006 | NT |
| 117 | 0.006 | NT |
| 118 | 0.016 | NT |
| 119 | 0.038 | NT |
| 120 | 0.009 | NT |
| 121 | 0.004 | NT |
| Comparative Example 1 | 46 | 8.4 |
| Comparative Example 2 | 7.7 | 2 |
| 122 | 0.004 | NT |
| 123 | 0.008 | NT |
| 124 | 0.021 | NT |
| 125 | 0.023 | NT |
| 126 | 0.005 | NT |
| 127 | 0.031 | NT |
| 128 | 0.234 | NT |
| 129 | 0.002 | NT |
| 130 | 0.054 | NT |
| 131 | 0.179 | NT |
| 132 | 0.190 | NT |
| 133 | 0.062 | NT |
| 134 | 0.005 | NT |
| 135 | 0.027 | NT |
| 136 | 0.007 | NT |
| 137 | 0.003 | NT |
| 138 | 0.015 | NT |
| 139 | 0.024 | NT |
| 140 | 0.146 | NT |
| 141 | 0.004 | NT |
| 142 | 0.178 | NT |
| 143 | 0.003 | NT |
| 144 | 0.005 | NT |
| 145 | 0.003 | NT |
| 146 | 0.061 | NT |
| 147 | 0.002 | NT |
| 148 | 0.005 | NT |
| 149 | 0.005 | NT |
| 150 | 0.137 | NT |
| 151 | 0.002 | NT |
| 152 | 0.008 | NT |
| 153 | 0.003 | NT |
| 154 | 0.010 | NT |

The Example Compounds tested were found to be potent inhibitors of HsNMT1 and PvNMT1 and many of the Example Compounds tested were more potent inhibitors than the Comparative Example Compounds 1 and 2.

Assay (b): Metabolic Activity Assay (MTS Assay)

Example NMT inhibitors of the present invention were tested for activity in an in vitro metabolic activity assay using the human Burkitt's Lymphoma cell line BL-41. Compounds having activity in inhibiting metabolic activity in the assay are expected to be useful as agents for preventing and/or treating cancer, by virtue of being inhibitors of human NMT1 and/or NMT2. The compounds with the highest activity in the assay are expected to be the most potent inhibitors of human NMT1 and/or NMT2.

Cell Preparation:

BL-41 cells (obtained from Cell Services at the Crick Institute; cell type: Burkitt's Lymphoma) were grown in DMEM media (supplemented with 10% FBS) and were seeded in a 96-well plate, 24 h prior to treatment. Cell suspensions were prepared by adjusting the cell density to the appropriate concentration (as stated in the Table 7 below) and 50 μL of the cell suspension was transferred to wells B-G in columns 2-11 of a 96-well plate.

TABLE 7

| Number of cells plated | |
| --- | --- |
| | BL-41 |
| Cell suspension concentration (cells/mL) | 500,000 |
| cells per well | 25,000 |

Assay Procedure:

100 μL of growth media (DMEM media) containing 0.2% DMSO was added to wells B-G in columns 2 and 11 as positive controls, and 100 μL of growth media containing Puromycin (3 μg/mL; final concentration in the plate 2 μg/mL) was added to wells B-G in column 3 as a negative control. Seven concentrations of NMT inhibitor stock solution were prepared for each Example Compound tested (the seven concentrations were prepared as follows: 400 μL 0.2% DMSO in DMEM was added to columns 2-7 of a 96 deep well plate; 598 μL DMEM (no DMSO) was added to column 1; 1.8 μL of drug stock (50 mM in DMSO) was added to column 1 and thoroughly mixed with a 1000 μL pipette; serial dilution was performed with 200 μL from column 1 until column 7). 100 μL of Example Compound stock solution was added to wells B-G in columns 4-10 of a 96-well plate (final concentration of Example Compound in the plate starting from 10 μM or 100 μM; total volume in each well was 150 μL). The plate was incubated at 37° C. with 5% $CO_2$ level.

After 72 h, 20 μL MTS reagent (G3580, prepared as follows: 200 μL of phenazine methosulfate (PMS) solution was added to 4 ml 3-(4,5-dimethylthiazol-2-yl)-5-(3-carboxymethoxyphenyl)-2-(4-sulfophenyl)-2H-tetrazolium inner salt (MTS) solution (16 mg in 10 ml PBS) and mix thoroughly) was added to each well of the 96-well plate. The plate was incubated at 37° C. for 1 to 4 h and the absorbance per well was measured at 490 nm with an EnVision plate reader. The average absorbance value of the negative control (Puromycin-treated cells) was subtracted from each value and the metabolic activity was calculated as a percentage relative to the positive control (DMSO-treated cells). $EC_{50}$ values were calculated using GraphPad.

Results:

$EC_{50}$ values for the Example Compounds tested in the BL-41 cell line in this assay are provided in Table 8 below.

TABLE 8

| Results of testing Example Compounds in the BL-41 cell line assay | |
| --- | --- |
| Example No. | BL-41 $EC_{50}$ (μM) |
| 2 | 0.22 |
| 3 | 0.56 |
| 10 | 0.24 |
| 11 | 0.89 |
| 20 | 1.16 |
| 51 | 0.08 |
| 54 | 2.31 |
| 55 | 1.07 |
| 56 | 0.8 |
| 57 | 1.25 |

As can be seen from these results, the Example Compounds tested showed high activity in the metabolic activity assay, indicating that these compounds are expected to be useful as anti-cancer agents.

Assay (c): Cell Cytotoxicity in SU-DHL-10 Cell Line

Example NMT inhibitors of the present invention were tested for the present invention were tested for activity in an in vitro metabolic activity assay using the human Large Cell Lymphoma cell line SU-DHL-10. Compounds having activity in inhibiting metabolic activity in the assay are expected to be useful as agents for preventing and/or treating cancer, by virtue of being inhibitors of human NMT1 and/or NMT2.

Cell Culture: SU-DHL-10 (ATCC CRL-2963) were cultured in RPMI-media (ATCC, 30-2001).

Cultures were maintained by the addition of fresh medium and inoculum of $8.0 \times 10^4$ to $2.0 \times 10^5$ cells/mL. Subculturing was done when the cell density was between $1.0 \times 10^6$ and $2.0 \times 10^6$ cells/mL.

Cell seeding: 5000 cells/well were plated in 384-white clear bottom plates (Greiner, 781098) for the assay in 20 μl growth media.

Compound Dilution:

Top dose: 1 mM stocks of each compound was prepared in 100% DMSO and thereafter diluted 333.33 fold in growth media to obtain 3 μM (0.3% DMSO) mid stock of each compound, from which 10 μl was added to assay wells (with 20 μl cells) for a final concentration of 1 μM (0.1% DMSO). For subsequent dose-response: 1 mM stock was diluted 3 fold in DMSO before subjecting to above dilution pattern to obtain final 0.1% DMSO concentration.

Treatment: Cells were incubated with the compounds for 48 h at 37° C. in presence of 5% $CO_2$.

Assay Procedure: The assay plate and its contents were equilibrated at room temperature for approximately 30 minutes. CellTiter-Glo® Reagent was added equal to the volume (1;1) of cell culture medium present in each well. The contents were mixed for 5 minutes on an orbital shaker to induce cell lysis. The plate was allowed to incubate at room temperature for 10 minutes to stabilize luminescent signal. The luminescence was recorded with an integration time of 0.25 seconds in EnVision 2104 Multilabel Plate Reader (Perkin Elmer).

Calculation: % Cytotoxicity was calculated considering 100% cell death in wells treated with 0.1% TritonX.

Results

TABLE 9

| Results of testing Example Compounds in the SU-DHL-10 assay | |
| --- | --- |
| Example No. | SU-DHL-10 $EC_{50}$ (μM) |
| 1 | 0.367 |
| 2 | 0.051 |
| 3 | 0.624 |

TABLE 9-continued

| Results of testing Example Compounds in the SU-DHL-10 assay | |
|---|---|
| Example No. | SU-DHL-10 $EC_{50}$ (μM) |
| 33 | 0.878 |
| 35 | 0.676 |
| 48 | 0.795 |
| 50 | 0.035 |
| 57 | 0.203 |
| 113 | 0.033 |
| 114 | 0.065 |
| 115 | 0.054 |
| 116 | 0.074 |
| 117 | 0.066 |
| 119 | 0.925 |
| 120 | 0.545 |
| 121 | 0.042 |
| 122 | 0.050 |
| 124 | 0.448 |
| 125 | 0.361 |
| 126 | 0.265 |
| 127 | 0.609 |
| 129 | 0.006 |
| 130 | 0.547 |
| 133 | 0.409 |
| 134 | 0.106 |
| 135 | 0.767 |
| 136 | 0.161 |
| 137 | 0.218 |
| 138 | 0.742 |
| 139 | 0.542 |
| 141 | 0.378 |
| 142 | 0.489 |
| 143 | 0.005 |
| 144 | 0.243 |
| 145 | 0.013 |
| 146 | 0.597 |
| 147 | 0.012 |
| 148 | 0.369 |
| 149 | 0.145 |
| 150 | >1.000 |
| 151 | 0.015 |
| 152 | 0.306 |
| 153 | 0.054 |
| 154 | 0.453 |

NT = not tested

As can be seen from these results, the Example Compounds tested showed high activity in the metabolic activity assay, indicating that these compounds are expected to be useful as anti-cancer agents.

Assay (d): CellTiter-Blue® Assay

Example Compounds 2 and 3 of the present invention were tested for activity in in vitro CellTiter-Blue® assays using the human cell lines BL-41, EL4, Ramos, Raji, A20, Shep-ER-N-Myc, SKNAS-ER-N-Myc, and P-493-6. Compounds having activity in inhibiting metabolic activity in the assay are expected to be useful as agents for preventing and/or treating cancer, by virtue of being inhibitors of human NMT1 and/or NMT2. The compounds with the highest activity in the assay are the most potent inhibitors of human NMT1 and/or NMT2.

BL-41, Ramos, Raji and A20 cells (obtained from Cell Services at the Crick Institute; cell type of BL-41, Ramos, Raji: Burkitt's Lymphoma; cell type of A20: murine B cell lymphoma cell line) were grown in RPMI-1640 media in 5% $CO_2$ (supplemented with 10% FBS). The cells were seeded in 96-well plates, 24 h prior to treatment. Cell suspensions were prepared by adjusting the cell density to the appropriate concentration (as stated in the Table 9 below) and 50 μL of the cell suspension was transferred to wells B-G in columns 2-11 of a 96-well plate.

Shep-ER-N-Myc cell line (cell type: human neuroblastoma) was sourced from Linda Valentijn, and firstly reported in Valentijn et. al., Cancer Res, 2005, 65(8), 3136-3145. SKNAS-ER-N-Myc cell line (cell type: human neuroblastoma) was sourced from Michael D. Hogarty, and firstly reported in Ushmorov et al., Oncogene, 2008, 27(24), 3424-3434. P-493-6 cell line was sourced from Chi Van Dang, and firstly reported in Pajic et. al., Int J Cancer, 2000, 87(6), 787-793. P-493-6 cell line is a non-transformed B cell line that can be genetically engineered to have either "low" levels of c-Myc, "medium" levels of c-Myc or "high" levels of c-Myc. The terms "low", "medium" and "high" are descriptors commonly used in the art and will be readily understood to mean:

i) "low" levels of c-Myc—a level of MYC expression which represents non-proliferating normal cells (i.e. a level of MYC expression not sufficient to cause the cycling of the cells);

ii) "medium" levels of c-Myc—a level of MYC expression which represents normal proliferating cells; and iii) "high" levels of c-Myc—a level of MYC expression which represents enforced/deregulated expression of c-Myc, typically observed in cancerous cells.

The EL4, Shep-ER-N-Myc, SKNAS-ER-N-Myc, and the P-493-6 cell lines were cultured in DMEM high glucose (D5671 (Sigma)), supplemented with 10% FBS at 5% CO2. Cell suspensions were prepared by adjusting the cell density to the appropriate concentration (as stated in the Table 10 below) and 50 μL of the cell suspension was transferred to wells B-G in columns 2-11 of a 96-well plate.

TABLE 10

| | Number of cells plated | | | | | | | |
|---|---|---|---|---|---|---|---|---|
| | BL-41 | EL4 | Ramos | Raji | A20 | Shep-ER-N-Myc | SKNAS-ER-N-Myc | P-493-6 |
| Cell suspension concentration (cells/mL) | 500,000 | 500,000 | 500,000 | 500,000 | 500,000 | 20,000 | 27,500 | 500,000 |
| cells per well | 35,000 | 35,000 | 35,000 | 35,000 | 35,000 | 1,000 | 5,500 | 25,000 |

For each the BL-41, Ramos, Raji, A20 cell lines and EL4, twenty-four hours later, 50 μL of the growth media for the respective cell line (positive control), a mix of Puromycin and Staurosporine (negative controls, final concentration 10 μg/mL and 1 μM respectively) or different concentrations of each Example compound being tested (dilution factor=3, starting at μM, final concentration in the plate starting from 10 μM) were prepared and added to a well of the 96-well plate. The plate was incubated at 37° C. with 5% $CO_2$ level.

72 hours later, 20 μl/well CellTiter-Blue® (G8081, Promega) were added to the plates according to the manufacturer's protocol, the plate was incubated at 37° C. for 2 or 3-4 h (A20, Ramos and Raji: 2 h; BL-41 and EL-4: 3-4 h), followed by measuring the absorbance per well at 570 nm using an EnVision plate reader. The negative control values were subtracted from every value. The metabolic activity was calculated as a percentage relative to the positive control. The $EC_{50}$ values were calculated using GraphPad Prism.

For the P-493-6 cell line, the experiment was performed in a 96 well plate and in technical quadruplicate. On day 0, 2500 cells/well in 50 μL media were seeded in, for the MYC high condition: just media; for the MYC medium condition: 1 μM β-Estradiol (Merck, E8875) and 0.1 μg/mL Doxycycline (Merck, D9891); for the MYC low condition: 0.1 μg/mL Doxycycline. On day 1, 50 μL of media for the respective MYC condition and 2× the Example Compound being tested, in the respective concentration, were added to the respective wells. On day 4 (for 72 hours) of incubation with the Example Compound being tested, 20 μL/well of the CellTiter Blue Assay (Promega, G8081) was added and the cells were incubated at 37° C. for 3 hours. The fluorescence was measured at 570 nM using an EnVision™ plate reader. As a positive control, the highest DMSO concentration was added to the cells (usually 0.4% DMSO); as a negative control, the cells were treated with 10 μg/mL Puromycin and 1 μM Staurosporine (Merck, P7255 and S4400, respectively).

For Shep cells, the experiment was performed in a 96 well plate and in technical quadruplicate. On day 0, 1000 cells/well were seeded in 50 μL media. On day 1, 50 μL media containing 200 nM Tamoxifen (Merck, H7904), to induce N-Myc, or Ethanol as control were added to the medium for 24 hours. On day 2, 100 μL of medium for the respective N-Myc condition and 2× the Example Compound being tested, in the respective concentration, were added to the wells. On day 4 (for 72 hours incubation), 20 μL/well of the CellTiter Blue Assay (Promega, G8081) was added and the cells were incubated at 37° C. for 3 hours. The fluorescence was measured at 570 nM using an EnVision™ plate reader. As a positive control, the highest DMSO concentration was added to the cells (usually 0.4% DMSO); as a negative control, the cells were treated with 10 μg/mL Puromycin and 1 μM Staurosporine (Merck, P7255 and S4400, respectively).

For SKNAS cells, the experiment was performed in a 48 well plate and in technical triplicate. On day 0, 5500 cells/well were seeded in 200 μL media. On day 1, the media was removed and 200 μL of media with Tamoxifen, to induce N-Myc, or Ethanol as control were added. On day 2, the media was removed and 200 μL of medium for the respective N-Myc condition and 1× the Example Compound being tested, in the respective concentration, were added. On day 6 (for 96 hours of incubation), 20 μL/well of the CellTiter Blue Assay (Promega, G8081) was added and the cells were incubated at 37° C. for 3 hours. The fluorescence was measured at 570 nM using an EnVision™ plate reader. As a positive control, the highest DMSO concentration was added to the cells (usually 0.4% DMSO); as a negative control, the cells were treated with 10 μg/mL Puromycin and 1 μM Staurosporine (Merck, P7255 and S4400, respectively).

Results:

$EC_{50}$ values for Example Compounds 2 and 3 in BL-41 EL4, Ramos, Raji, and A20 cell lines are provided in Table 11 below:

TABLE 11

Results of testing of certain Example Compounds in BL-41 EL4, Ramos, Raji, and A20 cell lines

| Cell line | Example 2 $EC_{50}$ (μM) | Example 3 $EC_{50}$ (μM) |
| --- | --- | --- |
| BL41 | 0.557 | 0.218 |
| EL4 | 0.139 | 1.24 |
| Ramos | 0.218 | 2.29 |
| Raji | 0.556 | 1.10 |
| A20 | 0.600 | 6.88 |

FIG. 1a shows metabolic viability of the P-493-6 cell line treated with Example Compound 3 at the shown concentrations for 72 hours, with different expression levels of c-Myc induced; and FIG. 1b shows metabolic viability of the P-493-6 cell line treated with Example Compound 2 at the shown concentrations for 72 hours, with different expression levels of c-Myc induced.

From FIGS. 1a and 1b it can be seen that there is a clear MYC-dependent loss in metabolic viability in the P-493-6 cell lines when the cells are exposed to Example Compound 3 or Example compound 2, with the highest loss in metabolic viability being recorded for P-493-6 cell lines with high MYC expression.

Figure 2:
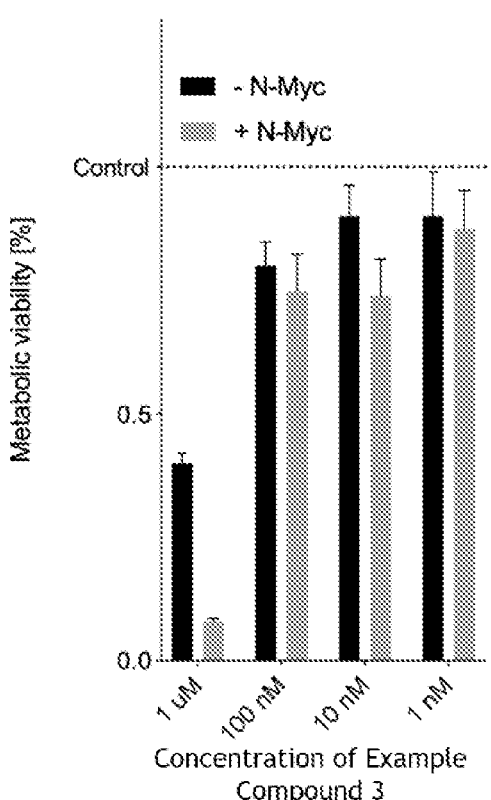
FIG. 2a shows the metabolic viability of the Shep-ER-MYCN cell line treated with Example Compound 3 at the shown concentrations for 72 hours, with and without induction of MYCN.
FIG. 2b shows the metabolic viability of the Shep-ER-MYCN cell line treated with Example Compound 2 at the shown concentrations for 72 hours, with and without induction of MYCN.
Figure 2:
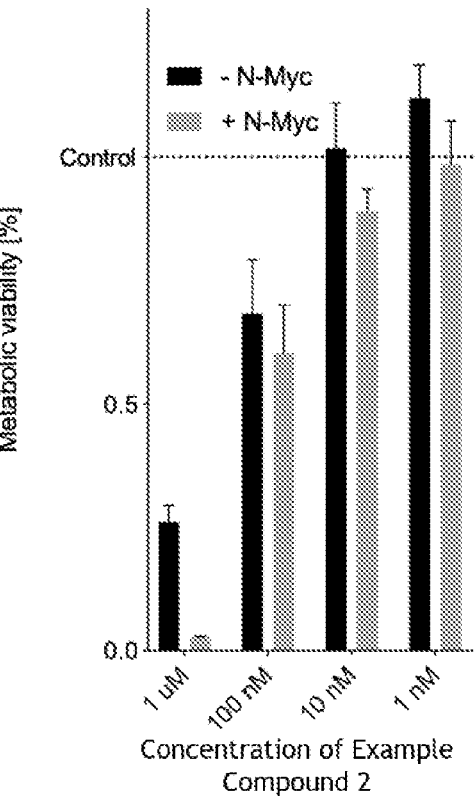

FIG. 2a shows metabolic viability of the Shep-ER-N-MYC cell line treated with Example Compound 3 at the shown concentrations for 72 hours, with (grey) or without (black) induction of MYCN; FIG. 2b shows metabolic viability of the Shep-ER-N-MYC cell line treated with Example Compound 2 at the shown concentrations for 72 hours, with (grey) or without (black) induction of MYCN.

Figure 3:
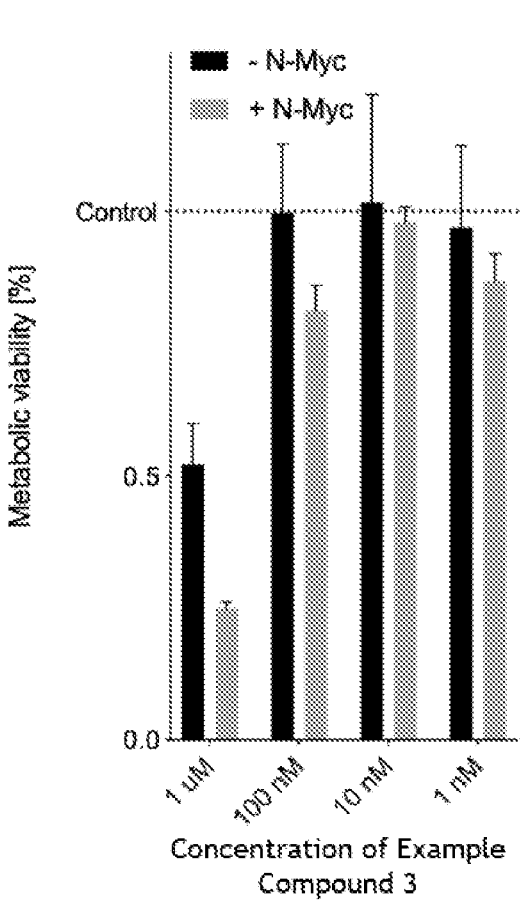
FIG. 3a shows the metabolic viability of the SKNAS-ER-MYCN cell line treated with Example Compound 3 at the shown concentrations for 92 hours, with and without induction of MYCN.
FIG. 3*b* shows the metabolic viability of the Shep-ER-MYCN cell line treated with Example Compound 2 at the shown concentrations for 72 hours, with and without induction of MYCN.
Figure 3:
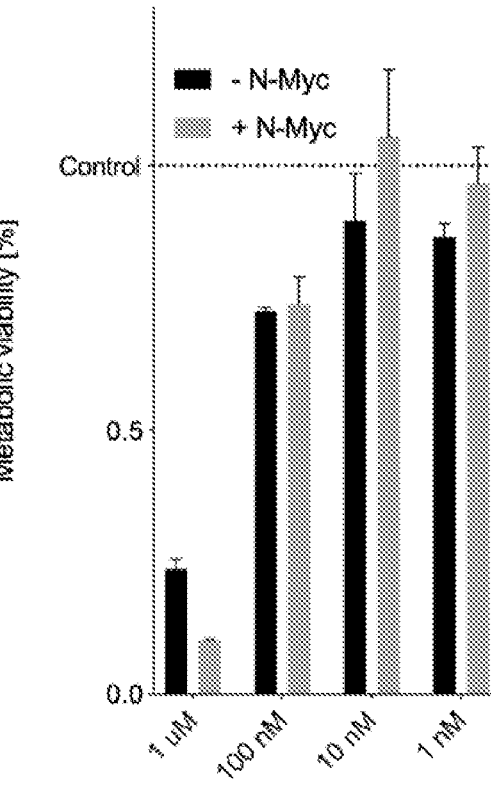

FIG. 3a shows metabolic viability of the SKNAS-ER-N-MYC cell line treated with Example Compound 3 at the shown concentrations for 96 hours, with (grey) or without (black) induction of MYCN; FIG. 3b shows metabolic viability of the SKNAS-ER-N-MYC cell line treated with Example Compound 2 at the shown concentrations for 72 hours, with (grey) or without (black) induction of MYCN.

From FIGS. 2a, 2b, 3a and 3b it can be seen that when the Shep-ER-N-MYC cell line and the SKNAS-ER-N-MYC cell line are exposed to Example Compound 2 or Example Compound 3, there is a clear loss in metabolic viability when the cells have induction of MYCN.

Assay (e): Rat Hepatocyte Half Life

Certain example compound of the present invention were tested for metabolic stability in rat metabolic assays using hepatocytes derived from pooled male Sprague-Dawley rats. Compounds having good metabolic stability in the assay are expected to be especially useful as agents for preventing and/or treating cancer, by having a long half-life in human patients.

Frozen pooled rat hepatocytes obtained from LifeTechnologies were thawed and purified according to the manufacturer's instructions. The test compound (4 mM) in DMSO was diluted with acetonitrile to provide a 100 μM sub-stock then further diluted with pH 7.4 Krebs-Henseleit buffer (supplemented with $CaCl_2$, $NaHCO_3$, HEPES, fructose and glycine) to provide a 2 μM working solution. 25 μL of working solution was incubated at 37° C., treated with 25 μL of rat hepatocyte suspension (containing $1×10^6$ cells/mL) and incubated at 37° C. with 5% $CO_2$ level at 95% relative humidity. Wells were incubated for an appropriate time (0, 15, 30, 45, 60 and 75 min) then quenched with 250 μL of acetonitrile containing reference standards diltiazem, 7-ethoxycoumarin and propranolol). The plates were shaken, sonicated for 5 min then cooled to 4° C. until all sampling was complete. All plates were centrifuged at 4000 rpm for 20 min to pellet the debris. 110 μL supernatant was diluted 110 μL water and quantitated using LC-MS/MS.

The results were used to calculate the % Remaining of the test compound at time point t=100×~[(AUC at time point t)/(AUC at T=0)]. A linear regression curve was fitted to a plot of natural logarithm (ln) of AUC against time. The T-half (min)=0.693/slope Results:

Rat hepatocyte half-life times for certain Example Compound of the invention are shown in Table 12 below:

TABLE 12

| Rat hepatocyte half-life times for certain Example Compounds of the invention | |
|---|---|
| Example No. | Rat hepatocyte $t_{1/2}$ (mins) |
| 2 | 91 |
| 3 | 123.1 |
| 4 | >180 |
| 10 | 122 |
| 16 | >375 |
| 42 | >180 |
| 43 | >180 |
| 44 | >180 |
| 53 | 24 |
| 54 | >180 |
| 55 | 140 |
| 56 | >180 |
| 57 | 151.2 |
| 60 | 144.3 |
| 61 | >180 |
| 65 | 144.3 |
| 66 | >180 |
| 67 | >180 |
| 69 | 49.2 |
| 70 | >180 |
| 71 | >180 |
| 72 | >180 |
| 73 | >180 |
| 74 | >180 |
| 75 | 22.5 |
| 76 | 93.4 |
| 77 | 89.6 |
| 78 | >180 |
| 80 | 44.6 |
| 84 | 144.7 |
| 85 | >180 |
| 88 | >180 |
| 89 | >180 |
| 90 | >180 |
| 95 | 90.8 |
| 96 | >180 |
| 99 | 29.8 |
| 100 | 32.8 |
| 101 | 104.2 |
| 102 | 14.5 |
| 108 | 58 |

All Example Compounds tested had a rat hepatocyte half-life of at least 22 minutes, with the majority of compound having significantly longer rat hepatocyte half-life, for example a rat hepatocyte half-life of over 60 minutes. These results show that Example Compounds of the invention have good metabolic stability in vitro. As such, it is expected that the compounds of the invention will be especially useful as medicaments, and in particular for use as medicaments for preventing and/or treating cancer by having a long half-life in human patients.

Assay (f): Rat Clearance and Bioavailability

Certain examples were tested for metabolic stability and in male Sprague-Dawley rats (Table 13 lists the example compounds tested). Half-life times and bioavailability was determined.

Male Sprague-Dawley rats were fasted for 4 h before dosing. Groups of 3 rats were dosed with Example compound(s) of the invention either as single compounds or by cassette dosing of 4 compounds at the same time (Table 13 indicates which compounds were administered as single compounds or administered by cassette dosing).

(i) intravenously (iv) at a dose of 1-3 mg/kg using a dose volume 2 mL/kg where the animals are anaesthetized using 3% v/v isoflurane: oxygen mixture and dose administered through lateral tail vein; or (ii) orally by gavage (OG) at a dose of 5-30 mg/kg using a dose volume 5 mL/kg to conscious animals.

In each case, the dose given for the particular Example Compound is shown in parentheses in Table 13.

~100 μL blood sample were collected after 5 min, 15 min, 30 min, 1 h, 2 h, 4 h, 8 h and 24 h (intravenous) and 15 min, 30 min, 1 h, 2 h, 4 h, 8 h and 24 h (oral) and transferred to heparinized capillary tubes, and subsequently into 0.5 mL microcentrifuge tubes. All blood samples are processed for plasma by centrifugation at 1640×g for 5 min at 4° C. within half an hour of collection. Plasma samples were stored at −20° C. until all samples were collected. All samples were mixed with ice-cold acetonitrile containing an internal standard (IS) in 1:4 v/v and centrifuged at 4000 rpm for 15 min at 15° C. Supernatant was then half diluted in water and loaded for LCMS/MS analysis. Analyte peak area/IS peak area (the ratio) was considered for further data analysis as described below.

Calibration curve and QC samples: Compound stock was prepared and further serial dilutions were carried out. The samples were spiked in blank plasma (1:50). Calibration curve ranged from 1 to 1250 ppb. Three quality control samples were also prepared—high QC (HQC), Mid QC (MQC and Low QC (LQC).

Oral bioavailability was calculated according to the formula:

$$F=(\text{oral AUC}_{last} \times \text{iv dose level}) \times 100/(\text{iv AUC}_{last} \times \text{oral dose level})$$

Results:

Rat iv half-life times and oral bioavailability values for certain Example Compounds tested are shown in Table 13 below:

TABLE 13

| Rat iv half-life times and oral bioavailabiliy values for certain Example Compounds | | |
|---|---|---|
| Example No. | Rat iv $t_{1/2}$ (h) (@mg/kg) | Rat oral bioavailability (%)(@mg/kg) |
| 2 | 3.5 (1*) | 28 (10*) |
| 3 | 4.3 (2*) | 24 (20*) |
| 11 | 4.4 (3*) | 0.35 (30*) |
| 16 | 5.9 (3*) | 0.5 (30*) |
| 51 | 9.1 (3*) | 0.07 (30*) |
| 54 | 3.5 (1**) | 33 (5**) |
| 55 | 3.1 (1**) | 38 (5**) |
| 57 | 6.6 (1**) | 6 (5**) |
| 72 | 2.7 (1**) | 34 (5**) |
| 73 | 3.6 (1**) | 65 (5**) |
| 74 | 2.2 (1*) | 28 (10*) |
| 76 | 3.0 (1**) | 70 (5**) |
| 78 | 2.3 (1**) | 73 (5**) |
| 101 | 5.4 (1**) | 32 (5**) |
| 107 | 1.7 (1**) | 37 (5**) |

*example compound administered as a single compound
**example compound administered by cassette dosing of 4 compounds at the same time The half life results show that the Example Compounds of the invention good metabolic stability in vivo. The bioavailability results show that the Example Compounds of the invention are bioavailable in vivo after oral administration. As such, it is expected that the compounds of the invention will be especially useful as medicaments, and in particular for use as medicaments for preventing and/or treating cancer by having a long half-life and good bioavailability in human patients.

Assay (g): SYBR Green Assay $EC_{50}$ values for *Plasmodium falciparum* (Pf) NMT strain 3D7 or NF54 were measured for certain compounds of the invention using an assay utilising SYBR Green dye. The assay for NMT strain 3D7 was carried out as follows:

Synchronous *Plasmodium falciparum* 3D7 late stage trophozoites at 33-36 h were used. Final parasitemia and haematocrit were between 0.1-0.2% and 2% respectively. Red blood cells used for the assay were centrifuged to remove the buffy coat and washed twice in Roswell Park Memorial Institute (RPMI) Media 1640 so that no white blood cells were present. The culture medium contained RPMI 1640 with 5 g/L Albumax, 0.025 g/L gentamycin and 0.292 g/L L-glutamine.

Sterile 96 well black tissue culture plates (Costar) were used routinely for every assay. The compounds of the invention tested in this assay were diluted in culture medium and used in duplicate wells for each dilution ranging from 10.000, 3.333, 1.111, 0.370, 0.123, 0.041 and 0.014 µM respectively in a final volume of 100 µL per well. Chloroquine was used as a standard with ten times reduced concentrations range as above. Two sets of control were used in duplicate wells, one set with no added compound of the invention or standard (positive control) and one with uninfected red blood cells (negative control).

The plates were incubated at 37° C. for 48 h in a gas chamber flushed with 5% $CO_2$, 5% $O_2$ and 90% $N_2$. After 48 h supernatants were taken out from each well and replaced with fresh drug and incubated for a further 48 h in the same manner. At the end of the 96 h incubation, 25 µL of SYBR Green I dye (SYBR Green I nucleic acid gel stain 10,000×, in DMSO from Invitrogen) in lysis buffer (1 µL dye to 1 mL lysis buffer) was added to each well and stored overnight at −20° C. The lysis buffer contained Tris (20 mM, pH 8.0), EDTA (2 mM), Saponin (0.16%) and Triton X-100 (1.6% v/v).

Plates were warmed to room temperature and fluorescence intensity was measured with a FLUOstar Omega Microplate fluorescence reader (BMG Labtech). Values were expressed in relative fluorescence units. Binding of SYBR Green is specific for parasite DNA as mature erythrocytes lack DNA and RNA. Fluorescence intensity unit was converted to percentage (%) of growth as follows:

% growth=(culture under drug)−(uninfected RBC)/
(culture with no drug)−(uninfected RBC)×100 and the $EC_{50}$ value was determined.

A similar protocol was used to determine activity against *Plasmodium falciparum* strain NF54.

All examples were tested against the 3D7 strain with the exception of the following Examples 6-9, 12-19, 22-28, 31, 36, 39, 41, 52-53, 81 and 112 which were assessed against the NF54 strain.

The *Plasmodium falciparum* (Pf) NMT $EC_{50}$ values for certain Example Compounds of the invention are shown in Table 14 below:

TABLE 14

*Plasmodium falciparum* (Pf) strain 3D7 or strain NF54) NMT $EC_{50}$ values for certain Example Compounds determined in the SYBR Green Assay

| Example No. | Pf $EC_{50}$ strain 3D7 (µM) | Pf $EC_{50}$ strain NF54 (µM) |
|---|---|---|
| 1 | 0.0063 | NT |
| 2 | 0.0024 | NT |
| 3 | 0.011 | NT |
| 4 | 0.1 | NT |
| 5 | 2.5 | NT |
| 6 | NT | >10 |
| 7 | NT | 3.2 |
| 8 | NT | >10 |
| 9 | NT | 2.1 |
| 10 | 0.51 | NT |
| 11 | 0.051 | NT |
| 12 | NT | >2.5 |
| 13 | NT | >10 |
| 16 | NT | >5 |
| 17 | NT | >5 |
| 18 | NT | 2.7 |
| 19 | NT | 3.6 |
| 20 | 0.15 | NT |
| 21 | 0.8 | NT |
| 22 | NT | 0.45 |
| 23 | NT | 0.34 |
| 24 | NT | 0.18 |
| 25 | NT | 1.09 |
| 26 | NT | >2.33 |
| 27 | NT | 2.82 |
| 28 | NT | 3.04 |
| 29 | 0.62 | NT |
| 30 | 0.96 | NT |
| 31 | NT | 1.3 |
| 32 | 0.064 | NT |
| 33 | 0.018 | NT |
| 34 | 0.14 | NT |
| 35 | 0.025 | NT |
| 36 | NT | 0.012 |
| 37 | 0.027 | NT |
| 38 | 0.15 | NT |
| 39 | NT | 0.085 |
| 40 | 0.25 | NT |
| 41 | NT | 0.045 |
| 42 | 0.24 | NT |
| 43 | 0.11 | NT |
| 44 | 0.54 | NT |
| 45 | 0.15 | NT |
| 46 | 0.057 | NT |
| 47 | 0.14 | NT |
| 48 | 0.065 | NT |
| 49 | 0.057 | NT |
| 50 | 0.026 | NT |
| 51 | 0.028 | NT |
| 52 | NT | >10 |
| 53 | NT | 0.26 |
| 54 | 0.16 | NT |
| 55 | 0.064 | NT |
| 56 | 0.025 | NT |
| 57 | 0.049 | |
| 58 | 0.41 | NT |
| 59 | 0.09 | NT |
| 60 | 0.24 | NT |
| 61 | 0.26 | NT |
| 62 | 0.011 | NT |
| 63 | 0.18 | NT |
| 64 | 0.85 | NT |
| 65 | >1 | NT |
| 66 | 0.32 | NT |
| 67 | 0.12 | NT |
| 68 | 0.074 | NT |
| 69 | 0.16 | NT |
| 70 | 0.41 | NT |
| 71 | 0.56 | NT |
| 72 | >0.590 | NT |
| 73 | 0.81 | NT |
| 74 | 0.12 | NT |
| 75 | >1 | NT |

TABLE 14-continued

| *Plasmodium falciparum* (Pf) strain 3D7 or strain NF54) NMT EC$_{50}$ values for certain Example Compounds determined in the SYBR Green Assay | | |
| --- | --- | --- |
| Example No. | Pf EC$_{50}$ strain 3D7 (μM) | Pf EC$_{50}$ strain NF54 (μM) |
| 76 | 0.41 | NT |
| 77 | >1 | NT |
| 78 | >1 | NT |
| 79 | 0.0022 | NT |
| 80 | 0.097 | NT |
| 82 | 0.094 | NT |
| 83 | 0.15 | NT |
| 84 | 0.034 | NT |
| 85 | 0.014 | NT |
| 86 | 0.2 | NT |
| 87 | >0.76 | NT |
| 88 | 0.076 | NT |
| 89 | 0.088 | NT |
| 90 | 0.3 | NT |
| 91 | 0.23 | NT |
| 92 | 0.26 | NT |
| 93 | 0.86 | NT |
| 94 | 0.44 | NT |
| 95 | 0.15 | NT |
| 96 | >0.910 | NT |
| 97 | 0.069 | NT |
| 98 | 0.007 | NT |
| 99 | 0.14 | NT |
| 100 | 0.04 | NT |
| 101 | >1 | NT |
| 102 | >1 | NT |
| 103 | 0.0053 | NT |
| 104 | 0.035 | NT |
| 105 | 0.018 | NT |
| 106 | >1 | NT |
| 107 | 0.14 | NT |
| 108 | 0.2 | NT |
| 109 | 0.12 | NT |
| 110 | 0.066 | NT |
| 111 | 0.45 | NT |
| 112 | NT | >10 |

NT = not tested

The Example Compounds tested were found to exhibit inihibitory activity against *Plasmodium falciparum* (Pf) NMT strain 3D7 and/or NF54. As such, it is expected that the compounds of the invention will be useful as medicaments, particularly in the treatment of conditions associated with such species, such as malaria, leishmaniasis, and sleeping sickness.

Assay (h): Mouse Malaria Model Protocol

The goal of this study was to evaluate the efficacy of compounds of the invention against *P. falciparum* Pf3D7$^{0087/N9}$ in NODscidIL2Rγ$^{null}$ mice engrafted with human erythrocytes.

The antimalarial efficacy was assessed in dose response model following administration of one oral (p.o.) dose of Example Compound 3 (30 or 10 or 3 mg/kg) or standard treatment (chloroquine (CQ), 50 mg/kg) per day for four consecutive days on day 3, 4, 5 and 6 post-infection (=4×30 mg/kg, or 4×10 mg/kg, or 4×3 mg/kg in total of Example compound 3; 4×50 mg/kg chloroquine) and measuring the effect on blood parasitemia by microscopic analysis of Giemsa-stained blood smears (on days 3, 4, 5, 6 and 7 post-infection). Mice were euthanized on day 7.

Figure 4:
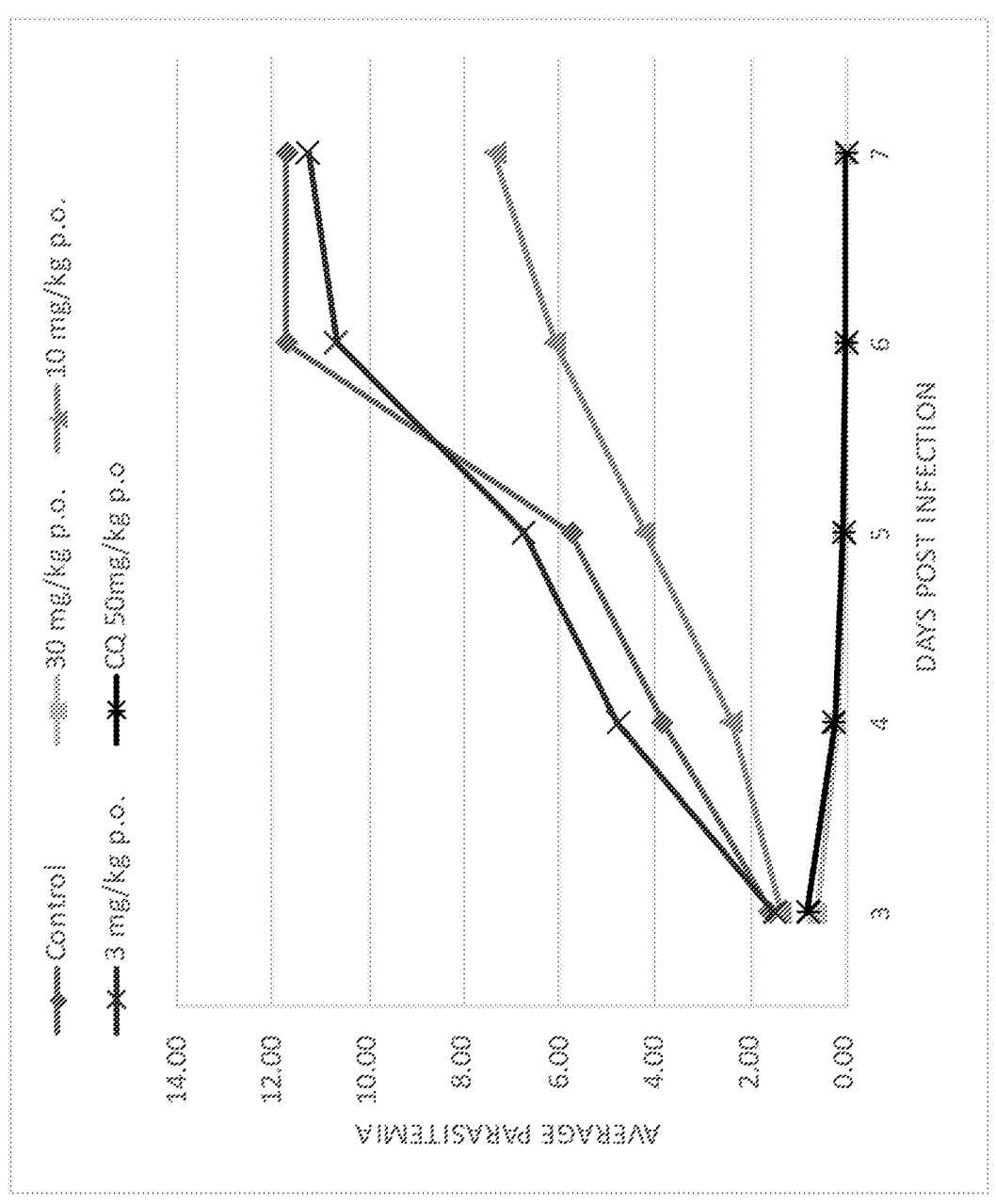
FIG. 4 shows the therapeutic efficacy (percentage reduction in the parasite burden) of 3 different doses of Example Compound 3 of the present invention against *P. falciparum* in vivo up to day 7 post-infection compared to standard treatment (chloroquine) and control mice (details of the mouse malaria model are provided at (g) of the 'Details of biological assays and results' section, below).

Results:

The therapeutic efficacy of Example 3 against *P. falciparum* in vivo up to day 7 post-infection compared to standard treatment and control mice is illustrated in FIG. 4 (graph). More specifically, the graph of FIG. 4 shows the percentage reduction in the parasite burden of the three different doses of Example 3 against *P. falciparum* in vivo up to day 7 post-infection compared to chloroquine standard treatment and control mice. Table 15 below shows the average parasitemia values presented in FIG. 4.

TABLE 15

| average percentage reduction in the parasite burden presented in FIG. 4. | | | | |
| --- | --- | --- | --- | --- |
| | average parasitemia values | | | |
| Post Infection (days) | Example Compound 3 - 3 mg/kg po per day on day 3, 4, 5 and 6 post-infection | Example Compound 3 - 10 mg/kg po per day on day 3, 4, 5 and 6 post-infection | Example Compound 3 - 30 mg/kg po per day on day 3, 4, 5 and 6 post-infection | Chloroquine (CQ) - 50 mg/kg po per day on day 3, 4, 5 and 6 post-infection | Control (no treatment) |
| 0 | 0.01 | 0.01 | 0.01 | 0.01 | 0.01 |
| 3 | 1.49 | 1.37 | 0.60 | 0.80 | 1.58 |
| 4 | 4.77 | 2.40 | 0.18 | 0.24 | 3.83 |
| 5 | 6.73 | 4.21 | 0.02 | 0.05 | 5.75 |
| 6 | 10.66 | 6.09 | 0.01 | 0.01 | 11.73 |
| 7 | 11.25 | 7.35 | 0.00* | 0.00* | 11.70 |

*2/2 (CQ) or 1/1 (Example compound 3 - 30 mg/kg dose) smears parasite free, respectively As can be seen from FIG. 4 and Table 15, at day 7 post-infection, 4×30, 4×10 mg/kg and 4×3 mg/kg p.o. of Example 3 showed >99.9% activity, minute (37%) activity and no significant (4%) activity respectively, compared to untreated control mice. In the 4×30 mg/kg group, all mice were parasite-free at day 7, which was the same results as for the mice treated with the standard treatment (chloroquine). The parasite detection limit in this study was 1 parasite in 10,000 erythrocytes (that is, 0.01%).

Assay (i): Mouse Xenograft Protocol

The in vivo efficacy was assess in a subcutaneous xenograft DOHH-2 Lymphoma Model using Female 6-8 week old CB17/SCID Mice. Each mouse was inoculated subcutaneously at the right front region with DOHH-2 tumor cells (5×106) in 0.1 ml of PBS mixed with matrigel (1:1 PBS: matrigel) for tumor development. The test compound administration started once the mean tumor size reached approximately 100-150 mm3. Compounds were administered either IP (vehicle 58% Na2HPO4 buffer (10 mM) (pH4.5)+40% PEG400+2% DMSO) or orally (vehicle Na2HPO4 buffer (10 mM) (pH 4.5)+0.2% tween 80). Tumor volumes were measured in two dimensions using a caliper, and the volume expressed in mm3 using the formula: V=(L×W×W)/2, where V is tumor volume, L is tumor length (the longest tumor dimension) and W is tumor width (the longest tumor dimension perpendicular to L).

Figure 5A:
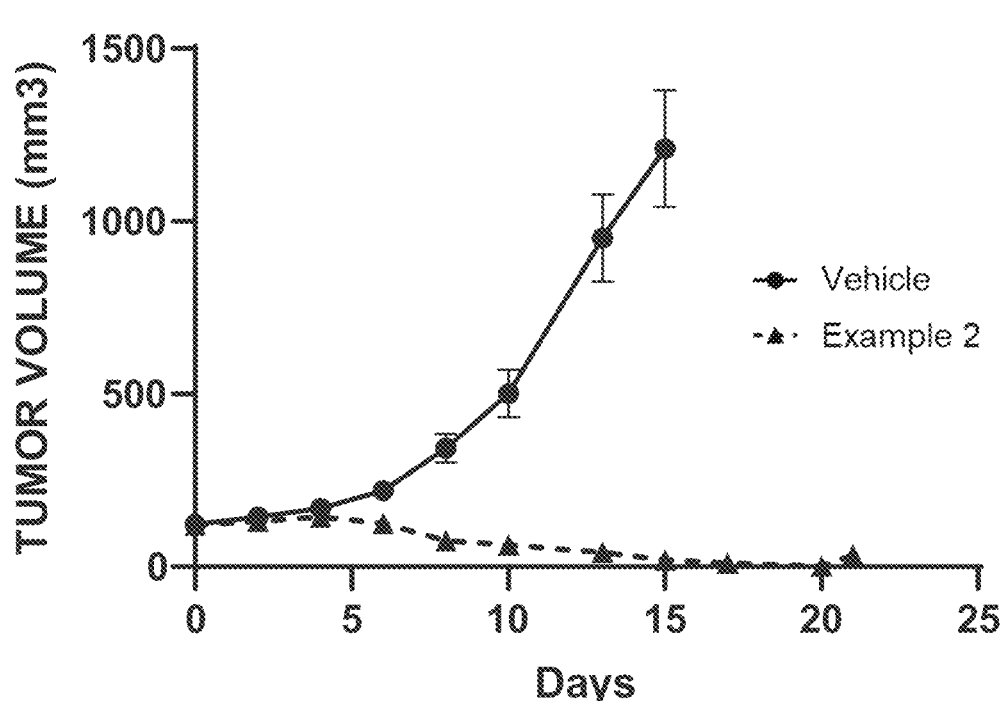
FIG. 5*a* shows the therapeutic efficacy (reduction in tumour size) of Example Compound 2 when dosed orally in a subcutaneous xenograft DOHH-2 Lymphoma Model using Female 6-8 week old CB17/SCID mice compared to a vehicle.
Figure 5B:
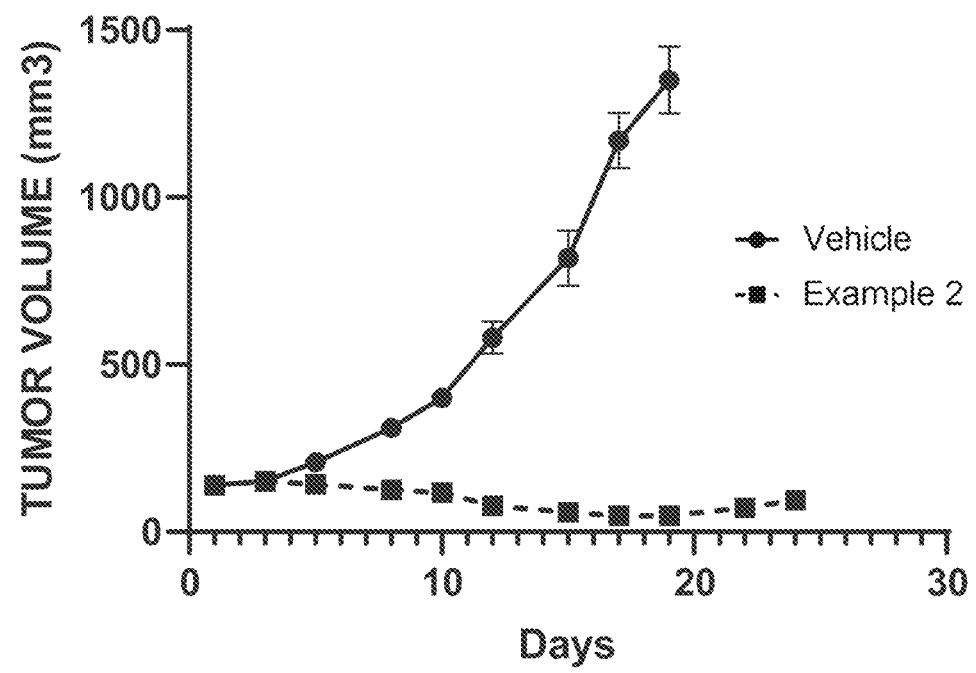
FIG. 5*b* shows the therapeutic efficacy of Example 2 when dosed intraperitonally in a subcutaneous xenograft DOHH-2 Lymphoma Model using Female 6-8 week old CB17/SCID mice compared to a vehicle.

Mice were dosed with Example 2 orally (50 mg/kg) once a day for 9 consecutive days (FIG. 5*a*), or Example 2 was dosed intraperitonally (25 mg/kg) in a cycle consisting of administration twice a day for three days followed by a four day no-dosing period (FIG. 5*b*). The cycle was repeated three times.

Mice were dosed with Example 129 intraperitonally (25 mg/kg) in a cycle consisting of administration twice a day for three days followed by a four day no-dosing period (Figure Sc). The cycle was repeated three times.

The protocol and any amendment(s) or procedures involving the care and use of animals in this study were reviewed and approved by the Institutional Animal Care and Use Committee (IACUC) of CrownBio prior to execution. During the study, the care and use of animals was conducted in accordance with the regulations of the Association for Assessment and Accreditation of Laboratory Animal Care (AAALAC).

Results

Figure 5C:
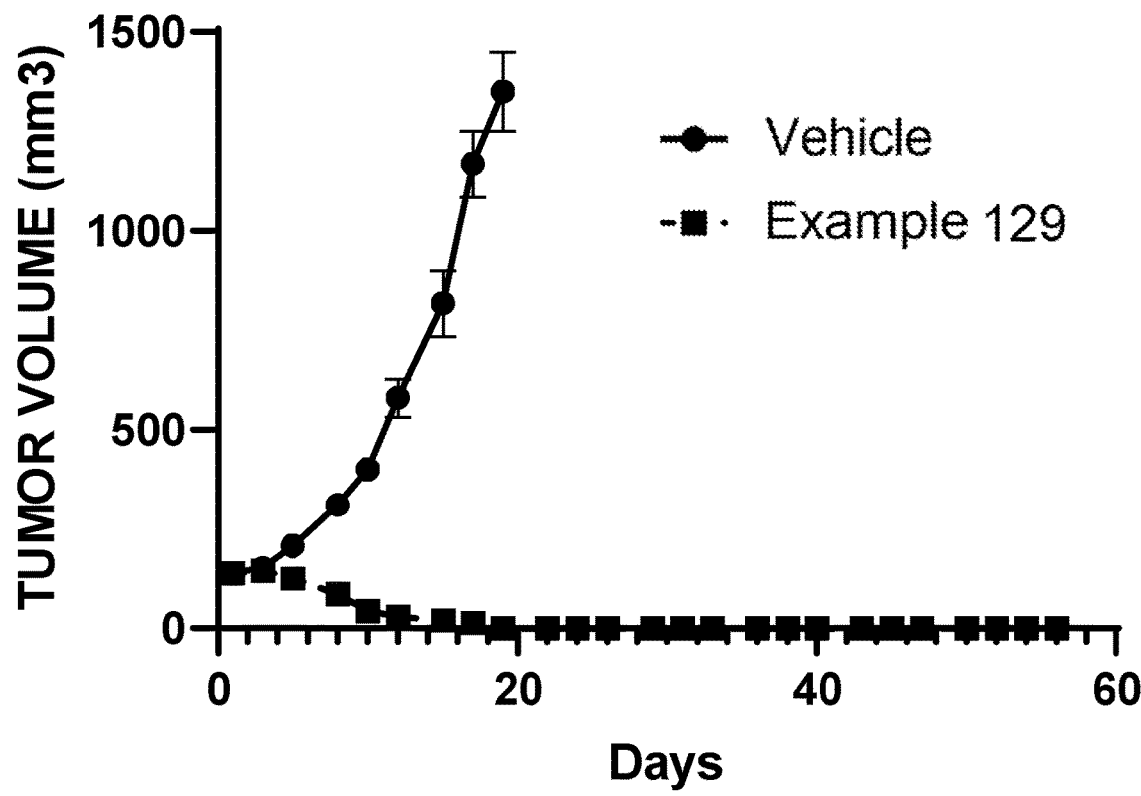
FIG. 5*c* shows the therapeutic efficacy of Example 129 when dosed intraperitonally in a subcutaneous xenograft DOHH-2 Lymphoma Model using Female 6-8 week old CB17/SCID mice compared to a vehicle.

FIGS. 5*a* and 5*b* show that oral or intraperitoneal dosing of Example 2 lead to a significant reduction in tumour volume, whilst treatment with vehicle resulted in a significant increase in tumour volume. Similarly, FIG. 5*c* shows that intraperitoneal dosing of Example 129 resulted in a significant decrease in tumour volume.

As such it is expected that the compounds are expected to be useful as medicaments, in particular the treatment of hyperproliferative disorders such as cancer.

Summary of Results

The compounds of Examples 1-158 exhibit one or more of the following:

(i) Inhibition of Human N-myristoyl transferase 1 in the range of $IC_{50}$ 0.00001 to 99.9 µM in assay (a);

(ii) inhibition of metabolic activity in BL-41 cells in the range of $EC_{50}$ 0.001 to 10 µM in assay (b);

(iii) inhibition of metabolic activity in SU-DHL-10 cells in the range of $EC_{50}$ 0.001 to 10 µM in assay (c);

(iv) inhibition of metabolic activity in BL-41 cells in the range of $EC_{50}$ 0.001 to 10 µM in assay (d);

(v) inhibition of metabolic activity in EL4 cells in the range of $EC_{50}$ 0.001 µM to 10 mM in assay (d);

(vi) inhibition of metabolic activity in Ramos cells in the range of $EC_{50}$ 0.001 µM to 10 mM in assay (d);

(vii) inhibition of metabolic activity in Raji cells in the range of $EC_{50}$ 0.001 µM to 10 mM in assay (d);

(viii) inhibition of metabolic activity in A20 cells in the range $EC_{50}$ 0.001 µM to 10 mM in assay (d);

(ix) inhibition of metabolic activity in Shep-ER-N-Myc cells in assay (d) in particular in the cell line with expression levels of c-MYC induced, and more especially in the cell line with high expression levels of c-MYC induced;

(x) inhibition of metabolic activity in SKNAS-ER-N-Myc cells in assay (d), in particular in the cell line with MYCN induction;

(xi) inhibition of metabolic activity in P-493-6 cells in in assay (d), in particular in the cell line with MYCN induction;

(xii) Inhibition of *Plasmodium vivax* (Pv) N-myristoyl transferase in the range of $IC_{50}$ 0.00001 to 99.9 µM in assay (a);

(xiii) inhibition of *Plasmodium falciparum* (Pf strains 3D7 or NF54) in the range of $EC_{50}$ 0.001 to 10 µM in assay (g);

(xiv) stability in rat liver hepatocytes with half-lives in excess of 22 mins, and suitably in excess of 60 mins (assay (e));

(xv) a long half-life in rat, suitably coupled with bioavailability >20% (assay (f));

(xvi) reduction in the parasite burden in the mouse malaria model (assay (h)) following daily oral administration at 210 mg/kg in the range 10-100%; and (xvii) reduction in mice xenograft tumor volume (assay (g)) following oral or intraperitoneal administration at 25-50 mg/kg.

Example Compounds of the invention suitably exhibit inhibitory activity for human N-myristoyl transferase 1 at lower concentrations within the $IC_{50}$ range shown above, for an $IC_{50}$ for Human N-myristoyl transferase 1 in the range of 0.00001 to 1.0 µM.

The Example Compounds of the invention for which $EC_{50}$ values were measured in the metabolic activity assay (assay (b)) all showed $EC_{50}$ for BL-41 cells in the range of $EC_{50}$ 0.01 to µM. Some of those examples exhibited inhibitory activity at lower concentrations within the $EC_{50}$ range shown above. For example, examples exhibit $EC_{50}$ in the range of from 0.001 to 1 µM in assay (b) for BL-41 cells. Example Compounds of the invention suitably exhibit an $EC_{50}$ of 1 µM or lower in assay (b) for BL-41 cells.

The Example Compounds of the invention for which $EC_{50}$ values were measured in the metabolic activity assay (assay (c)) all showed $E_{50}$ for SU-DHL-10 cells in the range of $EC_{50}$ 0.01 to 10 µM. Some of those examples exhibited inhibitory activity at lower concentrations within the $EC_{50}$ range shown above. For example, certain examples exhibit $EC_{50}$ in the range of from 0.001 to 1 µM in assay (c) for SU-DHL-10 cells. Example Compounds of the invention suitably exhibit an $EC_{50}$ of 1 µM or lower in assay (c) for SU-DHL-10 cells.

For the Example Compounds of the invention for which $EC_{50}$ values for *Plasmodium falciparum* (Pf) were measured using assay (g), the majority of the compounds showed $EC_{50}$ for *Plasmodium falciparum* (Pt) in the range of $EC_{50}$ 0.001 to 10 µM. Some of those examples exhibited inhibitory activity at lower concentrations within the $EC_{50}$ range shown above.

Example Compounds of the invention suitably exhibit inhibitory activity at lower concentrations within the $EC_{50}$ range shown above. For example, examples exhibit $EC_{50}$ at *Plasmodium falciparum* (3D7 or NF54 strains) in the range of $IC_{50}$ 0.0001 to 0.1 μM in assay (h).

The Example Compounds of the invention for which a reduction in parasite burden in the mouse malaria model was measured using the protocol described at (h) showed effects following once-daily administration at 10 mg/kg/dose, and optimum effects following once-daily administration at 30 mg/kg/dose. Example Compounds of the invention suitably lower the parasite burden by more than 50% following once-daily administration at 15 mg/kg or a higher dose, for example following once-daily administration at 20 mg/kg or a higher dose or following once-daily administration at 30 mg/kg or a higher dose.

Throughout the specification and the claims which follow, unless the context requires otherwise, the word 'comprise', and variations such as 'comprises' and 'comprising', will be understood to imply the inclusion of a stated integer, step, group of integers or group of steps but not to the exclusion of any other integer, step, group of integers or group of steps.

All patents, patent applications and references mentioned throughout the specification of the present invention are herein incorporated in their entirety by reference.

The invention embraces all combinations of preferred and more preferred groups and suitable and more suitable groups and embodiments of groups recited above.

The invention claimed is:

1. A compound of Formula (I), or a pharmaceutically acceptable ester, amide, carbamate or salt thereof, Formula (I)

wherein:

$n_1$ is 1 or 2; $n_2$ is 1 or 2;

$X^1$ is selected from the group consisting of $CR^x$ and N;

when present, Rx is selected from the group consisting of hydrogen, halogen, and —$C_{1-4}$alkyl optionally substituted by 1, 2 or 3 substituents, each substituent being independently selected from the group consisting of halogen, —OH, —$OCH_3$, and —$OCF_3$;

$R^1$ is selected from the group consisting of hydrogen; —$C_{1-4}$alkyl optionally substituted by 1, 2 or 3 substituents, each substituent being independently selected from the group consisting of halogen, —$OCH_3$, and —$OCF_3$; and —$C_{3-6}$cycloalkyl optionally substituted by 1, 2 or 3 substituents, each substituent being independently selected from the group consisting of halogen, —$CH_3$, —$OCH_3$, and —$OCF_3$;

$R^2$ is selected from the group consisting of hydrogen; —$C_{1-4}$alkyl optionally substituted by 1, 2 or 3 substituents, each substituent being independently selected from the group consisting of halogen, —$OCH_3$, and —OCF 3; and —$C_{3-6}$cycloalkyl optionally substituted by 1, 2 or 3 substituents, each substituent being independently selected from the group consisting of halogen, —$CH_3$, —$OCH_3$, and —$OCF_3$;

or $R^1$ and $R^2$ are linked such that together with the atom to which they are attached they form a $C_{3-6}$cycloalkyl group or a 3- to 6-membered non-aromatic heterocyclyl group comprising 1 heteroatom selected from the group consisting of O and N, wherein said $C_{3-6}$cycloalkyl group or 3- to 6-membered non-aromatic heterocyclyl group is optionally substituted by 1 or 2 substituents, each substituent being independently selected from the group consisting of halogen, —OH, —$CH_3$, —$OCH_3$, and —$OCF_3$;

$R^3$ is selected from the group consisting of hydrogen; —$C_{1-4}$alkyl optionally substituted by 1, 2 or 3 substituents, each substituent being independently selected from the group consisting of halogen, —OH, —$OCH_3$, and —$OCF_3$; and —$C_{3-6}$-cycloalkyl optionally substituted by 1, 2 or 3 substituents, each substituent being independently selected from the group consisting of halogen, —OH, —$CH_3$, —$OCH_3$, and —$OCF_3$;

or $R^1$ and $R^3$ are linked such that together with the atoms to which they are attached they form a 3- to 6-membered non-aromatic heterocyclyl group comprising 1 N heteroatom, wherein said 3- to 6-membered non-aromatic heterocyclyl group is optionally substituted by 1 or 2 substituents, each substituent being independently selected from the group consisting of halogen, —$CH_3$, —OH, —$OCH_3$, and —$OCF_3$;

$X^2$ is selected from the group consisting of $CR^4$ and N;

when present, $R^4$ is selected from the group consisting of hydrogen; halogen; —$C_{1-4}$alkyl optionally substituted by 1, 2 or 3 substituents, each substituent being independently selected from the group consisting of halogen, —OH, —$OCH_3$, —$OCF_3$, and —$NR^aR^b$;

$R^{5a}$ and $R^{5d}$ are independently selected from the group consisting of hydrogen; halogen; methyl optionally substituted by 1, 2 or 3 substituents, each substituent being independently selected from the group consisting of halogen, —OH, —$OCH_3$, and —$OCF_3$; and methoxy optionally substituted by 1, 2 or 3 substituents, each substituent being independently selected from the group consisting of halogen, —OH, —$OCH_3$, and —$OCF_3$;

$R^{5b}$ and $R^{5c}$ are independently selected from the group consisting of hydrogen; halogen; —$C_{1-4}$alkyl optionally substituted by 1, 2 or 3 substituents, each substituent being independently selected from the group consisting of halogen, —OH, —$OCH_3$, and —$OCF_3$; —O—$C_{1-4}$alkyl optionally substituted by 1, 2 or 3 substituents, each substituent being independently selected from the group consisting of halogen, —OH, —$OCH_3$, and —$OCF_3$; and $C_{3-6}$cycloalkyl optionally substituted by 1, 2 or 3 substituents, each substituent being independently selected from the group consisting of halogen, —$CH_3$, —OH, —$OCH_3$, and —$OCF_3$;

or $R^{5b}$ and $R^{5c}$ are linked such that together with the atoms to which they are attached they form a 6-membered aryl group or a 5- or 6-membered aromatic heterocyclyl group comprising 1 or 2 heteroatoms selected from the group consisting of S, O and N, wherein said 6-membered aryl group or 5- or 6-membered aromatic heterocyclyl group is optionally substituted by 1 or 2 substituents, each substituent being independently selected from the group consisting of halogen, —OH, —OCH$_3$, and —OCF$_3$;

R$^6$ is selected from the group consisting of hydrogen and methyl;

when present, each R$^7$ is —C$_{1-4}$alkyl optionally substituted by 1, 2 or 3 substituents, each substituent being independently selected from the group consisting of halogen, —OH, —OCH$_3$, and —OCF$_3$;

R$^8$ is selected from the group consisting of hydrogen; halogen; —OH; —CN; —C$_{1-4}$alkyl optionally substituted by 1, 2 or 3 substituents, each substituent being independently selected from the group consisting of halogen, —OH, —CN, and methoxy optionally substituted by 1, 2 or 3 halogen; —C$_{3-6}$cycloalkyl optionally substituted by 1, 2 or 3 substituents, each substituent being independently selected from the group consisting of halogen, —CH$_3$, —OH, —CN, and methoxy optionally substituted by 1, 2 or 3 halogen; —C$_{1-4}$alkenyl optionally substituted by 1, 2 or 3 substituents, each substituent being independently selected from the group consisting of halogen, —OH, —CN, and methoxy optionally substituted by 1, 2 or 3 halogen; and —O—C$_{1-4}$alkyl optionally substituted by 1, 2 or 3 substituents, each substituent being independently selected from the group consisting of halogen, —OH, CN and methoxy optionally substituted by 1, 2 or 3 halogen;

R$^9$ is selected from the group consisting of hydrogen, and —C$_{1-4}$alkyl optionally substituted by 1, 2 or 3 substituents, each substituent being independently selected from the group consisting of halogen, —OH, —OCH$_3$, and —OCF$_3$; or R$^8$ and R$^9$ are linked such that together with the atoms to which they are attached they form a 6-membered aryl group, a C$_{5-6}$cycloalkyl group, or a 5- or 6-membered aromatic heterocyclyl group comprising 1 or 2 heteroatoms selected from N, O and S, and wherein said 6-membered aryl group, C$_{5-6}$cycloalkyl group or 5- to 6-membered aromatic heterocyclyl group is optionally substituted by 1, 2 or 3 substituents, each substituent being independently selected from the group consisting of halogen; —OH; —CN; —C$_{1-4}$alkyl optionally substituted by 1, 2 or 3 substituents, each substituent being independently selected from the group consisting of halogen, —OH, and methoxy optionally substituted by 1, 2 or 3 halogen; and —O—C$_{1-4}$alkyl optionally substituted by 1, 2 or 3 substituents, each substituent being independently selected from the group consisting of -halogen, —OH, and methoxy optionally substituted by 1, 2 or 3 halogen;

p is 0, 1, or 2;

Z is a 5- to 13-membered non-aromatic heterocyclyl group comprising 1, 2 or 3 heteroatoms selected from N, O and S, wherein at least one of the heteroatoms is N, and wherein said 5- to 13-membered non-aromatic heterocyclyl group is optionally substituted with 1, 2, 3 or 4 substituents, each substituent being independently selected from the group consisting of halogen; —C$_{1-6}$alkyl optionally substituted by 1, 2 or 3 substituents, each substituent being independently selected from the group consisting of halogen, —OH, and —OC$_{1-3}$alkyl optionally substituted by 1, 2 or 3 halogen; —O—C$_{1-6}$alkyl optionally substituted by 1, 2 or 3 substituents, each substituent being independently selected from the group consisting of halogen, —OH, and —O—C$_{1-3}$alkyl optionally substituted by 1, 2 or 3 halogen; NR$^c$R$^d$; and C$_{3-6}$cycloalkyl optionally substituted by 1, 2 or 3 substituents, each substituent being independently selected from the group consisting of halogen, —OH, and —O—C$_{1-3}$alkyl optionally substituted by 1, 2 or 3 halogen; or when two substituents are on adjacent ring positions they may be linked such that together with the atoms to which they are attached they form a C$_{3-6}$cycloalkyl group or a 4- to 6-membered non-aromatic heterocyclyl group comprising 1 heteroatom selected from the group consisting of O and N, wherein said C$_{3-6}$cycloalkyl group or 4- to 6-membered non-aromatic heterocyclyl group is optionally substituted by 1 or 2 substituents, each substituent being independently selected from the group consisting of halogen; —C$_{1-6}$alkyl optionally substituted by 1, 2 or 3 substituents, each substituent being independently selected from the group consisting of halogen, —OH, and —OC$_{1-3}$alkyl optionally substituted by 1, 2 or 3 halogen; and —O—C$_{1-6}$alkyl optionally substituted by 1, 2 or 3 substituents, each substituent being independently selected from the group consisting of halogen, —OH, and —O—C$_{1-3}$alkyl optionally substituted by 1, 2 or 3 halogen;

R$^c$ and R$^d$ are independently selected from the group consisting of hydrogen; —C$_{1-6}$alkyl optionally substituted by 1, 2 or 3 substituents, each substituent being independently selected from the group consisting of halogen, —OCH$_3$, and —OCF$_3$; and C$_{3-6}$cycloalkyl optionally substituted by 1, 2 or 3 substituents, each substituent being independently selected from the group consisting of halogen, —CH$_3$, —OH, —OCH$_3$, and —OCF$_3$;

or Z is —NR$^{10}$R$^{11}$, wherein

R$^{10}$ is selected from the group consisting of hydrogen and —C$_{1-4}$alkyl; and R$^{11}$ is a 5- to 10-membered non-aromatic heterocyclyl group comprising 1, 2 or 3 heteroatoms selected from N, O and S, wherein at least one of the heteroatoms is N, and wherein said 5- to 10-membered non-aromatic heterocyclyl group is optionally substituted with 1, 2, 3 or 4 substituents independently selected from the group consisting of halogen; —OH; —C$_{1-6}$alkyl optionally substituted by 1, 2 or 3 substituents, each substituent being independently selected from the group consisting of halogen, —OH, and —OC$_{1-3}$alkyl optionally substituted by 1, 2 or 3 halogen; and —O—C$_{1-6}$alkyl optionally substituted by 1, 2 or 3 substituents, each substituent being independently selected from the group consisting of halogen, —OH, and —O—C$_{1-3}$alkyl optionally substituted by 1, 2 or 3 halogen; and when present, each R$^a$ and R$^b$ are independently selected from the group consisting of hydrogen and —C$_{1-4}$alkyl.

2. The compound or a pharmaceutically acceptable ester, amide, carbamate or salt thereof according to claim 1, which is a compound of Formula (I), or a pharmaceutically acceptable ester, amide, carbamate or salt thereof, Formula (I)

wherein:

$n_1$ is 1 or 2; $n_2$ is 1 or 2;

$X^1$ is selected from the group consisting of $CR^x$ and N;

when present, $R^x$ is selected from the group consisting of hydrogen, halogen, and —$C_{1-4}$alkyl optionally substituted by 1, 2 or 3 substituents, each substituent being independently selected from the group consisting of halogen, —OH, —OCH$_3$, and —OCF$_3$;

$R^1$ is selected from the group consisting of hydrogen; —$C_{1-4}$alkyl optionally substituted by 1, 2 or 3 substituents, each substituent being independently selected from the group consisting of halogen, —OCH$_3$, and —OCF$_3$; and —$C_{3-6}$cycloalkyl optionally substituted by 1, 2 or 3 substituents, each substituent being independently selected from the group consisting of halogen, —CH$_3$, —OCH$_3$, and —OCF$_3$;

$R^2$ is selected from the group consisting of hydrogen; —$C_{1-4}$alkyl optionally substituted by 1, 2 or 3 substituents, each substituent being independently selected from the group consisting of halogen, —OCH$_3$, and —OCF$_3$; and —$C_{3-6}$cycloalkyl optionally substituted by 1, 2 or 3 substituents, each substituent being independently selected from the group consisting of halogen, —CH$_3$, —OCH$_3$, and —OCF$_3$;

or $R^1$ and $R^2$ are linked such that together with the atom to which they are attached they form a $C_{3-6}$cycloalkyl group or a 3- to 6-membered non-aromatic heterocyclyl group comprising 1 heteroatom selected from the group consisting of O and N, wherein said $C_{3-6}$cycloalkyl group or 3- to 6-membered non-aromatic heterocyclyl group is optionally substituted by 1 or 2 substituents, each substituent being independently selected from the group consisting of halogen, —OH, —CH$_3$, —OCH$_3$, and —OCF$_3$;

$R^3$ is selected from the group consisting of hydrogen; —$C_{1-4}$alkyl optionally substituted by 1, 2 or 3 substituents, each substituent being independently selected from the group consisting of halogen, —OH, —OCH$_3$, and —OCF$_3$; and —$C_{3-6}$-cycloalkyl optionally substituted by 1, 2 or 3 substituents, each substituent being independently selected from the group consisting of halogen, —OH, —CH$_3$, —OCH$_3$, and —OCF$_3$;

or $R^1$ and $R^3$ are linked such that together with the atoms to which they are attached they form a 3- to 6-membered non-aromatic heterocyclyl group comprising 1 N heteroatom, wherein said 3- to 6-membered non-aromatic heterocyclyl group is optionally substituted by 1 or 2 substituents, each substituent being independently selected from the group consisting of halogen, —OH, —OCH$_3$, and —OCF$_3$;

$X^2$ is selected from the group consisting of $CR^4$ and N;

when present, $R^4$ is selected from the group consisting of hydrogen; halogen; —$C_{1-4}$alkyl optionally substituted by 1, 2 or 3 substituents, each substituent being independently selected from the group consisting of halogen, —OH, —OCH$_3$, and —OCF$_3$; and —$NR^aR^b$, $R^{5a}$ and $R^{5d}$ are independently selected from the group consisting of hydrogen; halogen; methyl optionally substituted by 1, 2 or 3 substituents, each substituent being independently selected from the group consisting of halogen, —OH, —OCH$_3$, and —OCF$_3$; and methoxy optionally substituted by 1, 2 or 3 substituents, each substituent being independently selected from the group consisting of halogen, —OH, —OCH$_3$, and —OCF$_3$;

$R^{5b}$ and $R^{5c}$ are independently selected from the group consisting of hydrogen; halogen; —$C_{1-4}$alkyl optionally substituted by 1, 2 or 3 substituents, each substituent being independently selected from the group consisting of halogen, —OH, —OCH$_3$, and —OCF$_3$; —O—$C_{1-4}$alkyl optionally substituted by 1, 2 or 3 substituents, each substituent being independently selected from the group consisting of halogen, —OH, —OCH$_3$, and —OCF$_3$; and $C_{3-6}$cycloalkyl optionally substituted by 1, 2 or 3 substituents, each substituent being independently selected from the group consisting of halogen, —CH$_3$, —OH, —OCH$_3$, and —OCF$_3$;

or $R^{5b}$ and $R^{5c}$ are linked such that together with the atoms to which they are attached they form a 6-membered aryl group or a 5- or 6-membered aromatic heterocyclyl group comprising 1 or 2 heteroatoms selected from the group consisting of S, O and N, wherein said 6-membered aryl group or 5- or 6-membered aromatic heterocyclyl group is optionally substituted by 1 or 2 substituents, each substituent being independently selected from the group consisting of halogen, —OH, —OCH$_3$, and —OCF$_3$;

$R^6$ is selected from the group consisting of hydrogen and methyl;

when present, each $R^7$ is —$C_{1-4}$alkyl optionally substituted by 1, 2 or 3 substituents, each substituent being independently selected from the group consisting of halogen, —OH, —OCH$_3$, and —OCF$_3$;

$R^8$ is selected from the group consisting of hydrogen; halogen; —OH; —CN; —$C_{1-4}$alkyl optionally substituted by 1, 2 or 3 substituents, each substituent being independently selected from the group consisting of halogen, —OH, —CN, and methoxy optionally substituted by 1, 2 or 3 halogen; —$C_{3-6}$cycloalkyl optionally substituted by 1, 2 or 3 substituents, each substituent being independently selected from the group consisting of halogen, —CH$_3$, —OH, —CN, and methoxy optionally substituted by 1, 2 or 3 halogen; —$C_{1-4}$alkenyl optionally substituted by 1, 2 or 3 substituents, each substituent being independently selected from the group consisting of halogen, —OH, —CN, and methoxy optionally substituted by 1, 2 or 3 halogen; and —O—$C_{1-4}$alkyl optionally substituted by 1, 2 or 3 substituents, each substituent being independently selected from the group consisting of halogen, —OH, CN and methoxy optionally substituted by 1, 2 or 3 halogen;

$R^9$ is selected from the group consisting of hydrogen, and —$C_{1-4}$alkyl optionally substituted by 1, 2 or 3 substituents, each substituent being independently selected from the group consisting of halogen, —OH, —OCH$_3$, and —OCF$_3$; or R$^8$ and R$^9$ are linked such that together with the atoms to which they are attached they form a 6-membered aryl group or a 5- or 6-membered aromatic heterocyclyl group comprising 1 or 2 heteroatoms selected from N, O and S, and wherein said 6-membered aryl group or 5- to 6-membered aromatic heterocyclyl group is optionally substituted by 1, 2 or 3 substituents, each substituent being independently selected from the group consisting of halogen; —OH; —CN; —C$_{1-4}$alkyl optionally substituted by 1, 2 or 3 substituents, each substituent being independently selected from the group consisting of halogen, —OH, and methoxy optionally substituted by 1, 2 or 3 halogen; and —O—C$_{1-4}$alkyl optionally substituted by 1, 2 or 3 substituents, each substituent being independently selected from the group consisting of -halogen, —OH, and methoxy optionally substituted by 1, 2 or 3 halogen;

p is 0, 1, or 2;

Z is a 5- to 13-membered non-aromatic heterocyclyl group comprising 1, 2 or 3 heteroatoms selected from N, O and S, wherein at least one of the heteroatoms is N, and wherein said 5- to 10-membered non-aromatic heterocyclyl group is optionally substituted with 1, 2, 3 or 4 substituents, each substituent being independently selected from the group consisting of halogen; —C$_{1-6}$alkyl optionally substituted by 1, 2 or 3 substituents, each substituent being independently selected from the group consisting of halogen, —OH, and —OC$_{1-3}$alkyl optionally substituted by 1, 2 or 3 halogen; and —O—C$_{1-6}$alkyl optionally substituted by 1, 2 or 3 substituents, each substituent being independently selected from the group consisting of halogen, —OH, and —O—C$_{1-3}$alkyl optionally substituted by 1, 2 or 3 halogen;

or Z is —NR$^{10}$R$^{11}$, wherein

R$^{10}$ is selected from the group consisting of hydrogen and —C$_{1-4}$alkyl; and R$^{11}$ is a 5- to 10-membered non-aromatic heterocyclyl group comprising 1, 2 or 3 heteroatoms selected from N, O and S, wherein at least one of the heteroatoms is N, and wherein said 5- to 10-membered non-aromatic heterocyclyl group is optionally substituted with 1, 2, 3 or 4 substituents independently selected from the group consisting of halogen; —OH; —C$_{1-6}$alkyl optionally substituted by 1, 2 or 3 substituents, each substituent being independently selected from the group consisting of halogen, —OH, and —OC$_{1-3}$alkyl optionally substituted by 1, 2 or 3 halogen; and —O—C$_{1-6}$alkyl optionally substituted by 1, 2 or 3 substituents, each substituent being independently selected from the group consisting of halogen, —OH, and —O—C$_{1-3}$alkyl optionally substituted by 1, 2 or 3 halogen; and when present, each R$^a$ and R$^b$ are independently selected from the group consisting of hydrogen and —C$_{1-4}$alkyl.

3. The compound or a pharmaceutically acceptable ester, amide, carbamate or salt thereof as claimed in claim 1, wherein Z is an optionally substituted 5- to 8-membered non-aromatic heterocyclyl group, and suitably Z is an optionally substituted 6-membered non-aromatic heterocyclyl group.

4. The compound or a pharmaceutically acceptable ester, amide, carbamate or salt thereof as claimed in claim 1, wherein Z is:

306 wherein

〰〰 denotes the point of attachment;

m is 0, 1, 2 or 3;

r is 0, 1, 2 or 3;

s is 0, 1 or 2;

R$^{12}$ is selected from the group consisting of hydrogen and —C$_{1-6}$alkyl optionally substituted by 1, 2 or 3 substituents, each substituent being independently selected from the group consisting of halogen and —OC$_{1-3}$alkyl optionally substituted by 1, 2 or 3 halogen; and when present, each R$^{13}$ is independently selected from the group consisting of halogen; —C$_{1-6}$alkyl optionally substituted by 1, 2 or 3 substituents, each substituent being independently selected from the group consisting of halogen, —OH, and —OC$_{1-3}$alkyl optionally substituted by 1, 2 or 3 halogen; and —O—C$_{1-6}$alkyl optionally substituted by 1, 2 or 3 substituents, each substituent being independently selected from the group consisting of halogen, —OH, and —O—C$_{1-3}$alkyl optionally substituted by 1, 2 or 3 halogen; NR$^c$R$^d$; and C$_{3-6}$cycloalkyl optionally substituted by 1, 2 or 3 substituents, each substituent being independently selected from the group consisting of halogen, —OH, and —O—C$_{1-3}$alkyl optionally substituted by 1, 2 or 3 halogen; or when two substituents are on adjacent ring positions they may be linked such that together with the atoms to which they are attached they form a C$_{3-6}$cycloalkyl group or a 4- to 6-membered non-aromatic heterocyclyl group comprising 1 heteroatom selected from the group consisting of O and N, wherein said C$_{3-6}$cycloalkyl group or 4- to 6-membered non-aromatic heterocyclyl group is optionally substituted by 1 or 2 substituents, each substituent being independently selected from the group consisting of halogen; —C$_{1-6}$alkyl optionally substituted by 1, 2 or 3 substituents, each substituent being independently selected from the group consisting of halogen, —OH, and —OC$_{1-3}$alkyl optionally substituted by 1, 2 or 3 halogen; and —O—C$_{1-6}$alkyl optionally substituted by 1, 2 or 3 substituents, each substituent being independently selected from the group consisting of halogen, —OH, and —O—C$_{1-3}$ alkyl optionally substituted by 1, 2 or 3 halogen;

R$^c$ and R$^d$ are independently selected from the group consisting of hydrogen; —C$_{1-6}$alkyl optionally substituted by 1, 2 or 3 substituents, each substituent being independently selected from the group consisting of halogen, —OCH$_3$, and —OCF$_3$; and C$_{3-6}$cycloalkyl optionally substituted by 1, 2 or 3 substituents, each substituent being independently selected from the group consisting of halogen, —CH$_3$, —OH, —OCH$_3$, and —OCF$_3$;

or, when m is 0 or 1, r is 2 or 3 and two R$^{13}$ groups are on adjacent ring positions, said two R$^{13}$ are linked such that together with the atoms to which they are attached they form a C$_{3-6}$cycloalkyl group or a 4- to 6-membered non-aromatic heterocyclyl group comprising 1 heteroatom selected from the group consisting of O and N, wherein said C$_{3-6}$cycloalkyl group or 4- to 6-membered non-aromatic heterocyclyl group is optionally substituted by 1 or 2 substituents, each substituent being independently selected from the group consisting of halogen; —C$_{1-6}$alkyl optionally substituted by 1, 2 or 3 substituents, each substituent being independently selected from the group consisting of halogen, —OH, and —OC$_{1-3}$alkyl optionally substituted by 1, 2 or 3 halogen; and —O—C$_{1-6}$alkyl optionally substituted by 1, 2 or 3 substituents, each substituent being independently selected from the group consisting of halogen, —OH, and —O—C$_{1-3}$alkyl optionally substituted by 1, 2 or 3 halogen;

or, when r is 1, 2 or 3 and one R$^{13}$ group is at an adjacent ring position to N—R$^{12}$, said R$^{13}$ and R$^{12}$ are linked such that together with the atoms to which they are attached they form a 5- or 6-membered non-aromatic heterocyclyl group comprising 1 N heteroatom and optionally 1 heteroatom selected from the group consisting of O and N, wherein said 5- or 6-membered non-aromatic heterocyclyl group is optionally substituted by 1 or 2 substituents, each substituent being independently selected from the group consisting of halogen; —C$_{1-6}$alkyl optionally substituted by 1, 2 or 3 substituents, each substituent being independently selected from the group consisting of halogen, —OH, and —OC$_{1-3}$alkyl optionally substituted by 1, 2 or 3 halogen; and —O—C$_{1-6}$alkyl optionally substituted by 1, 2 or 3 substituents, each substituent being independently selected from the group consisting of halogen, —OH, and —O—C$_{1-3}$alkyl optionally substituted by 1, 2 or 3 halogen; and when present, each R$^{14}$ is independently selected from the group consisting of halogen; —C$_{1-6}$alkyl optionally substituted by 1, 2 or 3 substituents, each substituent being independently selected from the group consisting of halogen, —OH, and —OC$_{1-3}$alkyl optionally substituted by 1, 2 or 3 halogen; and —O—C$_{1-6}$alkyl optionally substituted by 1, 2 or 3 substituents, each substituent being independently selected from the group consisting of halogen, —OH, and —O—C$_{1-3}$alkyl optionally substituted by 1, 2 or 3 halogen.

5. The compound or a pharmaceutically acceptable ester, amide, carbamate or salt thereof as claimed in claim 4, wherein m is 1 or 2;

r is 0, 1 or 2;

s is 0, 1 or 2;

R$^{12}$ is selected from the group consisting of hydrogen and —C$_{1-6}$alkyl optionally substituted by 1, 2 or 3 substituents, each substituent being independently selected from the group consisting of halogen and —OC$_{1-3}$alkyl optionally substituted by 1, 2 or 3 halogen;

when present, each R$^{13}$ is selected from the group consisting of independently selected from the group consisting of hydrogen; halogen; —C$_{1-6}$alkyl optionally substituted by 1, 2 or 3 substituents, each substituent being independently selected from the group consisting of halogen, —OH, and —OC$_{1-3}$alkyl optionally substituted by 1, 2 or 3 halogen; and —O—C$_{1-6}$alkyl optionally substituted by 1, 2 or 3 substituents, each substituent being independently selected from the group consisting of halogen, —OH, and —O—C$_{1-3}$alkyl optionally substituted by 1, 2 or 3 halogen; and when present, each R$^{14}$ is selected from the group consisting of independently selected from the group consisting of hydrogen; halogen; —C$_{1-6}$alkyl optionally substituted by 1, 2 or 3 substituents, each substituent being independently selected from the group consisting of halogen, —OH, and —OC$_{1-3}$alkyl optionally substituted by 1, 2 or 3 halogen; and —O—C$_{1-6}$alkyl optionally substituted by 1, 2 or 3 substituents, each substituent being independently selected from the group consisting of halogen, —OH, and —O—C$_{1-3}$alkyl optionally substituted by 1, 2 or 3 halogen.

6. The compound or a pharmaceutically acceptable ester, amide, carbamate or salt thereof as claimed in claim 5, wherein R$^{12}$ is —C$_{1-4}$alkyl optionally substituted by 1, 2 or 3 substituents, each substituent being independently selected from the group consisting of halogen and —OC$_{1-3}$alkyl optionally substituted by 1, 2 or 3 halogen, and R$^{13}$ is independently selected from the group consisting of —C$_{1-6}$alkyl optionally substituted by 1, 2 or 3 substituents, each substituent being independently selected from the group consisting of halogen, —OH, and —OC$_{1-3}$alkyl optionally substituted by 1, 2 or 3 halogen; and —O—C$_{1-6}$alkyl optionally substituted by 1, 2 or 3 substituents, each substituent being independently selected from the group consisting of halogen, —OH, and —O—C$_{1-3}$alkyl optionally substituted by 1, 2 or 3 halogen.

7. The compound or a pharmaceutically acceptable ester, amide, carbamate or salt thereof as claimed in claim 1, wherein Z is selected from the group consisting of:

-continued wherein 〰〰 denotes the point of attachment.

8. The compound or a pharmaceutically acceptable ester, amide, carbamate or salt thereof as claimed in claim 7, wherein Z is selected from the group consisting of:

and wherein 〰〰 denotes the point of attachment.

9. The compound or a pharmaceutically acceptable ester, amide, carbamate or salt thereof as claimed in claim 1, wherein $R^1$ is —$C_{1-4}$alkyl optionally substituted by 1, 2 or 3 substituents, each substituent being independently selected from the group consisting of halogen, —$OCH_3$, and —$OCF_3$; and $R^2$ is —$C_{1-4}$alkyl optionally substituted by 1, 2 or 3 substituents, each substituent being independently selected from the group consisting of halogen, —$OCH_3$, and —$OCF_3$; and suitably wherein $R^1$ is methyl and $R^2$ is methyl.

10. The compound or a pharmaceutically acceptable ester, amide, carbamate or salt thereof as claimed in claim 1, wherein $R^8$ is selected from the group consisting of hydrogen, halogen, methyl, $CF_3$, methoxy and $OCF_3$, and $R^9$ is hydrogen.

11. The compound or a pharmaceutically acceptable ester, amide, carbamate or salt thereof as claimed in claim 10, wherein $R^8$ is Cl.

12. The compound or a pharmaceutically acceptable ester, amide, carbamate or salt thereof as claimed in claim 1, wherein $n_1$ is 1, and $n_2$ is 1.

13. The compound or a pharmaceutically acceptable ester, amide, carbamate or salt thereof as claimed in claim 1, wherein $X^2$ is $CR^4$, $R^4$ is selected from the group consisting of hydrogen and methyl optionally substituted by 1, 2 or 3 F atoms and $X^1$ is N.

14. The compound or a pharmaceutically acceptable ester, amide, carbamate or salt thereof as claimed in claim 1, wherein $R^{5a}$, $R^{5b}$, $R^{5c}$ and $R^{5d}$ each represent hydrogen.

15. The compound or a pharmaceutically acceptable ester, amide, carbamate or salt thereof as claimed in claim 1, wherein $R^3$, $R^4$, $R^6$ and $R^9$ are each hydrogen; and p is 0.

16. A compound or a pharmaceutically acceptable ester, amide, carbamate or salt thereof as claimed in claim 1, wherein the compound or a pharmaceutically acceptable ester, amide, carbamate or salt thereof is selected from the group consisting of:

1-{5-chloro-2-[(3R)-3-methylpiperazin-1-yl]pyrimidin-4-yl}-N-(2-{imidazo[1,2-a]pyridin-3-yl}propan-2-yl)azetidine-3-carboxamide;

1-{5-chloro-2-[(2S)-2,4-dimethylpiperazin-1-yl]pyrimidin-4-yl}-N-(2-{imidazo[1,2-a]pyridin-3-yl}propan-2-yl)azetidine-3-carboxamide;

1-{5-chloro-2-[(3R)-3,4-dimethylpiperazin-1-yl]pyrimidin-4-yl}-N-(2-{imidazo[1,2-a]pyridin-3-yl}propan-2-yl)azetidine-3-carboxamide;

1-[5-fluoro-2-(4-methylpiperazin-1-yl) pyridin-4-yl]-N-(2-{imidazo[1,2-a]pyridin-3-yl}propan-2-yl)azetidine-3-carboxamide;

1-[5-chloro-2-(1,4-diazepan-1-yl)pyrimidin-4-yl]-N-{imidazo[1,2-a]pyridin-3-ylmethyl}azetidine-3-carboxamide;

1-[2-(1,4-diazepan-1-yl)-5-fluoropyrimidin-4-yl]-N-{imidazo[1,2-a]pyridin-3-ylmethyl}azetidine-3-carboxamide;

1-(5-chloro-2-{3,6-diazabicyclo[3.2.0]heptan-3-yl}pyrimidin-4-yl)-N-{imidazo[1,2-a]pyridin-3-ylmethyl}azetidine-3-carboxamide;

1-(2-{3,6-diazabicyclo[3.2.0]heptan-3-yl}-5-fluoropyrimidin-4-yl)-N-{imidazo[1,2-a]pyridin-3-ylmethyl}azetidine-3-carboxamide;

1-[2-(1,4-diazepan-1-yl)-5-fluoropyrimidin-4-yl]-N-(1-{imidazo[1,2-a]pyridin-3-yl}ethyl)azetidine-3-carboxamide;

1-[5-chloro-2-(1,4-diazepan-1-yl)pyrimidin-4-yl]-N-(1-{imidazo[1,2-a]pyridin-3-yl}ethyl)azetidine-3-carboxamide;

1-[2-(1,4-diazepan-1-yl)-5-fluoropyrimidin-4-yl]-N-(2-{imidazo[1,2-a]pyridin-3-yl}propan-2-yl)azetidine-3-carboxamide;

1-[2-(1,4-diazepan-1-yl)-5-fluoropyrimidin-4-yl]-N-({2-methylimidazo[1,2-a]pyridin-3-yl}methyl)azetidine-3-carboxamide;

1-(2-{3,6-diazabicyclo[3.2.0]heptan-3-yl}-5-fluoropyrimidin-4-yl)-N-({2-methylimidazo[1,2-a]pyridin-3-yl}methyl)azetidine-3-carboxamide;

1-{5-fluoro-2-[methyl(pyrrolidin-3-yl)amino]pyrimidin-4-yl}-N-{imidazo[1,2-a]pyridin-3-ylmethyl}azetidine-3-carboxamide;

1-[5-fluoro-2-(pyrrolidin-3-ylamino)pyrimidin-4-yl]-N-{imidazo[1,2-a]pyridin-3-ylmethyl}azetidine-3-carboxamide;

1-[5-fluoro-2-(piperazin-1-yl)pyrimidin-4-yl]-N-{imidazo[1,2-a]pyridin-3-ylmethyl}azetidine-3-carboxamide;

1-[5-chloro-2-(1,4-diazepan-1-yl)pyrimidin-4-yl]-N-{imidazo[1,2-a]pyridin-3-ylmethyl}-N-methylazetidine-3-carboxamide;

1-[5-chloro-2-(1,4-diazepan-1-yl)pyrimidin-4-yl]-N-({2-methylimidazo[1,2-a]pyridin-3-yl}methyl)azetidine-3-carboxamide;

1-[2-(1,4-diazepan-1-yl)-5-methoxypyrimidin-4-yl]-N-{imidazo[1,2-a]pyridin-3-ylmethyl}azetidine-3-carboxamide;

1-[2-(1,4-diazepan-1-yl)-5-methoxypyrimidin-4-yl]-N-(2-{imidazo[1,2-a]pyridin-3-yl}propan-2-yl)azetidine-3-carboxamide;

1-[5-chloro-2-(1,4-diazepan-1-yl)pyrimidin-4-yl]-N-({6-fluoroimidazo[1,2-a]pyridin-3-yl}methyl)azetidine-3-carboxamide;

1-[5-chloro-2-(1,4-diazepan-1-yl)pyrimidin-4-yl]-N-({6-chloroimidazo[1,2-a]pyridin-3-yl}methyl)azetidine-3-carboxamide;

1-[2-(1,4-diazepan-1-yl)-5-methoxypyrimidin-4-yl]-N-(1-{2-methylimidazo[1,2-a]pyridin-3-yl}ethyl)azetidine-3-carboxamide;

1-[5-chloro-2-(1,4-diazepan-1-yl)pyrimidin-4-yl]-N-(1-{2-methylimidazo[1,2-a]pyridin-3-yl}ethyl)azetidine-3-carboxamide;

1-[5-chloro-2-(piperazin-1-yl)pyrimidin-4-yl]-N-{imidazo[1,2-a]pyridin-3-ylmethyl}azetidine-3-carboxamide;

1-{5-fluoro-2-[(3S)-3-methylpiperazin-1-yl]pyrimidin-4-yl}-N-{imidazo[1,2-a]pyridin-3-ylmethyl}azetidine-3-carboxamide;

1-{5-chloro-2-[(3S)-3-methylpiperazin-1-yl]pyrimidin-4-yl}-N-{imidazo[1,2-a]pyridin-3-ylmethyl}azetidine-3-carboxamide;

1-{5-fluoro-2-[(3R)-3-methylpiperazin-1-yl]pyrimidin-4-yl}-N-{imidazo[1,2-a]pyridin-3-ylmethyl}azetidine-3-carboxamide;

1-{5-chloro-2-[(3R)-3-methylpiperazin-1-yl]pyrimidin-4-yl}-N-{imidazo[1,2-a]pyridin-3-ylmethyl}azetidine-3-carboxamide;

1-[5-chloro-2-(piperazin-1-yl)pyrimidin-4-yl]-N-(1-{imidazo[1,2-a]pyridin-3-yl}ethyl)azetidine-3-carboxamide;

1-[5-fluoro-2-(piperazin-1-yl)pyrimidin-4-yl]-N-(1-{imidazo[1,2-a]pyridin-3-yl}ethyl)azetidine-3-carboxamide;

1-[5-fluoro-2-(piperazin-1-yl)pyrimidin-4-yl]-N-(2-{imidazo[1,2-a]pyridin-3-yl}propan-2-yl)azetidine-3-carboxamide;

1-[5-chloro-2-(piperazin-1-yl)pyrimidin-4-yl]-N-(2-{imidazo[1,2-a]pyridin-3-yl}propan-2-yl)azetidine-3-carboxamide;

N-(2-{imidazo[1,2-a]pyridin-3-yl}propan-2-yl)-1-[5-methoxy-2-(piperazin-1-yl)pyrimidin-4-yl]azetidine-3-carboxamide;

1-{5-fluoro-2-[(3R)-3-methylpiperazin-1-yl]pyrimidin-4-yl}-N-(2-{imidazo[1,2-a]pyridin-3-yl}propan-2-yl)azetidine-3-carboxamide;

N-(2-{imidazo[1,2-a]pyridin-3-yl}propan-2-yl)-1-{5-methoxy-2-[(3R)-3-methylpiperazin-1-yl]pyrimidin-4-yl}azetidine-3-carboxamide;

1-{5-chloro-2-[(3S)-3-methylpiperazin-1-yl]pyrimidin-4-yl}-N-(2-{imidazo[1,2-a]pyridin-3-yl}propan-2-yl)azetidine-3-carboxamide;

1-{5-fluoro-2-[(3S)-3-methylpiperazin-1-yl]pyrimidin-4-yl}-N-(2-{imidazo[1,2-a]pyridin-3-yl}propan-2-yl)azetidine-3-carboxamide;

N-(2-{imidazo[1,2-a]pyridin-3-yl}propan-2-yl)-1-{5-methoxy-2-[(3S)-3-methylpiperazin-1-yl]pyrimidin-4-yl}azetidine-3-carboxamide;

1-{5-fluoro-2-[methyl(pyrrolidin-3-yl)amino]pyrimidin-4-yl}-N-(2-{imidazo[1,2-a]pyridin-3-yl}propan-2-yl)azetidine-3-carboxamide;

1-{5-chloro-2-[methyl(pyrrolidin-3-yl)amino]pyrimidin-4-yl}-N-(2-{imidazo[1,2-a]pyridin-3-yl}propan-2-yl)azetidine-3-carboxamide;

1-{2-[(3R,5S)-3,5-dimethylpiperazin-1-yl]-5-methoxy-pyrimidin-4-yl}-N-(2-{imidazo[1,2-a]pyridin-3-yl}propan-2-yl)azetidine-3-carboxamide;

1-{2-[(3R,5S)-3,5-dimethylpiperazin-1-yl]-5-chloropyrimidin-4-yl}-N-(2-{imidazo[1,2-a]pyridin-3-yl}propan-2-yl)azetidine-3-carboxamide;

1-{2-[(3R,5S)-3,5-dimethylpiperazin-1-yl]-5-fluoropyrimidin-4-yl}-N-(2-{imidazo[1,2-a]pyridin-3-yl}propan-2-yl)azetidine-3-carboxamide 1-{2-[(3S,5S)-3,5-dimethylpiperazin-1-yl]-5-methoxypyrimidin-4-yl}-N-(2-{imidazo[1,2-a]pyridin-3-yl}propan-2-yl)azetidine-3-carboxamide;

1-{5-chloro-2-[(3R,5R)-3,5-dimethylpiperazin-1-yl]pyrimidin-4-yl}-N-(2-{imidazo[1,2-a]pyridin-3-yl}propan-2-yl)azetidine-3-carboxamide;

1-{2-[(3R,5R)-3,5-dimethylpiperazin-1-yl]-5-fluoropyrimidin-4-yl}-N-(2-{imidazo[1,2-a]pyridin-3-yl}propan-2-yl)azetidine-3-carboxamide;

1-{5-chloro-2-[(3S,5S)-3,5-dimethylpiperazin-1-yl]pyrimidin-4-yl}-N-(2-{imidazo[1,2-a]pyridin-3-yl}propan-2-yl)azetidine-3-carboxamide;

1-{5-fluoro-2-[(3S,5S)-3,4,5-trimethylpiperazin-1-yl]pyrimidin-4-yl}-N-(2-{imidazo[1,2-a]pyridin-3-yl}propan-2-yl)azetidine-3-carboxamide;

1-{5-chloro-2-[(2S)-2-methylpiperazin-1-yl]pyrimidin-4-yl}-N-(2-{imidazo[1,2-a]pyridin-3-yl}propan-2-yl)-N-methylazetidine-3-carboxamide;

1-[5-chloro-2-(1,4-diazepan-1-yl)pyrimidin-4-yl]-N-(2-{imidazo[1,2-a]pyridin-3-yl}propan-2-yl)azetidine-3-carboxamide 1-[5-fluoro-2-(4-methyl-1,4-diazepan-1-yl)pyrimidin-4-yl]-N-{imidazo[1,2-a]pyridin-3-ylmethyl}azetidine-3-carboxamide;

1-[5-chloro-2-(4-methyl-1,4-diazepan-1-yl)pyrimidin-4-yl]-N-(1-{imidazo[1,2-a]pyridin-3-yl}ethyl)azetidine-3-carboxamide;

1-[5-fluoro-2-(4-methylpiperazin-1-yl)pyrimidin-4-yl]-N-(2-{imidazo[1,2-a]pyridin-3-yl}propan-2-yl)azetidine-3-carboxamide;

1-[5-chloro-2-(4-methylpiperazin-1-yl)pyrimidin-4-yl]-N-(2-{imidazo[1,2-a]pyridin-3-yl}propan-2-yl)azetidine-3-carboxamide;

1-[5-fluoro-2-(4-methyl-1,4-diazepan-1-yl)pyrimidin-4-yl]-N-(2-{imidazo[1,2-a]pyridin-3-yl}propan-2-yl)azetidine-3-carboxamide;

1-[5-chloro-2-(4-methyl-1,4-diazepan-1-yl)pyrimidin-4-yl]-N-(2-{imidazo[1,2-a]pyridin-3-yl}propan-2-yl)azetidine-3-carboxamide;

1-{5-fluoro-2-[methyl(1-methylpyrrolidin-3-yl)amino]pyrimidin-4-yl}-N-(2-{imidazo[1,2-a]pyridin-3-yl}propan-2-yl)azetidine-3-carboxamide;

1-{5-chloro-2-[methyl(1-methylpyrrolidin-3-yl)amino]pyrimidin-4-yl}-N-(2-{imidazo[1,2-a]pyridin-3-yl}propan-2-yl)azetidine-3-carboxamide;

1-[5-fluoro-2-(4-methylpiperazin-1-yl)pyrimidin-4-yl]-N-(2-{6-methylimidazo[1,2-a]pyridin-3-yl}propan-2-yl)azetidine-3-carboxamide;

1-[5-fluoro-2-(4-methylpiperazin-1-yl)pyrimidin-4-yl]-N-(2-{8-fluoroimidazo[1,2-a]pyridin-3-yl}propan-2-yl)azetidine-3-carboxamide;

N-(2-{imidazo[1,2-a]pyridin-3-yl}propan-2-yl)-1-[5-methoxy-2-(4-methyl-1,4-diazepan-1-yl)pyrimidin-4-yl]azetidine-3-carboxamide;

N-(2-{imidazo[1,2-a]pyridin-3-yl}propan-2-yl)-1-[5-methoxy-2-(4-methylpiperazin-1-yl)pyrimidin-4-yl]azetidine-3-carboxamide;

1-[5-fluoro-2-(4-methylpiperazin-1-yl)pyrimidin-4-yl]-N-(2-{imidazo[1,2-a]pyridin-3-yl}propan-2-yl) pyrrolidine-3-carboxamide;

1-[5-fluoro-2-(4-methylpiperazin-1-yl)pyrimidin-4-yl]-N-(2-{imidazo[1,2-a]pyridin-3-yl}propan-2-yl)-3-methylazetidine-3-carboxamide;

N-(2-{imidazo[1,2-a]pyridin-3-yl}propan-2-yl)-1-[5-methyl-2-(4-methylpiperazin-1-yl)pyrimidin-4-yl]azetidine-3-carboxamide;

1-[5-chloro-2-(4-methylpiperazin-1-yl)pyrimidin-4-yl]-N-(2-{6-methylimidazo[1,2-a]pyridin-3-yl}propan-2-yl)azetidine-3-carboxamide;

1-{5-chloro-2-[(2R)-2,4-dimethylpiperazin-1-yl]pyrimidin-4-yl}-N-(2-{imidazo[1,2-a]pyridin-3-yl}propan-2-yl)azetidine-3-carboxamide;

1-{5-chloro-2-[3-(fluoromethyl)-4-methylpiperazin-1-yl]pyrimidin-4-yl}-N-(2-{imidazo[1,2-a]pyridin-3-yl}propan-2-yl)azetidine-3-carboxamide;

1-[5-chloro-2-(4-ethylpiperazin-1-yl)pyrimidin-4-yl]-N-(2-{imidazo[1,2-a]pyridin-3-yl}propan-2-yl)azetidine-3-carboxamide;

1-{5-chloro-2-[4-(propan-2-yl) piperazin-1-yl]pyrimidin-4-yl}-N-(2-{imidazo[1,2-a]pyridin-3-yl}propan-2-yl)azetidine-3-carboxamide;

1-{5-chloro-2-[4-(2-methoxyethyl) piperazin-1-yl]pyrimidin-4-yl}-N-(2-{imidazo[1,2-a]pyridin-3-yl}propan-2-yl)azetidine-3-carboxamide;

1-[5-chloro-2-(4-methylpiperazin-1-yl)pyrimidin-4-yl]-N-(2-{imidazo[1,2-a]pyridin-3-yl}propan-2-yl)-N-methylazetidine-3-carboxamide;

1-{5-chloro-2-[(3R)-3,4-dimethylpiperazin-1-yl]pyrimidin-4-yl}-N-(2-{imidazo[1,2-a]pyridin-3-yl}propan-2-yl)-N-methylazetidine-3-carboxamide;

(3R)-1-[5-chloro-2-(4-methylpiperazin-1-yl)pyrimidin-4-yl]-N-(2-{imidazo[1,2-a]pyridin-3-yl}propan-2-yl)pyrrolidine-3-carboxamide;

(3S)-1-[5-chloro-2-(4-methylpiperazin-1-yl)pyrimidin-4-yl]-N-(2-{imidazo[1,2-a]pyridin-3-yl}propan-2-yl)pyrrolidine-3-carboxamide;

1-[5-chloro-2-(4-methylpiperazin-1-yl)pyrimidin-4-yl]-N-(2-{imidazo[1,2-a]pyridin-3-yl}propan-2-yl) piperidine-4-carboxamide;

1-[5-fluoro-2-(4-methylpiperazin-1-yl)pyrimidin-4-yl]-N-(2-{imidazo[1,2-a]pyridin-3-yl}propan-2-yl)-N-methylazetidine-3-carboxamide;

1-{5-chloro-2-[(2S,3R)-2,3-dimethylpiperazin-1-yl]pyrimidin-4-yl}-N-(2-{imidazo[1,2-a]pyridin-3-yl}propan-2-yl)azetidine-3-carboxamide;

1-{5-chloro-2-[3-(methoxymethyl)-4-methylpiperazin-1-yl]pyrimidin-4-yl}-N-(2-{imidazo[1,2-a]pyridin-3-yl}propan-2-yl)azetidine-3-carboxamide;

1-(5-fluoro-2-{6-methyl-3,6-diazabicyclo[3.2.0]heptan-3-yl}pyrimidin-4-yl)-N-{imidazo[1,2-a]pyridin-3-ylmethyl}azetidine-3-carboxamide;

1-{2-[(3S)-3,4-dimethylpiperazin-1-yl]-5-fluoropyrimidin-4-yl}-N-(2-{imidazo[1,2-a]pyridin-3-yl}propan-2-yl)azetidine-3-carboxamide;

1-{5-chloro-2-[(3S)-3,4-dimethylpiperazin-1-yl]pyrimidin-4-yl}-N-(2-{imidazo[1,2-a]pyridin-3-yl}propan-2-yl)azetidine-3-carboxamide;

1-{2-[(3R)-3,4-dimethylpiperazin-1-yl]-5-fluoropyrimidin-4-yl}-N-(2-{imidazo[1,2-a]pyridin-3-yl}propan-2-yl)azetidine-3-carboxamide;

1-{2-[(3R)-3,4-dimethylpiperazin-1-yl]-5-methoxypyrimidin-4-yl}-N-(2-{imidazo[1,2-a]pyridin-3-yl}propan-2-yl)azetidine-3-carboxamide;

1-{2-[(3R)-3,4-dimethylpiperazin-1-yl]-5-fluoropyrimidin-4-yl}-N-(2-{imidazo[1,2-a]pyridin-3-yl}propan-2-yl) pyrrolidine-3-carboxamide;

1-{2-[(3R)-3,4-dimethylpiperazin-1-yl]-5-fluoropyrimidin-4-yl}-N-(2-{imidazo[1,2-a]pyridin-3-yl}propan-2-yl)-3-methylazetidine-3-carboxamide;

N-(2-{imidazo[1,2-a]pyridin-3-yl}propan-2-yl)-1-{5-methoxy-2-[(3R,5S)-3,4,5-trimethylpiperazin-1-yl]pyrimidin-4-yl}azetidine-3-carboxamide;

1-{5-chloro-2-[(3R,5S)-3,4,5-trimethylpiperazin-1-yl]pyrimidin-4-yl}-N-(2-{imidazo[1,2-a]pyridin-3-yl}propan-2-yl)azetidine-3-carboxamide;

1-{5-fluoro-2-[(3R,5S)-3,4,5-trimethylpiperazin-1-yl]pyrimidin-4-yl}-N-(2-{imidazo[1,2-a]pyridin-3-yl}propan-2-yl)azetidine-3-carboxamide;

N-(2-{imidazo[1,2-a]pyridin-3-yl}propan-2-yl)-1-{5-methoxy-2-[(3R,5R)-3,4,5-trimethylpiperazin-1-yl]pyrimidin-4-yl}azetidine-3-carboxamide;

1-{5-chloro-2-[(3R,5R)-3,4,5-trimethylpiperazin-1-yl]pyrimidin-4-yl}-N-(2-{imidazo[1,2-a]pyridin-3-yl}propan-2-yl)azetidine-3-carboxamide;

1-{5-fluoro-2-[(3S,5S)-3,4,5-trimethylpiperazin-1-yl]pyrimidin-4-yl}-N-(2-{imidazo[1,2-a]pyridin-3-yl}propan-2-yl)azetidine-3-carboxamide;

N-(2-{imidazo[1,2-a]pyridin-3-yl}propan-2-yl)-1-{5-methoxy-2-[(3R,5R)-3,4,5-trimethylpiperazin-1-yl]pyrimidin-4-yl}azetidine-3-carboxamide;

1-{5-chloro-2-[(3R,5R)-3,4,5-trimethylpiperazin-1-yl]pyrimidin-4-yl}-N-(2-{imidazo[1,2-a]pyridin-3-yl}propan-2-yl)azetidine-3-carboxamide;

1-{5-fluoro-2-[(3S,5S)-3,4,5-trimethylpiperazin-1-yl]pyrimidin-4-yl}-N-(2-{imidazo[1,2-a]pyridin-3-yl}propan-2-yl)azetidine-3-carboxamide;

1-{2-[(3R)-3,4-dimethylpiperazin-1-yl]-5-fluoropyrimidin-4-yl}-N-(2-{6-methylimidazo[1,2-a]pyridin-3-yl}propan-2-yl)azetidine-3-carboxamide;

1-{5-chloro-2-[(3R)-3,4-dimethylpiperazin-1-yl]pyrimidin-4-yl}-N-(2-{6-methylimidazo[1,2-a]pyridin-3-yl}propan-2-yl)azetidine-3-carboxamide;

(3R)-1-{5-chloro-2-[(3R)-3,4-dimethylpiperazin-1-yl]pyrimidin-4-yl}-N-(2-{imidazo[1,2-a]pyridin-3-yl}propan-2-yl) pyrrolidine-3-carboxamide;

(3S)-1-{5-chloro-2-[(3R)-3,4-dimethylpiperazin-1-yl]pyrimidin-4-yl}-N-(2-{imidazo[1,2-a]pyridin-3-yl}propan-2-yl) pyrrolidine-3-carboxamide;

1-{5-chloro-2-[(3R)-3,4-dimethylpiperazin-1-yl]pyrimidin-4-yl}-N-(2-{imidazo[1,2-a]pyridin-3-yl}propan-2-yl) piperidine-4-carboxamide;

1-{2-[(3R)-3,4-dimethylpiperazin-1-yl]-5-fluoropyrimidin-4-yl}-N-(2-{imidazo[1,2-a]pyridin-3-yl}propan-2-yl)-N-methylazetidine-3-carboxamide;

1-{5-chloro-2-[(3R)-3,4-dimethylpiperazin-1-yl]pyridin-4-yl}-N-(2-{imidazo[1,2-a]pyridin-3-yl}propan-2-yl)azetidine-3-carboxamide;

1-{2-[(3R)-3,4-dimethylpiperazin-1-yl]-5-fluoropyridin-4-yl}-N-(2-{imidazo[1,2-a]pyridin-3-yl}propan-2-yl)azetidine-3-carboxamide;

1-[5-chloro-2-(4-methylpiperazin-1-yl) pyridin-4-yl]-N-(2-{imidazo[1,2-a]pyridin-3-yl}propan-2-yl)azetidine-3-carboxamide;

1-{5-chloro-2-[(2S)-2,4-dimethylpiperazin-1-yl]pyrimidin-4-yl}-N-{imidazo[1,2-a]pyridin-3-ylmethyl}-N-methylazetidine-3-carboxamide;

1-{5-chloro-2-[(2S)-2,4-dimethylpiperazin-1-yl]pyrimidin-4-yl}-N-(2-{imidazo[1,2-a]pyridin-3-yl}propan-2-yl)-N-methylazetidine-3-carboxamide;

1-{2-[(2S)-2,4-dimethylpiperazin-1-yl]-5-fluoropyrimidin-4-yl}-N-(2-{imidazo[1,2-a]pyridin-3-yl}propan-2-yl)-N-methylazetidine-3-carboxamide;

1-{5-chloro-2-[(2S,5R)-2,4,5-trimethylpiperazin-1-yl]pyrimidin-4-yl}-N-(2-{imidazo[1,2-a]pyridin-3-yl}propan-2-yl)azetidine-3-carboxamide;

1-{5-chloro-2-[(2R,5R)-2,4,5-trimethylpiperazin-1-yl] pyrimidin-4-yl}-N-(2-{imidazo[1,2-a]pyridin-3-yl}propan-2-yl)azetidine-3-carboxamide;

1-{5-fluoro-2-[(2S,5R)-2,4,5-trimethylpiperazin-1-yl]pyrimidin-4-yl}-N-(2-{imidazo[1,2-a]pyridin-3-yl}propan-2-yl)azetidine-3-carboxamide;

1-[5-chloro-2-(1,4-diazepan-1-yl)pyrimidin-4-yl]-N-{[1,2,4]triazolo[4,3-a]pyridin-3-ylmethyl}azetidine-3-carboxamide;

N-(2-(imidazo[1,2-a]pyridin-3-yl)propan-2-yl)-1-(2-(4-methyl-1,4-diazepan-1-yl)quinazolin-4-yl)azetidine-3-carboxamide;

N-(2-(imidazo[1,2-a]pyridin-3-yl)propan-2-yl)-1-(2-(4-methyl-1,4-diazepan-1-yl)thieno[2,3-d]pyrimidin-4-yl)azetidine-3-carboxamide;

N-(2-(imidazo[1,2-a]pyridin-3-yl)propan-2-yl)-1-(2-(4-methyl-1,4-diazepan-1-yl)-6,7-dihydro-5H-cyclopenta[d]pyrimidin-4-yl)azetidine-3-carboxamide;

1-(5-chloro-6-methyl-2-(4-methyl-1,4-diazepan-1-yl)pyrimidin-4-yl)-N-(2-(imidazo[1,2-a]pyridin-3-yl)propan-2-yl)azetidine-3-carboxamide;

N-(2-(imidazo[1,2-a]pyridin-3-yl)propan-2-yl)-1-(6-methyl-2-(4-methyl-1,4-diazepan-1-yl)thieno[3,2-d]pyrimidin-4-yl)azetidine-3-carboxamide;

N-(2-(imidazo[1,2-a]pyridin-3-yl)propan-2-yl)-1-(6-methyl-2-(4-methyl-1,4-diazepan-1-yl)thieno[2,3-d]pyrimidin-4-yl)azetidine-3-carboxamide;

1-(2-(1,4-diazepan-1-yl)thieno[3,2-d]pyrimidin-4-yl)-N-(2-(imidazo[1,2-a]pyridin-3-yl)propan-2-yl)azetidine-3-carboxamide;

1-(5-chloro-2-(piperazin-1-yl)pyrimidin-4-yl)-N-(2-(imidazo[1,2-a]pyridin-3-yl)propan-2-yl)-N-methylazetidine-3-carboxamide;

1-(5-chloro-2-(1,4-diazepan-1-yl)pyrimidin-4-yl)-N-(2-(imidazo[1,2-a]pyridin-3-yl)propan-2-yl)-N-methyl-azetidine-3-carboxamide;

1-(5-chloro-2-(4-methyl-1,4-diazepan-1-yl)pyrimidin-4-yl)-N-(2-(imidazo[1,2-a]pyridin-3-yl)propan-2-yl)-N-methylazetidine-3-carboxamide;

N-(2-(imidazo[1,2-a]pyridin-3-yl)propan-2-yl)-N-methyl-1-(2-(4-methyl-1,4-diazepan-1-yl)thieno[3,2-d]pyrimidin-4-yl)azetidine-3-carboxamide;

(R)-1-(5-chloro-2-(3-methylpiperazin-1-yl)pyrimidin-4-yl)-N-(2-(imidazo[1,2-a]pyridin-3-yl)propan-2-yl)-N-methylazetidine-3-carboxamide;

(S)—N-(2-(imidazo[1,2-a]pyridin-3-yl)propan-2-yl)-N-methyl-1-(2-(2-methylpiperazin-1-yl)thieno[3,2-d]pyrimidin-4-yl)azetidine-3-carboxamide;

(S)—N-(2-(imidazo[1,2-a]pyridin-3-yl)propan-2-yl)-1-(2-(2-methylpiperazin-1-yl)thieno[3,2-d]pyrimidin-4-yl)azetidine-3-carboxamide;

1-(5-chloro-2-(3,3-dimethylpiperazin-1-yl)pyrimidin-4-yl)-N-(2-(imidazo[1,2-a]pyridin-3-yl)propan-2-yl)-N-methylazetidine-3-carboxamide;

1-(2-(4-aminopiperidin-1-yl)-5-chloropyrimidin-4-yl)-N-(2-(imidazo[1,2-a]pyridin-3-yl)propan-2-yl)-N-methylazetidine-3-carboxamide;

1-(5-chloro-2-(4,7-diazaspiro[2.5]octan-7-yl)pyrimidin-4-yl)-N-(2-(imidazo[1,2-a]pyridin-3-yl)propan-2-yl)-N-methylazetidine-3-carboxamide;

1-(2-(4-aminoazepan-1-yl)-5-chloropyrimidin-4-yl)-N-(2-(imidazo[1,2-a]pyridin-3-yl)propan-2-yl)-N-methylazetidine-3-carboxamide;

1-(2-(2,5-diazabicyclo[2.2.1]heptan-2-yl)-5-chloropyrimidin-4-yl)-N-(2-(imidazo[1,2-a]pyridin-3-yl)propan-2-yl)-N-methylazetidine-3-carboxamide;

1-(2-(3,8-diazabicyclo[3.2.1]octan-3-yl)-5-chloropyrimidin-4-yl)-N-(2-(imidazo[1,2-a]pyridin-3-yl)propan-2-yl)-N-methylazetidine-3-carboxamide;

1-(5-chloro-2-(2,3-dimethylpiperazin-1-yl)pyrimidin-4-yl)-N-(2-(imidazo[1,2-a]pyridin-3-yl)propan-2-yl)-N-methylazetidine-3-carboxamide;

(S)—N-(2-(imidazo[1,2-a]pyridin-3-yl)propan-2-yl)-N-methyl-1-(2-(2-methylpiperazin-1-yl)-5-(trifluoromethyl)pyrimidin-4-yl)azetidine-3-carboxamide;

1-(5-chloro-2-(piperazin-1-yl)pyrimidin-4-yl)-N-ethyl-N-(2-(imidazo[1,2-a]pyridin-3-yl)propan-2-yl)azetidine-3-carboxamide;

1-(5-chloro-2-(3-ethylpiperazin-1-yl)pyrimidin-4-yl)-N-(2-(imidazo[1,2-a]pyridin-3-yl)propan-2-yl)azetidine-3-carboxamide;

(R)-1-(5-chloro-2-(2-methylpiperazin-1-yl)pyrimidin-4-yl)-N-(2-(imidazo[1,2-a]pyridin-3-yl)propan-2-yl)-N-methylazetidine-3-carboxamide;

(R)-1-(5-chloro-2-(2,4-dimethylpiperazin-1-yl)pyrimidin-4-yl)-N-(2-(imidazo[1,2-a]pyridin-3-yl)propan-2-yl)-N-methylazetidine-3-carboxamide;

(S)-1-(5-chloro-2-(3-methylpiperazin-1-yl)pyrimidin-4-yl)-N-(2-(imidazo[1,2-a]pyridin-3-yl)propan-2-yl)-N-methylazetidine-3-carboxamide;

(S)-1-(5-chloro-2-(3,4-dimethylpiperazin-1-yl)pyrimidin-4-yl)-N-(2-(imidazo[1,2-a]pyridin-3-yl)propan-2-yl)-N-methylazetidine-3-carboxamide;

(R)-1-(5-chloro-2-(2-methylpiperazin-1-yl)pyrimidin-4-yl)-N-(2-(imidazo[1,2-a]pyridin-3-yl)propan-2-yl)azetidine-3-carboxamide;

1-(5-chloro-2-(2,3-dimethylpiperazin-1-yl)pyrimidin-4-yl)-N-(2-(imidazo[1,2-a]pyridin-3-yl)propan-2-yl)aze-tidine-3-carboxamide;

(S)-1-(5-chloro-2-(2-methylpiperazin-1-yl)pyrimidin-4-yl)-N-ethyl-N-(2-(imidazo[1,2-a]pyridin-3-yl)propan-2-yl)azetidine-3-carboxamide;

1-(2-(3,8-diazabicyclo[3.2.1]octan-3-yl)-5-chloropyrimi-din-4-yl)-N-(2-(imidazo[1,2-a]pyridin-3-yl)propan-2-yl)azetidine-3-carboxamide;

1-(2-(2,5-diazabicyclo[4.1.0]heptan-2-yl)-5-chloropy-rimidin-4-yl)-N-(2-(imidazo[1,2-a]pyridin-3-yl)pro-pan-2-yl)-N-methylazetidine-3-carboxamide;

(S)-1-(5-chloro-2-(2-methylpiperazin-1-yl)pyrimidin-4-yl)-N-(2-(imidazo[1,2-a]pyridin-3-yl)propan-2-yl)aze-tidine-3-carboxamide;

(S)-1-(5-chloro-2-(2-ethylpiperazin-1-yl)pyrimidin-4-yl)-N-(2-(imidazo[1,2-a]pyridin-3-yl)propan-2-yl)azeti-dine-3-carboxamide;

(S)-1-(5-chloro-2-(2-ethylpiperazin-1-yl)pyrimidin-4-yl)-N-(2-(imidazo[1,2-a]pyridin-3-yl)propan-2-yl)-N-methylazetidine-3-carboxamide:

1-(5-chloro-2-(2,2-dimethylpiperazin-1-yl)pyrimidin-4-yl)-N-(2-(imidazo[1,2-a]pyridin-3-yl)propan-2-yl)-N-methylazetidine-3-carboxamide;

1-(5-chloro-2-(4,7-diazaspiro[2.5]octan-4-yl)pyrimidin-4-yl)-N-(2-(imidazo[1,2-a]pyridin-3-yl)propan-2-yl)-N-methylazetidine-3-carboxamide;

1-(5-chloro-2-((2S,5S)-2,5-dimethylpiperazin-1-yl)py-rimidin-4-yl)-N-(2-(imidazo[1,2-a]pyridin-3-yl)pro-pan-2-yl)azetidine-3-carboxamide;

1-(5-chloro-2-((2S,5S)-2,4,5-trimethylpiperazin-1-yl)py-rimidin-4-yl)-N-(2-(imidazo[1,2-a]pyridin-3-yl)pro-pan-2-yl)azetidine-3-carboxamide;

1-(5-chloro-2-((2S,5R)-2,5-dimethylpiperazin-1-yl)py-rimidin-4-yl)-N-(2-(imidazo[1,2-a]pyridin-3-yl)pro-pan-2-yl)azetidine-3-carboxamide; and 1-(5-chloro-2-((2S,5R)-2,4,5-trimethylpiperazin-1-yl)py-rimidin-4-yl)-N-(2-(imidazo[1,2-a]pyridin-3-yl)pro-pan-2-yl)azetidine-3-carboxamide;

or a pharmaceutically acceptable ester, amide, carbamate and salt thereof.

17. A compound or a pharmaceutically acceptable ester, amide, carbamage or salt thereof as claimed in claim 2, wherein the compound or a pharmaceutically acceptable ester, amide, carbamate or salt thereof is selected from the group consisting of:

1-{5-chloro-2-[(3R)-3-methylpiperazin-1-yl]pyrimidin-4-yl}-N-(2-{imidazo[1,2-a]pyridin-3-yl}propan-2-yl)azetidine-3-carboxamide;

1-{5-chloro-2-[(2R)-2,4-dimethylpiperazin-1-yl]pyrimi-din-4-yl}-N-(2-{imidazo[1,2-a]pyridin-3-yl}propan-2-yl)azetidine-3-carboxamide;

1-{5-chloro-2-[(3R)-3,4-dimethylpiperazin-1-yl]pyrimi-din-4-yl}-N-(2-{imidazo[1,2-a]pyridin-3-yl}propan-2-yl)azetidine-3-carboxamide;

1-[5-fluoro-2-(4-methylpiperazin-1-yl)  pyridin-4-yl]-N-(2-{imidazo[1,2-a]pyridin-3-yl}propan-2-yl)azetidine-3-carboxamide;

1-[5-chloro-2-(1,4-diazepan-1-yl)pyrimidin-4-yl]-N-{imidazo[1,2-a]pyridin-3-ylmethyl}azetidine-3-car-boxamide;

1-[2-(1,4-diazepan-1-yl)-5-fluoropyrimidin-4-yl]-N-{imidazo[1,2-a]pyridin-3-ylmethyl}azetidine-3-car-boxamide;

1-(5-chloro-2-{3,6-diazabicyclo[3.2.0]heptan-3-yl}pyrimidin-4-yl)-N-{imidazo[1,2-a]pyridin-3-ylmethyl}azetidine-3-carboxamide;

1-(2-{3,6-diazabicyclo[3.2.0]heptan-3-yl}-5-fluoropy-rimidin-4-yl)-N-{imidazo[1,2-a]pyridin-3-ylmethyl}azetidine-3-carboxamide;

1-[2-(1,4-diazepan-1-yl)-5-fluoropyrimidin-4-yl]-N-(1-{imidazo[1,2-a]pyridin-3-yl}ethyl)azetidine-3-carbox-amide;

1-[5-chloro-2-(1,4-diazepan-1-yl)pyrimidin-4-yl]-N-(1-{imidazo[1,2-a]pyridin-3-yl}ethyl)azetidine-3-carbox-amide;

1-[2-(1,4-diazepan-1-yl)-5-fluoropyrimidin-4-yl]-N-(2-{imidazo[1,2-a]pyridin-3-yl}propan-2-yl)azetidine-3-carboxamide;

1-[2-(1,4-diazepan-1-yl)-5-fluoropyrimidin-4-yl]-N-({2-methylimidazo[1,2-a]pyridin-3-yl}methyl)azetidine-3-carboxamide;

1-(2-{3,6-diazabicyclo[3.2.0]heptan-3-yl}-5-fluoropy-rimidin-4-yl)-N-({2-methylimidazo[1,2-a]pyridin-3-yl}methyl)azetidine-3-carboxamide;

1-{5-fluoro-2-[methyl(pyrrolidin-3-yl)amino]pyrimidin-4-yl}-N-{imidazo[1,2-a]pyridin-3-ylmethyl}azetidine-3-carboxamide;

1-[5-fluoro-2-(pyrrolidin-3-ylamino)pyrimidin-4-yl]-N-{imidazo[1,2-a]pyridin-3-ylmethyl}azetidine-3-car-boxamide;

1-[5-fluoro-2-(piperazin-1-yl)pyrimidin-4-yl]-N-{imi-dazo[1,2-a]pyridin-3-ylmethyl}azetidine-3-carboxam-ide;

1-[5-chloro-2-(1,4-diazepan-1-yl)pyrimidin-4-yl]-N-{imidazo[1,2-a]pyridin-3-ylmethyl}-N-methylazeti-dine-3-carboxamide;

1-[5-chloro-2-(1,4-diazepan-1-yl)pyrimidin-4-yl]-N-({2-methylimidazo[1,2-a]pyridin-3-yl}methyl)azetidine-3-carboxamide;

1-[2-(1,4-diazepan-1-yl)-5-methoxypyrimidin-4-yl]-N-{imidazo[1,2-a]pyridin-3-ylmethyl}azetidine-3-car-boxamide;

1-[2-(1,4-diazepan-1-yl)-5-methoxypyrimidin-4-yl]-N-(2-{imidazo[1,2-a]pyridin-3-yl}propan-2-yl)azetidine-3-carboxamide;

1-[5-chloro-2-(1,4-diazepan-1-yl)pyrimidin-4-yl]-N-({6-fluoroimidazo[1,2-a]pyridin-3-yl}methyl)azetidine-3-carboxamide;

1-[5-chloro-2-(1,4-diazepan-1-yl)pyrimidin-4-yl]-N-({6-chloroimidazo[1,2-a]pyridin-3-yl}methyl)azetidine-3-carboxamide;

1-[2-(1,4-diazepan-1-yl)-5-methoxypyrimidin-4-yl]-N-(1-{2-methylimidazo[1,2-a]pyridin-3-yl}ethyl)azeti-dine-3-carboxamide;

1-[5-chloro-2-(1,4-diazepan-1-yl)pyrimidin-4-yl]-N-(1-{2-methylimidazo[1,2-a]pyridin-3-yl}ethyl)azetidine-3-carboxamide;

1-[5-chloro-2-(piperazin-1-yl)pyrimidin-4-yl]-N-{imi-dazo[1,2-a]pyridin-3-ylmethyl}azetidine-3-carboxam-ide;

1-{5-fluoro-2-[(3S)-3-methylpiperazin-1-yl]pyrimidin-4-yl}-N-{imidazo[1,2-a]pyridin-3-ylmethyl}azetidine-3-carboxamide;

1-{5-chloro-2-[(3S)-3-methylpiperazin-1-yl]pyrimidin-4-yl}-N-{imidazo[1,2-a]pyridin-3-ylmethyl}azetidine-3-carboxamide;

1-{5-fluoro-2-[(3R)-3-methylpiperazin-1-yl]pyrimidin-4-yl}-N-{imidazo[1,2-a]pyridin-3-ylmethyl}azetidine-3-carboxamide;

1-{5-chloro-2-[(3R)-3-methylpiperazin-1-yl]pyrimidin-4-yl}-N-{imidazo[1,2-a]pyridin-3-ylmethyl}azetidine-3-carboxamide;

1-[5-chloro-2-(piperazin-1-yl)pyrimidin-4-yl]-N-(1-{imidazo[1,2-a]pyridin-3-yl}ethyl)azetidine-3-carboxamide;

1-[5-fluoro-2-(piperazin-1-yl)pyrimidin-4-yl]-N-(1-{imidazo[1,2-a]pyridin-3-yl}ethyl)azetidine-3-carboxamide;

1-[5-fluoro-2-(piperazin-1-yl)pyrimidin-4-yl]-N-(2-{imidazo[1,2-a]pyridin-3-yl}propan-2-yl)azetidine-3-carboxamide;

1-[5-chloro-2-(piperazin-1-yl)pyrimidin-4-yl]-N-(2-{imidazo[1,2-a]pyridin-3-yl}propan-2-yl)azetidine-3-carboxamide;

N-(2-{imidazo[1,2-a]pyridin-3-yl}propan-2-yl)-1-[5-methoxy-2-(piperazin-1-yl)pyrimidin-4-yl]azetidine-3-carboxamide;

1-{5-fluoro-2-[(3R)-3-methylpiperazin-1-yl]pyrimidin-4-yl}-N-(2-{imidazo[1,2-a]pyridin-3-yl}propan-2-yl)azetidine-3-carboxamide;

N-(2-{imidazo[1,2-a]pyridin-3-yl}propan-2-yl)-1-{5-methoxy-2-[(3R)-3-methylpiperazin-1-yl]pyrimidin-4-yl}azetidine-3-carboxamide;

1-{5-chloro-2-[(3S)-3-methylpiperazin-1-yl]pyrimidin-4-yl}-N-(2-{imidazo[1,2-a]pyridin-3-yl}propan-2-yl)azetidine-3-carboxamide;

1-{5-fluoro-2-[(3S)-3-methylpiperazin-1-yl]pyrimidin-4-yl}-N-(2-{imidazo[1,2-a]pyridin-3-yl}propan-2-yl)azetidine-3-carboxamide;

N-(2-{imidazo[1,2-a]pyridin-3-yl}propan-2-yl)-1-{5-methoxy-2-[(3S)-3-methylpiperazin-1-yl]pyrimidin-4-yl}azetidine-3-carboxamide;

1-{5-fluoro-2-[methyl(pyrrolidin-3-yl)amino]pyrimidin-4-yl}-N-(2-{imidazo[1,2-a]pyridin-3-yl}propan-2-yl)azetidine-3-carboxamide;

1-{5-chloro-2-[methyl(pyrrolidin-3-yl)amino]pyrimidin-4-yl}-N-(2-{imidazo[1,2-a]pyridin-3-yl}propan-2-yl)azetidine-3-carboxamide;

1-{2-[(3R,5S)-3,5-dimethylpiperazin-1-yl]-5-methoxy-pyrimidin-4-yl}-N-(2-{imidazo[1,2-a]pyridin-3-yl}propan-2-yl)azetidine-3-carboxamide;

1-{2-[(3R,5S)-3,5-dimethylpiperazin-1-yl]-5-chloropyrimidin-4-yl}-N-(2-{imidazo[1,2-a]pyridin-3-yl}propan-2-yl)azetidine-3-carboxamide;

1-{2-[(3R,5S)-3,5-dimethylpiperazin-1-yl]-5-fluoropyrimidin-4-yl}-N-(2-{imidazo[1,2-a]pyridin-3-yl}propan-2-yl)azetidine-3-carboxamide;

1-{2-[(3S,5S)-3,5-dimethylpiperazin-1-yl]-5-methoxypyrimidin-4-yl}-N-(2-{imidazo[1,2-a]pyridin-3-yl}propan-2-yl)azetidine-3-carboxamide;

1-{5-chloro-2-[(3S,5S)-3,5-dimethylpiperazin-1-yl]pyrimidin-4-yl}-N-(2-{imidazo[1,2-a]pyridin-3-yl}propan-2-yl)azetidine-3-carboxamide;

1-{2-[(3S,5S)-3,5-dimethylpiperazin-1-yl]-5-fluoropyrimidin-4-yl}-N-(2-{imidazo[1,2-a]pyridin-3-yl}propan-2-yl)azetidine-3-carboxamide;

1-{5-chloro-2-[(3R,5R)-3,5-dimethylpiperazin-1-yl]pyrimidin-4-yl}-N-(2-{imidazo[1,2-a]pyridin-3-yl}propan-2-yl)azetidine-3-carboxamide;

1-{5-fluoro-2-[(3R,5R)-3,4,5-trimethylpiperazin-1-yl]pyrimidin-4-yl}-N-(2-{imidazo[1,2-a]pyridin-3-yl}propan-2-yl)azetidine-3-carboxamide;

1-{5-fluoro-2-[(3S,5S)-3,5-dimethylpiperazin-1-yl]pyrimidin-4-yl}-N-(2-{imidazo[1,2-a]pyridin-3-yl}propan-2-yl)azetidine-3-carboxamide;

1-{5-chloro-2-[(2R)-2-methylpiperazin-1-yl]pyrimidin-4-yl}-N-(2-{imidazo[1,2-a]pyridin-3-yl}propan-2-yl)-N-methylazetidine-3-carboxamide;

1-[5-chloro-2-(1,4-diazepan-1-yl)pyrimidin-4-yl]-N-(2-{imidazo[1,2-a]pyridin-3-yl}propan-2-yl)azetidine-3-carboxamide 1-[5-fluoro-2-(4-methyl-1,4-diazepan-1-yl)pyrimidin-4-yl]-N-{imidazo[1,2-a]pyridin-3-ylmethyl}azetidine-3-carboxamide;

1-[5-chloro-2-(4-methyl-1,4-diazepan-1-yl)pyrimidin-4-yl]-N-(1-{imidazo[1,2-a]pyridin-3-yl}ethyl)azetidine-3-carboxamide;

1-[5-fluoro-2-(4-methylpiperazin-1-yl)pyrimidin-4-yl]-N-(2-{imidazo[1,2-a]pyridin-3-yl}propan-2-yl)azetidine-3-carboxamide;

1-[5-chloro-2-(4-methylpiperazin-1-yl)pyrimidin-4-yl]-N-(2-{imidazo[1,2-a]pyridin-3-yl}propan-2-yl)azetidine-3-carboxamide;

1-[5-fluoro-2-(4-methyl-1,4-diazepan-1-yl)pyrimidin-4-yl]-N-(2-{imidazo[1,2-a]pyridin-3-yl}propan-2-yl)azetidine-3-carboxamide;

1-[5-chloro-2-(4-methyl-1,4-diazepan-1-yl)pyrimidin-4-yl]-N-(2-{imidazo[1,2-a]pyridin-3-yl}propan-2-yl)azetidine-3-carboxamide;

1-{5-fluoro-2-[methyl(1-methylpyrrolidin-3-yl)amino]pyrimidin-4-yl}-N-(2-{imidazo[1,2-a]pyridin-3-yl}propan-2-yl)azetidine-3-carboxamide;

1-{5-chloro-2-[methyl(1-methylpyrrolidin-3-yl)amino]pyrimidin-4-yl}-N-(2-{imidazo[1,2-a]pyridin-3-yl}propan-2-yl)azetidine-3-carboxamide;

1-[5-fluoro-2-(4-methylpiperazin-1-yl)pyrimidin-4-yl]-N-(2-{6-methylimidazo[1,2-a]pyridin-3-yl}propan-2-yl)azetidine-3-carboxamide;

1-[5-fluoro-2-(4-methylpiperazin-1-yl)pyrimidin-4-yl]-N-(2-{8-fluoroimidazo[1,2-a]pyridin-3-yl}propan-2-yl)azetidine-3-carboxamide;

N-(2-{imidazo[1,2-a]pyridin-3-yl}propan-2-yl)-1-[5-methoxy-2-(4-methyl-1,4-diazepan-1-yl)pyrimidin-4-yl]azetidine-3-carboxamide;

N-(2-{imidazo[1,2-a]pyridin-3-yl}propan-2-yl)-1-[5-methoxy-2-(4-methylpiperazin-1-yl)pyrimidin-4-yl]azetidine-3-carboxamide;

1-[5-fluoro-2-(4-methylpiperazin-1-yl)pyrimidin-4-yl]-N-(2-{imidazo[1,2-a]pyridin-3-yl}propan-2-yl) pyrrolidine-3-carboxamide;

1-[5-fluoro-2-(4-methylpiperazin-1-yl)pyrimidin-4-yl]-N-(2-{imidazo[1,2-a]pyridin-3-yl}propan-2-yl)-3-methylazetidine-3-carboxamide;

N-(2-{imidazo[1,2-a]pyridin-3-yl}propan-2-yl)-1-[5-methyl-2-(4-methylpiperazin-1-yl)pyrimidin-4-yl]azetidine-3-carboxamide;

1-[5-chloro-2-(4-methylpiperazin-1-yl)pyrimidin-4-yl]-N-(2-{6-methylimidazo[1,2-a]pyridin-3-yl}propan-2-yl)azetidine-3-carboxamide;

1-{5-chloro-2-[(2S)-2,4-dimethylpiperazin-1-yl]pyrimidin-4-yl}-N-(2-{imidazo[1,2-a]pyridin-3-yl}propan-2-yl)azetidine-3-carboxamide;

1-{5-chloro-2-[3-(fluoromethyl)-4-methylpiperazin-1-yl]pyrimidin-4-yl}-N-(2-{imidazo[1,2-a]pyridin-3-yl}propan-2-yl)azetidine-3-carboxamide;

1-[5-chloro-2-(4-ethylpiperazin-1-yl)pyrimidin-4-yl]-N-(2-{imidazo[1,2-a]pyridin-3-yl}propan-2-yl)azetidine-3-carboxamide;

1-{5-chloro-2-[4-(propan-2-yl) piperazin-1-yl]pyrimidin-4-yl}-N-(2-{imidazo[1,2-a]pyridin-3-yl}propan-2-yl)azetidine-3-carboxamide;

1-{5-chloro-2-[4-(2-methoxyethyl) piperazin-1-yl]pyrimidin-4-yl}-N-(2-{imidazo[1,2-a]pyridin-3-yl}propan-2-yl)azetidine-3-carboxamide;

1-[5-chloro-2-(4-methylpiperazin-1-yl)pyrimidin-4-yl]-N-(2-{imidazo[1,2-a]pyridin-3-yl}propan-2-yl)-N-methylazetidine-3-carboxamide;

1-{5-chloro-2-[(3R)-3,4-dimethylpiperazin-1-yl]pyrimidin-4-yl}-N-(2-{imidazo[1,2-a]pyridin-3-yl}propan-2-yl)-N-methylazetidine-3-carboxamide;

(3R)-1-[5-chloro-2-(4-methylpiperazin-1-yl)pyrimidin-4-yl]-N-(2-{imidazo[1,2-a]pyridin-3-yl}propan-2-yl)pyrrolidine-3-carboxamide;

(3S)-1-[5-chloro-2-(4-methylpiperazin-1-yl)pyrimidin-4-yl]-N-(2-{imidazo[1,2-a]pyridin-3-yl}propan-2-yl)pyrrolidine-3-carboxamide;

1-[5-chloro-2-(4-methylpiperazin-1-yl)pyrimidin-4-yl]-N-(2-{imidazo[1,2-a]pyridin-3-yl}propan-2-yl) piperidine-4-carboxamide;

1-[5-fluoro-2-(4-methylpiperazin-1-yl)pyrimidin-4-yl]-N-(2-{imidazo[1,2-a]pyridin-3-yl}propan-2-yl)-N-methylazetidine-3-carboxamide;

1-{5-chloro-2-[(2S,3R)-2,3-dimethylpiperazin-1-yl]pyrimidin-4-yl}-N-(2-{imidazo[1,2-a]pyridin-3-yl}propan-2-yl)azetidine-3-carboxamide;

1-{5-chloro-2-[3-(methoxymethyl)-4-methylpiperazin-1-yl]pyrimidin-4-yl}-N-(2-{imidazo[1,2-a]pyridin-3-yl}propan-2-yl)azetidine-3-carboxamide;

1-(5-fluoro-2-{6-methyl-3,6-diazabicyclo[3.2.0]heptan-3-yl}pyrimidin-4-yl)-N-{imidazo[1,2-a]pyridin-3-ylmethyl}azetidine-3-carboxamide;

1-{2-[(3S)-3,4-dimethylpiperazin-1-yl]-5-fluoropyrimidin-4-yl}-N-(2-{imidazo[1,2-a]pyridin-3-yl}propan-2-yl)azetidine-3-carboxamide;

1-{5-chloro-2-[(3S)-3,4-dimethylpiperazin-1-yl]pyrimidin-4-yl}-N-(2-{imidazo[1,2-a]pyridin-3-yl}propan-2-yl)azetidine-3-carboxamide;

1-{2-[(3R)-3,4-dimethylpiperazin-1-yl]-5-fluoropyrimidin-4-yl}-N-(2-{imidazo[1,2-a]pyridin-3-yl}propan-2-yl)azetidine-3-carboxamide;

1-{2-[(3S)-3,4-dimethylpiperazin-1-yl]-5-methoxypyrimidin-4-yl}-N-(2-{imidazo[1,2-a]pyridin-3-yl}propan-2-yl)azetidine-3-carboxamide;

1-{2-[(3R)-3,4-dimethylpiperazin-1-yl]-5-fluoropyrimidin-4-yl}-N-(2-{imidazo[1,2-a]pyridin-3-yl}propan-2-yl) pyrrolidine-3-carboxamide;

1-{2-[(3S)-3,4-dimethylpiperazin-1-yl]-5-fluoropyrimidin-4-yl}-N-(2-{imidazo[1,2-a]pyridin-3-yl}propan-2-yl)-3-methylazetidine-3-carboxamide;

N-(2-{imidazo[1,2-a]pyridin-3-yl}propan-2-yl)-1-{5-methoxy-2-[(3R,5S)-3,4,5-trimethylpiperazin-1-yl]pyrimidin-4-yl}azetidine-3-carboxamide;

1-{5-chloro-2-[(3R,5S)-3,4,5-trimethylpiperazin-1-yl]pyrimidin-4-yl}-N-(2-{imidazo[1,2-a]pyridin-3-yl}propan-2-yl)azetidine-3-carboxamide;

1-{5-fluoro-2-[(3R,5S)-3,4,5-trimethylpiperazin-1-yl]pyrimidin-4-yl}-N-(2-{imidazo[1,2-a]pyridin-3-yl}propan-2-yl)azetidine-3-carboxamide;

N-(2-{imidazo[1,2-a]pyridin-3-yl}propan-2-yl)-1-{5-methoxy-2-[(3S,5S)-3,4,5-trimethylpiperazin-1-yl]pyrimidin-4-yl}azetidine-3-carboxamide;

1-{5-chloro-2-[(3S,5S)-3,4,5-trimethylpiperazin-1-yl]pyrimidin-4-yl}-N-(2-{imidazo[1,2-a]pyridin-3-yl}propan-2-yl)azetidine-3-carboxamide;

1-{5-fluoro-2-[(3S,5S)-3,4,5-trimethylpiperazin-1-yl]pyrimidin-4-yl}-N-(2-{imidazo[1,2-a]pyridin-3-yl}propan-2-yl)azetidine-3-carboxamide;

N-(2-{imidazo[1,2-a]pyridin-3-yl}propan-2-yl)-1-{5-methoxy-2-[(3R,5R)-3,4,5-trimethylpiperazin-1-yl]pyrimidin-4-yl}azetidine-3-carboxamide;

1-{5-chloro-2-[(3R,5R)-3,4,5-trimethylpiperazin-1-yl]pyrimidin-4-yl}-N-(2-{imidazo[1,2-a]pyridin-3-yl}propan-2-yl)azetidine-3-carboxamide;

1-{5-fluoro-2-[(3R,5R)-3,4,5-trimethylpiperazin-1-yl]pyrimidin-4-yl}-N-(2-{imidazo[1,2-a]pyridin-3-yl}propan-2-yl)azetidine-3-carboxamide;

1-{2-[(3R)-3,4-dimethylpiperazin-1-yl]-5-fluoropyrimidin-4-yl}-N-(2-{6-methylimidazo[1,2-a]pyridin-3-yl}propan-2-yl)azetidine-3-carboxamide;

1-{5-chloro-2-[(3R)-3,4-dimethylpiperazin-1-yl]pyrimidin-4-yl}-N-(2-{6-methylimidazo[1,2-a]pyridin-3-yl}propan-2-yl)azetidine-3-carboxamide;

(3R)-1-{5-chloro-2-[(3R)-3,4-dimethylpiperazin-1-yl]pyrimidin-4-yl}-N-(2-{imidazo[1,2-a]pyridin-3-yl}propan-2-yl) pyrrolidine-3-carboxamide;

(3S)-1-{5-chloro-2-[(3R)-3,4-dimethylpiperazin-1-yl]pyrimidin-4-yl}-N-(2-{imidazo[1,2-a]pyridin-3-yl}propan-2-yl) pyrrolidine-3-carboxamide;

1-{5-chloro-2-[(3S)-3,4-dimethylpiperazin-1-yl]pyrimidin-4-yl}-N-(2-{imidazo[1,2-a]pyridin-3-yl}propan-2-yl) piperidine-4-carboxamide;

1-{2-[(3R)-3,4-dimethylpiperazin-1-yl]-5-fluoropyrimidin-4-yl}-N-(2-{imidazo[1,2-a]pyridin-3-yl}propan-2-yl)-N-methylazetidine-3-carboxamide;

1-{5-chloro-2-[(3S)-3,4-dimethylpiperazin-1-yl]pyrimidin-4-yl}-N-(2-{imidazo[1,2-a]pyridin-3-yl}propan-2-yl)azetidine-3-carboxamide;

1-{2-[(3S)-3,4-dimethylpiperazin-1-yl]-5-fluoropyridin-4-yl}-N-(2-{imidazo[1,2-a]pyridin-3-yl}propan-2-yl)azetidine-3-carboxamide;

1-[5-chloro-2-(4-methylpiperazin-1-yl) pyridin-4-yl]-N-(2-{imidazo[1,2-a]pyridin-3-yl}propan-2-yl)azetidine-3-carboxamide;

1-{5-chloro-2-[(2S)-2,4-dimethylpiperazin-1-yl]pyrimidin-4-yl}-N-{imidazo[1,2-a]pyridin-3-ylmethyl}-N-methylazetidine-3-carboxamide;

1-{5-chloro-2-[(2S)-2,4-dimethylpiperazin-1-yl]pyrimidin-4-yl}-N-(2-{imidazo[1,2-a]pyridin-3-yl}propan-2-yl)-N-methylazetidine-3-carboxamide;

1-{2-[(2S)-2,4-dimethylpiperazin-1-yl]-5-fluoropyrimidin-4-yl}-N-(2-{imidazo[1,2-a]pyridin-3-yl}propan-2-yl)-N-methylazetidine-3-carboxamide;

1-{5-chloro-2-[(2S,5R)-2,4,5-trimethylpiperazin-1-yl]pyrimidin-4-yl}-N-(2-{imidazo[1,2-a]pyridin-3-yl}propan-2-yl)azetidine-3-carboxamide;

1-{5-chloro-2-[(2S,5S)-2,4,5-trimethylpiperazin-1-yl]pyrimidin-4-yl}-N-(2-{imidazo[1,2-a]pyridin-3-yl}propan-2-yl)azetidine-3-carboxamide;

1-{5-fluoro-2-[(2S,5R)-2,4,5-trimethylpiperazin-1-yl]pyrimidin-4-yl}-N-(2-{imidazo[1,2-a]pyridin-3-yl}propan-2-yl)azetidine-3-carboxamide; and 1-[5-chloro-2-(1,4-diazepan-1-yl)pyrimidin-4-yl]-N-{[1,2,4]triazolo[4,3-a]pyridin-3-ylmethyl}azetidine-3-carboxamide;

or a pharmaceutically acceptable amide, carbamate and salt of any one thereof.

18. A pharmaceutical composition comprising a compound or a pharmaceutically acceptable ester, amide, carbamate or salt thereof as claimed in claim 1, together with a pharmaceutically suitable carrier; and optionally also comprising a further therapeutic agent.

19. A method for the prevention or treatment of a disease or disorder in which inhibition of N-myristoyl transferase provides a therapeutic or prophylactic effect, which comprises administering to a subject in need thereof a therapeutically effective amount of a compound or a pharmaceutically acceptable ester, amide, carbamate or salt thereof according to claim 1.

20. A compound selected from the group consisting of:

a compound of formula (II)

(II)

wherein $R^1$, $R^2$, $R^3$, $R^{5a}$, $R^{5b}$, $R^{5c}$, $R^{5d}$, $R^6$, $R^7$, $R^8$, $R^9$, $X^1$, $X^2$, m, p, r, $n_1$, $n_2$ and $R^{13}$ are as defined for the compound of formula (I) and Q is a nitrogen protecting group such as tert-butyloxycarbonyl (BOC);

a compound of formula (V)

(V)

wherein D is halo such as chloro and $R^1$, $R^2$, $R^3$, $R^{5a}$, $R^{5b}$, $R^{5c}$, $R^{5d}$, $R^6$, $R^7$, $R^8$, $R^9$, $X^1$, $X^2$, p, $n_1$ and n2 are as defined for the compound of formula (I); and a compound of formula (X)

(X)

wherein $X^2$ is CH and $R^1$, $R^2$, $R^3$, $R^{5a}$, $R^{5b}$, $R^{5c}$, $R^{5d}$, $R^8$, $R^7$, p, $n_1$ and $n_2$ are as defined for the compound of formula (I); or salts thereof.

21. A compound of Formula (I), or a pharmaceutically acceptable salt thereof, Formula (I)

wherein:

$n_1$ is 1 or 2; $n_2$ is 1 or 2;

$X^1$ is selected from the group consisting of $CR^x$ and N;

when present, Rx is selected from the group consisting of hydrogen, halogen, and —$C_{1-4}$alkyl optionally substituted by 1, 2 or 3 substituents, each substituent being independently selected from the group consisting of halogen, —OH, —OCH$_3$, and —OCF$_3$;

$R^1$ is selected from the group consisting of hydrogen; —$C_{1-4}$alkyl optionally substituted by 1, 2 or 3 substituents, each substituent being independently selected from the group consisting of halogen, —OCH$_3$, and —OCF$_3$; and —$C_{3-6}$Cycloalkyl optionally substituted by 1, 2 or 3 substituents, each substituent being independently selected from the group consisting of halogen, —CH$_3$, —OCH$_3$, and —OCF$_3$;

$R_2$ is selected from the group consisting of hydrogen; —$C_{1-4}$alkyl optionally substituted by 1, 2 or 3 substituents, each substituent being independently selected from the group consisting of halogen, —OCH$_3$, and —OCF$_3$; and —$C_{3-6}$cycloalkyl optionally substituted by 1, 2 or 3 substituents, each substituent being independently selected from the group consisting of halogen, —CH$_3$, —OCH$_3$, and —OCF$_3$;

or $R^1$ and $R^2$ are linked such that together with the atom to which they are attached they form a $C_{3-6}$cycloalkyl group or a 3- to 6-membered non-aromatic heterocyclyl group comprising 1 heteroatom selected from the group consisting of O and N, wherein said $C_{3-6}$cycloalkyl group or 3- to 6-membered non-aromatic heterocyclyl group is optionally substituted by 1 or 2 substituents, each substituent being independently selected from the group consisting of halogen, —OH, —$CH_3$, —$OCH_3$, and —$OCF_3$;

$R^3$ is selected from the group consisting of hydrogen; —$C_{1-4}$alkyl optionally substituted by 1, 2 or 3 substituents, each substituent being independently selected from the group consisting of halogen, —$OCH_3$, and —$OCF_3$; and —$C_{3-6}$Cycloalkyl optionally substituted by 1, 2 or 3 substituents, each substituent being independently selected from the group consisting of halogen, —$CH_3$, —$OCH_3$, and —$OCF_3$;

or $R^1$ and $R^3$ are linked such that together with the atom to which they are attached they form a $C_{3-6}$cycloalkyl group or a 3- to 6-membered non-aromatic heterocyclyl group comprising 1 heteroatom selected from the group consisting of O and N, wherein said $C_{3-6}$cycloalkyl group or 3- to 6-membered non-aromatic heterocyclyl group is optionally substituted by 1 or 2 substituents, each substituent being independently selected from the group consisting of halogen, —OH, —$CH_3$, —$OCH_3$, and —$OCF_3$;

$X^2$ is selected from the group consisting of $CR^4$ and N;

when present, $R^4$ is selected from the group consisting of hydrogen; halogen; —$C_{1-4}$alkyl optionally substituted by 1, 2 or 3 substituents, each substituent being independently selected from the group consisting of halogen, —OH, —$OCH_3$, —$OCF_3$, and —$NR^aR^b$;

$R^{5a}$ and $R^{5d}$ are independently selected from the group consisting of hydrogen; halogen; methyl optionally substituted by 1, 2 or 3 substituents, each substituent being independently selected from the group consisting of halogen, —OH, —$OCH_3$, and —$OCF_3$; and methoxy optionally substituted by 1, 2 or 3 substituents, each substituent being independently selected from the group consisting of halogen, —OH, —$OCH_3$, and —$OCF_3$;

$R^{5b}$ and $R^{5c}$ are independently selected from the group consisting of hydrogen; halogen; —$C_{1-4}$alkyl optionally substituted by 1, 2 or 3 substituents, each substituent being independently selected from the group consisting of halogen, —OH, —$OCH_3$, and —$OCF_3$; —O—$C_{1-4}$alkyl optionally substituted by 1, 2 or 3 substituents, each substituent being independently selected from the group consisting of halogen, —OH, —$OCH_3$, and —$OCF_3$; and $C_{3-6}$cycloalkyl optionally substituted by 1, 2 or 3 substituents, each substituent being independently selected from the group consisting of halogen, —$CH_3$, —OH, —$OCH_3$, and —$OCF_3$;

or $R^{5b}$ and $R^{5c}$ are linked such that together with the atoms to which they are attached they form a 6-membered aryl group or a 5- or 6-membered aromatic heterocyclyl group comprising 1 or 2 heteroatoms selected from the group consisting of S, O and N, wherein said 6-membered aryl group or 5- or 6-membered aromatic heterocyclyl group is optionally substituted by 1 or 2 substituents, each substituent being independently selected from the group consisting of halogen, —OH, —$OCH_3$, and —$OCF_3$;

$R^6$ is selected from the group consisting of hydrogen and methyl;

when present, each $R^7$ is —$C_{1-4}$alkyl optionally substituted by 1, 2 or 3 substituents, each substituent being independently selected from the group consisting of halogen, —OH, —$OCH_3$, and —$OCF_3$;

$R^8$ is selected from the group consisting of hydrogen; halogen; —OH; —CN; —$C_{1-4}$alkyl optionally substituted by 1, 2 or 3 substituents, each substituent being independently selected from the group consisting of halogen, —OH, —CN, and methoxy optionally substituted by 1, 2 or 3 halogen; —$C_{3-6}$cycloalkyl optionally substituted by 1, 2 or 3 substituents, each substituent being independently selected from the group consisting of halogen, —$CH_3$, —OH, —CN, and methoxy optionally substituted by 1, 2 or 3 halogen; —$C_{1-4}$alkenyl optionally substituted by 1, 2 or 3 substituents, each substituent being independently selected from the group consisting of halogen, —OH, —CN, and methoxy optionally substituted by 1, 2 or 3 halogen; and —O—$C_{1-4}$alkyl optionally substituted by 1, 2 or 3 substituents, each substituent being independently selected from the group consisting of halogen, —OH, CN and methoxy optionally substituted by 1, 2 or 3 halogen;

$R^9$ is selected from the group consisting of hydrogen, and —$C_{1-4}$alkyl optionally substituted by 1, 2 or 3 substituents, each substituent being independently selected from the group consisting of halogen, —OH, —$OCH_3$, and —$OCF_3$; or $R^8$ and $R^9$ are linked such that together with the atoms to which they are attached they form a 6-membered aryl group, a $C_{5-6}$cycloalkyl group, or a 5- or 6-membered aromatic heterocyclyl group comprising 1 or 2 heteroatoms selected from N, O and S, and wherein said 6-membered aryl group, $C_{5-6}$cycloalkyl group or 5- to 6-membered aromatic heterocyclyl group is optionally substituted by 1, 2 or 3 substituents, each substituent being independently selected from the group consisting of halogen; —OH; —CN; —$C_{1-4}$alkyl optionally substituted by 1, 2 or 3 substituents, each substituent being independently selected from the group consisting of halogen, —OH, and methoxy optionally substituted by 1, 2 or 3 halogen; and —O—$C_{1-4}$alkyl optionally substituted by 1, 2 or 3 substituents, each substituent being independently selected from the group consisting of -halogen, —OH, and methoxy optionally substituted by 1, 2 or 3 halogen;

p is 0, 1, or 2;

Z is a 5- to 13-membered non-aromatic heterocyclyl group comprising 1, 2 or 3 heteroatoms selected from N, O and S, wherein at least one of the heteroatoms is N, and wherein said 5- to 13-membered non-aromatic heterocyclyl group is optionally substituted with 1, 2, 3 or 4 substituents, each substituent being independently selected from the group consisting of halogen; —$C_{1-6}$alkyl optionally substituted by 1, 2 or 3 substituents, each substituent being independently selected from the group consisting of halogen, —OH, and —$OC_{1-3}$alkyl optionally substituted by 1, 2 or 3 halogen; —O—$C_{1-6}$alkyl optionally substituted by 1, 2 or 3 substituents, each substituent being independently selected from the group consisting of halogen, —OH, and —O—$C_{1-3}$alkyl optionally substituted by 1, 2 or 3 halogen; $NR^cR^d$; and $C_{3-6}$cycloalkyl optionally substituted by 1, 2 or 3 substituents, each substituent being independently selected from the group consisting of halogen, —OH, and —O—$C_{1-3}$alkyl optionally substituted by 1, 2 or 3 halogen; or when two substituents are on adjacent ring positions they may be linked such that together with the atoms to which they are attached they form a $C_{3-6}$cycloalkyl group or a 4- to 6-membered non-aromatic heterocyclyl group comprising 1 heteroatom selected from the group consisting of O and N, wherein said $C_{3-6}$cycloalkyl group or 4- to 6-membered non-aromatic heterocyclyl group is optionally substituted by 1 or 2 substituents, each substituent being independently selected from the group consisting of halogen; —$C_{1-6}$alkyl optionally substituted by 1, 2 or 3 substituents, each substituent being independently selected from the group consisting of halogen, —OH, and —$OC_{1-3}$alkyl optionally substituted by 1, 2 or 3 halogen; and —O—$C_{1-6}$alkyl optionally substituted by 1, 2 or 3 substituents, each substituent being independently selected from the group consisting of halogen, —OH, and —O—$C_{1-3}$alkyl optionally substituted by 1, 2 or 3 halogen;

$R^e$ and $R^d$ are independently selected from the group consisting of hydrogen; —$C_{1-6}$alkyl optionally substituted by 1, 2 or 3 substituents, each substituent being independently selected from the group consisting of halogen, —$OCH_3$, and —$OCF_3$; and $C_{3-6}$cycloalkyl optionally substituted by 1, 2 or 3 substituents, each substituent being independently selected from the group consisting of halogen, —$CH_3$, —OH, —$OCH_3$, and —$OCF_3$;

or Z is —$NR^{10}R^{11}$ wherein $R^{10}$ is selected from the group consisting of hydrogen and —$C_{1-4}$alkyl; and $R^{11}$ is a 5- to 10-membered non-aromatic heterocyclyl group comprising 1, 2 or 3 heteroatoms selected from N, O and S, wherein at least one of the heteroatoms is N, and wherein said 5- to 10-membered non-aromatic heterocyclyl group is optionally substituted with 1, 2, 3 or 4 substituents independently selected from the group consisting of halogen; —OH; —$C_{1-6}$alkyl optionally substituted by 1, 2 or 3 substituents, each substituent being independently selected from the group consisting of halogen, —OH, and —$OC_{1-3}$alkyl optionally substituted by 1, 2 or 3 halogen; and —O—$C_{1-6}$alkyl optionally substituted by 1, 2 or 3 substituents, each substituent being independently selected from the group consisting of halogen, —OH, and —O—$C_{1-3}$alkyl optionally substituted by 1, 2 or 3 halogen; and when present, each $R^a$ and $R^b$ are independently selected from the group consisting of hydrogen and —$C_{1-4}$alkyl.

22. A compound or a pharmaceutically acceptable salt thereof as claimed in claim 1, wherein the compound or a pharmaceutically acceptable salt thereof is selected from the group consisting of:

1-{5-chloro-2-[(3R)-3-methylpiperazin-1-yl]pyrimidin-4-yl}-N-(2-{imidazo[1,2-a]pyridin-3-yl}propan-2-yl)azetidine-3-carboxamide;

1-{5-chloro-2-[(2S)-2,4-dimethylpiperazin-1-yl]pyrimidin-4-yl}-N-(2-{imidazo[1,2-a]pyridin-3-yl}propan-2-yl)azetidine-3-carboxamide;

1-{5-chloro-2-[(3R)-3,4-dimethylpiperazin-1-yl]pyrimidin-4-yl}-N-(2-{imidazo[1,2-a]pyridin-3-yl}propan-2-yl)azetidine-3-carboxamide;

1-[5-fluoro-2-(4-methylpiperazin-1-yl)pyridin-4-yl]-N-(2-{imidazo[1,2-a]pyridin-3-yl}propan-2-yl)azetidine-3-carboxamide;

1-[5-chloro-2-(1,4-diazepan-1-yl)pyrimidin-4-yl]-N-{imidazo[1,2-a]pyridin-3-ylmethyl}azetidine-3-carboxamide;

1-[2-(1,4-diazepan-1-yl)-5-fluoropyrimidin-4-yl]-N-{imidazo[1,2-a]pyridin-3-ylmethyl}azetidine-3-carboxamide;

1-(5-chloro-2-{3,6-diazabicyclo[3.2.0]heptan-3-yl}pyrimidin-4-yl)-N-{imidazo[1,2-a]pyridin-3-ylmethyl}azetidine-3-carboxamide;

1-(2-{3,6-diazabicyclo[3.2.0]heptan-3-yl}-5-fluoropyrimidin-4-yl)-N-{imidazo[1,2-a]pyridin-3-ylmethyl}azetidine-3-carboxamide;

1-[2-(1,4-diazepan-1-yl)-5-fluoropyrimidin-4-yl]-N-(1-{imidazo[1,2-a]pyridin-3-yl}ethyl)azetidine-3-carboxamide;

1-[5-chloro-2-(1,4-diazepan-1-yl)pyrimidin-4-yl]-N-(1-{imidazo[1,2-a]pyridin-3-yl}ethyl)azetidine-3-carboxamide;

1-[2-(1,4-diazepan-1-yl)-5-fluoropyrimidin-4-yl]-N-(2-{imidazo[1,2-a]pyridin-3-yl}propan-2-yl)azetidine-3-carboxamide;

1-[2-(1,4-diazepan-1-yl)-5-fluoropyrimidin-4-yl]-N-({2-methylimidazo[1,2-a]pyridin-3-yl}methyl)azetidine-3-carboxamide;

1-(2-{3,6-diazabicyclo[3.2.0]heptan-3-yl}-5-fluoropyrimidin-4-yl)-N-({2-methylimidazo[1,2-a]pyridin-3-yl}methyl)azetidine-3-carboxamide;

1-{5-fluoro-2-[methyl(pyrrolidin-3-yl)amino]pyrimidin-4-yl}-N{imidazo[1,2-a]pyridin-3-ylmethyl}azetidine-3-carboxamide;

1-[5-fluoro-2-(pyrrolidin-3-ylamino)pyrimidin-4-yl]-N{imidazo[1,2-a]pyridin-3-ylmethyl}azetidine-3-carboxamide;

1-[5-fluoro-2-(piperazin-1-yl)pyrimidin-4-yl]-N-{imidazo[1,2-a]pyridin-3-ylmethyl}azetidine-3-carboxamide;

1-[5-chloro-2-(1,4-diazepan-1-yl)pyrimidin-4-yl]-N-{imidazo[1,2-a]pyridin-3-ylmethyl}-N-methylazetidine-3-carboxamide;

1-[5-chloro-2-(1,4-diazepan-1-yl)pyrimidin-4-yl]-N-({2-methylimidazo[1,2-a]pyridin-3-yl}methyl)azetidine-3-carboxamide;

1-[2-(1,4-diazepan-1-yl)-5-methoxypyrimidin-4-yl]-N-{imidazo[1,2-a]pyridin-3-ylmethyl}azetidine-3-carboxamide;

1-[2-(1,4-diazepan-1-yl)-5-methoxypyrimidin-4-yl]-N-(2{imidazo[1,2-a]pyridin-3-yl}propan-2-yl)azetidine-3-carboxamide;

1-[5-chloro-2-(1,4-diazepan-1-yl)pyrimidin-4-yl]-N-({6-fluoroimidazo[1,2-a]pyridin-3-yl}methyl)azetidine-3-carboxamide;

1-[5-chloro-2-(1,4-diazepan-1-yl)pyrimidin-4-yl]-N-({6-chloroimidazo[1,2-a]pyridin-3-yl}methyl)azetidine-3-carboxamide;

1-[2-(1,4-diazepan-1-yl)-5-methoxypyrimidin-4-yl]-N-(1-{2-methylimidazo[1,2-a]pyridin-3-yl}ethyl)azetidine-3-carboxamide;

1-[5-chloro-2-(1,4-diazepan-1-yl)pyrimidin-4-yl]-N-(1-{2-methylimidazo[1,2-a]pyridin-3-yl}ethyl)azetidine-3-carboxamide;

1-[5-chloro-2-(piperazin-1-yl)pyrimidin-4-yl]-N-{imidazo[1,2-a]pyridin-3-ylmethyl}azetidine-3-carboxamide;

1-{5-fluoro-2-[(3S)-3-methylpiperazin-1-yl]pyrimidin-4-yl}-N{imidazo[1,2-a]pyridin-3-ylmethyl}azetidine-3-carboxamide;

1-{5-chloro-2-[(3S)-3-methylpiperazin-1-yl]pyrimidin-4-yl}-N-{imidazo[1,2-a]pyridin-3-ylmethyl}azetidine-3-carboxamide;

1-{5-fluoro-2-[(3R)-3-methylpiperazin-1-yl]pyrimidin-4-yl}-N-{imidazo[1,2-a]pyridin-3-ylmethyl}azetidine-3-carboxamide;

1-{5-chloro-2-[(3R)-3-methylpiperazin-1-yl]pyrimidin-4-yl}-N-{imidazo[1,2-a]pyridin-3-ylmethyl}azetidine-3-carboxamide;

1-[5-chloro-2-(piperazin-1-yl)pyrimidin-4-yl]-N-(1-{imidazo[1,2-a]pyridin-3-yl}ethyl)azetidine-3-carboxamide;

1-[5-fluoro-2-(piperazin-1-yl)pyrimidin-4-yl]-N-(1-{imidazo[1,2-a]pyridin-3-yl}ethyl)azetidine-3-carboxamide;

1-[5-fluoro-2-(piperazin-1-yl)pyrimidin-4-yl]-N-(2-{imidazo[1,2-a]pyridin-3-yl}propan-2-yl)azetidine-3-carboxamide;

1-[5-chloro-2-(piperazin-1-yl)pyrimidin-4-yl]-N-(2-{imidazo[1,2-a]pyridin-3-yl}propan-2-yl)azetidine-3-carboxamide;

N-(2-{imidazo[1,2-a]pyridin-3-yl}propan-2-yl)-1-[5-methoxy-2-(piperazin-1-yl)pyrimidin-4-yl]azetidine-3-carboxamide;

1-{5-fluoro-2-[(3R)-3-methylpiperazin-1-yl]pyrimidin-4-yl}-N-(2-{imidazo[1,2-a]pyridin-3-yl}propan-2-yl)azetidine-3-carboxamide;

N-(2-{imidazo[1,2-a]pyridin-3-yl}propan-2-yl)-1-{5-methoxy-2-[(3R)-3-methylpiperazin-1-yl]pyrimidin-4-yl}azetidine-3-carboxamide;

1-{5-chloro-2-[(3S)-3-methylpiperazin-1-yl]pyrimidin-4-yl}-N-(2-{imidazo[1,2-a]pyridin-3-yl}propan-2-yl)azetidine-3-carboxamide;

1-{5-fluoro-2-[(3S)-3-methylpiperazin-1-yl]pyrimidin-4-yl}-N-(2-{imidazo[1,2-a]pyridin-3-yl}propan-2-yl)azetidine-3-carboxamide;

N-(2-{imidazo[1,2-a]pyridin-3-yl}propan-2-yl)-1-{5-methoxy-2-[(3S)-3-methylpiperazin-1-yl]pyrimidin-4-yl}azetidine-3-carboxamide;

1-{5-fluoro-2-[methyl(pyrrolidin-3-yl)amino]pyrimidin-4-yl}-N-(2{imidazo[1,2-a]pyridin-3-yl}propan-2-yl)azetidine-3-carboxamide;

1-{5-chloro-2-[methyl(pyrrolidin-3-yl)amino]pyrimidin-4-yl}-N-(2-{imidazo[1,2-a]pyridin-3-yl}propan-2-yl)azetidine-3-carboxamide;

1-{2-[(3R,5S)-3,5-dimethylpiperazin-1-yl]-5-methoxy-pyrimidin-4-yl}-N-(2-{imidazo[1,2-a]pyridin-3-yl}propan-2-yl)azetidine-3-carboxamide;

1-{2-[(3R,5S)-3,5-dimethylpiperazin-1-yl]-5-chloropy-rimidin-4-yl}-N-(2-{imidazo[1,2-a]pyridin-3-yl}propan-2-yl)azetidine-3-carboxamide;

1-{2-[(3R,5S)-3,5-dimethylpiperazin-1-yl]-5-fluoropy-rimidin-4-yl}-N-(2-{imidazo[1,2-a]pyridin-3-yl}propan-2-yl)azetidine-3-carboxamide 1-{2-[(3S,5S)-3,5-dimethylpiperazin-1-yl]-5-methoxypy-rimidin-4-yl}-N-(2-{imidazo[1,2-a]pyridin-3-yl}propan-2-yl)azetidine-3-carboxamide;

1-{5-chloro-2-[(3R,5R)-3,5-dimethylpiperazin-1-yl]py-rimidin-4-yl}-N-(2-{imidazo[1,2-a]pyridin-3-yl}propan-2-yl)azetidine-3-carboxamide;

1-{2-[(3R,5R)-3,5-dimethylpiperazin-1-yl]-5-fluoropy-rimidin-4-yl}-N-(2-{imidazo[1,2-a]pyridin-3-yl}propan-2-yl)azetidine-3-carboxamide;

1-{5-chloro-2-[(3S,5S)-3,5-dimethylpiperazin-1-yl]py-rimidin-4-yl}-N-(2-{imidazo[1,2-a]pyridin-3-yl}propan-2-yl)azetidine-3-carboxamide;

1-{5-fluoro-2-[(3S,5S)-3,4,5-trimethylpiperazin-1-yl]py-rimidin-4-yl}-N-(2-{imidazo[1,2-a]pyridin-3-yl}propan-2-yl)azetidine-3-carboxamide;

1-{5-chloro-2-[(2S)-2-methylpiperazin-1-yl]pyrimidin-4-yl}-N-(2-{imidazo[1,2-a]pyridin-3-yl}propan-2-yl)-N-methylazetidine-3-carboxamide;

1-[5-chloro-2-(1,4-diazepan-1-yl)pyrimidin-4-yl]-N-(2-{imidazo[1,2-a]pyridin-3-yl}propan-2-yl)azetidine-3-carboxamide 1-[5-fluoro-2-(4-methyl-1,4-diazepan-1-yl)pyrimidin-4-yl]-N-{imidazo[1,2-a]pyridin-3-ylmethyl}azetidine-3-carboxamide;

1-[5-chloro-2-(4-methyl-1,4-diazepan-1-yl)pyrimidin-4-yl]-N-(1-{imidazo[1,2-a]pyridin-3-yl}ethyl)azetidine-3-carboxamide;

1-[5-fluoro-2-(4-methylpiperazin-1-yl)pyrimidin-4-yl]-N-(2-{imidazo[1,2-a]pyridin-3-yl}propan-2-yl)azetidine-3-carboxamide;

1-[5-chloro-2-(4-methylpiperazin-1-yl)pyrimidin-4-yl]-N-(2-{imidazo[1,2-a]pyridin-3-yl}propan-2-yl)azetidine-3-carboxamide;

1-[5-fluoro-2-(4-methyl-1,4-diazepan-1-yl)pyrimidin-4-yl]-N-(2-{imidazo[1,2-a]pyridin-3-yl}propan-2-yl)azetidine-3-carboxamide;

1-[5-chloro-2-(4-methyl-1,4-diazepan-1-yl)pyrimidin-4-yl]-N-(2-{imidazo[1,2-a]pyridin-3-yl}propan-2-yl)azetidine-3-carboxamide;

1-{5-fluoro-2-[methyl(1-methylpyrrolidin-3-yl)amino]pyrimidin-4-yl}-N-(2-{imidazo[1,2-a]pyridin-3-yl}propan-2-yl)azetidine-3-carboxamide;

1-{5-chloro-2-[methyl(1-methylpyrrolidin-3-yl)amino]pyrimidin-4-yl}-N-(2-{imidazo[1,2-a]pyridin-3-yl}propan-2-yl)azetidine-3-carboxamide;

1-[5-fluoro-2-(4-methylpiperazin-1-yl)pyrimidin-4-yl]-N-(2-{6-methylimidazo[1,2-a]pyridin-3-yl}propan-2-yl)azetidine-3-carboxamide;

1-[5-fluoro-2-(4-methylpiperazin-1-yl)pyrimidin-4-yl]-N-(2-{8-fluoroimidazo[1,2-a]pyridin-3-yl}propan-2-yl)azetidine-3-carboxamide;

N-(2-{imidazo[1,2-a]pyridin-3-yl}propan-2-yl)-1-[5-methoxy-2-(4-methyl-1,4-diazepan-1-yl)pyrimidin-4-yl]azetidine-3-carboxamide;

N-(2-{imidazo[1,2-a]pyridin-3-yl}propan-2-yl)-1-[5-methoxy-2-(4-methylpiperazin-1-yl)pyrimidin-4-yl]azetidine-3-carboxamide;

1-[5-fluoro-2-(4-methylpiperazin-1-yl)pyrimidin-4-yl]-N-(2-{imidazo[1,2-a]pyridin-3-yl}propan-2-yl)pyrro-lidine-3-carboxamide;

1-[5-fluoro-2-(4-methylpiperazin-1-yl)pyrimidin-4-yl]-N-(2-{imidazo[1,2-a]pyridin-3-yl}propan-2-yl)-3-methylazetidine-3-carboxamide;

N-(2-{imidazo[1,2-a]pyridin-3-yl}propan-2-yl)-1-[5-methyl-2-(4-methylpiperazin-1-yl)pyrimidin-4-yl]aze-tidine-3-carboxamide;

1-[5-chloro-2-(4-methylpiperazin-1-yl)pyrimidin-4-yl]-N-(2-{6-methylimidazo[1,2-a]pyridin-3-yl}propan-2-yl)azetidine-3-carboxamide;

1-{5-chloro-2-[(2R)-2,4-dimethylpiperazin-1-yl]pyrimi-din-4-yl}-N-(2-{imidazo[1,2-a]pyridin-3-yl}propan-2-yl)azetidine-3-carboxamide;

1-{5-chloro-2-[3-(fluoromethyl)-4-methylpiperazin-1-yl]pyrimidin-4-yl}-N-(2-{imidazo[1,2-a]pyridin-3-yl}propan-2-yl)azetidine-3-carboxamide;

1-[5-chloro-2-(4-ethylpiperazin-1-yl)pyrimidin-4-yl]-N-(2-{imidazo[1,2-a]pyridin-3-yl}propan-2-yl)azetidine-3-carboxamide;

1-{5-chloro-2-[4-(propan-2-yl)piperazin-1-yl]pyrimidin-4-yl}-N-(2-{imidazo[1,2-a]pyridin-3-yl}propan-2-yl)azetidine-3-carboxamide;

1-{5-chloro-2-[4-(2-methoxyethyl)piperazin-1-yl]py-rimidin-4-yl}-N-(2-{imidazo[1,2-a]pyridin-3-yl}propan-2-yl)azetidine-3-carboxamide;

1-[5-chloro-2-(4-methylpiperazin-1-yl)pyrimidin-4-yl]-N-(2-{imidazo[1,2-a]pyridin-3-yl}propan-2-yl)-N-methylazetidine-3-carboxamide;

1-{5-chloro-2-[(3R)-3,4-dimethylpiperazin-1-yl]pyrimidin-4-yl}-N-(2-{imidazo[1,2-a]pyridin-3-yl}propan-2-yl)-N-methylazetidine-3-carboxamide;

(3R)-1-[5-chloro-2-(4-methylpiperazin-1-yl)pyrimidin-4-yl]-N-(2-{imidazo[1,2-a]pyridin-3-yl}propan-2-yl)pyrrolidine-3-carboxamide;

(3S)-1-[5-chloro-2-(4-methylpiperazin-1-yl)pyrimidin-4-yl]-N-(2-{imidazo[1,2-a]pyridin-3-yl}propan-2-yl)pyrrolidine-3-carboxamide;

1-[5-chloro-2-(4-methylpiperazin-1-yl)pyrimidin-4-yl]-N-(2-{imidazo[1,2-a]pyridin-3-yl}propan-2-yl)piperidine-4-carboxamide;

1-[5-fluoro-2-(4-methylpiperazin-1-yl)pyrimidin-4-yl]-N-(2-{imidazo[1,2-a]pyridin-3-yl}propan-2-yl)-N-methylazetidine-3-carboxamide;

1-{5-chloro-2-[(2S,3R)-2,3-dimethylpiperazin-1-yl]pyrimidin-4-yl}-N-(2-{imidazo[1,2-a]pyridin-3-yl}propan-2-yl)azetidine-3-carboxamide;

1-{5-chloro-2-[3-(methoxymethyl)-4-methylpiperazin-1-yl]pyrimidin-4-yl}-N-(2-{imidazo[1,2-a]pyridin-3-yl}propan-2-yl)azetidine-3-carboxamide;

1-(5-fluoro-2-{6-methyl-3,6-diazabicyclo[3.2.0]heptan-3-yl}pyrimidin-4-yl)-N-{imidazo[1,2-a]pyridin-3-ylmethyl}azetidine-3-carboxamide;

1-{2-[(3S)-3,4-dimethylpiperazin-1-yl]-5-fluoropyrimidin-4-yl}-N-(2-{imidazo[1,2-a]pyridin-3-yl}propan-2-yl)azetidine-3-carboxamide;

1-{5-chloro-2-[(3S)-3,4-dimethylpiperazin-1-yl]pyrimidin-4-yl}-N-(2-{imidazo[1,2-a]pyridin-3-yl}propan-2-yl)azetidine-3-carboxamide;

1-{2-[(3R)-3,4-dimethylpiperazin-1-yl]-5-fluoropyrimidin-4-yl}-N-(2-{imidazo[1,2-a]pyridin-3-yl}propan-2-yl)azetidine-3-carboxamide;

1-{2-[(3R)-3,4-dimethylpiperazin-1-yl]-5-methoxypyrimidin-4-yl}-N-(2-{imidazo[1,2-a]pyridin-3-yl}propan-2-yl)azetidine-3-carboxamide;

1-{2-[(3R)-3,4-dimethylpiperazin-1-yl]-5-fluoropyrimidin-4-yl}-N-(2-{imidazo[1,2-a]pyridin-3-yl}propan-2-yl)pyrrolidine-3-carboxamide;

1-{2-[(3R)-3,4-dimethylpiperazin-1-yl]-5-fluoropyrimidin-4-yl}-N-(2-{imidazo[1,2-a]pyridin-3-yl}propan-2-yl)-3-methylazetidine-3-carboxamide;

N-(2-{imidazo[1,2-a]pyridin-3-yl}propan-2-yl)-1-{5-methoxy-2-[(3R,5S)-3,4,5-trimethylpiperazin-1-yl]pyrimidin-4-yl}azetidine-3-carboxamide;

1-{5-chloro-2-[(3R,5S)-3,4,5-trimethylpiperazin-1-yl]pyrimidin-4-yl}-N-(2-{imidazo[1,2-a]pyridin-3-yl}propan-2-yl)azetidine-3-carboxamide;

1-{5-fluoro-2-[(3R,5S)-3,4,5-trimethylpiperazin-1-yl]pyrimidin-4-yl}-N-(2-{imidazo[1,2-a]pyridin-3-yl}propan-2-yl)azetidine-3-carboxamide;

N-(2-{imidazo[1,2-a]pyridin-3-yl}propan-2-yl)-1-{5-methoxy-2-[(3R,5R)-3,4,5-trimethylpiperazin-1-yl]pyrimidin-4-yl}azetidine-3-carboxamide;

1-{5-chloro-2-[(3R,5R)-3,4,5-trimethylpiperazin-1-yl]pyrimidin-4-yl}-N-(2-{imidazo[1,2-a]pyridin-3-yl}propan-2-yl)azetidine-3-carboxamide;

1-{5-fluoro-2-[(3S,5S)-3,4,5-trimethylpiperazin-1-yl]pyrimidin-4-yl}-N-(2-{imidazo[1,2-a]pyridin-3-yl}propan-2-yl)azetidine-3-carboxamide;

N-(2-{imidazo[1,2-a]pyridin-3-yl}propan-2-yl)-1-{5-methoxy-2-[(3R,5R)-3,4,5-trimethylpiperazin-1-yl]pyrimidin-4-yl}azetidine-3-carboxamide;

1-{5-chloro-2-[(3R,5R)-3,4,5-trimethylpiperazin-1-yl]pyrimidin-4-yl}-N-(2-{imidazo[1,2-a]pyridin-3-yl}propan-2-yl)azetidine-3-carboxamide;

1-{5-fluoro-2-[(3S,5S)-3,4,5-trimethylpiperazin-1-yl]pyrimidin-4-yl}-N-(2-{imidazo[1,2-a]pyridin-3-yl}propan-2-yl)azetidine-3-carboxamide;

1-{2-[(3R)-3,4-dimethylpiperazin-1-yl]-5-fluoropyrimidin-4-yl}-N-(2-{6-methylimidazo[1,2-a]pyridin-3-yl}propan-2-yl)azetidine-3-carboxamide;

1-{5-chloro-2-[(3R)-3,4-dimethylpiperazin-1-yl]pyrimidin-4-yl}-N-(2-{6-methylimidazo[1,2-a]pyridin-3-yl}propan-2-yl)azetidine-3-carboxamide;

(3R)-1-{5-chloro-2-[(3R)-3,4-dimethylpiperazin-1-yl]pyrimidin-4-yl}-N-(2-{imidazo[1,2-a]pyridin-3-yl}propan-2-yl)pyrrolidine-3-carboxamide;

(3S)-1-{5-chloro-2-[(3R)-3,4-dimethylpiperazin-1-yl]pyrimidin-4-yl}-N-(2-{imidazo[1,2-a]pyridin-3-yl}propan-2-yl)pyrrolidine-3-carboxamide;

1-{5-chloro-2-[(3R)-3,4-dimethylpiperazin-1-yl]pyrimidin-4-yl}-N-(2-{imidazo[1,2-a]pyridin-3-yl}propan-2-yl)piperidine-4-carboxamide;

1-{2-[(3R)-3,4-dimethylpiperazin-1-yl]-5-fluoropyrimidin-4-yl}-N-(2-{imidazo[1,2-a]pyridin-3-yl}propan-2-yl)-N-methylazetidine-3-carboxamide;

1-{5-chloro-2-[(3R)-3,4-dimethylpiperazin-1-yl]pyrimidin-4-yl}-N-(2-{imidazo[1,2-a]pyridin-3-yl}propan-2-yl)azetidine-3-carboxamide;

1-{2-[(3R)-3,4-dimethylpiperazin-1-yl]-5-fluoropyridin-4-yl}-N-(2-{imidazo[1,2-a]pyridin-3-yl}propan-2-yl)azetidine-3-carboxamide;

1-[5-chloro-2-(4-methylpiperazin-1-yl)pyridin-4-yl]-N-(2{imidazo[1,2-a]pyridin-3-yl}propan-2-yl)azetidine-3-carboxamide;

1-{5-chloro-2-[(2S)-2,4-dimethylpiperazin-1-yl]pyrimidin-4-yl}-N{imidazo[1,2-a]pyridin-3-ylmethyl}-N-methylazetidine-3-carboxamide;

1-{5-chloro-2-[(2S)-2,4-dimethylpiperazin-1-yl]pyrimidin-4-yl}-N-(2{imidazo[1,2-a]pyridin-3-yl}propan-2-yl)-N-methylazetidine-3-carboxamide;

1-{2-[(2S)-2,4-dimethylpiperazin-1-yl]-5-fluoropyrimidin-4-yl}-N-(2-{imidazo[1,2-a]pyridin-3-yl}propan-2-yl)-N-methylazetidine-3-carboxamide;

1-{5-chloro-2-[(2S,5R)-2,4,5-trimethylpiperazin-1-yl]pyrimidin-4-yl}-N-(2-{imidazo[1,2-a]pyridin-3-yl}propan-2-yl)azetidine-3-carboxamide;

1-{5-chloro-2-[(2R,5R)-2,4,5-trimethylpiperazin-1-yl]pyrimidin-4-yl}-N-(2{imidazo[1,2-a]pyridin-3-yl}propan-2-yl)azetidine-3-carboxamide;

1-{5-fluoro-2-[(2S,5R)-2,4,5-trimethylpiperazin-1-yl]pyrimidin-4-yl}-N-(2-{imidazo[1,2-a]pyridin-3-yl}propan-2-yl)azetidine-3-carboxamide; and 1-[5-chloro-2-(1,4-diazepan-1-yl)pyrimidin-4-yl]-N-{[1,2,4]triazolo[4,3-a]pyridin-3-ylmethyl}azetidine-3-carboxamide;

N-(2-(imidazo[1,2-a]pyridin-3-yl)propan-2-yl)-1-(2-(4-methyl-1,4-diazepan-1-yl)quinazolin-4-yl)azetidine-3-carboxamide;

N-(2-(imidazo[1,2-a]pyridin-3-yl)propan-2-yl)-1-(2-(4-methyl-1,4-diazepan-1-yl)thieno[2,3-d]pyrimidin-4-yl)azetidine-3-carboxamide;

N-(2-(imidazo[1,2-a]pyridin-3-yl)propan-2-yl)-1-(2-(4-methyl-1,4-diazepan-1-yl)-6,7-dihydro-5H-cyclopenta[d]pyrimidin-4-yl)azetidine-3-carboxamide;

1-(5-chloro-6-methyl-2-(4-methyl-1,4-diazepan-1-yl)pyrimidin-4-yl)-N-(2-(imidazo[1,2-a]pyridin-3-yl)propan-2-yl)azetidine-3-carboxamide;

N-(2-(imidazo[1,2-a]pyridin-3-yl)propan-2-yl)-1-(6-methyl-2-(4-methyl-1,4-diazepan-1-yl)thieno[3,2-d]pyrimidin-4-yl)azetidine-3-carboxamide;

N-(2-(imidazo[1,2-a]pyridin-3-yl)propan-2-yl)-1-(6-methyl-2-(4-methyl-1,4-diazepan-1-yl)thieno[2,3-d]pyrimidin-4-yl)azetidine-3-carboxamide;

1-(2-(1,4-diazepan-1-yl)thieno[3,2-d]pyrimidin-4-yl)-N-(2-(imidazo[1,2-a]pyridin-3-yl)propan-2-yl)azetidine-3-carboxamide;

1-(5-chloro-2-(piperazin-1-yl)pyrimidin-4-yl)-N-(2-(imidazo[1,2-a]pyridin-3-yl)propan-2-yl)-N-methylazetidine-3-carboxamide;

1-(5-chloro-2-(1,4-diazepan-1-yl)pyrimidin-4-yl)-N-(2-(imidazo[1,2-a]pyridin-3-yl)propan-2-yl)-N-methylazetidine-3-carboxamide;

1-(5-chloro-2-(4-methyl-1,4-diazepan-1-yl)pyrimidin-4-yl)-N-(2-(imidazo[1,2-a]pyridin-3-yl)propan-2-yl)-N-methylazetidine-3-carboxamide;

N-(2-(imidazo[1,2-a]pyridin-3-yl)propan-2-yl)-N-methyl-1-(2-(4-methyl-1,4-diazepan-1-yl)thieno[3,2-d]pyrimidin-4-yl)azetidine-3-carboxamide;

(R)-1-(5-chloro-2-(3-methylpiperazin-1-yl)pyrimidin-4-yl)-N-(2-(imidazo[1,2-a]pyridin-3-yl)propan-2-yl)-N-methylazetidine-3-carboxamide;

(S)—N-(2-(imidazo[1,2-a]pyridin-3-yl)propan-2-yl)-N-methyl-1-(2-(2-methylpiperazin-1-yl)thieno[3,2-d]pyrimidin-4-yl)azetidine-3-carboxamide;

(S)—N-(2-(imidazo[1,2-a]pyridin-3-yl)propan-2-yl)-1-(2-(2-methylpiperazin-1-yl)thieno[3,2-d]pyrimidin-4-yl)azetidine-3-carboxamide;

1-(5-chloro-2-(3,3-dimethylpiperazin-1-yl)pyrimidin-4-yl)-N-(2-(imidazo[1,2-a]pyridin-3-yl)propan-2-yl)-N-methylazetidine-3-carboxamide;

1-(2-(4-aminopiperidin-1-yl)-5-chloropyrimidin-4-yl)-N-(2-(imidazo[1,2-a]pyridin-3-yl)propan-2-yl)-N-methylazetidine-3-carboxamide;

1-(5-chloro-2-(4,7-diazaspiro[2.5]octan-7-yl)pyrimidin-4-yl)-N-(2-(imidazo[1,2-a]pyridin-3-yl)propan-2-yl)-N-methylazetidine-3-carboxamide;

1-(2-(4-aminoazepan-1-yl)-5-chloropyrimidin-4-yl)-N-(2-(imidazo[1,2-a]pyridin-3-yl)propan-2-yl)-N-methylazetidine-3-carboxamide;

1-(2-(2,5-diazabicyclo[2.2.1]heptan-2-yl)-5-chloropyrimidin-4-yl)-N-(2-(imidazo[1,2-a]pyridin-3-yl)propan-2-yl)-N-methylazetidine-3-carboxamide;

1-(2-(3,8-diazabicyclo[3.2.1]octan-3-yl)-5-chloropyrimidin-4-yl)-N-(2-(imidazo[1,2-a]pyridin-3-yl)propan-2-yl)-N-methylazetidine-3-carboxamide;

1-(5-chloro-2-(2,3-dimethylpiperazin-1-yl)pyrimidin-4-yl)-N-(2-(imidazo[1,2-a]pyridin-3-yl)propan-2-yl)-N-methylazetidine-3-carboxamide;

(S)—N-(2-(imidazo[1,2-a]pyridin-3-yl)propan-2-yl)-N-methyl-1-(2-(2-methylpiperazin-1-yl)-5-(trifluoromethyl)pyrimidin-4-yl)azetidine-3-carboxamide;

1-(5-chloro-2-(piperazin-1-yl)pyrimidin-4-yl)-N-ethyl-N-(2-(imidazo[1,2-a]pyridin-3-yl)propan-2-yl)azetidine-3-carboxamide;

1-(5-chloro-2-(3-ethylpiperazin-1-yl)pyrimidin-4-yl)-N-(2-(imidazo[1,2-a]pyridin-3-yl)propan-2-yl)azetidine-3-carboxamide;

(R)-1-(5-chloro-2-(2-methylpiperazin-1-yl)pyrimidin-4-yl)-N-(2-(imidazo[1,2-a]pyridin-3-yl)propan-2-yl)-N-methylazetidine-3-carboxamide;

(R)-1-(5-chloro-2-(2,4-dimethylpiperazin-1-yl)pyrimidin-4-yl)-N-(2-(imidazo[1,2-a]pyridin-3-yl)propan-2-yl)-N-methylazetidine-3-carboxamide;

(S)-1-(5-chloro-2-(3-methylpiperazin-1-yl)pyrimidin-4-yl)-N-(2-(imidazo[1,2-a]pyridin-3-yl)propan-2-yl)-N-methylazetidine-3-carboxamide;

(S)-1-(5-chloro-2-(3,4-dimethylpiperazin-1-yl)pyrimidin-4-yl)-N-(2-(imidazo[1,2-a]pyridin-3-yl)propan-2-yl)-N-methylazetidine-3-carboxamide;

(R)-1-(5-chloro-2-(2-methylpiperazin-1-yl)pyrimidin-4-yl)-N-(2-(imidazo[1,2-a]pyridin-3-yl)propan-2-yl)azetidine-3-carboxamide;

1-(5-chloro-2-(2,3-dimethylpiperazin-1-yl)pyrimidin-4-yl)-N-(2-(imidazo[1,2-a]pyridin-3-yl)propan-2-yl)azetidine-3-carboxamide;

(S)-1-(5-chloro-2-(2-methylpiperazin-1-yl)pyrimidin-4-yl)-N-ethyl-N-(2-(imidazo[1,2-a]pyridin-3-yl)propan-2-yl)azetidine-3-carboxamide;

1-(2-(3,8-diazabicyclo[3.2.1]octan-3-yl)-5-chloropyrimidin-4-yl)-N-(2-(imidazo[1,2-a]pyridin-3-yl)propan-2-yl)azetidine-3-carboxamide;

1-(2-(2,5-diazabicyclo[4.1.0]heptan-2-yl)-5-chloropyrimidin-4-yl)-N-(2-(imidazo[1,2-a]pyridin-3-yl)propan-2-yl)-N-methylazetidine-3-carboxamide;

(S)-1-(5-chloro-2-(2-methylpiperazin-1-yl)pyrimidin-4-yl)-N-(2-(imidazo[1,2-a]pyridin-3-yl)propan-2-yl)azetidine-3-carboxamide;

(S)-1-(5-chloro-2-(2-ethylpiperazin-1-yl)pyrimidin-4-yl)-N-(2-(imidazo[1,2-a]pyridin-3-yl)propan-2-yl)azetidine-3-carboxamide;

(S)-1-(5-chloro-2-(2-ethylpiperazin-1-yl)pyrimidin-4-yl)-N-(2-(imidazo[1,2-a]pyridin-3-yl)propan-2-yl)-N-methylazetidine-3-carboxamide:

1-(5-chloro-2-(2,2-dimethylpiperazin-1-yl)pyrimidin-4-yl)-N-(2-(imidazo[1,2-a]pyridin-3-yl)propan-2-yl)-N-methylazetidine-3-carboxamide;

1-(5-chloro-2-(4,7-diazaspiro[2.5]octan-4-yl)pyrimidin-4-yl)-N-(2-(imidazo[1,2-a]pyridin-3-yl)propan-2-yl)-N-methylazetidine-3-carboxamide;

1-(5-chloro-2-((2S,5S)-2,5-dimethylpiperazin-1-yl)pyrimidin-4-yl)-N-(2-(imidazo[1,2-a]pyridin-3-yl)propan-2-yl)azetidine-3-carboxamide;

1-(5-chloro-2-((2S,5S)-2,4,5-trimethylpiperazin-1-yl)pyrimidin-4-yl)-N-(2-(imidazo[1,2-a]pyridin-3-yl)propan-2-yl)azetidine-3-carboxamide;

1-(5-chloro-2-((2S,5R)-2,5-dimethylpiperazin-1-yl)pyrimidin-4-yl)-N-(2-(imidazo[1,2-a]pyridin-3-yl)propan-2-yl)azetidine-3-carboxamide; and 1-(5-chloro-2-((2S,5R)-2,4,5-trimethylpiperazin-1-yl)pyrimidin-4-yl)-N-(2-(imidazo[1,2-a]pyridin-3-yl)propan-2-yl)azetidine-3-carboxamide;

or a pharmaceutically acceptable salt thereof.

23. A compound or a pharmaceutically acceptable ester, amide, carbamate or salt thereof as claimed in claim 2, wherein the compound or a pharmaceutically acceptable salt thereof is selected from the group consisting of:

1-{5-chloro-2-[(3R)-3-methylpiperazin-1-yl]pyrimidin-4-yl}-N-(2-{imidazo[1,2-a]pyridin-3-yl}propan-2-yl)azetidine-3-carboxamide;

1-{5-chloro-2-[(2S)-2,4-dimethylpiperazin-1-yl]pyrimidin-4-yl}-N-(2-{imidazo[1,2-a]pyridin-3-yl}propan-2-yl)azetidine-3-carboxamide;

1-{5-chloro-2-[(3R)-3,4-dimethylpiperazin-1-yl]pyrimidin-4-yl}-N-(2-{imidazo[1,2-a]pyridin-3-yl}propan-2-yl)azetidine-3-carboxamide;

1-[5-fluoro-2-(4-methylpiperazin-1-yl)pyridin-4-yl]-N-(2-{imidazo[1,2-a]pyridin-3-yl}propan-2-yl)azetidine-3-carboxamide;

1-[5-chloro-2-(1,4-diazepan-1-yl)pyrimidin-4-yl]-N-{imidazo[1,2-a]pyridin-3-ylmethyl}azetidine-3-carboxamide;

1-[2-(1,4-diazepan-1-yl)-5-fluoropyrimidin-4-yl]-N-{imidazo[1,2-a]pyridin-3-ylmethyl}azetidine-3-carboxamide;

1-(5-chloro-2-{3,6-diazabicyclo[3.2.0]heptan-3-yl}pyrimidin-4-yl)-N-{imidazo[1,2-a]pyridin-3-ylmethyl}azetidine-3-carboxamide;

1-(2-{3,6-diazabicyclo[3.2.0]heptan-3-yl}-5-fluoropyrimidin-4-yl)-N-{imidazo[1,2-a]pyridin-3-ylmethyl}azetidine-3-carboxamide;

1-[2-(1,4-diazepan-1-yl)-5-fluoropyrimidin-4-yl]-N-(1-{imidazo[1,2-a]pyridin-3-yl}ethyl)azetidine-3-carboxamide;

1-[5-chloro-2-(1,4-diazepan-1-yl)pyrimidin-4-yl]-N-(1-{imidazo[1,2-a]pyridin-3-yl}ethyl)azetidine-3-carboxamide;

1-[2-(1,4-diazepan-1-yl)-5-fluoropyrimidin-4-yl]-N-(2-{imidazo[1,2-a]pyridin-3-yl}propan-2-yl)azetidine-3-carboxamide;

1-[2-(1,4-diazepan-1-yl)-5-fluoropyrimidin-4-yl]-N-({2-methylimidazo[1,2-a]pyridin-3-yl}methyl)azetidine-3-carboxamide;

1-(2-{3,6-diazabicyclo[3.2.0]heptan-3-yl}-5-fluoropyrimidin-4-yl)-N-({2-methylimidazo[1,2-a]pyridin-3-yl}methyl)azetidine-3-carboxamide;

1-{5-fluoro-2-[methyl(pyrrolidin-3-yl)amino]pyrimidin-4-yl}-N{imidazo[1,2-a]pyridin-3-ylmethyl}azetidine-3-carboxamide;

1-[5-fluoro-2-(pyrrolidin-3-ylamino)pyrimidin-4-yl]-N{imidazo[1,2-a]pyridin-3-ylmethyl}azetidine-3-carboxamide;

1-[5-fluoro-2-(piperazin-1-yl)pyrimidin-4-yl]-N-{imidazo[1,2-a]pyridin-3-ylmethyl}azetidine-3-carboxamide;

1-[5-chloro-2-(1,4-diazepan-1-yl)pyrimidin-4-yl]-N-{imidazo[1,2-a]pyridin-3-ylmethyl}-N-methylazetidine-3-carboxamide;

1-[5-chloro-2-(1,4-diazepan-1-yl)pyrimidin-4-yl]-N-({2-methylimidazo[1,2-a]pyridin-3-yl}methyl)azetidine-3-carboxamide;

1-[2-(1,4-diazepan-1-yl)-5-methoxypyrimidin-4-yl]-N-{imidazo[1,2-a]pyridin-3-ylmethyl}azetidine-3-carboxamide;

1-[2-(1,4-diazepan-1-yl)-5-methoxypyrimidin-4-yl]-N-(2{imidazo[1,2-a]pyridin-3-yl}propan-2-yl)azetidine-3-carboxamide;

1-[5-chloro-2-(1,4-diazepan-1-yl)pyrimidin-4-yl]-N-({6-fluoroimidazo[1,2-a]pyridin-3-yl}methyl)azetidine-3-carboxamide;

1-[5-chloro-2-(1,4-diazepan-1-yl)pyrimidin-4-yl]-N-({6-chloroimidazo[1,2-a]pyridin-3-yl}methyl)azetidine-3-carboxamide;

1-[2-(1,4-diazepan-1-yl)-5-methoxypyrimidin-4-yl]-N-(1-{2-methylimidazo[1,2-a]pyridin-3-yl}ethyl)azetidine-3-carboxamide;

1-[5-chloro-2-(1,4-diazepan-1-yl)pyrimidin-4-yl]-N-(1-{2-methylimidazo[1,2-a]pyridin-3-yl}ethyl)azetidine-3-carboxamide;

1-[5-chloro-2-(piperazin-1-yl)pyrimidin-4-yl]-N-{imidazo[1,2-a]pyridin-3-ylmethyl}azetidine-3-carboxamide;

1-{5-fluoro-2-[(3S)-3-methylpiperazin-1-yl]pyrimidin-4-yl}-N{imidazo[1,2-a]pyridin-3-ylmethyl}azetidine-3-carboxamide;

1-{5-chloro-2-[(3S)-3-methylpiperazin-1-yl]pyrimidin-4-yl}-N-{imidazo[1,2-a]pyridin-3-ylmethyl}azetidine-3-carboxamide;

1-{5-fluoro-2-[(3R)-3-methylpiperazin-1-yl]pyrimidin-4-yl}-N-{imidazo[1,2-a]pyridin-3-ylmethyl}azetidine-3-carboxamide;

1-{5-chloro-2-[(3R)-3-methylpiperazin-1-yl]pyrimidin-4-yl}-N-{imidazo[1,2-a]pyridin-3-ylmethyl}azetidine-3-carboxamide;

1-[5-chloro-2-(piperazin-1-yl)pyrimidin-4-yl]-N-(1-{imidazo[1,2-a]pyridin-3-yl}ethyl)azetidine-3-carboxamide;

1-[5-fluoro-2-(piperazin-1-yl)pyrimidin-4-yl]-N-(1-{imidazo[1,2-a]pyridin-3-yl}ethyl)azetidine-3-carboxamide;

1-[5-fluoro-2-(piperazin-1-yl)pyrimidin-4-yl]-N-(2-{imidazo[1,2-a]pyridin-3-yl}propan-2-yl)azetidine-3-carboxamide;

1-[5-chloro-2-(piperazin-1-yl)pyrimidin-4-yl]-N-(2-{imidazo[1,2-a]pyridin-3-yl}propan-2-yl)azetidine-3-carboxamide;

N-(2-{imidazo[1,2-a]pyridin-3-yl}propan-2-yl)-1-[5-methoxy-2-(piperazin-1-yl)pyrimidin-4-yl]azetidine-3-carboxamide;

1-{5-fluoro-2-[(3R)-3-methylpiperazin-1-yl]pyrimidin-4-yl}-N-(2-{imidazo[1,2-a]pyridin-3-yl}propan-2-yl)azetidine-3-carboxamide;

N-(2-{imidazo[1,2-a]pyridin-3-yl}propan-2-yl)-1-{5-methoxy-2-[(3R)-3-methylpiperazin-1-yl]pyrimidin-4-yl}azetidine-3-carboxamide;

1-{5-chloro-2-[(3S)-3-methylpiperazin-1-yl]pyrimidin-4-yl}-N-(2-{imidazo[1,2-a]pyridin-3-yl}propan-2-yl)azetidine-3-carboxamide;

1-{5-fluoro-2-[(3S)-3-methylpiperazin-1-yl]pyrimidin-4-yl}-N-(2-{imidazo[1,2-a]pyridin-3-yl}propan-2-yl)azetidine-3-carboxamide;

N-(2-{imidazo[1,2-a]pyridin-3-yl}propan-2-yl)-1-{5-methoxy-2-[(3S)-3-methylpiperazin-1-yl]pyrimidin-4-yl}azetidine-3-carboxamide;

1-{5-fluoro-2-[methyl(pyrrolidin-3-yl)amino]pyrimidin-4-yl}-N-(2{imidazo[1,2-a]pyridin-3-yl}propan-2-yl)azetidine-3-carboxamide;

1-{5-chloro-2-[methyl(pyrrolidin-3-yl)amino]pyrimidin-4-yl}-N-(2-{imidazo[1,2-a]pyridin-3-yl}propan-2-yl)azetidine-3-carboxamide;

1-{2-[(3R,5S)-3,5-dimethylpiperazin-1-yl]-5-methoxy-pyrimidin-4-yl}-N-(2-{imidazo[1,2-a]pyridin-3-yl}propan-2-yl)azetidine-3-carboxamide;

1-{2-[(3R,5S)-3,5-dimethylpiperazin-1-yl]-5-chloropyrimidin-4-yl}-N-(2-{imidazo[1,2-a]pyridin-3-yl}propan-2-yl)azetidine-3-carboxamide;

1-{2-[(3R,5S)-3,5-dimethylpiperazin-1-yl]-5-fluoropyrimidin-4-yl}-N-(2-{imidazo[1,2-a]pyridin-3-yl}propan-2-yl)azetidine-3-carboxamide;

1-{2-[(3S,5S)-3,5-dimethylpiperazin-1-yl]-5-methoxypyrimidin-4-yl}-N-(2-{imidazo[1,2-a]pyridin-3-yl}propan-2-yl)azetidine-3-carboxamide;

1-{5-chloro-2-[(3R,5R)-3,5-dimethylpiperazin-1-yl]pyrimidin-4-yl}-N-(2-{imidazo[1,2-a]pyridin-3-yl}propan-2-yl)azetidine-3-carboxamide;

1-{2-[(3R,5R)-3,5-dimethylpiperazin-1-yl]-5-fluoropyrimidin-4-yl}-N-(2-{imidazo[1,2-a]pyridin-3-yl}propan-2-yl)azetidine-3-carboxamide;

1-{5-chloro-2-[(3S,5S)-3,5-dimethylpiperazin-1-yl]pyrimidin-4-yl}-N-(2-{imidazo[1,2-a]pyridin-3-yl}propan-2-yl)azetidine-3-carboxamide;

1-{5-fluoro-2-[(3S,5S)-3,4,5-trimethylpiperazin-1-yl]py-rimidin-4-yl}-N-(2-{imidazo[1,2-a]pyridin-3-yl}propan-2-yl)azetidine-3-carboxamide;

1-{5-fluoro-2-[(3S,5S)-3,4,5-dimethylpiperazine-1-yl]pyrimidin-4-yl}-N-(2-{imidazo[1,2-a]pyridin-3-yl}propan-2-yl)azetidine-3-carboxamide;

1-{5-chloro-2-[(2S)-2-methylpiperazin-1-yl]pyrimidin-4-yl}-N-(2-{imidazo[1,2-a]pyridin-3-yl}propan-2-yl)-N-methylazetidine-3-carboxamide;

1-[5-chloro-2-(1,4-diazepan-1-yl)pyrimidin-4-yl]-N-(2-{imidazo[1,2-a]pyridin-3-yl}propan-2-yl)azetidine-3-carboxamide 1-[5-fluoro-2-(4-methyl-1,4-diazepan-1-yl)pyrimidin-4-yl]-N-{imidazo[1,2-a]pyridin-3-ylmethyl}azetidine-3-carboxamide;

1-[5-chloro-2-(4-methyl-1,4-diazepan-1-yl)pyrimidin-4-yl]-N-(1-{imidazo[1,2-a]pyridin-3-yl}ethyl)azetidine-3-carboxamide;

1-[5-fluoro-2-(4-methylpiperazin-1-yl)pyrimidin-4-yl]-N-(2-{imidazo[1,2-a]pyridin-3-yl}propan-2-yl)azetidine-3-carboxamide;

1-[5-chloro-2-(4-methylpiperazin-1-yl)pyrimidin-4-yl]-N-(2-{imidazo[1,2-a]pyridin-3-yl}propan-2-yl)azetidine-3-carboxamide;

1-[5-fluoro-2-(4-methyl-1,4-diazepan-1-yl)pyrimidin-4-yl]-N-(2-{imidazo[1,2-a]pyridin-3-yl}propan-2-yl)azetidine-3-carboxamide;

1-[5-chloro-2-(4-methyl-1,4-diazepan-1-yl)pyrimidin-4-yl]-N-(2-{imidazo[1,2-a]pyridin-3-yl}propan-2-yl)azetidine-3-carboxamide;

1-{5-fluoro-2-[methyl(1-methylpyrrolidin-3-yl)amino]pyrimidin-4-yl}-N-(2-{imidazo[1,2-a]pyridin-3-yl}propan-2-yl)azetidine-3-carboxamide;

1-{5-chloro-2-[methyl(1-methylpyrrolidin-3-yl)amino]pyrimidin-4-yl}-N-(2-{imidazo[1,2-a]pyridin-3-yl}propan-2-yl)azetidine-3-carboxamide;

1-[5-fluoro-2-(4-methylpiperazin-1-yl)pyrimidin-4-yl]-N-(2-{6-methylimidazo[1,2-a]pyridin-3-yl}propan-2-yl)azetidine-3-carboxamide;

1-[5-fluoro-2-(4-methylpiperazin-1-yl)pyrimidin-4-yl]-N-(2-{8-fluoroimidazo[1,2-a]pyridin-3-yl}propan-2-yl)azetidine-3-carboxamide;

N-(2-{imidazo[1,2-a]pyridin-3-yl}propan-2-yl)-1-[5-methoxy-2-(4-methyl-1,4-diazepan-1-yl)pyrimidin-4-yl]azetidine-3-carboxamide;

N-(2-{imidazo[1,2-a]pyridin-3-yl}propan-2-yl)-1-[5-methoxy-2-(4-methylpiperazin-1-yl)pyrimidin-4-yl]azetidine-3-carboxamide;

1-[5-fluoro-2-(4-methylpiperazin-1-yl)pyrimidin-4-yl]-N-(2-{imidazo[1,2-a]pyridin-3-yl}propan-2-yl)pyrrolidine-3-carboxamide;

1-[5-fluoro-2-(4-methylpiperazin-1-yl)pyrimidin-4-yl]-N-(2-{imidazo[1,2-a]pyridin-3-yl}propan-2-yl)-3-methylazetidine-3-carboxamide;

N-(2-{imidazo[1,2-a]pyridin-3-yl}propan-2-yl)-1-[5-methyl-2-(4-methylpiperazin-1-yl)pyrimidin-4-yl]azetidine-3-carboxamide;

1-[5-chloro-2-(4-methylpiperazin-1-yl)pyrimidin-4-yl]-N-(2-{6-methylimidazo[1,2-a]pyridin-3-yl}propan-2-yl)azetidine-3-carboxamide;

1-{5-chloro-2-[(2R)-2,4-dimethylpiperazin-1-yl]pyrimidin-4-yl}-N-(2-{imidazo[1,2-a]pyridin-3-yl}propan-2-yl)azetidine-3-carboxamide;

1-{5-chloro-2-[3-(fluoromethyl)-4-methylpiperazin-1-yl]pyrimidin-4-yl}-N-(2-{imidazo[1,2-a]pyridin-3-yl}propan-2-yl)azetidine-3-carboxamide;

1-[5-chloro-2-(4-ethylpiperazin-1-yl)pyrimidin-4-yl]-N-(2-{imidazo[1,2-a]pyridin-3-yl}propan-2-yl)azetidine-3-carboxamide;

1-{5-chloro-2-[4-(propan-2-yl)piperazin-1-yl]pyrimidin-4-yl}-N-(2-{imidazo[1,2-a]pyridin-3-yl}propan-2-yl)azetidine-3-carboxamide;

1-[5-chloro-2-[4-(2-methoxyethyl)piperazin-1-yl]py-rimidin-4-yl]-N-(2-{imidazo[1,2-a]pyridin-3-yl}propan-2-yl)azetidine-3-carboxamide;

1-[5-chloro-2-(4-methylpiperazin-1-yl)pyrimidin-4-yl]-N-(2-{imidazo[1,2-a]pyridin-3-yl}propan-2-yl)-N-methylazetidine-3-carboxamide;

1-{5-chloro-2-[(3R)-3,4-dimethylpiperazin-1-yl]pyrimi-din-4-yl}-N-(2-{imidazo[1,2-a]pyridin-3-yl}propan-2-yl)-N-methylazetidine-3-carboxamide;

(3R)-1-[5-chloro-2-(4-methylpiperazin-1-yl)pyrimidin-4-yl]-N-(2-{imidazo[1,2-a]pyridin-3-yl}propan-2-yl)pyrrolidine-3-carboxamide;

(3S)-1-[5-chloro-2-(4-methylpiperazin-1-yl)pyrimidin-4-yl]-N-(2-{imidazo[1,2-a]pyridin-3-yl}propan-2-yl)pyrrolidine-3-carboxamide;

1-[5-chloro-2-(4-methylpiperazin-1-yl)pyrimidin-4-yl]-N-(2-{imidazo[1,2-a]pyridin-3-yl}propan-2-yl)piperi-dine-4-carboxamide;

1-[5-fluoro-2-(4-methylpiperazin-1-yl)pyrimidin-4-yl]-N-(2-{imidazo[1,2-a]pyridin-3-yl}propan-2-yl)-N-methylazetidine-3-carboxamide;

1-{5-chloro-2-[(2S,3R)-2,3-dimethylpiperazin-1-yl]py-rimidin-4-yl}-N-(2-{imidazo[1,2-a]pyridin-3-yl}propan-2-yl)azetidine-3-carboxamide;

1-{5-chloro-2-[3-(methoxymethyl)-4-methylpiperazin-1-yl]pyrimidin-4-yl}-N-(2-{imidazo[1,2-a]pyridin-3-yl}propan-2-yl)azetidine-3-carboxamide;

1-(5-fluoro-2-{6-methyl-3,6-diazabicyclo[3.2.0]heptan-3-yl}pyrimidin-4-yl)-N-{imidazo[1,2-a]pyridin-3-ylmethyl}azetidine-3-carboxamide;

1-{2-[(3S)-3,4-dimethylpiperazin-1-yl]-5-fluoropyrimi-din-4-yl}-N-(2-{imidazo[1,2-a]pyridin-3-yl}propan-2-yl)azetidine-3-carboxamide;

1-{5-chloro-2-[(3S)-3,4-dimethylpiperazin-1-yl]pyrimi-din-4-yl}-N-(2-{imidazo[1,2-a]pyridin-3-yl}propan-2-yl)azetidine-3-carboxamide;

1-{2-[(3R)-3,4-dimethylpiperazin-1-yl]-5-fluoropyrimi-din-4-yl}-N-(2-{imidazo[1,2-a]pyridin-3-yl}propan-2-yl)azetidine-3-carboxamide;

1-{2-[(3R)-3,4-dimethylpiperazin-1-yl]-5-methoxypy-rimidin-4-yl}-N-(2-{imidazo[1,2-a]pyridin-3-yl}propan-2-yl)azetidine-3-carboxamide;

1-{2-[(3R)-3,4-dimethylpiperazin-1-yl]-5-fluoropyrimi-din-4-yl}-N-(2-{imidazo[1,2-a]pyridin-3-yl}propan-2-yl)pyrrolidine-3-carboxamide;

1-{2-[(3R)-3,4-dimethylpiperazin-1-yl]-5-fluoropyrimi-din-4-yl}-N-(2-{imidazo[1,2-a]pyridin-3-yl}propan-2-yl)-3-methylazetidine-3-carboxamide;

N-(2-{imidazo[1,2-a]pyridin-3-yl}propan-2-yl)-1-{5-methoxy-2-[(3R,5S)-3,4,5-trimethylpiperazin-1-yl]py-rimidin-4-yl}azetidine-3-carboxamide;

1-{5-chloro-2-[(3R,5S)-3,4,5-trimethylpiperazin-1-yl]py-rimidin-4-yl}-N-(2-{imidazo[1,2-a]pyridin-3-yl}propan-2-yl)azetidine-3-carboxamide;

1-{5-fluoro-2-[(3R,5S)-3,4,5-trimethylpiperazin-1-yl]py-rimidin-4-yl}-N-(2-{imidazo[1,2-a]pyridin-3-yl}propan-2-yl)azetidine-3-carboxamide;

N-(2-{imidazo[1,2-a]pyridin-3-yl}propan-2-yl)-1-{5-methoxy-2-[(3R,5R)-3,4,5-trimethylpiperazin-1-yl]py-rimidin-4-yl}azetidine-3-carboxamide;

1-{5-chloro-2-[(3R,5R)-3,4,5-trimethylpiperazin-1-yl]
pyrimidin-4-yl}-N-(2-{imidazo[1,2-a]pyridin-3-
yl}propan-2-yl)azetidine-3-carboxamide;

1-{5-fluoro-2-[(3S,5S)-3,4,5-trimethylpiperazin-1-yl]py-
rimidin-4-yl}-N-(2-{imidazo[1,2-a]pyridin-3-
yl}propan-2-yl)azetidine-3-carboxamide;

N-(2-{imidazo[1,2-a]pyridin-3-yl}propan-2-yl)-1-{5-
methoxy-2-[(3R,5R)-3,4,5-trimethylpiperazin-1-yl]py-
rimidin-4-yl}azetidine-3-carboxamide;

1-{5-chloro-2-[(3R,5R)-3,4,5-trimethylpiperazin-1-yl]
pyrimidin-4-yl}-N-(2-{imidazo[1,2-a]pyridin-3-
yl}propan-2-yl)azetidine-3-carboxamide;

1-{5-fluoro-2-[(3S,5S)-3,4,5-trimethylpiperazin-1-yl]py-
rimidin-4-yl}-N-(2-{imidazo[1,2-a]pyridin-3-
yl}propan-2-yl)azetidine-3-carboxamide;

1-{2-[(3R)-3,4-dimethylpiperazin-1-yl]-5-fluoropyrimi-
din-4-yl}-N-(2-{6-methylimidazo[1,2-a]pyridin-3-
yl}propan-2-yl)azetidine-3-carboxamide;

1-{5-chloro-2-[(3R)-3,4-dimethylpiperazin-1-yl]pyrimi-
din-4-yl}-N-(2-{6-methylimidazo[1,2-a]pyridin-3-
yl}propan-2-yl)azetidine-3-carboxamide;

(3R)-1-{5-chloro-2-[(3R)-3,4-dimethylpiperazin-1-yl]py-
rimidin-4-yl}-N-(2-{imidazo[1,2-a]pyridin-3-
yl}propan-2-yl)pyrrolidine-3-carboxamide;

(3S)-1-{5-chloro-2-[(3R)-3,4-dimethylpiperazin-1-yl]py-
rimidin-4-yl}-N-(2-{imidazo[1,2-a]pyridin-3-
yl}propan-2-yl)pyrrolidine-3-carboxamide;

1-{5-chloro-2-[(3R)-3,4-dimethylpiperazin-1-yl]pyrimi-
din-4-yl}-N-(2-{imidazo[1,2-a]pyridin-3-yl}propan-2-
yl)piperidine-4-carboxamide;

1-{2-[(3R)-3,4-dimethylpiperazin-1-yl]-5-fluoropyrimi-
din-4-yl}-N-(2-{imidazo[1,2-a]pyridin-3-yl}propan-2-
yl)-N-methylazetidine-3-carboxamide;

1-{5-chloro-2-[(3R)-3,4-dimethylpiperazin-1-yl]pyridin-
4-yl}-N-(2-{imidazo[1,2-a]pyridin-3-yl}propan-2-yl)
azetidine-3-carboxamide;

1-{2-[(3R)-3,4-dimethylpiperazin-1-yl]-5-fluoropyridin-
4-yl}-N-(2-{imidazo[1,2-a]pyridin-3-yl}propan-2-yl)
azetidine-3-carboxamide;

1-[5-chloro-2-(4-methylpiperazin-1-yl)pyridin-4-yl]-N-
(2{imidazo[1,2-a]pyridin-3-yl}propan-2-yl)azetidine-
3-carboxamide;

1-{5-chloro-2-[(2S)-2,4-dimethylpiperazin-1-yl]pyrimi-
din-4-yl}-N{imidazo[1,2-a]pyridin-3-ylmethyl}-N-
methylazetidine-3-carboxamide;

1-{5-chloro-2-[(2S)-2,4-dimethylpiperazin-1-yl]pyrimi-
din-4-yl}-N-(2{imidazo[1,2-a]pyridin-3-yl}propan-2-
yl)-N-methylazetidine-3-carboxamide;

1-{2-[(2S)-2,4-dimethylpiperazin-1-yl]-5-fluoropyrimi-
din-4-yl}-N-(2-{imidazo[1,2-a]pyridin-3-yl}propan-2-
yl)-N-methylazetidine-3-carboxamide;

1-{5-chloro-2-[(2S,5R)-2,4,5-trimethylpiperazin-1-yl]py-
rimidin-4-yl}-N-(2-{imidazo[1,2-a]pyridin-3-
yl}propan-2-yl)azetidine-3-carboxamide;

1-{5-chloro-2-[(2R,5R)-2,4,5-trimethylpiperazin-1-yl]
pyrimidin-4-yl}-N-(2{imidazo[1,2-a]pyridin-3-
yl}propan-2-yl)azetidine-3-carboxamide;

1-{5-fluoro-2-[(2S,5R)-2,4,5-trimethylpiperazin-1-yl]py-
rimidin-4-yl}-N-(2-{imidazo[1,2-a]pyridin-3-
yl}propan-2-yl)azetidine-3-carboxamide; and 1-[5-chloro-2-(1,4-diazepan-1-yl)pyrimidin-4-yl]-N-{[1,
2,4]triazolo[4,3-a]pyridin-3-ylmethyl}azetidine-3-car-
boxamide;

or a pharmaceutically acceptable salt thereof.

* * * * *